(12) United States Patent
Zhang

(10) Patent No.: US 11,795,203 B2
(45) Date of Patent: Oct. 24, 2023

(54) PROTEIN HETERODIMER AND USE THEREOF

(71) Applicant: Jinyu Zhang, Chongqing (CN)

(72) Inventor: Jinyu Zhang, Chongqing (CN)

( * ) Notice: Subject to any disclaimer, the term of this patent is extended or adjusted under 35 U.S.C. 154(b) by 0 days.

(21) Appl. No.: 17/264,193

(22) PCT Filed: Jul. 30, 2019

(86) PCT No.: PCT/CN2019/098300
§ 371 (c)(1),
(2) Date: Jan. 28, 2021

(87) PCT Pub. No.: WO2020/024922
PCT Pub. Date: Feb. 6, 2020

(65) Prior Publication Data
US 2021/0395320 A1 Dec. 23, 2021

(30) Foreign Application Priority Data

Jul. 30, 2018 (CN) .......................... 201810853384.X

(51) Int. Cl.
| | | |
|---|---|---|
| *C07K 14/475* | (2006.01) | |
| *C07K 14/535* | (2006.01) | |
| *C07K 14/54* | (2006.01) | |
| *C07K 14/55* | (2006.01) | |
| *A61P 35/00* | (2006.01) | |
| *A61K 38/00* | (2006.01) | |

(52) U.S. Cl.
CPC ............ *C07K 14/475* (2013.01); *A61P 35/00* (2018.01); *C07K 14/535* (2013.01); *C07K 14/5418* (2013.01); *C07K 14/5434* (2013.01); *C07K 14/5443* (2013.01); *C07K 14/55* (2013.01); *A61K 38/00* (2013.01)

(58) Field of Classification Search
CPC combination set(s) only.
See application file for complete search history.

(56) References Cited

U.S. PATENT DOCUMENTS

| | | | |
|---|---|---|---|
| 6,022,535 A | 2/2000 | Bauer et al. | |
| 6,030,812 A | 2/2000 | Bauer et al. | |
| 6,057,133 A | 5/2000 | Bauer et al. | |
| 8,507,222 B2 | 8/2013 | Wong et al. | |
| 9,255,141 B2 | 2/2016 | Wong et al. | |
| 9,328,159 B2 | 5/2016 | Wong et al. | |
| 9,428,573 B2 | 8/2016 | Wong et al. | |
| 10,150,805 B2 | 12/2018 | Wong et al. | |
| 10,358,478 B2 | 7/2019 | Wong et al. | |
| 2004/0072299 A1* | 4/2004 | Gillies .................. | C07K 16/30 530/391.1 |
| 2005/0053579 A1 | 3/2005 | Galipeau et al. | |
| 2012/0177595 A1 | 7/2012 | Wong et al. | |
| 2014/0134128 A1 | 5/2014 | Wong et al. | |
| 2014/0205560 A1 | 7/2014 | Wong et al. | |
| 2014/0242025 A1 | 8/2014 | Wong et al. | |
| 2016/0213750 A1 | 7/2016 | Wong et al. | |
| 2016/0355567 A1 | 12/2016 | Wong et al. | |
| 2019/0023766 A1 | 1/2019 | Wong et al. | |

FOREIGN PATENT DOCUMENTS

| | | |
|---|---|---|
| CN | 1227604 A | 9/1999 |
| CN | 1288059 A | 3/2001 |
| CN | 1316518 A | 10/2001 |
| CN | 101166760 A | 4/2008 |
| CN | 103370339 A | 10/2013 |
| CN | 105518143 A | 4/2016 |
| EP | 1 731 531 A2 | 12/2006 |
| EP | 1 731 531 A3 | 12/2006 |
| JP | 2003-507012 | 2/2003 |
| WO | WO 01/10912 A1 | 2/2001 |
| WO | WO 2018/129404 A1 | 7/2018 |

OTHER PUBLICATIONS

Merck Manual Bladder Cancer accessed Aug. 21, 2014 at URL: merckmanuals.com/home/kidney_and_urinary_tract_disorders/cancers_of_the_kidney_and_genitourinary_tract/bladder_cancer.html, 2 pages (Year: 2014).*
Merck Manuals Lung Carcinoma accessed Mar. 12, 2017 at URL merckmanuals.com/professional/pulmonary-disorders/tumors-of-the-lungs/lung-carcinoma, 18 pages (Year: 2017).*
Merck Manual Colorectal Cancer accessed Aug. 21, 2014 at URL merckmanuals.com/home/digestive_disorders/tumors_of_the_digestive_system/colorectal_cancer.htm, 5 pages (Year: 2014).*
National Institute of Cancer—understanding and related topics, accessed Aug. 21, 2014 at URL: cancer.gov/cancertopics/understandingcancer, 63 pages (Year: 2014).*
Thyroid cancer accessed Mar. 12, 2017 at URL www.merckmanuals.com/professional/endocrine-and-metabolic-disorders/thyroid-disorders/thyroid-cancers, 4 pages (Year: 2017).*
Renal cell carcinoma, accessed Mar. 12, 2017 at URL merckmanuals.com/professional/genitourinary-disorders/genitourinary-cancer/renal-cell-carcinoma, 6 pages (Year: 2017).*
Merck Manual Prostate Cancer accessed Aug. 21, 2014 at URL: merckmanuals.com/home/kidney_and_urinary_tract_disorders/cancers_of_the_kidney_and_genitourinary_tract/prostate_cancer.html?qt=prostate cancer&alt=sh, 8 pages (Year: 2014).*

(Continued)

*Primary Examiner* — Julie Ha
*Assistant Examiner* — Kristina M Hellman
(74) *Attorney, Agent, or Firm* — Oblon, McClelland, Maier & Neustadt, L.L.P.

(57) ABSTRACT

Disclosed are a protein heterodimer and the use thereof. The protein heterodimer comprises a first polypeptide chain and a second polypeptide chain different from the first polypeptide chain, wherein the first polypeptide chain comprises IL(interleukin)12a and a first factor fused to IL12a, the second polypeptide chain comprises IL12b and a second factor fused to IL12b, and the first factor and the second factor are each independently selected from a group consisting of: IL2, GMCSF(granulocyte-macrophage colony-stimulating factor), IL7, IL15, IL21 and FLT3L(FMS-like tyrosine kinase 3 ligand). The protein heterodimer can be used for treating tumors.

8 Claims, 19 Drawing Sheets
Specification includes a Sequence Listing.

(56) References Cited

OTHER PUBLICATIONS

Merck Manuals Neuroblastoma accessed Mar. 12, 2017 at URL merckmanuals.com/professional/ pediatrics/pediatric-cancers/neuroblastoma, 4 pages (Year: 2017).*
Cholangiocarcinoma accessed Mar. 12, 2017 at URL surgery.usc.edu/divisions/tumor/pancreasdiseases/web%20pages/BILIARY%20SYSTEM/cholangiocarcinoma, 2 pages (Year: 2017).*
Skin cancer, accessed Jun. 9, 2015 at merckmanuals.com/professional/dermatologic-disorders/cancers-of-the-skin/overview-of-skin-cancer, 3 pages (Year: 2015).*
Bowie et al, "Deciphering the message in protein sequences: tolerance to amino acid substitutions," Science 247:1306-1310 (1990)) (Year: 1990).*
Wen et al., Fusion cytokine IL-2-GMCSF enhances anticancer immune responses through promoting cell-cell interactions, J Transl Med 14:41, pp. 1-13 (2016) (Year: 2016).*
Brombacher et al., "Novel IL-12 family members shed light on the orchestration of Th1 responses,"Trends Immunol. 24:207-212 (2003) (Year: 2003).*
Yoon et al., "Charged residues dominate a unique interlocking topography in the hydrodynamic cytokine interleukin 12," EMBO J. 19: 3530-3541 (2000) (Year: 2000).*
International Search Report dated Oct. 30, 2019 in PCT/CN2019/098300 filed Jul. 30, 2019, 5 pages.
Zhou, He-feng et al., "Co-expression of p40 and p35 Gene of Human Interleukin-12 in Pichia pastoris and Its Bioactivity", China Biotechnology, vol. 28, No. 3, 2008, pp. 20-24, 6 total pages (with English Abstract).

Williams, P. et al., "A Fusion of GMCSF and IL-21 Initiates Hypersignaling Through the IL-21 Rα Chain With Immune Activating and Tumoricidal Effects In Vivo", Molecular Therapy., vol. 18, No. 7, 2010, pp. 1293-1301.
Extended European Search Report dated Apr. 7, 2022 in European Patent Application No. 19843948.1, 8 pages.
Verena Gafner, et al., "An engineered antibody-interleukin-12 fusion protein with enhanced tumor vascular targeting properties," International Journal of Cancer, vol. 119, 2006, pp. 2205-2212.
Japanese Office Action dated Apr. 18, 2023, in Japanese Paten Application No. 2021-505757 (with English Translation).
Weiss et al., Immunotherapy of Cancer by IL-12-based Cytokine Combinations, Expert Opinion on Biological Therapy, Nov. 2007, vol. 7, No. 11, p. 1705-1721, DOI: 10.1517/14715898.7.11.1705.
Esche et al., Interleukin-12 and Flt3 ligand differentially promote dendropoiesis in vivo, European Journal of Immunology, 2000, vol. 30, No. 9, p. 2565-2575, DOI: 10.1002/1521-4141(200009)30:93.0.CO;2-V.
Schilbach et al., Cancer-targeted IL-12 controls human rhabdomyosarcoma by senescence induction and myogenic differentiation, OncoImmunology, 2015 year and vol. 4, No. 7, e1014760, DOI: 10.1080/2162402X.2015.1014760.
Tian et al., IL-21 and IL-12 Inhibit Differentiation of Treg and $T_H17$ Cells and Enhance Cytotoxicity of Peripheral Blood Mononuclear Cells in Patients With Cervical Cancer, International Journal of Gynecologic Cancer, 2011, vol. 21, No. 9, p. 1672/1678, DOI: 10.1097/IGC.0B013e3182358955.

* cited by examiner

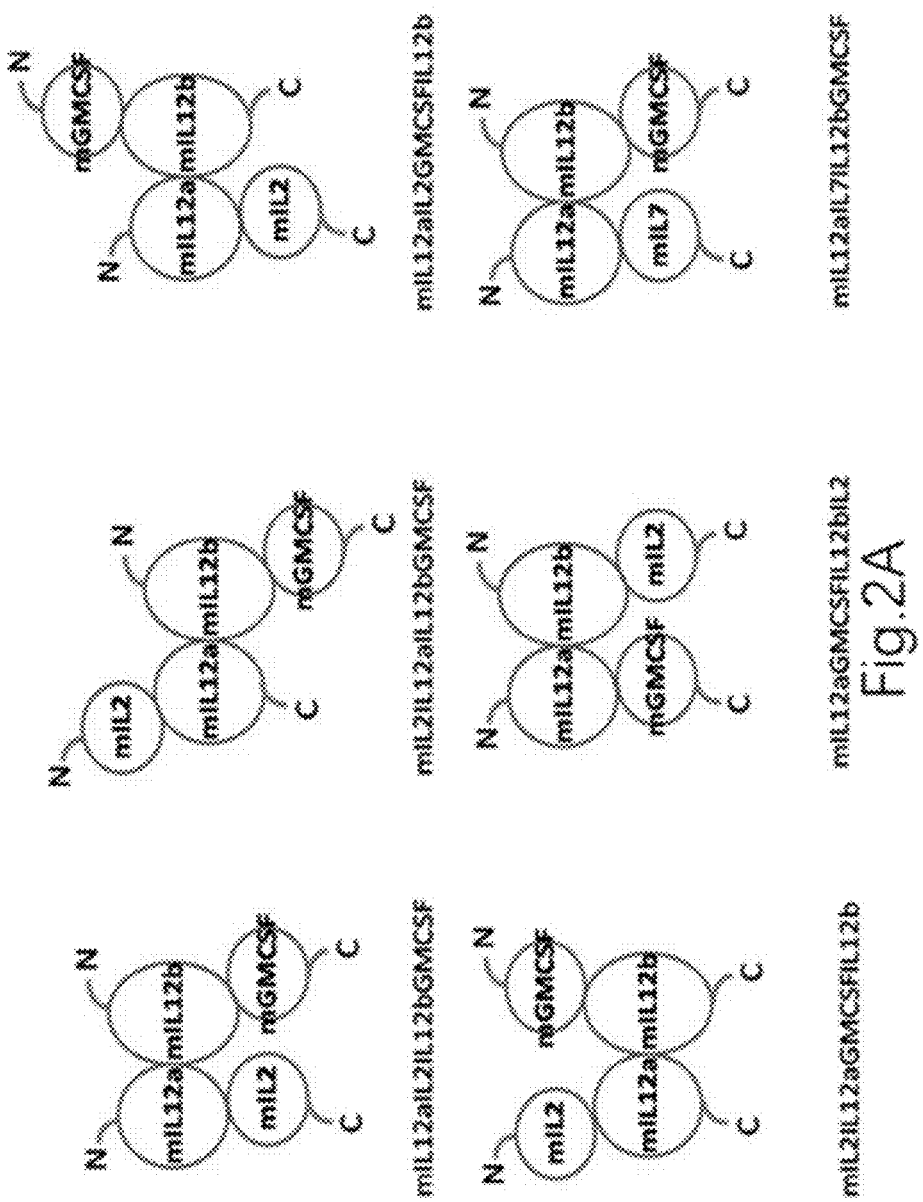

SEQUENCE LISTING

<160> NUMBER OF SEQ ID NOS: 75

<210> SEQ ID NO 1
<211> LENGTH: 193
<212> TYPE: PRT
<213> ORGANISM: Mus musculus

<400> SEQUENCE: 1

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

-continued

```
Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Ile Ile
            115                 120                 125

Leu Asp Lys Gly Met Leu Val Ala Ile Asp Glu Leu Met Gln Ser Leu
            130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala
```

<210> SEQ ID NO 2
<211> LENGTH: 313
<212> TYPE: PRT
<213> ORGANISM: Mus musculus

<400> SEQUENCE: 2

```
Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
            35                  40                  45

Ser Gly Lys Thr Leu Thr Ile Thr Val Lys Glu Phe Leu Asp Ala Gly
        50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
            115                 120                 125

Phe Asn Ile Lys Ser Ser Ser Ser Pro Asp Ser Arg Ala Val Thr
            130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
            195                 200                 205

Ile Lys Pro Asp Pro Pro Lys Asn Leu Gln Met Lys Pro Leu Lys Asn
        210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270
```

```
Leu Val Glu Lys Thr Ser Thr Glu Val Gln Cys Lys Gly Gly Asn Val
            275                 280                 285

Cys Val Gln Ala Gln Asp Arg Tyr Tyr Asn Ser Ser Cys Ser Lys Trp
290                 295                 300

Ala Cys Val Pro Cys Arg Val Arg Ser
305                 310
```

<210> SEQ ID NO 3
<211> LENGTH: 149
<212> TYPE: PRT
<213> ORGANISM: Mus musculus

<400> SEQUENCE: 3

```
Ala Pro Thr Ser Ser Thr Ser Ser Thr Ala Glu Ala Gln Gln
1               5                   10                  15

Gln Gln Gln Gln Gln Gln Gln Gln Gln His Leu Glu Gln Leu Leu
                20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145
```

<210> SEQ ID NO 4
<211> LENGTH: 114
<212> TYPE: PRT
<213> ORGANISM: Mus musculus

<400> SEQUENCE: 4

```
Asn Trp Ile Asp Val Arg Tyr Asp Leu Glu Lys Ile Glu Ser Leu Ile
1               5                   10                  15

Gln Ser Ile His Ile Asp Thr Thr Leu Tyr Thr Asp Ser Asp Phe His
                20                  25                  30

Pro Ser Cys Lys Val Thr Ala Met Asn Cys Phe Leu Leu Glu Leu Gln
            35                  40                  45

Val Ile Leu His Glu Tyr Ser Asn Met Thr Leu Asn Glu Thr Val Arg
    50                  55                  60

Asn Val Leu Tyr Leu Ala Asn Ser Thr Leu Ser Ser Asn Lys Asn Val
65                  70                  75                  80

Ala Glu Ser Gly Cys Lys Glu Cys Glu Glu Leu Glu Glu Lys Thr Phe
                85                  90                  95

Thr Glu Phe Leu Gln Ser Phe Ile Arg Ile Val Gln Met Phe Ile Asn
            100                 105                 110

Thr Ser
```

<210> SEQ ID NO 5
<211> LENGTH: 129
<212> TYPE: PRT
<213> ORGANISM: Mus musculus

<400> SEQUENCE: 5

```
Glu Cys His Ile Lys Asp Lys Glu Gly Lys Ala Tyr Glu Ser Val Leu
1               5                   10                  15
Met Ile Ser Ile Asp Glu Leu Asp Lys Met Thr Gly Thr Asp Ser Asn
            20                  25                  30
Cys Pro Asn Asn Glu Pro Asn Phe Phe Arg Lys His Val Cys Asp Asp
        35                  40                  45
Thr Lys Glu Ala Ala Phe Leu Asn Arg Ala Arg Lys Leu Lys Gln
    50                  55                  60
Phe Leu Lys Met Asn Ile Ser Glu Glu Phe Asn Val His Leu Leu Thr
65                  70                  75                  80
Val Ser Gln Gly Thr Gln Thr Leu Val Asn Cys Thr Ser Lys Glu Glu
                85                  90                  95
Lys Asn Val Lys Glu Gln Lys Lys Asn Asp Ala Cys Phe Leu Lys Arg
            100                 105                 110
Leu Leu Arg Glu Ile Lys Thr Cys Trp Asn Lys Ile Leu Lys Gly Ser
        115                 120                 125
Ile
```

<210> SEQ ID NO 6
<211> LENGTH: 129
<212> TYPE: PRT
<213> ORGANISM: Mus musculus

<400> SEQUENCE: 6

```
His Lys Ser Ser Pro Gln Gly Pro Asp Arg Leu Leu Ile Arg Leu Arg
1               5                   10                  15
His Leu Ile Asp Ile Val Glu Gln Leu Lys Ile Tyr Glu Asn Asp Leu
            20                  25                  30
Asp Pro Glu Leu Leu Ser Ala Pro Gln Asp Val Lys Gly His Cys Glu
        35                  40                  45
His Ala Ala Phe Ala Cys Phe Gln Lys Ala Lys Leu Lys Pro Ser Asn
    50                  55                  60
Pro Gly Asn Asn Lys Thr Phe Ile Ile Asp Leu Val Ala Gln Leu Arg
65                  70                  75                  80
Arg Arg Leu Pro Ala Arg Arg Gly Gly Lys Lys Gln Lys His Ile Ala
                85                  90                  95
Lys Cys Pro Ser Cys Asp Ser Tyr Glu Lys Arg Thr Pro Lys Glu Phe
            100                 105                 110
Leu Glu Arg Leu Lys Trp Leu Leu Gln Lys Met Ile His Gln His Leu
        115                 120                 125
Ser
```

<210> SEQ ID NO 7
<211> LENGTH: 206
<212> TYPE: PRT
<213> ORGANISM: Mus musculus

<400> SEQUENCE: 7

```
Gly Thr Pro Asp Cys Tyr Phe Ser His Ser Pro Ile Ser Ser Asn Phe
1               5                   10                  15
```

Lys Val Lys Phe Arg Glu Leu Thr Asp His Leu Leu Lys Asp Tyr Pro
            20                  25                  30

Val Thr Val Ala Val Asn Leu Gln Asp Glu Lys His Cys Lys Ala Leu
        35                  40                  45

Trp Ser Leu Phe Leu Ala Gln Arg Trp Ile Glu Gln Leu Lys Thr Val
    50                  55                  60

Ala Gly Ser Lys Met Gln Thr Leu Leu Glu Asp Val Asn Thr Glu Ile
65                  70                  75                  80

His Phe Val Thr Ser Cys Thr Phe Gln Pro Leu Pro Glu Cys Leu Arg
                85                  90                  95

Phe Val Gln Thr Asn Ile Ser His Leu Leu Lys Asp Thr Cys Thr Gln
            100                 105                 110

Leu Leu Ala Leu Lys Pro Cys Ile Gly Lys Ala Cys Gln Asn Phe Ser
        115                 120                 125

Arg Cys Leu Glu Val Gln Cys Gln Pro Asp Ser Ser Thr Leu Leu Pro
    130                 135                 140

Pro Arg Ser Pro Ile Ala Leu Glu Ala Thr Glu Leu Pro Glu Pro Arg
145                 150                 155                 160

Pro Arg Gln Leu Leu Leu Leu Leu Leu Leu Leu Pro Leu Thr Leu
                165                 170                 175

Val Leu Leu Ala Ala Ala Trp Gly Leu Arg Trp Gln Arg Ala Arg Arg
            180                 185                 190

Arg Gly Glu Leu His Pro Gly Val Pro Leu Pro Ser His Pro
        195                 200                 205

<210> SEQ ID NO 8
<211> LENGTH: 124
<212> TYPE: PRT
<213> ORGANISM: Mus musculus

<400> SEQUENCE: 8

Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
            20                  25                  30

Leu Asn Glu Glu Val Glu Val Val Ser Asn Glu Phe Ser Phe Lys Lys
        35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Gly Gln Lys
        115                 120

<210> SEQ ID NO 9
<211> LENGTH: 197
<212> TYPE: PRT
<213> ORGANISM: Homo sapiens

<400> SEQUENCE: 9

Arg Asn Leu Pro Val Ala Thr Pro Asp Pro Gly Met Phe Pro Cys Leu
1               5                   10                  15

```
His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 10
<211> LENGTH: 306
<212> TYPE: PRT
<213> ORGANISM: Homo sapiens

<400> SEQUENCE: 10

Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190
```

```
Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
                260                 265                 270

Ser Ala Thr Val Ile Cys Arg Lys Asn Ala Ser Ile Ser Val Arg Ala
                275                 280                 285

Gln Asp Arg Tyr Tyr Ser Ser Ser Trp Ser Glu Trp Ala Ser Val Pro
    290                 295                 300

Cys Ser
305

<210> SEQ ID NO 11
<211> LENGTH: 133
<212> TYPE: PRT
<213> ORGANISM: Homo sapiens

<400> SEQUENCE: 11

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 12
<211> LENGTH: 114
<212> TYPE: PRT
<213> ORGANISM: Homo sapiens

<400> SEQUENCE: 12

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60
```

```
Asn Leu Ile Ile Leu Ala Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 13
<211> LENGTH: 152
<212> TYPE: PRT
<213> ORGANISM: Homo sapiens

<400> SEQUENCE: 13

Asp Cys Asp Ile Glu Gly Lys Asp Gly Lys Gln Tyr Glu Ser Val Leu
 1               5                  10                  15

Met Val Ser Ile Asp Gln Leu Leu Asp Ser Met Lys Glu Ile Gly Ser
                20                  25                  30

Asn Cys Leu Asn Asn Glu Phe Asn Phe Phe Lys Arg His Ile Cys Asp
             35                  40                  45

Ala Asn Lys Glu Gly Met Phe Leu Phe Arg Ala Ala Arg Lys Leu Arg
     50                  55                  60

Gln Phe Leu Lys Met Asn Ser Thr Gly Asp Phe Asp Leu His Leu Leu
 65                  70                  75                  80

Lys Val Ser Glu Gly Thr Thr Ile Leu Leu Asn Cys Thr Gly Gln Val
                 85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150

<210> SEQ ID NO 14
<211> LENGTH: 133
<212> TYPE: PRT
<213> ORGANISM: Homo sapiens

<400> SEQUENCE: 14

Gln Gly Gln Asp Arg His Met Ile Arg Met Arg Gln Leu Ile Asp Ile
 1               5                  10                  15

Val Asp Gln Leu Lys Asn Tyr Val Asn Asp Leu Val Pro Glu Phe Leu
                20                  25                  30

Pro Ala Pro Glu Asp Val Glu Thr Asn Cys Glu Trp Ser Ala Phe Ser
             35                  40                  45

Cys Phe Gln Lys Ala Gln Leu Lys Ser Ala Asn Thr Gly Asn Asn Glu
     50                  55                  60

Arg Ile Ile Asn Val Ser Ile Lys Lys Leu Lys Arg Lys Pro Pro Ser
 65                  70                  75                  80

Thr Asn Ala Gly Arg Arg Gln Lys His Arg Leu Thr Cys Pro Ser Cys
                 85                  90                  95

Asp Ser Tyr Glu Lys Lys Pro Pro Lys Glu Phe Leu Glu Arg Phe Lys
            100                 105                 110
```

```
Ser Leu Leu Gln Lys Met Ile His Gln His Leu Ser Ser Arg Thr His
        115                 120                 125

Gly Ser Glu Asp Ser
    130
```

<210> SEQ ID NO 15
<211> LENGTH: 209
<212> TYPE: PRT
<213> ORGANISM: Homo sapiens

<400> SEQUENCE: 15

```
Thr Gln Asp Cys Ser Phe Gln His Ser Pro Ile Ser Ser Asp Phe Ala
1               5                   10                  15

Val Lys Ile Arg Glu Leu Ser Asp Tyr Leu Leu Gln Asp Tyr Pro Val
            20                  25                  30

Thr Val Ala Ser Asn Leu Gln Asp Glu Glu Leu Cys Gly Gly Leu Trp
        35                  40                  45

Arg Leu Val Leu Ala Gln Arg Trp Met Glu Arg Leu Lys Thr Val Ala
50                  55                  60

Gly Ser Lys Met Gln Gly Leu Leu Glu Arg Val Asn Thr Glu Ile His
65                  70                  75                  80

Phe Val Thr Lys Cys Ala Phe Gln Pro Pro Ser Cys Leu Arg Phe
                85                  90                  95

Val Gln Thr Asn Ile Ser Arg Leu Leu Gln Glu Thr Ser Glu Gln Leu
            100                 105                 110

Val Ala Leu Lys Pro Trp Ile Thr Arg Gln Asn Phe Ser Arg Cys Leu
        115                 120                 125

Glu Leu Gln Cys Gln Pro Asp Ser Ser Thr Leu Pro Pro Pro Trp Ser
    130                 135                 140

Pro Arg Pro Leu Glu Ala Thr Ala Pro Thr Ala Pro Gln Pro Pro Leu
145                 150                 155                 160

Leu Leu Leu Leu Leu Leu Pro Val Gly Leu Leu Leu Leu Ala Ala Ala
                165                 170                 175

Trp Cys Leu His Trp Gln Arg Thr Arg Arg Arg Thr Pro Arg Pro Gly
            180                 185                 190

Glu Gln Val Pro Pro Val Pro Ser Pro Gln Asp Leu Leu Leu Val Glu
        195                 200                 205

His
```

<210> SEQ ID NO 16
<211> LENGTH: 127
<212> TYPE: PRT
<213> ORGANISM: Homo sapiens

<400> SEQUENCE: 16

```
Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
```

```
                85                  90                  95
Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
            115                 120                 125

<210> SEQ ID NO 17
<211> LENGTH: 15
<212> TYPE: PRT
<213> ORGANISM: Artificial Sequence
<220> FEATURE:
<223> OTHER INFORMATION: joint peptide

<400> SEQUENCE: 17

Gly Gly Gly Gly Ser Gly Gly Gly Gly Ser Gly Gly Gly Gly Ser
1               5                   10                  15

<210> SEQ ID NO 18
<211> LENGTH: 809
<212> TYPE: PRT
<213> ORGANISM: Artificial Sequence
<220> FEATURE:
<223> OTHER INFORMATION: mIL12aIL2IL12bGMCSF protein heterodimer

<400> SEQUENCE: 18

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65              70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145             150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Gly Ser Gly Gly Gly Gly Ser Gly Gly Gly Gly Ser
        195                 200                 205

Ala Pro Thr Ser Ser Ser Thr Ser Ser Ser Thr Ala Glu Ala Gln Gln
    210                 215                 220

Gln Gln Gln Gln Gln Gln Gln Gln Gln Gln His Leu Glu Gln Leu Leu
225             230                 235                 240

Met Asp Leu Gln Glu Leu Leu Ser Arg Met Glu Asn Tyr Arg Asn Leu
                245                 250                 255
```

```
Lys Leu Pro Arg Met Leu Thr Phe Lys Phe Tyr Leu Pro Lys Gln Ala
                260                 265                 270

Thr Glu Leu Lys Asp Leu Gln Cys Leu Glu Asp Glu Leu Gly Pro Leu
            275                 280                 285

Arg His Val Leu Asp Leu Thr Gln Ser Lys Ser Phe Gln Leu Glu Asp
        290                 295                 300

Ala Glu Asn Phe Ile Ser Asn Ile Arg Val Thr Val Val Lys Leu Lys
305                 310                 315                 320

Gly Ser Asp Asn Thr Phe Glu Cys Gln Phe Asp Glu Ser Ala Thr
                325                 330                 335

Val Val Asp Phe Leu Arg Arg Trp Ile Ala Phe Cys Gln Ser Ile Ile
                340                 345                 350

Ser Thr Ser Pro Gln Met Trp Glu Leu Glu Lys Asp Val Tyr Val Val
            355                 360                 365

Glu Val Asp Trp Thr Pro Asp Ala Pro Gly Glu Thr Val Asn Leu Thr
        370                 375                 380

Cys Asp Thr Pro Glu Glu Asp Asp Ile Thr Trp Thr Ser Asp Gln Arg
385                 390                 395                 400

His Gly Val Ile Gly Ser Gly Lys Thr Leu Thr Ile Thr Val Lys Glu
                405                 410                 415

Phe Leu Asp Ala Gly Gln Tyr Thr Cys His Lys Gly Gly Glu Thr Leu
                420                 425                 430

Ser His Ser His Leu Leu Leu His Lys Lys Glu Asn Gly Ile Trp Ser
            435                 440                 445

Thr Glu Ile Leu Lys Asn Phe Lys Asn Lys Thr Phe Leu Lys Cys Glu
        450                 455                 460

Ala Pro Asn Tyr Ser Gly Arg Phe Thr Cys Ser Trp Leu Val Gln Arg
465                 470                 475                 480

Asn Met Asp Leu Lys Phe Asn Ile Lys Ser Ser Ser Ser Pro Asp
                485                 490                 495

Ser Arg Ala Val Thr Cys Gly Met Ala Ser Leu Ser Ala Glu Lys Val
            500                 505                 510

Thr Leu Asp Gln Arg Asp Tyr Glu Lys Tyr Ser Val Ser Cys Gln Glu
        515                 520                 525

Asp Val Thr Cys Pro Thr Ala Glu Glu Thr Leu Pro Ile Glu Leu Ala
530                 535                 540

Leu Glu Ala Arg Gln Gln Asn Lys Tyr Glu Asn Tyr Ser Thr Ser Phe
545                 550                 555                 560

Phe Ile Arg Asp Ile Ile Lys Pro Asp Pro Pro Lys Asn Leu Gln Met
                565                 570                 575

Lys Pro Leu Lys Asn Ser Gln Val Glu Val Ser Trp Glu Tyr Pro Asp
            580                 585                 590

Ser Trp Ser Thr Pro His Ser Tyr Phe Ser Leu Lys Phe Phe Val Arg
        595                 600                 605

Ile Gln Arg Lys Lys Glu Lys Met Lys Glu Thr Glu Glu Gly Cys Asn
            610                 615                 620

Gln Lys Gly Ala Phe Leu Val Glu Lys Thr Ser Thr Glu Val Gln Cys
625                 630                 635                 640

Lys Gly Gly Asn Val Cys Val Gln Ala Gln Asp Arg Tyr Tyr Asn Ser
                645                 650                 655

Ser Cys Ser Lys Trp Ala Cys Val Pro Cys Arg Val Arg Ser Gly Gly
            660                 665                 670

Gly Gly Ser Gly Gly Gly Gly Ser Gly Gly Gly Ser Ala Pro Thr
```

```
                675                 680                 685
Arg Ser Pro Ile Thr Val Thr Arg Pro Trp Lys His Val Glu Ala Ile
        690                 695                 700
Lys Glu Ala Leu Asn Leu Leu Asp Asp Met Pro Val Thr Leu Asn Glu
705                 710                 715                 720
Glu Val Glu Val Val Ser Asn Glu Phe Ser Phe Lys Lys Leu Thr Cys
                725                 730                 735
Val Gln Thr Arg Leu Lys Ile Phe Glu Gln Gly Leu Arg Gly Asn Phe
        740                 745                 750
Thr Lys Leu Lys Gly Ala Leu Asn Met Thr Ala Ser Tyr Tyr Gln Thr
        755                 760                 765
Tyr Cys Pro Pro Thr Pro Glu Thr Asp Cys Glu Thr Gln Val Thr Thr
        770                 775                 780
Tyr Ala Asp Phe Ile Asp Ser Leu Lys Thr Phe Leu Thr Asp Ile Pro
785                 790                 795                 800
Phe Glu Cys Lys Lys Pro Gly Gln Lys
                805

<210> SEQ ID NO 19
<211> LENGTH: 809
<212> TYPE: PRT
<213> ORGANISM: Artificial Sequence
<220> FEATURE:
<223> OTHER INFORMATION: mIL2IL12aIL12bGMCSF protein heterodimer

<400> SEQUENCE: 19

Ala Pro Thr Ser Ser Ser Thr Ser Ser Ser Thr Ala Glu Ala Gln Gln
1               5                   10                  15
Gln Gln Gln Gln Gln Gln Gln Gln Gln Gln His Leu Glu Gln Leu Leu
            20                  25                  30
Met Asp Leu Gln Glu Leu Leu Ser Arg Met Glu Asn Tyr Arg Asn Leu
        35                  40                  45
Lys Leu Pro Arg Met Leu Thr Phe Lys Phe Tyr Leu Pro Lys Gln Ala
50                  55                  60
Thr Glu Leu Lys Asp Leu Gln Cys Leu Glu Asp Glu Leu Gly Pro Leu
65                  70                  75                  80
Arg His Val Leu Asp Leu Thr Gln Ser Lys Ser Phe Gln Leu Glu Asp
                85                  90                  95
Ala Glu Asn Phe Ile Ser Asn Ile Arg Val Thr Val Val Lys Leu Lys
            100                 105                 110
Gly Ser Asp Asn Thr Phe Glu Cys Gln Phe Asp Asp Glu Ser Ala Thr
        115                 120                 125
Val Val Asp Phe Leu Arg Arg Trp Ile Ala Phe Cys Gln Ser Ile Ile
130                 135                 140
Ser Thr Ser Pro Gln Gly Gly Gly Ser Gly Gly Gly Gly Ser Gly
145                 150                 155                 160
Gly Gly Gly Ser Arg Val Ile Pro Val Ser Gly Pro Ala Arg Cys Leu
                165                 170                 175
Ser Gln Ser Arg Asn Leu Leu Lys Thr Thr Asp Asp Met Val Lys Thr
            180                 185                 190
Ala Arg Glu Lys Leu Lys His Tyr Ser Cys Thr Ala Glu Asp Ile Asp
        195                 200                 205
His Glu Asp Ile Thr Arg Asp Gln Thr Ser Thr Leu Lys Thr Cys Leu
        210                 215                 220
Pro Leu Glu Leu His Lys Asn Glu Ser Cys Leu Ala Thr Arg Glu Thr
```

-continued

```
                225                 230                 235                 240
        Ser Ser Thr Thr Arg Gly Ser Cys Leu Pro Pro Gln Lys Thr Ser Leu
                        245                 250                 255

Met Met Thr Leu Cys Leu Gly Ser Ile Tyr Glu Asp Leu Lys Met Tyr
                        260                 265                 270

Gln Thr Glu Phe Gln Ala Ile Asn Ala Ala Leu Gln Asn His Asn His
                        275                 280                 285

Gln Gln Ile Ile Leu Asp Lys Gly Met Leu Val Ala Ile Asp Glu Leu
                        290                 295                 300

Met Gln Ser Leu Asn His Asn Gly Glu Thr Leu Arg Gln Lys Pro Pro
        305                 310                 315                 320

Val Gly Glu Ala Asp Pro Tyr Arg Val Lys Met Lys Leu Cys Ile Leu
                        325                 330                 335

Leu His Ala Phe Ser Thr Arg Val Val Thr Ile Asn Arg Val Met Gly
                        340                 345                 350

Tyr Leu Ser Ser Ala Met Trp Glu Leu Glu Lys Asp Val Tyr Val Val
                        355                 360                 365

Glu Val Asp Trp Thr Pro Asp Ala Pro Gly Glu Thr Val Asn Leu Thr
                        370                 375                 380

Cys Asp Thr Pro Glu Glu Asp Asp Ile Thr Trp Thr Ser Asp Gln Arg
        385                 390                 395                 400

His Gly Val Ile Gly Ser Gly Lys Thr Leu Thr Ile Thr Val Lys Glu
                        405                 410                 415

Phe Leu Asp Ala Gly Gln Tyr Thr Cys His Lys Gly Gly Glu Thr Leu
                        420                 425                 430

Ser His Ser His Leu Leu Leu His Lys Lys Glu Asn Gly Ile Trp Ser
                        435                 440                 445

Thr Glu Ile Leu Lys Asn Phe Lys Asn Lys Thr Phe Leu Lys Cys Glu
                        450                 455                 460

Ala Pro Asn Tyr Ser Gly Arg Phe Thr Cys Ser Trp Leu Val Gln Arg
        465                 470                 475                 480

Asn Met Asp Leu Lys Phe Asn Ile Lys Ser Ser Ser Ser Ser Pro Asp
                        485                 490                 495

Ser Arg Ala Val Thr Cys Gly Met Ala Ser Leu Ser Ala Glu Lys Val
                        500                 505                 510

Thr Leu Asp Gln Arg Asp Tyr Glu Lys Tyr Ser Val Ser Cys Gln Glu
                        515                 520                 525

Asp Val Thr Cys Pro Thr Ala Glu Glu Thr Leu Pro Ile Glu Leu Ala
                        530                 535                 540

Leu Glu Ala Arg Gln Gln Asn Lys Tyr Glu Asn Tyr Ser Thr Ser Phe
        545                 550                 555                 560

Phe Ile Arg Asp Ile Ile Lys Pro Asp Pro Pro Lys Asn Leu Gln Met
                        565                 570                 575

Lys Pro Leu Lys Asn Ser Gln Val Glu Val Ser Trp Glu Tyr Pro Asp
                        580                 585                 590

Ser Trp Ser Thr Pro His Ser Tyr Phe Ser Leu Lys Phe Phe Val Arg
                        595                 600                 605

Ile Gln Arg Lys Lys Glu Lys Met Lys Glu Thr Glu Glu Gly Cys Asn
                        610                 615                 620

Gln Lys Gly Ala Phe Leu Val Glu Lys Thr Ser Thr Glu Val Gln Cys
        625                 630                 635                 640

Lys Gly Gly Asn Val Cys Val Gln Ala Gln Asp Arg Tyr Tyr Asn Ser
                        645                 650                 655
```

```
Ser Cys Ser Lys Trp Ala Cys Val Pro Cys Arg Val Arg Ser Gly Gly
            660                 665                 670

Gly Gly Ser Gly Gly Gly Ser Gly Gly Gly Ser Ala Pro Thr
        675                 680                 685

Arg Ser Pro Ile Thr Val Thr Arg Pro Trp Lys His Val Glu Ala Ile
    690                 695                 700

Lys Glu Ala Leu Asn Leu Leu Asp Asp Met Pro Val Thr Leu Asn Glu
705                 710                 715                 720

Glu Val Glu Val Val Ser Asn Glu Phe Ser Phe Lys Lys Leu Thr Cys
                725                 730                 735

Val Gln Thr Arg Leu Lys Ile Phe Glu Gln Gly Leu Arg Gly Asn Phe
            740                 745                 750

Thr Lys Leu Lys Gly Ala Leu Asn Met Thr Ala Ser Tyr Tyr Gln Thr
        755                 760                 765

Tyr Cys Pro Pro Thr Pro Glu Thr Asp Cys Glu Thr Gln Val Thr Thr
    770                 775                 780

Tyr Ala Asp Phe Ile Asp Ser Leu Lys Thr Phe Leu Thr Asp Ile Pro
785                 790                 795                 800

Phe Glu Cys Lys Lys Pro Gly Gln Lys
                805
```

<210> SEQ ID NO 20
<211> LENGTH: 809
<212> TYPE: PRT
<213> ORGANISM: Artificial Sequence
<220> FEATURE:
<223> OTHER INFORMATION: mIL12aIL2GMCSFIL12b protein heterodimer

<400> SEQUENCE: 20

```
Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Ile Ile
        115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Gly Ser Gly Gly Gly Ser Gly Gly Gly Ser
        195                 200                 205
```

```
Ala Pro Thr Ser Ser Thr Ser Ser Ser Thr Ala Glu Ala Gln Gln
    210                 215                 220

Gln Gln Gln Gln Gln Gln Gln Gln Gln His Leu Glu Gln Leu Leu
225                 230                 235                 240

Met Asp Leu Gln Glu Leu Leu Ser Arg Met Glu Asn Tyr Arg Asn Leu
            245                 250                 255

Lys Leu Pro Arg Met Leu Thr Phe Lys Phe Tyr Leu Pro Lys Gln Ala
            260                 265                 270

Thr Glu Leu Lys Asp Leu Gln Cys Leu Glu Asp Glu Leu Gly Pro Leu
        275                 280                 285

Arg His Val Leu Asp Leu Thr Gln Ser Lys Ser Phe Gln Leu Glu Asp
    290                 295                 300

Ala Glu Asn Phe Ile Ser Asn Ile Arg Val Thr Val Val Lys Leu Lys
305                 310                 315                 320

Gly Ser Asp Asn Thr Phe Glu Cys Gln Phe Asp Asp Glu Ser Ala Thr
                325                 330                 335

Val Val Asp Phe Leu Arg Arg Trp Ile Ala Phe Cys Gln Ser Ile Ile
            340                 345                 350

Ser Thr Ser Pro Gln Ala Pro Thr Arg Ser Pro Ile Thr Val Thr Arg
    355                 360                 365

Pro Trp Lys His Val Glu Ala Ile Lys Glu Ala Leu Asn Leu Leu Asp
370                 375                 380

Asp Met Pro Val Thr Leu Asn Glu Glu Val Glu Val Val Ser Asn Glu
385                 390                 395                 400

Phe Ser Phe Lys Lys Leu Thr Cys Val Gln Thr Arg Leu Lys Ile Phe
                405                 410                 415

Glu Gln Gly Leu Arg Gly Asn Phe Thr Lys Leu Lys Gly Ala Leu Asn
            420                 425                 430

Met Thr Ala Ser Tyr Tyr Gln Thr Tyr Cys Pro Pro Thr Pro Glu Thr
        435                 440                 445

Asp Cys Glu Thr Gln Val Thr Thr Tyr Ala Asp Phe Ile Asp Ser Leu
    450                 455                 460

Lys Thr Phe Leu Thr Asp Ile Pro Phe Glu Cys Lys Lys Pro Gly Gln
465                 470                 475                 480

Lys Gly Gly Gly Gly Ser Gly Gly Gly Ser Gly Gly Gly Gly Ser
                485                 490                 495

Met Trp Glu Leu Glu Lys Asp Val Tyr Val Val Glu Val Asp Trp Thr
            500                 505                 510

Pro Asp Ala Pro Gly Glu Thr Val Asn Leu Thr Cys Asp Thr Pro Glu
        515                 520                 525

Glu Asp Asp Ile Thr Trp Thr Ser Asp Gln Arg His Gly Val Ile Gly
    530                 535                 540

Ser Gly Lys Thr Leu Thr Ile Thr Val Lys Glu Phe Leu Asp Ala Gly
545                 550                 555                 560

Gln Tyr Thr Cys His Lys Gly Gly Glu Thr Leu Ser His Ser His Leu
                565                 570                 575

Leu Leu His Lys Lys Glu Asn Gly Ile Trp Ser Thr Glu Ile Leu Lys
            580                 585                 590

Asn Phe Lys Asn Lys Thr Phe Leu Lys Cys Glu Ala Pro Asn Tyr Ser
        595                 600                 605

Gly Arg Phe Thr Cys Ser Trp Leu Val Gln Arg Asn Met Asp Leu Lys
    610                 615                 620
```

```
Phe Asn Ile Lys Ser Ser Ser Ser Pro Asp Ser Arg Ala Val Thr
625                 630                 635                 640

Cys Gly Met Ala Ser Leu Ser Ala Glu Lys Val Thr Leu Asp Gln Arg
            645                 650                 655

Asp Tyr Glu Lys Tyr Ser Val Ser Cys Gln Glu Asp Val Thr Cys Pro
            660                 665                 670

Thr Ala Glu Glu Thr Leu Pro Ile Glu Leu Ala Leu Glu Ala Arg Gln
            675                 680                 685

Gln Asn Lys Tyr Glu Asn Tyr Ser Thr Ser Phe Phe Ile Arg Asp Ile
            690                 695                 700

Ile Lys Pro Asp Pro Lys Asn Leu Gln Met Lys Pro Leu Lys Asn
705                 710                 715                 720

Ser Gln Val Glu Val Ser Trp Glu Tyr Pro Asp Ser Trp Ser Thr Pro
            725                 730                 735

His Ser Tyr Phe Ser Leu Lys Phe Phe Val Arg Ile Gln Arg Lys Lys
            740                 745                 750

Glu Lys Met Lys Glu Thr Glu Glu Gly Cys Asn Gln Lys Gly Ala Phe
            755                 760                 765

Leu Val Glu Lys Thr Ser Thr Glu Val Gln Cys Lys Gly Gly Asn Val
            770                 775                 780

Cys Val Gln Ala Gln Asp Arg Tyr Tyr Asn Ser Ser Cys Ser Lys Trp
785                 790                 795                 800

Ala Cys Val Pro Cys Arg Val Arg Ser
            805

<210> SEQ ID NO 21
<211> LENGTH: 809
<212> TYPE: PRT
<213> ORGANISM: Artificial Sequence
<220> FEATURE:
<223> OTHER INFORMATION: mIL2IL12aGMCSFIL12b protein heterodimer

<400> SEQUENCE: 21

Ala Pro Thr Ser Ser Ser Thr Ser Ser Ser Thr Ala Glu Ala Gln Gln
1               5                   10                  15

Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
            85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
            115                 120                 125

Val Val Asp Phe Leu Arg Arg Trp Ile Ala Phe Cys Gln Ser Ile Ile
            130                 135                 140

Ser Thr Ser Pro Gln Gly Gly Gly Gly Ser Gly Gly Gly Gly Ser Gly
145                 150                 155                 160

Gly Gly Gly Ser Arg Val Ile Pro Val Ser Gly Pro Ala Arg Cys Leu
            165                 170                 175
```

-continued

Ser Gln Ser Arg Asn Leu Leu Lys Thr Thr Asp Asp Met Val Lys Thr
            180                 185                 190
Ala Arg Glu Lys Leu Lys His Tyr Ser Cys Thr Ala Glu Asp Ile Asp
        195                 200                 205
His Glu Asp Ile Thr Arg Asp Gln Thr Ser Thr Leu Lys Thr Cys Leu
    210                 215                 220
Pro Leu Glu Leu His Lys Asn Glu Ser Cys Leu Ala Thr Arg Glu Thr
225                 230                 235                 240
Ser Ser Thr Thr Arg Gly Ser Cys Leu Pro Pro Gln Lys Thr Ser Leu
                245                 250                 255
Met Met Thr Leu Cys Leu Gly Ser Ile Tyr Glu Asp Leu Lys Met Tyr
            260                 265                 270
Gln Thr Glu Phe Gln Ala Ile Asn Ala Ala Leu Gln Asn His Asn His
        275                 280                 285
Gln Gln Ile Ile Leu Asp Lys Gly Met Leu Val Ala Ile Asp Glu Leu
    290                 295                 300
Met Gln Ser Leu Asn His Asn Gly Glu Thr Leu Arg Gln Lys Pro Pro
305                 310                 315                 320
Val Gly Glu Ala Asp Pro Tyr Arg Val Lys Met Lys Leu Cys Ile Leu
                325                 330                 335
Leu His Ala Phe Ser Thr Arg Val Val Thr Ile Asn Arg Val Met Gly
            340                 345                 350
Tyr Leu Ser Ser Ala Ala Pro Thr Arg Ser Pro Ile Thr Val Thr Arg
        355                 360                 365
Pro Trp Lys His Val Glu Ala Ile Lys Glu Ala Leu Asn Leu Leu Asp
    370                 375                 380
Asp Met Pro Val Thr Leu Asn Glu Glu Val Glu Val Val Ser Asn Glu
385                 390                 395                 400
Phe Ser Phe Lys Lys Leu Thr Cys Val Gln Thr Arg Leu Lys Ile Phe
                405                 410                 415
Glu Gln Gly Leu Arg Gly Asn Phe Thr Lys Leu Lys Gly Ala Leu Asn
            420                 425                 430
Met Thr Ala Ser Tyr Tyr Gln Thr Tyr Cys Pro Pro Thr Pro Glu Thr
        435                 440                 445
Asp Cys Glu Thr Gln Val Thr Thr Tyr Ala Asp Phe Ile Asp Ser Leu
    450                 455                 460
Lys Thr Phe Leu Thr Asp Ile Pro Phe Glu Cys Lys Lys Pro Gly Gln
465                 470                 475                 480
Lys Gly Gly Gly Ser Gly Gly Gly Ser Gly Gly Gly Ser
                485                 490                 495
Met Trp Glu Leu Glu Lys Asp Val Tyr Val Val Glu Val Asp Trp Thr
            500                 505                 510
Pro Asp Ala Pro Gly Glu Thr Val Asn Leu Thr Cys Asp Thr Pro Glu
        515                 520                 525
Glu Asp Asp Ile Thr Trp Thr Ser Asp Gln Arg His Gly Val Ile Gly
    530                 535                 540
Ser Gly Lys Thr Leu Thr Ile Thr Val Lys Glu Phe Leu Asp Ala Gly
545                 550                 555                 560
Gln Tyr Thr Cys His Lys Gly Gly Glu Thr Leu Ser His Ser His Leu
                565                 570                 575
Leu Leu His Lys Lys Glu Asn Gly Ile Trp Ser Thr Glu Ile Leu Lys
            580                 585                 590
Asn Phe Lys Asn Lys Thr Phe Leu Lys Cys Glu Ala Pro Asn Tyr Ser

```
                595                 600                 605
Gly Arg Phe Thr Cys Ser Trp Leu Val Gln Arg Asn Met Asp Leu Lys
    610                 615                 620

Phe Asn Ile Lys Ser Ser Ser Ser Pro Asp Ser Arg Ala Val Thr
625                 630                 635                 640

Cys Gly Met Ala Ser Leu Ser Ala Glu Lys Val Thr Leu Asp Gln Arg
                    645                 650                 655

Asp Tyr Glu Lys Tyr Ser Val Ser Cys Gln Glu Asp Val Thr Cys Pro
                660                 665                 670

Thr Ala Glu Glu Thr Leu Pro Ile Glu Leu Ala Leu Glu Ala Arg Gln
                    675                 680                 685

Gln Asn Lys Tyr Glu Asn Tyr Ser Thr Ser Phe Phe Ile Arg Asp Ile
    690                 695                 700

Ile Lys Pro Asp Pro Pro Lys Asn Leu Gln Met Lys Pro Leu Lys Asn
705                 710                 715                 720

Ser Gln Val Glu Val Ser Trp Glu Tyr Pro Asp Ser Trp Ser Thr Pro
                    725                 730                 735

His Ser Tyr Phe Ser Leu Lys Phe Phe Val Arg Ile Gln Arg Lys Lys
                740                 745                 750

Glu Lys Met Lys Glu Thr Glu Glu Gly Cys Asn Gln Lys Gly Ala Phe
            755                 760                 765

Leu Val Glu Lys Thr Ser Thr Glu Val Gln Cys Lys Gly Gly Asn Val
        770                 775                 780

Cys Val Gln Ala Gln Asp Arg Tyr Tyr Asn Ser Ser Cys Ser Lys Trp
785                 790                 795                 800

Ala Cys Val Pro Cys Arg Val Arg Ser
                    805

<210> SEQ ID NO 22
<211> LENGTH: 809
<212> TYPE: PRT
<213> ORGANISM: Artificial Sequence
<220> FEATURE:
<223> OTHER INFORMATION: mIL12aGMCSFIL12bIL2 protein heterodimer

<400> SEQUENCE: 22

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
                20                  25                  30

Leu Lys His Tyr Ser Cys Thr Ala Glu Asp Ile Asp His Glu Asp Ile
            35                  40                  45

Thr Arg Asp Gln Thr Ser Thr Leu Lys Thr Cys Leu Pro Leu Glu Leu
        50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
```

-continued

```
              145                 150                 155                 160
Asp Pro Tyr Arg Val Lys Met Lys Leu Cys Ile Leu His Ala Phe
                    165                 170                 175
Ser Thr Arg Val Val Thr Ile Asn Arg Val Met Gly Tyr Leu Ser Ser
                180                 185                 190
Ala Gly Gly Gly Ser Gly Gly Gly Ser Gly Gly Gly Ser
                195                 200                 205
Ala Pro Thr Arg Ser Pro Ile Thr Val Thr Arg Pro Trp Lys His Val
        210                 215                 220
Glu Ala Ile Lys Glu Ala Leu Asn Leu Leu Asp Asp Met Pro Val Thr
225                 230                 235                 240
Leu Asn Glu Glu Val Glu Val Val Ser Asn Glu Phe Ser Phe Lys Lys
                    245                 250                 255
Leu Thr Cys Val Gln Thr Arg Leu Lys Ile Phe Glu Gln Gly Leu Arg
                260                 265                 270
Gly Asn Phe Thr Lys Leu Lys Gly Ala Leu Asn Met Thr Ala Ser Tyr
                275                 280                 285
Tyr Gln Thr Tyr Cys Pro Pro Thr Pro Glu Thr Asp Cys Glu Thr Gln
            290                 295                 300
Val Thr Thr Tyr Ala Asp Phe Ile Asp Ser Leu Lys Thr Phe Leu Thr
305                 310                 315                 320
Asp Ile Pro Phe Glu Cys Lys Lys Pro Gly Gln Lys Met Trp Glu Leu
                    325                 330                 335
Glu Lys Asp Val Tyr Val Val Glu Val Asp Trp Thr Pro Asp Ala Pro
                340                 345                 350
Gly Glu Thr Val Asn Leu Thr Cys Asp Thr Pro Glu Glu Asp Asp Ile
                355                 360                 365
Thr Trp Thr Ser Asp Gln Arg His Gly Val Ile Gly Ser Gly Lys Thr
            370                 375                 380
Leu Thr Ile Thr Val Lys Glu Phe Leu Asp Ala Gly Gln Tyr Thr Cys
385                 390                 395                 400
His Lys Gly Gly Glu Thr Leu Ser His Ser His Leu Leu Leu His Lys
                    405                 410                 415
Lys Glu Asn Gly Ile Trp Ser Thr Glu Ile Leu Lys Asn Phe Lys Asn
                420                 425                 430
Lys Thr Phe Leu Lys Cys Glu Ala Pro Asn Tyr Ser Gly Arg Phe Thr
            435                 440                 445
Cys Ser Trp Leu Val Gln Arg Asn Met Asp Leu Lys Phe Asn Ile Lys
450                 455                 460
Ser Ser Ser Ser Ser Pro Asp Ser Arg Ala Val Thr Cys Gly Met Ala
465                 470                 475                 480
Ser Leu Ser Ala Glu Lys Val Thr Leu Asp Gln Arg Asp Tyr Glu Lys
                    485                 490                 495
Tyr Ser Val Ser Cys Gln Glu Asp Val Thr Cys Pro Thr Ala Glu Glu
                500                 505                 510
Thr Leu Pro Ile Glu Leu Ala Leu Glu Ala Arg Gln Gln Asn Lys Tyr
            515                 520                 525
Glu Asn Tyr Ser Thr Ser Phe Phe Ile Arg Asp Ile Ile Lys Pro Asp
                530                 535                 540
Pro Pro Lys Asn Leu Gln Met Lys Pro Leu Lys Asn Ser Gln Val Glu
545                 550                 555                 560
Val Ser Trp Glu Tyr Pro Asp Ser Trp Ser Thr Pro His Ser Tyr Phe
                    565                 570                 575
```

```
Ser Leu Lys Phe Phe Val Arg Ile Gln Arg Lys Lys Glu Lys Met Lys
            580                 585                 590

Glu Thr Glu Glu Gly Cys Asn Gln Lys Gly Ala Phe Leu Val Glu Lys
            595                 600                 605

Thr Ser Thr Glu Val Gln Cys Lys Gly Gly Asn Val Cys Val Gln Ala
610                 615                 620

Gln Asp Arg Tyr Tyr Asn Ser Ser Cys Ser Lys Trp Ala Cys Val Pro
625                 630                 635                 640

Cys Arg Val Arg Ser Gly Gly Gly Ser Gly Gly Gly Ser Gly
                    645                 650                 655

Gly Gly Gly Ser Ala Pro Thr Ser Ser Ser Thr Ser Ser Ser Thr Ala
            660                 665                 670

Glu Ala Gln Gln Gln Gln Gln Gln Gln Gln Gln Gln Gln His Leu
            675                 680                 685

Glu Gln Leu Leu Met Asp Leu Gln Glu Leu Leu Ser Arg Met Glu Asn
            690                 695                 700

Tyr Arg Asn Leu Lys Leu Pro Arg Met Leu Thr Phe Lys Phe Tyr Leu
705                 710                 715                 720

Pro Lys Gln Ala Thr Glu Leu Lys Asp Leu Gln Cys Leu Glu Asp Glu
                    725                 730                 735

Leu Gly Pro Leu Arg His Val Leu Asp Leu Thr Gln Ser Lys Ser Phe
            740                 745                 750

Gln Leu Glu Asp Ala Glu Asn Phe Ile Ser Asn Ile Arg Val Thr Val
            755                 760                 765

Val Lys Leu Lys Gly Ser Asp Asn Thr Phe Glu Cys Gln Phe Asp Asp
770                 775                 780

Glu Ser Ala Thr Val Val Asp Phe Leu Arg Arg Trp Ile Ala Phe Cys
785                 790                 795                 800

Gln Ser Ile Ile Ser Thr Ser Pro Gln
                    805

<210> SEQ ID NO 23
<211> LENGTH: 789
<212> TYPE: PRT
<213> ORGANISM: Artificial Sequence
<220> FEATURE:
<223> OTHER INFORMATION: mIL12aIL7IL12bGMCSF protein heterodimer

<400> SEQUENCE: 23

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125
```

```
Leu Asp Lys Gly Met Leu Val Ala Ile Asp Glu Leu Met Gln Ser Leu
    130                 135                 140
Asn His Asn Gly Glu Thr Leu Arg Gln Lys Pro Pro Val Gly Glu Ala
145                 150                 155                 160
Asp Pro Tyr Arg Val Lys Met Lys Leu Cys Ile Leu Leu His Ala Phe
                165                 170                 175
Ser Thr Arg Val Val Thr Ile Asn Arg Val Met Gly Tyr Leu Ser Ser
                180                 185                 190
Ala Gly Gly Gly Ser Gly Gly Gly Ser Gly Gly Gly Gly Ser
                195                 200                 205
Glu Cys His Ile Lys Asp Lys Glu Gly Lys Ala Tyr Glu Ser Val Leu
    210                 215                 220
Met Ile Ser Ile Asp Glu Leu Asp Lys Met Thr Gly Thr Asp Ser Asn
225                 230                 235                 240
Cys Pro Asn Asn Glu Pro Asn Phe Phe Arg Lys His Val Cys Asp Asp
                245                 250                 255
Thr Lys Glu Ala Ala Phe Leu Asn Arg Ala Ala Arg Lys Leu Lys Gln
                260                 265                 270
Phe Leu Lys Met Asn Ile Ser Glu Glu Phe Asn Val His Leu Leu Thr
                275                 280                 285
Val Ser Gln Gly Thr Gln Thr Leu Val Asn Cys Thr Ser Lys Glu Glu
    290                 295                 300
Lys Asn Val Lys Glu Gln Lys Lys Asn Asp Ala Cys Phe Leu Lys Arg
305                 310                 315                 320
Leu Leu Arg Glu Ile Lys Thr Cys Trp Asn Lys Ile Leu Lys Gly Ser
                325                 330                 335
Ile Met Trp Glu Leu Gly Lys Asp Val Tyr Val Glu Val Asp Trp
                340                 345                 350
Thr Pro Asp Ala Pro Gly Glu Thr Val Asn Leu Thr Cys Asp Thr Pro
                355                 360                 365
Glu Glu Asp Asp Ile Thr Trp Thr Ser Asp Gln Arg His Gly Val Ile
    370                 375                 380
Gly Ser Gly Lys Thr Leu Thr Ile Thr Val Lys Glu Phe Leu Asp Ala
385                 390                 395                 400
Gly Gln Tyr Thr Cys His Lys Gly Gly Glu Thr Leu Ser His Ser His
                405                 410                 415
Leu Leu Leu His Lys Lys Glu Asn Gly Ile Trp Ser Thr Glu Ile Leu
                420                 425                 430
Lys Asn Phe Lys Asn Lys Thr Phe Leu Lys Cys Glu Ala Pro Asn Tyr
    435                 440                 445
Ser Gly Arg Phe Thr Cys Ser Trp Leu Val Gln Arg Asn Met Asp Leu
450                 455                 460
Lys Phe Asn Ile Lys Ser Ser Ser Ser Ser Pro Asp Ser Arg Ala Val
465                 470                 475                 480
Thr Cys Gly Met Ala Ser Leu Ser Ala Glu Lys Val Thr Leu Asp Gln
                485                 490                 495
Arg Asp Tyr Glu Lys Tyr Ser Val Ser Cys Gln Glu Asp Val Thr Cys
                500                 505                 510
Pro Thr Ala Glu Glu Thr Leu Pro Ile Glu Leu Ala Leu Glu Ala Arg
                515                 520                 525
Gln Gln Asn Lys Tyr Glu Asn Tyr Ser Thr Ser Phe Phe Ile Arg Asp
    530                 535                 540
```

```
Ile Ile Lys Pro Asp Pro Lys Asn Leu Gln Met Lys Pro Leu Lys
545                 550                 555                 560

Asn Ser Gln Val Glu Val Ser Trp Glu Tyr Pro Asp Ser Trp Ser Thr
                565                 570                 575

Pro His Ser Tyr Phe Ser Leu Lys Phe Phe Val Arg Ile Gln Arg Lys
                580                 585                 590

Lys Glu Lys Met Lys Glu Thr Glu Glu Gly Cys Asn Gln Lys Gly Ala
            595                 600                 605

Phe Leu Val Glu Lys Thr Ser Thr Glu Val Gln Cys Lys Gly Gly Asn
        610                 615                 620

Val Cys Val Gln Ala Gln Asp Arg Tyr Tyr Asn Ser Ser Cys Ser Lys
625                 630                 635                 640

Trp Ala Cys Val Pro Cys Arg Val Arg Ser Gly Gly Gly Ser Gly
                645                 650                 655

Gly Gly Gly Ser Gly Gly Gly Ser Ala Pro Thr Arg Ser Pro Ile
            660                 665                 670

Thr Val Thr Arg Pro Trp Lys His Val Glu Ala Ile Lys Glu Ala Leu
                675                 680                 685

Asn Leu Leu Asp Asp Met Pro Val Thr Leu Asn Glu Glu Val Glu Val
        690                 695                 700

Val Ser Asn Glu Phe Ser Phe Lys Lys Leu Thr Cys Val Gln Thr Arg
705                 710                 715                 720

Leu Lys Ile Phe Glu Gln Gly Leu Arg Gly Asn Phe Thr Lys Leu Lys
                725                 730                 735

Gly Ala Leu Asn Met Thr Ala Ser Tyr Tyr Gln Thr Tyr Cys Pro Pro
            740                 745                 750

Thr Pro Glu Thr Asp Cys Glu Thr Gln Val Thr Thr Tyr Ala Asp Phe
        755                 760                 765

Ile Asp Ser Leu Lys Thr Phe Leu Thr Asp Ile Pro Phe Glu Cys Lys
                770                 775                 780

Lys Pro Gly Gln Lys
785

<210> SEQ ID NO 24
<211> LENGTH: 793
<212> TYPE: PRT
<213> ORGANISM: Artificial Sequence
<220> FEATURE:
<223> OTHER INFORMATION: mIL12aIL15IL12bGMCSF protein heterodimer

<400> SEQUENCE: 24

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
                20                  25                  30

Leu Lys His Tyr Ser Cys Thr Ala Glu Asp Ile Asp His Glu Asp Ile
            35                  40                  45

Thr Arg Asp Gln Thr Ser Thr Leu Lys Thr Cys Leu Pro Leu Glu Leu
        50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110
```

-continued

```
Gln Ala Ile Asn Ala Ala Leu Gln Asn His Asn His Gln Ile Ile
            115                 120                 125
Leu Asp Lys Gly Met Leu Val Ala Ile Asp Glu Leu Met Gln Ser Leu
130                 135                 140
Asn His Asn Gly Glu Thr Leu Arg Gln Lys Pro Pro Val Gly Glu Ala
145                 150                 155                 160
Asp Pro Tyr Arg Val Lys Met Lys Leu Cys Ile Leu Leu His Ala Phe
                165                 170                 175
Ser Thr Arg Val Val Thr Ile Asn Arg Val Met Gly Tyr Leu Ser Ser
            180                 185                 190
Ala Gly Gly Gly Gly Ser Gly Gly Gly Ser Gly Gly Gly Gly Ser
            195                 200                 205
Gly Ile His Val Phe Ile Leu Gly Cys Val Ser Val Gly Leu Pro Lys
            210                 215                 220
Thr Glu Ala Asn Trp Ile Asp Val Arg Tyr Asp Leu Glu Lys Ile Glu
225                 230                 235                 240
Ser Leu Ile Gln Ser Ile His Ile Asp Thr Thr Leu Tyr Thr Asp Ser
                245                 250                 255
Asp Phe His Pro Ser Cys Lys Val Thr Ala Met Asn Cys Phe Leu Leu
            260                 265                 270
Glu Leu Gln Val Ile Leu His Glu Tyr Ser Asn Met Thr Leu Asn Glu
            275                 280                 285
Thr Val Arg Asn Val Leu Tyr Leu Ala Asn Ser Thr Leu Ser Ser Asn
            290                 295                 300
Lys Asn Val Ala Glu Ser Gly Cys Lys Glu Cys Glu Glu Leu Glu Glu
305                 310                 315                 320
Lys Thr Phe Thr Glu Phe Leu Gln Ser Phe Ile Arg Ile Val Gln Met
                325                 330                 335
Phe Ile Asn Thr Ser Met Trp Glu Leu Glu Lys Asp Val Tyr Val Val
            340                 345                 350
Glu Val Asp Trp Thr Pro Asp Ala Pro Gly Glu Thr Val Asn Leu Thr
            355                 360                 365
Cys Asp Thr Pro Glu Glu Asp Asp Ile Thr Trp Thr Ser Asp Gln Arg
370                 375                 380
His Gly Val Ile Gly Ser Gly Lys Thr Leu Thr Ile Thr Val Lys Glu
385                 390                 395                 400
Phe Leu Asp Ala Gly Gln Tyr Thr Cys His Lys Gly Gly Glu Thr Leu
                405                 410                 415
Ser His Ser His Leu Leu Leu His Lys Lys Glu Asn Gly Ile Trp Ser
            420                 425                 430
Thr Glu Ile Leu Lys Asn Phe Lys Asn Lys Thr Phe Leu Lys Cys Glu
            435                 440                 445
Ala Pro Asn Tyr Ser Gly Arg Phe Thr Cys Ser Trp Leu Val Gln Arg
            450                 455                 460
Asn Met Asp Leu Lys Phe Asn Ile Lys Ser Ser Ser Ser Pro Asp
465                 470                 475                 480
Ser Arg Ala Val Thr Cys Gly Met Ala Ser Leu Ser Ala Glu Lys Val
                485                 490                 495
Thr Leu Asp Gln Arg Asp Tyr Glu Lys Tyr Ser Val Ser Cys Gln Glu
            500                 505                 510
Asp Val Thr Cys Pro Thr Ala Glu Glu Thr Leu Pro Ile Glu Leu Ala
            515                 520                 525
Leu Glu Ala Arg Gln Gln Asn Lys Tyr Glu Asn Tyr Ser Thr Ser Phe
```

-continued

```
                530                 535                 540
Phe Ile Arg Asp Ile Ile Lys Pro Asp Pro Lys Asn Leu Gln Met
545                 550                 555                 560

Lys Pro Leu Lys Asn Ser Gln Val Glu Val Ser Trp Glu Tyr Pro Asp
                565                 570                 575

Ser Trp Ser Thr Pro His Ser Tyr Phe Ser Leu Lys Phe Phe Val Arg
                580                 585                 590

Ile Gln Arg Lys Lys Glu Lys Met Lys Glu Thr Glu Glu Gly Cys Asn
                595                 600                 605

Gln Lys Gly Ala Phe Leu Val Glu Lys Thr Ser Thr Glu Val Gln Cys
                610                 615                 620

Lys Gly Gly Asn Val Cys Val Gln Ala Gln Asp Arg Tyr Tyr Asn Ser
625                 630                 635                 640

Ser Cys Ser Lys Trp Ala Cys Val Pro Cys Arg Val Arg Ser Gly Gly
                645                 650                 655

Gly Gly Ser Gly Gly Gly Gly Ser Gly Gly Gly Gly Ser Ala Pro Thr
                660                 665                 670

Arg Ser Pro Ile Thr Val Thr Arg Pro Trp Lys His Val Glu Ala Ile
                675                 680                 685

Lys Glu Ala Leu Asn Leu Leu Asp Asp Met Pro Val Thr Leu Asn Glu
                690                 695                 700

Glu Val Glu Val Val Ser Asn Glu Phe Ser Phe Lys Lys Leu Thr Cys
705                 710                 715                 720

Val Gln Thr Arg Leu Lys Ile Phe Glu Gln Gly Leu Arg Gly Asn Phe
                725                 730                 735

Thr Lys Leu Lys Gly Ala Leu Asn Met Thr Ala Ser Tyr Tyr Gln Thr
                740                 745                 750

Tyr Cys Pro Pro Thr Pro Glu Thr Asp Cys Glu Thr Gln Val Thr Thr
                755                 760                 765

Tyr Ala Asp Phe Ile Asp Ser Leu Lys Thr Phe Leu Thr Asp Ile Pro
                770                 775                 780

Phe Glu Cys Lys Lys Pro Gly Gln Lys
785                 790
```

<210> SEQ ID NO 25
<211> LENGTH: 789
<212> TYPE: PRT
<213> ORGANISM: Artificial Sequence
<220> FEATURE:
<223> OTHER INFORMATION: mIL12aIL21IL12bGMCSF protein heterodimer

<400> SEQUENCE: 25

```
Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
                20                  25                  30

Leu Lys His Tyr Ser Cys Thr Ala Glu Asp Ile Asp His Glu Asp Ile
                35                  40                  45

Thr Arg Asp Gln Thr Ser Thr Leu Lys Thr Cys Leu Pro Leu Glu Leu
                50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
```

```
              100                 105                 110
    Gln Ala Ile Asn Ala Ala Leu Gln Asn His Asn His Gln Gln Ile Ile
        115                 120                 125
    Leu Asp Lys Gly Met Leu Val Ala Ile Asp Glu Leu Met Gln Ser Leu
        130                 135                 140
    Asn His Asn Gly Glu Thr Leu Arg Gln Lys Pro Pro Val Gly Glu Ala
    145                 150                 155                 160
    Asp Pro Tyr Arg Val Lys Met Lys Leu Cys Ile Leu Leu His Ala Phe
                    165                 170                 175
    Ser Thr Arg Val Val Thr Ile Asn Arg Val Met Gly Tyr Leu Ser Ser
                    180                 185                 190
    Ala Gly Gly Gly Ser Gly Gly Gly Ser Gly Gly Gly Gly Ser
        195                 200                 205
    His Lys Ser Ser Pro Gln Gly Pro Asp Arg Leu Leu Ile Arg Leu Arg
        210                 215                 220
    His Leu Ile Asp Ile Val Glu Gln Leu Lys Ile Tyr Glu Asn Asp Leu
    225                 230                 235                 240
    Asp Pro Glu Leu Leu Ser Ala Pro Gln Asp Val Lys Gly His Cys Glu
                    245                 250                 255
    His Ala Ala Phe Ala Cys Phe Gln Lys Ala Lys Leu Lys Pro Ser Asn
                    260                 265                 270
    Pro Gly Asn Asn Lys Thr Phe Ile Ile Asp Leu Val Ala Gln Leu Arg
                    275                 280                 285
    Arg Arg Leu Pro Ala Arg Arg Gly Gly Lys Lys Gln Lys His Ile Ala
        290                 295                 300
    Lys Cys Pro Ser Cys Asp Ser Tyr Glu Lys Arg Thr Pro Lys Glu Phe
    305                 310                 315                 320
    Leu Glu Arg Leu Lys Trp Leu Leu Gln Lys Met Ile His Gln His Leu
                    325                 330                 335
    Ser Met Trp Glu Leu Glu Lys Asp Val Tyr Val Val Glu Val Asp Trp
                    340                 345                 350
    Thr Pro Asp Ala Pro Gly Glu Thr Val Asn Leu Thr Cys Asp Thr Pro
                    355                 360                 365
    Glu Glu Asp Asp Ile Thr Trp Thr Ser Asp Gln Arg His Gly Val Ile
        370                 375                 380
    Gly Ser Gly Lys Thr Leu Thr Ile Thr Val Lys Glu Phe Leu Asp Ala
    385                 390                 395                 400
    Gly Gln Tyr Thr Cys His Lys Gly Gly Glu Thr Leu Ser His Ser His
                    405                 410                 415
    Leu Leu Leu His Lys Lys Glu Asn Gly Ile Trp Ser Thr Glu Ile Leu
                    420                 425                 430
    Lys Asn Phe Lys Asn Lys Thr Phe Leu Lys Cys Glu Ala Pro Asn Tyr
        435                 440                 445
    Ser Gly Arg Phe Thr Cys Ser Trp Leu Val Gln Arg Asn Met Asp Leu
        450                 455                 460
    Lys Phe Asn Ile Lys Ser Ser Ser Ser Pro Asp Ser Arg Ala Val
    465                 470                 475                 480
    Thr Cys Gly Met Ala Ser Leu Ser Ala Glu Lys Val Thr Leu Asp Gln
                    485                 490                 495
    Arg Asp Tyr Glu Lys Tyr Ser Val Ser Cys Gln Glu Asp Val Thr Cys
                    500                 505                 510
    Pro Thr Ala Glu Glu Thr Leu Pro Ile Glu Leu Ala Leu Glu Ala Arg
        515                 520                 525
```

Gln Gln Asn Lys Tyr Glu Asn Tyr Ser Thr Ser Phe Phe Ile Arg Asp
            530                 535                 540

Ile Ile Lys Pro Asp Pro Lys Asn Leu Gln Met Lys Pro Leu Lys
545                 550                 555                 560

Asn Ser Gln Val Glu Val Ser Trp Glu Tyr Pro Asp Ser Trp Ser Thr
                565                 570                 575

Pro His Ser Tyr Phe Ser Leu Lys Phe Phe Val Arg Ile Gln Arg Lys
                580                 585                 590

Lys Glu Lys Met Lys Glu Thr Glu Glu Gly Cys Asn Gln Lys Gly Ala
                595                 600                 605

Phe Leu Val Glu Lys Thr Ser Thr Glu Val Gln Cys Lys Gly Gly Asn
                610                 615                 620

Val Cys Val Gln Ala Gln Asp Arg Tyr Tyr Asn Ser Ser Cys Ser Lys
625                 630                 635                 640

Trp Ala Cys Val Pro Cys Arg Val Arg Ser Gly Gly Gly Ser Gly
                645                 650                 655

Gly Gly Gly Ser Gly Gly Gly Ser Ala Pro Thr Arg Ser Pro Ile
                660                 665                 670

Thr Val Thr Arg Pro Trp Lys His Val Glu Ala Ile Lys Glu Ala Leu
                675                 680                 685

Asn Leu Leu Asp Asp Met Pro Val Thr Leu Asn Glu Glu Val Glu Val
690                 695                 700

Val Ser Asn Glu Phe Ser Phe Lys Lys Leu Thr Cys Val Gln Thr Arg
705                 710                 715                 720

Leu Lys Ile Phe Glu Gln Gly Leu Arg Gly Asn Phe Thr Lys Leu Lys
                725                 730                 735

Gly Ala Leu Asn Met Thr Ala Ser Tyr Tyr Gln Thr Tyr Cys Pro Pro
                740                 745                 750

Thr Pro Glu Thr Asp Cys Glu Thr Gln Val Thr Thr Tyr Ala Asp Phe
                755                 760                 765

Ile Asp Ser Leu Lys Thr Phe Leu Thr Asp Ile Pro Phe Glu Cys Lys
                770                 775                 780

Lys Pro Gly Gln Lys
785

<210> SEQ ID NO 26
<211> LENGTH: 891
<212> TYPE: PRT
<213> ORGANISM: Artificial Sequence
<220> FEATURE:
<223> OTHER INFORMATION: mIL12aIL2IL12bFLT3L protein heterodimer

<400> SEQUENCE: 26

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
                20                  25                  30

Leu Lys His Tyr Ser Cys Thr Ala Glu Asp Ile Asp His Glu Asp Ile
                35                  40                  45

Thr Arg Asp Gln Thr Ser Thr Leu Lys Thr Cys Leu Pro Leu Glu Leu
            50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

```
Cys Leu Gly Ser Ile Tyr Glu Asp Leu Lys Met Tyr Gln Thr Glu Phe
                100                 105                 110

Gln Ala Ile Asn Ala Ala Leu Gln Asn His Asn His Gln Gln Ile Ile
            115                 120                 125

Leu Asp Lys Gly Met Leu Val Ala Ile Asp Glu Leu Met Gln Ser Leu
        130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Gly Ser Gly Gly Gly Ser Gly Gly Gly Gly Ser
        195                 200                 205

Ala Pro Thr Ser Ser Ser Thr Ser Ser Ser Thr Ala Glu Ala Gln Gln
        210                 215                 220

Gln Gln Gln Gln Gln Gln Gln Gln Gln His Leu Glu Gln Leu Leu
225                 230                 235                 240

Met Asp Leu Gln Glu Leu Leu Ser Arg Met Glu Asn Tyr Arg Asn Leu
                245                 250                 255

Lys Leu Pro Arg Met Leu Thr Phe Lys Phe Tyr Leu Pro Lys Gln Ala
            260                 265                 270

Thr Glu Leu Lys Asp Leu Gln Cys Leu Glu Asp Glu Leu Gly Pro Leu
        275                 280                 285

Arg His Val Leu Asp Leu Thr Gln Ser Lys Ser Phe Gln Leu Glu Asp
        290                 295                 300

Ala Glu Asn Phe Ile Ser Asn Ile Arg Val Thr Val Val Lys Leu Lys
305                 310                 315                 320

Gly Ser Asp Asn Thr Phe Glu Cys Gln Phe Asp Asp Glu Ser Ala Thr
                325                 330                 335

Val Val Asp Phe Leu Arg Arg Trp Ile Ala Phe Cys Gln Ser Ile Ile
            340                 345                 350

Ser Thr Ser Pro Gln Met Trp Glu Leu Glu Lys Asp Val Tyr Val Val
        355                 360                 365

Glu Val Asp Trp Thr Pro Asp Ala Pro Gly Glu Thr Val Asn Leu Thr
370                 375                 380

Cys Asp Thr Pro Glu Glu Asp Asp Ile Thr Trp Thr Ser Asp Gln Arg
385                 390                 395                 400

His Gly Val Ile Gly Ser Gly Lys Thr Leu Thr Ile Thr Val Lys Glu
                405                 410                 415

Phe Leu Asp Ala Gly Gln Tyr Thr Cys His Lys Gly Gly Glu Thr Leu
            420                 425                 430

Ser His Ser His Leu Leu Leu His Lys Lys Glu Asn Gly Ile Trp Ser
        435                 440                 445

Thr Glu Ile Leu Lys Asn Phe Lys Asn Lys Thr Phe Leu Lys Cys Glu
        450                 455                 460

Ala Pro Asn Tyr Ser Gly Arg Phe Thr Cys Ser Trp Leu Val Gln Arg
465                 470                 475                 480

Asn Met Asp Leu Lys Phe Asn Ile Lys Ser Ser Ser Ser Pro Asp
                485                 490                 495

Ser Arg Ala Val Thr Cys Gly Met Ala Ser Leu Ser Ala Glu Lys Val
            500                 505                 510
```

Thr Leu Asp Gln Arg Asp Tyr Glu Lys Tyr Ser Val Ser Cys Gln Glu
515                 520                 525

Asp Val Thr Cys Pro Thr Ala Glu Glu Thr Leu Pro Ile Glu Leu Ala
530                 535                 540

Leu Glu Ala Arg Gln Gln Asn Lys Tyr Glu Asn Tyr Ser Thr Ser Phe
545                 550                 555                 560

Phe Ile Arg Asp Ile Ile Lys Pro Asp Pro Pro Lys Asn Leu Gln Met
            565                 570                 575

Lys Pro Leu Lys Asn Ser Gln Val Glu Val Ser Trp Glu Tyr Pro Asp
                580                 585                 590

Ser Trp Ser Thr Pro His Ser Tyr Phe Ser Leu Lys Phe Phe Val Arg
            595                 600                 605

Ile Gln Arg Lys Lys Glu Lys Met Lys Glu Thr Glu Glu Gly Cys Asn
            610                 615                 620

Gln Lys Gly Ala Phe Leu Val Glu Lys Thr Ser Thr Glu Val Gln Cys
625                 630                 635                 640

Lys Gly Gly Asn Val Cys Val Gln Ala Gln Asp Arg Tyr Tyr Asn Ser
                645                 650                 655

Ser Cys Ser Lys Trp Ala Cys Val Pro Cys Arg Val Arg Ser Gly Gly
            660                 665                 670

Gly Gly Ser Gly Gly Gly Gly Ser Gly Gly Gly Gly Ser Gly Thr Pro
            675                 680                 685

Asp Cys Tyr Phe Ser His Ser Pro Ile Ser Ser Asn Phe Lys Val Lys
            690                 695                 700

Phe Arg Glu Leu Thr Asp His Leu Leu Lys Asp Tyr Pro Val Thr Val
705                 710                 715                 720

Ala Val Asn Leu Gln Asp Glu Lys His Cys Lys Ala Leu Trp Ser Leu
                725                 730                 735

Phe Leu Ala Gln Arg Trp Ile Glu Gln Leu Lys Thr Val Ala Gly Ser
            740                 745                 750

Lys Met Gln Thr Leu Leu Glu Asp Val Asn Thr Glu Ile His Phe Val
            755                 760                 765

Thr Ser Cys Thr Phe Gln Pro Leu Pro Glu Cys Leu Arg Phe Val Gln
770                 775                 780

Thr Asn Ile Ser His Leu Leu Lys Asp Thr Cys Thr Gln Leu Leu Ala
785                 790                 795                 800

Leu Lys Pro Cys Ile Gly Lys Ala Cys Gln Asn Phe Ser Arg Cys Leu
                805                 810                 815

Glu Val Gln Cys Gln Pro Asp Ser Ser Thr Leu Leu Pro Pro Arg Ser
            820                 825                 830

Pro Ile Ala Leu Glu Ala Thr Glu Leu Pro Glu Pro Arg Pro Arg Gln
            835                 840                 845

Leu Leu Leu Leu Leu Leu Leu Leu Pro Leu Thr Leu Val Leu Leu
850                 855                 860

Ala Ala Ala Trp Gly Leu Arg Trp Gln Arg Ala Arg Arg Arg Gly Glu
865                 870                 875                 880

Leu His Pro Gly Val Pro Leu Pro Ser His Pro
                885                 890

<210> SEQ ID NO 27
<211> LENGTH: 871
<212> TYPE: PRT
<213> ORGANISM: Artificial Sequence
<220> FEATURE:
<223> OTHER INFORMATION: mIL12aIL7IL12bFLT3L protein heterodimer

<400> SEQUENCE: 27

```
Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Ser Gly Gly Gly Ser Gly Gly Gly Ser
        195                 200                 205

Glu Cys His Ile Lys Asp Lys Glu Gly Lys Ala Tyr Glu Ser Val Leu
210                 215                 220

Met Ile Ser Ile Asp Glu Leu Asp Lys Met Thr Gly Thr Asp Ser Asn
225                 230                 235                 240

Cys Pro Asn Asn Glu Pro Asn Phe Phe Arg Lys His Val Cys Asp Asp
                245                 250                 255

Thr Lys Glu Ala Ala Phe Leu Asn Arg Ala Ala Arg Lys Leu Lys Gln
            260                 265                 270

Phe Leu Lys Met Asn Ile Ser Glu Glu Phe Asn Val His Leu Leu Thr
        275                 280                 285

Val Ser Gln Gly Thr Gln Thr Leu Val Asn Cys Thr Ser Lys Glu Glu
290                 295                 300

Lys Asn Val Lys Glu Gln Lys Lys Asn Asp Ala Cys Phe Leu Lys Arg
305                 310                 315                 320

Leu Leu Arg Glu Ile Lys Thr Cys Trp Asn Lys Ile Leu Lys Gly Ser
                325                 330                 335

Ile Met Trp Glu Leu Glu Lys Asp Val Tyr Val Val Glu Val Asp Trp
            340                 345                 350

Thr Pro Asp Ala Pro Gly Glu Thr Val Asn Leu Thr Cys Asp Thr Pro
        355                 360                 365

Glu Glu Asp Asp Ile Thr Trp Thr Ser Asp Gln Arg His Gly Val Ile
    370                 375                 380

Gly Ser Gly Lys Thr Leu Thr Ile Thr Val Lys Glu Phe Leu Asp Ala
385                 390                 395                 400

Gly Gln Tyr Thr Cys His Lys Gly Gly Glu Thr Leu Ser His Ser His
```

405                 410                 415
Leu Leu Leu His Lys Lys Glu Asn Gly Ile Trp Ser Thr Glu Ile Leu
            420                 425                 430

Lys Asn Phe Lys Asn Lys Thr Phe Leu Lys Cys Glu Ala Pro Asn Tyr
            435                 440                 445

Ser Gly Arg Phe Thr Cys Ser Trp Leu Val Gln Arg Asn Met Asp Leu
    450                 455                 460

Lys Phe Asn Ile Lys Ser Ser Ser Ser Pro Asp Ser Arg Ala Val
465                 470                 475                 480

Thr Cys Gly Met Ala Ser Leu Ser Ala Glu Lys Val Thr Leu Asp Gln
                485                 490                 495

Arg Asp Tyr Glu Lys Tyr Ser Val Ser Cys Gln Glu Asp Val Thr Cys
            500                 505                 510

Pro Thr Ala Glu Glu Thr Leu Pro Ile Glu Leu Ala Leu Glu Ala Arg
            515                 520                 525

Gln Gln Asn Lys Tyr Glu Asn Tyr Ser Thr Ser Phe Phe Ile Arg Asp
    530                 535                 540

Ile Ile Lys Pro Asp Pro Pro Lys Asn Leu Gln Met Lys Pro Leu Lys
545                 550                 555                 560

Asn Ser Gln Val Glu Val Ser Trp Glu Tyr Pro Asp Ser Trp Ser Thr
                565                 570                 575

Pro His Ser Tyr Phe Ser Leu Lys Phe Phe Val Arg Ile Gln Arg Lys
            580                 585                 590

Lys Glu Lys Met Lys Glu Thr Glu Glu Gly Cys Asn Gln Lys Gly Ala
            595                 600                 605

Phe Leu Val Glu Lys Thr Ser Thr Glu Val Gln Cys Lys Gly Gly Asn
    610                 615                 620

Val Cys Val Gln Ala Gln Asp Arg Tyr Tyr Asn Ser Ser Cys Ser Lys
625                 630                 635                 640

Trp Ala Cys Val Pro Cys Arg Val Arg Ser Gly Gly Gly Ser Gly
                645                 650                 655

Gly Gly Gly Ser Gly Gly Gly Ser Gly Thr Pro Asp Cys Tyr Phe
            660                 665                 670

Ser His Ser Pro Ile Ser Ser Asn Phe Lys Val Lys Phe Arg Glu Leu
    675                 680                 685

Thr Asp His Leu Leu Lys Asp Tyr Pro Val Thr Val Ala Val Asn Leu
            690                 695                 700

Gln Asp Glu Lys His Cys Lys Ala Leu Trp Ser Leu Phe Leu Ala Gln
705                 710                 715                 720

Arg Trp Ile Glu Gln Leu Lys Thr Val Ala Gly Ser Lys Met Gln Thr
                725                 730                 735

Leu Leu Glu Asp Val Asn Thr Glu Ile His Phe Val Thr Ser Cys Thr
            740                 745                 750

Phe Gln Pro Leu Pro Glu Cys Leu Arg Phe Val Gln Thr Asn Ile Ser
            755                 760                 765

His Leu Leu Lys Asp Thr Cys Thr Gln Leu Leu Ala Leu Lys Pro Cys
    770                 775                 780

Ile Gly Lys Ala Cys Gln Asn Phe Ser Arg Cys Leu Glu Val Gln Cys
785                 790                 795                 800

Gln Pro Asp Ser Ser Thr Leu Leu Pro Pro Arg Ser Pro Ile Ala Leu
                805                 810                 815

Glu Ala Thr Glu Leu Pro Glu Pro Arg Pro Arg Gln Leu Leu Leu Leu
            820                 825                 830

```
Leu Leu Leu Leu Leu Pro Leu Thr Leu Val Leu Leu Ala Ala Ala Trp
            835                 840                 845

Gly Leu Arg Trp Gln Arg Ala Arg Arg Arg Gly Glu Leu His Pro Gly
    850                 855                 860

Val Pro Leu Pro Ser His Pro
865                 870

<210> SEQ ID NO 28
<211> LENGTH: 875
<212> TYPE: PRT
<213> ORGANISM: Artificial Sequence
<220> FEATURE:
<223> OTHER INFORMATION: mIL12aIL15IL12bFLT3L protein heterodimer

<400> SEQUENCE: 28

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Ser Gly Gly Gly Ser Gly Gly Gly Ser
        195                 200                 205

Gly Ile His Val Phe Ile Leu Gly Cys Val Ser Val Gly Leu Pro Lys
    210                 215                 220

Thr Glu Ala Asn Trp Ile Asp Val Arg Tyr Asp Leu Glu Lys Ile Glu
225                 230                 235                 240

Ser Leu Ile Gln Ser Ile His Ile Asp Thr Thr Leu Tyr Thr Asp Ser
                245                 250                 255

Asp Phe His Pro Ser Cys Lys Val Thr Ala Met Asn Cys Phe Leu Leu
            260                 265                 270

Glu Leu Gln Val Ile Leu His Glu Tyr Ser Asn Met Thr Leu Asn Glu
        275                 280                 285

Thr Val Arg Asn Val Leu Tyr Leu Ala Asn Ser Thr Leu Ser Ser Asn
    290                 295                 300

Lys Asn Val Ala Glu Ser Gly Cys Lys Glu Cys Glu Glu Leu Glu Glu
305                 310                 315                 320
```

-continued

Lys Thr Phe Thr Glu Phe Leu Gln Ser Phe Ile Arg Ile Val Gln Met
            325                 330                 335

Phe Ile Asn Thr Ser Met Trp Glu Leu Glu Lys Asp Val Tyr Val Val
            340                 345                 350

Glu Val Asp Trp Thr Pro Asp Ala Pro Gly Glu Thr Val Asn Leu Thr
            355                 360                 365

Cys Asp Thr Pro Glu Glu Asp Ile Thr Trp Thr Ser Asp Gln Arg
            370                 375                 380

His Gly Val Ile Gly Ser Gly Lys Thr Leu Thr Ile Thr Val Lys Glu
385                 390                 395                 400

Phe Leu Asp Ala Gly Gln Tyr Thr Cys His Lys Gly Gly Glu Thr Leu
            405                 410                 415

Ser His Ser His Leu Leu Leu His Lys Lys Glu Asn Gly Ile Trp Ser
            420                 425                 430

Thr Glu Ile Leu Lys Asn Phe Lys Asn Lys Thr Phe Leu Lys Cys Glu
            435                 440                 445

Ala Pro Asn Tyr Ser Gly Arg Phe Thr Cys Ser Trp Leu Val Gln Arg
            450                 455                 460

Asn Met Asp Leu Lys Phe Asn Ile Lys Ser Ser Ser Ser Ser Pro Asp
465                 470                 475                 480

Ser Arg Ala Val Thr Cys Gly Met Ala Ser Leu Ser Ala Glu Lys Val
            485                 490                 495

Thr Leu Asp Gln Arg Asp Tyr Glu Lys Tyr Ser Val Ser Cys Gln Glu
            500                 505                 510

Asp Val Thr Cys Pro Thr Ala Glu Glu Thr Leu Pro Ile Glu Leu Ala
            515                 520                 525

Leu Glu Ala Arg Gln Gln Asn Lys Tyr Glu Asn Tyr Ser Thr Ser Phe
            530                 535                 540

Phe Ile Arg Asp Ile Ile Lys Pro Asp Pro Pro Lys Asn Leu Gln Met
545                 550                 555                 560

Lys Pro Leu Lys Asn Ser Gln Val Glu Val Ser Trp Glu Tyr Pro Asp
            565                 570                 575

Ser Trp Ser Thr Pro His Ser Tyr Phe Ser Leu Lys Phe Phe Val Arg
            580                 585                 590

Ile Gln Arg Lys Lys Glu Lys Met Lys Glu Thr Glu Glu Gly Cys Asn
            595                 600                 605

Gln Lys Gly Ala Phe Leu Val Glu Lys Thr Ser Thr Glu Val Gln Cys
            610                 615                 620

Lys Gly Gly Asn Val Cys Val Gln Ala Gln Asp Arg Tyr Tyr Asn Ser
625                 630                 635                 640

Ser Cys Ser Lys Trp Ala Cys Val Pro Cys Arg Val Arg Ser Gly Gly
            645                 650                 655

Gly Gly Ser Gly Gly Gly Gly Ser Gly Gly Gly Gly Ser Gly Thr Pro
            660                 665                 670

Asp Cys Tyr Phe Ser His Ser Pro Ile Ser Ser Asn Phe Lys Val Lys
            675                 680                 685

Phe Arg Glu Leu Thr Asp His Leu Leu Lys Asp Tyr Pro Val Thr Val
            690                 695                 700

Ala Val Asn Leu Gln Asp Glu Lys His Cys Lys Ala Leu Trp Ser Leu
705                 710                 715                 720

Phe Leu Ala Gln Arg Trp Ile Glu Gln Leu Lys Thr Val Ala Gly Ser
            725                 730                 735

```
Lys Met Gln Thr Leu Leu Glu Asp Val Asn Thr Glu Ile His Phe Val
            740                 745                 750

Thr Ser Cys Thr Phe Gln Pro Leu Pro Glu Cys Leu Arg Phe Val Gln
        755                 760                 765

Thr Asn Ile Ser His Leu Leu Lys Asp Thr Cys Thr Gln Leu Leu Ala
    770                 775                 780

Leu Lys Pro Cys Ile Gly Lys Ala Cys Gln Asn Phe Ser Arg Cys Leu
785                 790                 795                 800

Glu Val Gln Cys Gln Pro Asp Ser Ser Thr Leu Leu Pro Pro Arg Ser
                805                 810                 815

Pro Ile Ala Leu Glu Ala Thr Glu Leu Pro Glu Pro Arg Pro Arg Gln
            820                 825                 830

Leu Leu Leu Leu Leu Leu Leu Leu Pro Leu Thr Leu Val Leu Leu
            835                 840                 845

Ala Ala Ala Trp Gly Leu Arg Trp Gln Arg Ala Arg Arg Arg Gly Glu
    850                 855                 860

Leu His Pro Gly Val Pro Leu Pro Ser His Pro
865                 870                 875

<210> SEQ ID NO 29
<211> LENGTH: 871
<212> TYPE: PRT
<213> ORGANISM: Artificial Sequence
<220> FEATURE:
<223> OTHER INFORMATION: mIL12aIL21IL12bFLT3L protein heterodimer

<400> SEQUENCE: 29

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Gly Ser Gly Gly Gly Gly Ser Gly Gly Gly Gly Ser
        195                 200                 205

His Lys Ser Ser Pro Gln Gly Pro Asp Arg Leu Leu Ile Arg Leu Arg
    210                 215                 220
```

```
His Leu Ile Asp Ile Val Glu Gln Leu Lys Ile Tyr Glu Asn Asp Leu
225                 230                 235                 240

Asp Pro Glu Leu Leu Ser Ala Pro Gln Asp Val Lys Gly His Cys Glu
            245                 250                 255

His Ala Ala Phe Ala Cys Phe Gln Lys Ala Lys Leu Lys Pro Ser Asn
        260                 265                 270

Pro Gly Asn Asn Lys Thr Phe Ile Ile Asp Leu Val Ala Gln Leu Arg
    275                 280                 285

Arg Arg Leu Pro Ala Arg Arg Gly Gly Lys Lys Gln Lys His Ile Ala
290                 295                 300

Lys Cys Pro Ser Cys Asp Ser Tyr Glu Lys Arg Thr Pro Lys Glu Phe
305                 310                 315                 320

Leu Glu Arg Leu Lys Trp Leu Leu Gln Lys Met Ile His Gln His Leu
                325                 330                 335

Ser Met Trp Glu Leu Glu Lys Asp Val Tyr Val Val Glu Val Asp Trp
            340                 345                 350

Thr Pro Asp Ala Pro Gly Glu Thr Val Asn Leu Thr Cys Asp Thr Pro
        355                 360                 365

Glu Glu Asp Asp Ile Thr Trp Thr Ser Asp Gln Arg His Gly Val Ile
    370                 375                 380

Gly Ser Gly Lys Thr Leu Thr Ile Thr Val Lys Glu Phe Leu Asp Ala
385                 390                 395                 400

Gly Gln Tyr Thr Cys His Lys Gly Gly Glu Thr Leu Ser His Ser His
                405                 410                 415

Leu Leu Leu His Lys Lys Glu Asn Gly Ile Trp Ser Thr Glu Ile Leu
            420                 425                 430

Lys Asn Phe Lys Asn Lys Thr Phe Leu Lys Cys Glu Ala Pro Asn Tyr
        435                 440                 445

Ser Gly Arg Phe Thr Cys Ser Trp Leu Val Gln Arg Asn Met Asp Leu
    450                 455                 460

Lys Phe Asn Ile Lys Ser Ser Ser Ser Pro Asp Ser Arg Ala Val
465                 470                 475                 480

Thr Cys Gly Met Ala Ser Leu Ser Ala Glu Lys Val Thr Leu Asp Gln
                485                 490                 495

Arg Asp Tyr Glu Lys Tyr Ser Val Ser Cys Gln Glu Asp Val Thr Cys
            500                 505                 510

Pro Thr Ala Glu Glu Thr Leu Pro Ile Glu Leu Ala Leu Glu Ala Arg
        515                 520                 525

Gln Gln Asn Lys Tyr Glu Asn Tyr Ser Thr Ser Phe Phe Ile Arg Asp
    530                 535                 540

Ile Ile Lys Pro Asp Pro Pro Lys Asn Leu Gln Met Lys Pro Leu Lys
545                 550                 555                 560

Asn Ser Gln Val Glu Val Ser Trp Glu Tyr Pro Asp Ser Trp Ser Thr
                565                 570                 575

Pro His Ser Tyr Phe Ser Leu Lys Phe Phe Val Arg Ile Gln Arg Lys
            580                 585                 590

Lys Glu Lys Met Lys Glu Thr Glu Glu Gly Cys Asn Gln Lys Gly Ala
        595                 600                 605

Phe Leu Val Glu Lys Thr Ser Thr Glu Val Gln Cys Lys Gly Gly Asn
    610                 615                 620

Val Cys Val Gln Ala Gln Asp Arg Tyr Tyr Asn Ser Ser Cys Ser Lys
625                 630                 635                 640

Trp Ala Cys Val Pro Cys Arg Val Arg Ser Gly Gly Gly Gly Ser Gly
```

```
                    645                 650                 655
Gly Gly Gly Ser Gly Gly Gly Ser Gly Thr Pro Asp Cys Tyr Phe
                660                 665                 670
Ser His Ser Pro Ile Ser Ser Asn Phe Lys Val Lys Phe Arg Glu Leu
                675                 680                 685
Thr Asp His Leu Leu Lys Asp Tyr Pro Val Thr Val Ala Val Asn Leu
            690                 695                 700
Gln Asp Glu Lys His Cys Lys Ala Leu Trp Ser Leu Phe Leu Ala Gln
705                 710                 715                 720
Arg Trp Ile Glu Gln Leu Lys Thr Val Ala Gly Ser Lys Met Gln Thr
                725                 730                 735
Leu Leu Glu Asp Val Asn Thr Glu Ile His Phe Val Thr Ser Cys Thr
            740                 745                 750
Phe Gln Pro Leu Pro Glu Cys Leu Arg Phe Val Gln Thr Asn Ile Ser
            755                 760                 765
His Leu Leu Lys Asp Thr Cys Thr Gln Leu Leu Ala Leu Lys Pro Cys
        770                 775                 780
Ile Gly Lys Ala Cys Gln Asn Phe Ser Arg Cys Leu Glu Val Gln Cys
785                 790                 795                 800
Gln Pro Asp Ser Ser Thr Leu Leu Pro Pro Arg Ser Pro Ile Ala Leu
                805                 810                 815
Glu Ala Thr Glu Leu Pro Glu Pro Arg Pro Arg Gln Leu Leu Leu Leu
            820                 825                 830
Leu Leu Leu Leu Leu Pro Leu Thr Leu Val Leu Leu Ala Ala Ala Trp
            835                 840                 845
Gly Leu Arg Trp Gln Arg Ala Arg Arg Arg Gly Glu Leu His Pro Gly
        850                 855                 860
Val Pro Leu Pro Ser His Pro
865                 870

<210> SEQ ID NO 30
<211> LENGTH: 793
<212> TYPE: PRT
<213> ORGANISM: Artificial Sequence
<220> FEATURE:
<223> OTHER INFORMATION: hIL12aIL2IL12bGMCSF protein heterodimer

<400> SEQUENCE: 30

Arg Asn Leu Pro Val Ala Thr Pro Asp Pro Gly Met Phe Pro Cys Leu
1               5                   10                  15
His His Ser Gln Asn Leu Leu Arg Ala Val Ser Asn Met Leu Gln Lys
            20                  25                  30
Ala Arg Gln Thr Leu Glu Phe Tyr Pro Cys Thr Ser Glu Glu Ile Asp
        35                  40                  45
His Glu Asp Ile Thr Lys Asp Lys Thr Ser Thr Val Glu Ala Cys Leu
    50                  55                  60
Pro Leu Glu Leu Thr Lys Asn Glu Ser Cys Leu Asn Ser Arg Glu Thr
65                  70                  75                  80
Ser Phe Ile Thr Asn Gly Ser Cys Leu Ala Ser Arg Lys Thr Ser Phe
                85                  90                  95
Met Met Ala Leu Cys Leu Ser Ser Ile Tyr Glu Asp Leu Lys Met Tyr
            100                 105                 110
Gln Val Glu Phe Lys Thr Met Asn Ala Lys Leu Leu Met Asp Pro Lys
        115                 120                 125
Arg Gln Ile Phe Leu Asp Gln Asn Met Leu Ala Val Ile Asp Glu Leu
```

```
              130                 135                 140
Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
                180                 185                 190

Tyr Leu Asn Ala Ser Gly Gly Gly Ser Gly Gly Gly Ser Gly
            195                 200                 205

Gly Gly Gly Ser Ala Pro Thr Ser Ser Ser Thr Lys Lys Thr Gln Leu
            210                 215                 220

Gln Leu Glu His Leu Leu Leu Asp Leu Gln Met Ile Leu Asn Gly Ile
225                 230                 235                 240

Asn Asn Tyr Lys Asn Pro Lys Leu Thr Arg Met Leu Thr Phe Lys Phe
                245                 250                 255

Tyr Met Pro Lys Lys Ala Thr Glu Leu Lys His Leu Gln Cys Leu Glu
                260                 265                 270

Glu Glu Leu Lys Pro Leu Glu Glu Val Leu Asn Leu Ala Gln Ser Lys
            275                 280                 285

Asn Phe His Leu Arg Pro Arg Asp Leu Ile Ser Asn Ile Asn Val Ile
            290                 295                 300

Val Leu Glu Leu Lys Gly Ser Glu Thr Thr Phe Met Cys Glu Tyr Ala
305                 310                 315                 320

Asp Glu Thr Ala Thr Ile Val Glu Phe Leu Asn Arg Trp Ile Thr Phe
                325                 330                 335

Cys Gln Ser Ile Ile Ser Thr Leu Thr Ile Trp Glu Leu Lys Lys Asp
                340                 345                 350

Val Tyr Val Val Glu Leu Asp Trp Tyr Pro Asp Ala Pro Gly Glu Met
            355                 360                 365

Val Val Leu Thr Cys Asp Thr Pro Glu Glu Asp Gly Ile Thr Trp Thr
            370                 375                 380

Leu Asp Gln Ser Ser Glu Val Leu Gly Ser Gly Lys Thr Leu Thr Ile
385                 390                 395                 400

Gln Val Lys Glu Phe Gly Asp Ala Gly Gln Tyr Thr Cys His Lys Gly
                405                 410                 415

Gly Glu Val Leu Ser His Ser Leu Leu Leu Leu His Lys Lys Glu Asp
            420                 425                 430

Gly Ile Trp Ser Thr Asp Ile Leu Lys Asp Gln Lys Glu Pro Lys Asn
            435                 440                 445

Lys Thr Phe Leu Arg Cys Glu Ala Lys Asn Tyr Ser Gly Arg Phe Thr
            450                 455                 460

Cys Trp Trp Leu Thr Thr Ile Ser Thr Asp Leu Thr Phe Ser Val Lys
465                 470                 475                 480

Ser Ser Arg Gly Ser Ser Asp Pro Gln Gly Val Thr Cys Gly Ala Ala
                485                 490                 495

Thr Leu Ser Ala Glu Arg Val Arg Gly Asp Asn Lys Glu Tyr Glu Tyr
            500                 505                 510

Ser Val Glu Cys Gln Glu Asp Ser Ala Cys Pro Ala Ala Glu Glu Ser
            515                 520                 525

Leu Pro Ile Glu Val Met Val Asp Ala Val His Lys Leu Lys Tyr Glu
            530                 535                 540

Asn Tyr Thr Ser Ser Phe Phe Ile Arg Asp Ile Ile Lys Pro Asp Pro
545                 550                 555                 560
```

-continued

```
Pro Lys Asn Leu Gln Leu Lys Pro Leu Lys Asn Ser Arg Gln Val Glu
                565                 570                 575

Val Ser Trp Glu Tyr Pro Asp Thr Trp Ser Thr Pro His Ser Tyr Phe
            580                 585                 590

Ser Leu Thr Phe Cys Val Gln Val Gln Gly Lys Ser Lys Arg Glu Lys
        595                 600                 605

Lys Asp Arg Val Phe Thr Asp Lys Thr Ser Ala Thr Val Ile Cys Arg
    610                 615                 620

Lys Asn Ala Ser Ile Ser Val Arg Ala Gln Asp Arg Tyr Tyr Ser Ser
625                 630                 635                 640

Ser Trp Ser Glu Trp Ala Ser Val Pro Cys Ser Gly Gly Gly Gly Ser
                645                 650                 655

Gly Gly Gly Gly Ser Gly Gly Gly Ser Ala Pro Ala Arg Ser Pro
                660                 665                 670

Ser Pro Ser Thr Gln Pro Trp Glu His Val Asn Ala Ile Gln Glu Ala
        675                 680                 685

Arg Arg Leu Leu Asn Leu Ser Arg Asp Thr Ala Ala Glu Met Asn Glu
    690                 695                 700

Thr Val Glu Val Ile Ser Glu Met Phe Asp Leu Gln Glu Pro Thr Cys
705                 710                 715                 720

Leu Gln Thr Arg Leu Glu Leu Tyr Lys Gln Gly Leu Arg Gly Ser Leu
                725                 730                 735

Thr Lys Leu Lys Gly Pro Leu Thr Met Met Ala Ser His Tyr Lys Gln
            740                 745                 750

His Cys Pro Pro Thr Pro Glu Thr Ser Cys Ala Thr Gln Ile Ile Thr
        755                 760                 765

Phe Glu Ser Phe Lys Glu Asn Leu Lys Asp Phe Leu Leu Val Ile Pro
    770                 775                 780

Phe Asp Cys Trp Glu Pro Val Gln Glu
785                 790

<210> SEQ ID NO 31
<211> LENGTH: 812
<212> TYPE: PRT
<213> ORGANISM: Artificial Sequence
<220> FEATURE:
<223> OTHER INFORMATION: hIL12aIL7IL12bGMCSF protein heterodimer

<400> SEQUENCE: 31

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125
```

```
Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly
        195                 200                 205

Gly Gly Gly Ser Asp Cys Asp Ile Glu Gly Lys Asp Gly Lys Gln Tyr
        210                 215                 220

Glu Ser Val Leu Met Val Ser Ile Asp Gln Leu Leu Asp Ser Met Lys
225                 230                 235                 240

Glu Ile Gly Ser Asn Cys Leu Asn Asn Glu Phe Asn Phe Lys Arg
                245                 250                 255

His Ile Cys Asp Ala Asn Lys Glu Gly Met Phe Leu Phe Arg Ala Ala
            260                 265                 270

Arg Lys Leu Arg Gln Phe Leu Lys Met Asn Ser Thr Gly Asp Phe Asp
        275                 280                 285

Leu His Leu Leu Lys Val Ser Glu Gly Thr Thr Ile Leu Leu Asn Cys
    290                 295                 300

Thr Gly Gln Val Lys Gly Arg Lys Pro Ala Ala Leu Gly Glu Ala Gln
305                 310                 315                 320

Pro Thr Lys Ser Leu Glu Glu Asn Lys Ser Leu Lys Glu Gln Lys Lys
                325                 330                 335

Leu Asn Asp Leu Cys Phe Leu Lys Arg Leu Leu Gln Glu Ile Lys Thr
            340                 345                 350

Cys Trp Asn Lys Ile Leu Met Gly Thr Lys Glu His Ile Trp Glu Leu
        355                 360                 365

Lys Lys Asp Val Tyr Val Val Glu Leu Asp Trp Tyr Pro Asp Ala Pro
370                 375                 380

Gly Glu Met Val Val Leu Thr Cys Asp Thr Pro Glu Glu Asp Gly Ile
385                 390                 395                 400

Thr Trp Thr Leu Asp Gln Ser Ser Glu Val Leu Gly Ser Gly Lys Thr
                405                 410                 415

Leu Thr Ile Gln Val Lys Glu Phe Gly Asp Ala Gly Gln Tyr Thr Cys
            420                 425                 430

His Lys Gly Gly Glu Val Leu Ser His Ser Leu Leu Leu Leu His Lys
        435                 440                 445

Lys Glu Asp Gly Ile Trp Ser Thr Asp Ile Leu Lys Asp Gln Lys Glu
450                 455                 460

Pro Lys Asn Lys Thr Phe Leu Arg Cys Glu Ala Lys Asn Tyr Ser Gly
465                 470                 475                 480

Arg Phe Thr Cys Trp Trp Leu Thr Thr Ile Ser Thr Asp Leu Thr Phe
                485                 490                 495

Ser Val Lys Ser Ser Arg Gly Ser Ser Asp Pro Gln Gly Val Thr Cys
            500                 505                 510

Gly Ala Ala Thr Leu Ser Ala Glu Arg Val Arg Gly Asp Asn Lys Glu
        515                 520                 525

Tyr Glu Tyr Ser Val Glu Cys Gln Glu Asp Ser Ala Cys Pro Ala Ala
530                 535                 540
```

```
Glu Glu Ser Leu Pro Ile Glu Val Met Val Asp Ala Val His Lys Leu
545                 550                 555                 560

Lys Tyr Glu Asn Tyr Thr Ser Ser Phe Phe Ile Arg Asp Ile Ile Lys
                565                 570                 575

Pro Asp Pro Lys Asn Leu Gln Leu Lys Pro Leu Lys Asn Ser Arg
            580                 585                 590

Gln Val Glu Val Ser Trp Glu Tyr Pro Asp Thr Trp Ser Thr Pro His
            595                 600                 605

Ser Tyr Phe Ser Leu Thr Phe Cys Val Gln Val Gln Gly Lys Ser Lys
            610                 615                 620

Arg Glu Lys Lys Asp Arg Val Phe Thr Asp Lys Thr Ser Ala Thr Val
625                 630                 635                 640

Ile Cys Arg Lys Asn Ala Ser Ile Ser Val Arg Ala Gln Asp Arg Tyr
                645                 650                 655

Tyr Ser Ser Ser Trp Ser Glu Trp Ala Ser Val Pro Cys Ser Gly Gly
                660                 665                 670

Gly Gly Ser Gly Gly Gly Gly Ser Gly Gly Gly Gly Ser Ala Pro Ala
            675                 680                 685

Arg Ser Pro Ser Pro Ser Thr Gln Pro Trp Glu His Val Asn Ala Ile
690                 695                 700

Gln Glu Ala Arg Arg Leu Leu Asn Leu Ser Arg Asp Thr Ala Ala Glu
705                 710                 715                 720

Met Asn Glu Thr Val Glu Val Ile Ser Glu Met Phe Asp Leu Gln Glu
                725                 730                 735

Pro Thr Cys Leu Gln Thr Arg Leu Glu Leu Tyr Lys Gln Gly Leu Arg
                740                 745                 750

Gly Ser Leu Thr Lys Leu Lys Gly Pro Leu Thr Met Met Ala Ser His
            755                 760                 765

Tyr Lys Gln His Cys Pro Pro Thr Pro Glu Thr Ser Cys Ala Thr Gln
            770                 775                 780

Ile Ile Thr Phe Glu Ser Phe Lys Glu Asn Leu Lys Asp Phe Leu Leu
785                 790                 795                 800

Val Ile Pro Phe Asp Cys Trp Glu Pro Val Gln Glu
                805                 810
```

<210> SEQ ID NO 32
<211> LENGTH: 793
<212> TYPE: PRT
<213> ORGANISM: Artificial Sequence
<220> FEATURE:
<223> OTHER INFORMATION: hIL12aIL15IL12bGMCSF protein heterodimer

<400> SEQUENCE: 32

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95
```

```
Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
        130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly
            195                 200                 205

Gly Gly Gly Ser Gly Ile His Val Phe Ile Leu Gly Cys Phe Ser Ala
            210                 215                 220

Gly Leu Pro Lys Thr Glu Ala Asn Trp Val Asn Val Ile Ser Asp Leu
225                 230                 235                 240

Lys Lys Ile Glu Asp Leu Ile Gln Ser Met His Ile Asp Ala Thr Leu
                245                 250                 255

Tyr Thr Glu Ser Asp Val His Pro Ser Cys Lys Val Thr Ala Met Lys
            260                 265                 270

Cys Phe Leu Leu Glu Leu Gln Val Ile Ser Leu Glu Ser Gly Asp Ala
            275                 280                 285

Ser Ile His Asp Thr Val Glu Asn Leu Ile Ile Leu Ala Asn Asn Ser
290                 295                 300

Leu Ser Ser Asn Gly Asn Val Thr Glu Ser Gly Cys Lys Glu Cys Glu
305                 310                 315                 320

Glu Leu Glu Glu Lys Asn Ile Lys Glu Phe Leu Gln Ser Phe Val His
                325                 330                 335

Ile Val Gln Met Phe Ile Asn Thr Ser Ile Trp Glu Leu Lys Lys Asp
            340                 345                 350

Val Tyr Val Val Glu Leu Asp Trp Tyr Pro Asp Ala Pro Gly Glu Met
            355                 360                 365

Val Val Leu Thr Cys Asp Thr Pro Glu Glu Asp Gly Ile Thr Trp Thr
            370                 375                 380

Leu Asp Gln Ser Ser Glu Val Leu Gly Ser Gly Lys Thr Leu Thr Ile
385                 390                 395                 400

Gln Val Lys Glu Phe Gly Asp Ala Gly Gln Tyr Thr Cys His Lys Gly
                405                 410                 415

Gly Glu Val Leu Ser His Ser Leu Leu Leu Leu His Lys Lys Glu Asp
            420                 425                 430

Gly Ile Trp Ser Thr Asp Ile Leu Lys Asp Gln Lys Glu Pro Lys Asn
            435                 440                 445

Lys Thr Phe Leu Arg Cys Glu Ala Lys Asn Tyr Ser Gly Arg Phe Thr
            450                 455                 460

Cys Trp Trp Leu Thr Thr Ile Ser Thr Asp Leu Thr Phe Ser Val Lys
465                 470                 475                 480

Ser Ser Arg Gly Ser Ser Asp Pro Gln Gly Val Thr Cys Gly Ala Ala
                485                 490                 495

Thr Leu Ser Ala Glu Arg Val Arg Gly Asp Asn Lys Glu Tyr Glu Tyr
            500                 505                 510

Ser Val Glu Cys Gln Glu Asp Ser Ala Cys Pro Ala Ala Glu Glu Ser
```

```
            515                 520                 525
Leu Pro Ile Glu Val Met Val Asp Ala Val His Lys Leu Lys Tyr Glu
    530                 535                 540

Asn Tyr Thr Ser Ser Phe Phe Ile Arg Asp Ile Ile Lys Pro Asp Pro
545                 550                 555                 560

Pro Lys Asn Leu Gln Leu Lys Pro Leu Lys Asn Ser Arg Gln Val Glu
                565                 570                 575

Val Ser Trp Glu Tyr Pro Asp Thr Trp Ser Thr Pro His Ser Tyr Phe
            580                 585                 590

Ser Leu Thr Phe Cys Val Gln Val Gln Gly Lys Ser Lys Arg Glu Lys
        595                 600                 605

Lys Asp Arg Val Phe Thr Asp Lys Thr Ser Ala Thr Val Ile Cys Arg
    610                 615                 620

Lys Asn Ala Ser Ile Ser Val Arg Ala Gln Asp Arg Tyr Tyr Ser Ser
625                 630                 635                 640

Ser Trp Ser Glu Trp Ala Ser Val Pro Cys Ser Gly Gly Gly Gly Ser
                645                 650                 655

Gly Gly Gly Gly Ser Gly Gly Gly Ser Ala Pro Ala Arg Ser Pro
            660                 665                 670

Ser Pro Ser Thr Gln Pro Trp Glu His Val Asn Ala Ile Gln Glu Ala
        675                 680                 685

Arg Arg Leu Leu Asn Leu Ser Arg Asp Thr Ala Ala Glu Met Asn Glu
    690                 695                 700

Thr Val Glu Val Ile Ser Glu Met Phe Asp Leu Gln Glu Pro Thr Cys
705                 710                 715                 720

Leu Gln Thr Arg Leu Glu Leu Tyr Lys Gln Gly Leu Arg Gly Ser Leu
                725                 730                 735

Thr Lys Leu Lys Gly Pro Leu Thr Met Met Ala Ser His Tyr Lys Gln
            740                 745                 750

His Cys Pro Pro Thr Pro Glu Thr Ser Cys Ala Thr Gln Ile Ile Thr
        755                 760                 765

Phe Glu Ser Phe Lys Glu Asn Leu Lys Asp Phe Leu Leu Val Ile Pro
    770                 775                 780

Phe Asp Cys Trp Glu Pro Val Gln Glu
785                 790

<210> SEQ ID NO 33
<211> LENGTH: 793
<212> TYPE: PRT
<213> ORGANISM: Artificial Sequence
<220> FEATURE:
<223> OTHER INFORMATION: hIL12aIL21IL12bGMCSF protein heterodimer

<400> SEQUENCE: 33

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
```

```
                    85                  90                  95
Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
            130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
                180                 185                 190

Tyr Leu Asn Ala Ser Gly Gly Gly Ser Gly Gly Gly Ser Gly
                195                 200                 205

Gly Gly Gly Ser Gln Gly Gln Asp Arg His Met Ile Arg Met Arg Gln
            210                 215                 220

Leu Ile Asp Ile Val Asp Gln Leu Lys Asn Tyr Val Asn Asp Leu Val
225                 230                 235                 240

Pro Glu Phe Leu Pro Ala Pro Glu Asp Val Glu Thr Asn Cys Glu Trp
                245                 250                 255

Ser Ala Phe Ser Cys Phe Gln Lys Ala Gln Leu Lys Ser Ala Asn Thr
                260                 265                 270

Gly Asn Asn Glu Arg Ile Ile Asn Val Ser Ile Lys Lys Leu Lys Arg
            275                 280                 285

Lys Pro Pro Ser Thr Asn Ala Gly Arg Arg Gln Lys His Arg Leu Thr
290                 295                 300

Cys Pro Ser Cys Asp Ser Tyr Glu Lys Lys Pro Pro Lys Glu Phe Leu
305                 310                 315                 320

Glu Arg Phe Lys Ser Leu Leu Gln Lys Met Ile His Gln His Leu Ser
                325                 330                 335

Ser Arg Thr His Gly Ser Glu Asp Ser Ile Trp Glu Leu Lys Lys Asp
            340                 345                 350

Val Tyr Val Val Glu Leu Asp Trp Tyr Pro Asp Ala Pro Gly Glu Met
            355                 360                 365

Val Val Leu Thr Cys Asp Thr Pro Glu Glu Asp Gly Ile Thr Trp Thr
            370                 375                 380

Leu Asp Gln Ser Ser Glu Val Leu Gly Ser Gly Lys Thr Leu Thr Ile
385                 390                 395                 400

Gln Val Lys Glu Phe Gly Asp Ala Gly Gln Tyr Thr Cys His Lys Gly
                405                 410                 415

Gly Glu Val Leu Ser His Ser Leu Leu Leu Leu His Lys Lys Glu Asp
            420                 425                 430

Gly Ile Trp Ser Thr Asp Ile Leu Lys Asp Gln Lys Glu Pro Lys Asn
            435                 440                 445

Lys Thr Phe Leu Arg Cys Glu Ala Lys Asn Tyr Ser Gly Arg Phe Thr
            450                 455                 460

Cys Trp Trp Leu Thr Thr Ile Ser Thr Asp Leu Thr Phe Ser Val Lys
465                 470                 475                 480

Ser Ser Arg Gly Ser Ser Asp Pro Gln Gly Val Thr Cys Gly Ala Ala
                485                 490                 495

Thr Leu Ser Ala Glu Arg Val Arg Gly Asp Asn Lys Glu Tyr Glu Tyr
            500                 505                 510
```

Ser Val Glu Cys Gln Glu Asp Ser Ala Cys Pro Ala Ala Glu Glu Ser
          515                 520                 525

Leu Pro Ile Glu Val Met Val Asp Ala Val His Lys Leu Lys Tyr Glu
    530                 535                 540

Asn Tyr Thr Ser Ser Phe Phe Ile Arg Asp Ile Ile Lys Pro Asp Pro
545                 550                 555                 560

Pro Lys Asn Leu Gln Leu Lys Pro Leu Lys Asn Ser Arg Gln Val Glu
                565                 570                 575

Val Ser Trp Glu Tyr Pro Asp Thr Trp Ser Thr Pro His Ser Tyr Phe
            580                 585                 590

Ser Leu Thr Phe Cys Val Gln Val Gln Gly Lys Ser Lys Arg Glu Lys
            595                 600                 605

Lys Asp Arg Val Phe Thr Asp Lys Thr Ser Ala Thr Val Ile Cys Arg
        610                 615                 620

Lys Asn Ala Ser Ile Ser Val Arg Ala Gln Asp Arg Tyr Tyr Ser Ser
625                 630                 635                 640

Ser Trp Ser Glu Trp Ala Ser Val Pro Cys Ser Gly Gly Gly Gly Ser
                645                 650                 655

Gly Gly Gly Gly Ser Gly Gly Gly Ser Ala Pro Ala Arg Ser Pro
            660                 665                 670

Ser Pro Ser Thr Gln Pro Trp Glu His Val Asn Ala Ile Gln Glu Ala
        675                 680                 685

Arg Arg Leu Leu Asn Leu Ser Arg Asp Thr Ala Ala Glu Met Asn Glu
        690                 695                 700

Thr Val Glu Val Ile Ser Glu Met Phe Asp Leu Gln Glu Pro Thr Cys
705                 710                 715                 720

Leu Gln Thr Arg Leu Glu Leu Tyr Lys Gln Gly Leu Arg Gly Ser Leu
                725                 730                 735

Thr Lys Leu Lys Gly Pro Leu Thr Met Met Ala Ser His Tyr Lys Gln
            740                 745                 750

His Cys Pro Pro Thr Pro Glu Thr Ser Cys Ala Thr Gln Ile Ile Thr
        755                 760                 765

Phe Glu Ser Phe Lys Glu Asn Leu Lys Asp Phe Leu Leu Val Ile Pro
    770                 775                 780

Phe Asp Cys Trp Glu Pro Val Gln Glu
785                 790

<210> SEQ ID NO 34
<211> LENGTH: 875
<212> TYPE: PRT
<213> ORGANISM: Artificial Sequence
<220> FEATURE:
<223> OTHER INFORMATION: hIL12aIL2IL12bFLT3L protein heterodimer

<400> SEQUENCE: 34

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

```
Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly
        195                 200                 205

Gly Gly Gly Ser Ala Pro Thr Ser Ser Ser Thr Lys Lys Thr Gln Leu
210                 215                 220

Gln Leu Glu His Leu Leu Leu Asp Leu Gln Met Ile Leu Asn Gly Ile
225                 230                 235                 240

Asn Asn Tyr Lys Asn Pro Lys Leu Thr Arg Met Leu Thr Phe Lys Phe
                245                 250                 255

Tyr Met Pro Lys Lys Ala Thr Glu Leu Lys His Leu Gln Cys Leu Glu
            260                 265                 270

Glu Glu Leu Lys Pro Leu Glu Glu Val Leu Asn Leu Ala Gln Ser Lys
        275                 280                 285

Asn Phe His Leu Arg Pro Arg Asp Leu Ile Ser Asn Ile Asn Val Ile
    290                 295                 300

Val Leu Glu Leu Lys Gly Ser Glu Thr Thr Phe Met Cys Glu Tyr Ala
305                 310                 315                 320

Asp Glu Thr Ala Thr Ile Val Glu Phe Leu Asn Arg Trp Ile Thr Phe
                325                 330                 335

Cys Gln Ser Ile Ile Ser Thr Leu Thr Ile Trp Glu Leu Lys Lys Asp
            340                 345                 350

Val Tyr Val Val Glu Leu Asp Trp Tyr Pro Asp Ala Pro Gly Glu Met
        355                 360                 365

Val Val Leu Thr Cys Asp Thr Pro Glu Glu Asp Gly Ile Thr Trp Thr
    370                 375                 380

Leu Asp Gln Ser Ser Glu Val Leu Gly Ser Gly Lys Thr Leu Thr Ile
385                 390                 395                 400

Gln Val Lys Glu Phe Gly Asp Ala Gly Gln Tyr Thr Cys His Lys Gly
                405                 410                 415

Gly Glu Val Leu Ser His Ser Leu Leu Leu Leu His Lys Lys Glu Asp
            420                 425                 430

Gly Ile Trp Ser Thr Asp Ile Leu Lys Asp Gln Lys Glu Pro Lys Asn
        435                 440                 445

Lys Thr Phe Leu Arg Cys Glu Ala Lys Asn Tyr Ser Gly Arg Phe Thr
    450                 455                 460

Cys Trp Trp Leu Thr Thr Ile Ser Thr Asp Leu Thr Phe Ser Val Lys
465                 470                 475                 480

Ser Ser Arg Gly Ser Ser Asp Pro Gln Gly Val Thr Cys Gly Ala Ala
                485                 490                 495
```

```
Thr Leu Ser Ala Glu Arg Val Arg Gly Asp Asn Lys Glu Tyr Glu Tyr
            500                 505                 510
Ser Val Glu Cys Gln Glu Asp Ser Ala Cys Pro Ala Ala Glu Glu Ser
        515                 520                 525
Leu Pro Ile Glu Val Met Val Asp Ala Val His Lys Leu Lys Tyr Glu
    530                 535                 540
Asn Tyr Thr Ser Ser Phe Phe Ile Arg Asp Ile Ile Lys Pro Asp Pro
545                 550                 555                 560
Pro Lys Asn Leu Gln Leu Lys Pro Leu Lys Asn Ser Arg Gln Val Glu
                565                 570                 575
Val Ser Trp Glu Tyr Pro Asp Thr Trp Ser Thr Pro His Ser Tyr Phe
            580                 585                 590
Ser Leu Thr Phe Cys Val Gln Val Gln Gly Lys Ser Lys Arg Glu Lys
        595                 600                 605
Lys Asp Arg Val Phe Thr Asp Lys Thr Ser Ala Thr Val Ile Cys Arg
    610                 615                 620
Lys Asn Ala Ser Ile Ser Val Arg Ala Gln Asp Arg Tyr Tyr Ser Ser
625                 630                 635                 640
Ser Trp Ser Glu Trp Ala Ser Val Pro Cys Ser Gly Gly Gly Ser
                645                 650                 655
Gly Gly Gly Gly Ser Gly Gly Gly Ser Thr Gln Asp Cys Ser Phe
            660                 665                 670
Gln His Ser Pro Ile Ser Ser Asp Phe Ala Val Lys Ile Arg Glu Leu
        675                 680                 685
Ser Asp Tyr Leu Leu Gln Asp Tyr Pro Val Thr Val Ala Ser Asn Leu
    690                 695                 700
Gln Asp Glu Glu Leu Cys Gly Gly Leu Trp Arg Leu Val Leu Ala Gln
705                 710                 715                 720
Arg Trp Met Glu Arg Leu Lys Thr Val Ala Gly Ser Lys Met Gln Gly
                725                 730                 735
Leu Leu Glu Arg Val Asn Thr Glu Ile His Phe Val Thr Lys Cys Ala
            740                 745                 750
Phe Gln Pro Pro Pro Ser Cys Leu Arg Phe Val Gln Thr Asn Ile Ser
        755                 760                 765
Arg Leu Leu Gln Glu Thr Ser Glu Gln Leu Val Ala Leu Lys Pro Trp
    770                 775                 780
Ile Thr Arg Gln Asn Phe Ser Arg Cys Leu Glu Leu Gln Cys Gln Pro
785                 790                 795                 800
Asp Ser Ser Thr Leu Pro Pro Pro Trp Ser Pro Arg Pro Leu Glu Ala
                805                 810                 815
Thr Ala Pro Thr Ala Pro Gln Pro Pro Leu Leu Leu Leu Leu Leu Leu
            820                 825                 830
Pro Val Gly Leu Leu Leu Leu Ala Ala Ala Trp Cys Leu His Trp Gln
        835                 840                 845
Arg Thr Arg Arg Arg Thr Pro Arg Pro Gly Glu Gln Val Pro Pro Val
    850                 855                 860
Pro Ser Pro Gln Asp Leu Leu Leu Val Glu His
865                 870                 875

<210> SEQ ID NO 35
<211> LENGTH: 894
<212> TYPE: PRT
<213> ORGANISM: Artificial Sequence
<220> FEATURE:
<223> OTHER INFORMATION: hIL12aIL7IL12bFLT3L protein heterodimer
```

<400> SEQUENCE: 35

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly
        195                 200                 205

Gly Gly Gly Ser Asp Cys Asp Ile Glu Gly Lys Asp Gly Lys Gln Tyr
    210                 215                 220

Glu Ser Val Leu Met Val Ser Ile Asp Gln Leu Leu Asp Ser Met Lys
225                 230                 235                 240

Glu Ile Gly Ser Asn Cys Leu Asn Asn Glu Phe Asn Phe Phe Lys Arg
                245                 250                 255

His Ile Cys Asp Ala Asn Lys Glu Gly Met Phe Leu Phe Arg Ala Ala
            260                 265                 270

Arg Lys Leu Arg Gln Phe Leu Lys Met Asn Ser Thr Gly Asp Phe Asp
        275                 280                 285

Leu His Leu Leu Lys Val Ser Glu Gly Thr Thr Ile Leu Leu Asn Cys
    290                 295                 300

Thr Gly Gln Val Lys Gly Arg Lys Pro Ala Ala Leu Gly Glu Ala Gln
305                 310                 315                 320

Pro Thr Lys Ser Leu Glu Glu Asn Lys Ser Leu Lys Glu Gln Lys Lys
                325                 330                 335

Leu Asn Asp Leu Cys Phe Leu Lys Arg Leu Leu Gln Glu Ile Lys Thr
            340                 345                 350

Cys Trp Asn Lys Ile Leu Met Gly Thr Lys Glu His Ile Trp Glu Leu
        355                 360                 365

Lys Lys Asp Val Tyr Val Val Glu Leu Asp Trp Tyr Pro Asp Ala Pro
    370                 375                 380

Gly Glu Met Val Val Leu Thr Cys Asp Thr Pro Glu Glu Asp Gly Ile
385                 390                 395                 400

Thr Trp Thr Leu Asp Gln Ser Ser Glu Val Leu Gly Ser Gly Lys Thr
```

```
            405                 410                 415
Leu Thr Ile Gln Val Lys Glu Phe Gly Asp Ala Gly Gln Tyr Thr Cys
        420                 425                 430

His Lys Gly Gly Glu Val Leu Ser His Ser Leu Leu Leu His Lys
        435                 440                 445

Lys Glu Asp Gly Ile Trp Ser Thr Asp Ile Leu Lys Asp Gln Lys Glu
        450                 455                 460

Pro Lys Asn Lys Thr Phe Leu Arg Cys Glu Ala Lys Asn Tyr Ser Gly
465                 470                 475                 480

Arg Phe Thr Cys Trp Trp Leu Thr Thr Ile Ser Thr Asp Leu Thr Phe
                485                 490                 495

Ser Val Lys Ser Ser Arg Gly Ser Ser Asp Pro Gln Gly Val Thr Cys
                500                 505                 510

Gly Ala Ala Thr Leu Ser Ala Glu Arg Val Arg Gly Asp Asn Lys Glu
                515                 520                 525

Tyr Glu Tyr Ser Val Glu Cys Gln Glu Asp Ser Ala Cys Pro Ala Ala
        530                 535                 540

Glu Glu Ser Leu Pro Ile Glu Val Met Val Asp Ala Val His Lys Leu
545                 550                 555                 560

Lys Tyr Glu Asn Tyr Thr Ser Ser Phe Phe Ile Arg Asp Ile Ile Lys
                565                 570                 575

Pro Asp Pro Pro Lys Asn Leu Gln Leu Lys Pro Leu Lys Asn Ser Arg
                580                 585                 590

Gln Val Glu Val Ser Trp Glu Tyr Pro Asp Thr Trp Ser Thr Pro His
                595                 600                 605

Ser Tyr Phe Ser Leu Thr Phe Cys Val Gln Val Gln Gly Lys Ser Lys
        610                 615                 620

Arg Glu Lys Lys Asp Arg Val Phe Thr Asp Lys Thr Ser Ala Thr Val
625                 630                 635                 640

Ile Cys Arg Lys Asn Ala Ser Ile Ser Val Arg Ala Gln Asp Arg Tyr
                645                 650                 655

Tyr Ser Ser Ser Trp Ser Glu Trp Ala Ser Val Pro Cys Ser Gly Gly
                660                 665                 670

Gly Gly Ser Gly Gly Gly Gly Ser Gly Gly Gly Gly Ser Thr Gln Asp
                675                 680                 685

Cys Ser Phe Gln His Ser Pro Ile Ser Ser Asp Phe Ala Val Lys Ile
        690                 695                 700

Arg Glu Leu Ser Asp Tyr Leu Leu Gln Asp Tyr Pro Val Thr Val Ala
705                 710                 715                 720

Ser Asn Leu Gln Asp Glu Glu Leu Cys Gly Gly Leu Trp Arg Leu Val
                725                 730                 735

Leu Ala Gln Arg Trp Met Glu Arg Leu Lys Thr Val Ala Gly Ser Lys
                740                 745                 750

Met Gln Gly Leu Leu Glu Arg Val Asn Thr Glu Ile His Phe Val Thr
                755                 760                 765

Lys Cys Ala Phe Gln Pro Pro Pro Ser Cys Leu Arg Phe Val Gln Thr
        770                 775                 780

Asn Ile Ser Arg Leu Leu Gln Glu Thr Ser Glu Gln Leu Val Ala Leu
785                 790                 795                 800

Lys Pro Trp Ile Thr Arg Gln Asn Phe Ser Arg Cys Leu Glu Leu Gln
                805                 810                 815

Cys Gln Pro Asp Ser Ser Thr Leu Pro Pro Pro Trp Ser Pro Arg Pro
                820                 825                 830
```

```
Leu Glu Ala Thr Ala Pro Thr Ala Pro Gln Pro Pro Leu Leu Leu
            835                 840                 845

Leu Leu Leu Pro Val Gly Leu Leu Leu Ala Ala Ala Trp Cys Leu
        850                 855                 860

His Trp Gln Arg Thr Arg Arg Arg Thr Pro Arg Pro Gly Glu Gln Val
865             870                 875                 880

Pro Pro Val Pro Ser Pro Gln Asp Leu Leu Leu Val Glu His
            885                 890
```

<210> SEQ ID NO 36
<211> LENGTH: 875
<212> TYPE: PRT
<213> ORGANISM: Artificial Sequence
<220> FEATURE:
<223> OTHER INFORMATION: hIL12aIL15IL12bFLT3L protein heterodimer

<400> SEQUENCE: 36

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Gly Ser Gly
        195                 200                 205

Gly Gly Gly Ser Gly Ile His Val Phe Ile Leu Gly Cys Phe Ser Ala
    210                 215                 220

Gly Leu Pro Lys Thr Glu Ala Asn Trp Val Asn Val Ile Ser Asp Leu
225                 230                 235                 240

Lys Lys Ile Glu Asp Leu Ile Gln Ser Met His Ile Asp Ala Thr Leu
                245                 250                 255

Tyr Thr Glu Ser Asp Val His Pro Ser Cys Lys Val Thr Ala Met Lys
            260                 265                 270

Cys Phe Leu Leu Glu Leu Gln Val Ile Ser Leu Glu Ser Gly Asp Ala
        275                 280                 285

Ser Ile His Asp Thr Val Glu Asn Leu Ile Ile Leu Ala Asn Asn Ser
    290                 295                 300
```

-continued

```
Leu Ser Ser Asn Gly Asn Val Thr Glu Ser Gly Cys Lys Glu Cys Glu
305                 310                 315                 320

Glu Leu Glu Glu Lys Asn Ile Lys Glu Phe Leu Gln Ser Phe Val His
            325                 330                 335

Ile Val Gln Met Phe Ile Asn Thr Ser Ile Trp Glu Leu Lys Lys Asp
        340                 345                 350

Val Tyr Val Glu Leu Asp Trp Tyr Pro Asp Ala Pro Gly Glu Met
            355                 360                 365

Val Val Leu Thr Cys Asp Thr Pro Glu Glu Asp Gly Ile Thr Trp Thr
370                 375                 380

Leu Asp Gln Ser Ser Glu Val Leu Gly Ser Gly Lys Thr Leu Thr Ile
385                 390                 395                 400

Gln Val Lys Glu Phe Gly Asp Ala Gly Gln Tyr Thr Cys His Lys Gly
            405                 410                 415

Gly Glu Val Leu Ser His Ser Leu Leu Leu Leu His Lys Lys Glu Asp
        420                 425                 430

Gly Ile Trp Ser Thr Asp Ile Leu Lys Asp Gln Lys Glu Pro Lys Asn
            435                 440                 445

Lys Thr Phe Leu Arg Cys Glu Ala Lys Asn Tyr Ser Gly Arg Phe Thr
450                 455                 460

Cys Trp Trp Leu Thr Thr Ile Ser Thr Asp Leu Thr Phe Ser Val Lys
465                 470                 475                 480

Ser Ser Arg Gly Ser Ser Asp Pro Gln Gly Val Thr Cys Gly Ala Ala
            485                 490                 495

Thr Leu Ser Ala Glu Arg Val Arg Gly Asp Asn Lys Glu Tyr Glu Tyr
        500                 505                 510

Ser Val Glu Cys Gln Glu Asp Ser Ala Cys Pro Ala Ala Glu Glu Ser
    515                 520                 525

Leu Pro Ile Glu Val Met Val Asp Ala Val His Lys Leu Lys Tyr Glu
530                 535                 540

Asn Tyr Thr Ser Ser Phe Phe Ile Arg Asp Ile Ile Lys Pro Asp Pro
545                 550                 555                 560

Pro Lys Asn Leu Gln Leu Lys Pro Leu Lys Asn Ser Arg Gln Val Glu
            565                 570                 575

Val Ser Trp Glu Tyr Pro Asp Thr Trp Ser Thr Pro His Ser Tyr Phe
        580                 585                 590

Ser Leu Thr Phe Cys Val Gln Val Gln Gly Lys Ser Lys Arg Glu Lys
    595                 600                 605

Lys Asp Arg Val Phe Thr Asp Lys Thr Ser Ala Thr Val Ile Cys Arg
610                 615                 620

Lys Asn Ala Ser Ile Ser Val Arg Ala Gln Asp Arg Tyr Tyr Ser Ser
625                 630                 635                 640

Ser Trp Ser Glu Trp Ala Ser Val Pro Cys Ser Gly Gly Gly Ser
            645                 650                 655

Gly Gly Gly Gly Ser Gly Gly Gly Ser Thr Gln Asp Cys Ser Phe
        660                 665                 670

Gln His Ser Pro Ile Ser Ser Asp Phe Ala Val Lys Ile Arg Glu Leu
    675                 680                 685

Ser Asp Tyr Leu Leu Gln Asp Tyr Pro Val Thr Val Ala Ser Asn Leu
690                 695                 700

Gln Asp Glu Glu Leu Cys Gly Gly Leu Trp Arg Leu Val Leu Ala Gln
705                 710                 715                 720
```

```
Arg Trp Met Glu Arg Leu Lys Thr Val Ala Gly Ser Lys Met Gln Gly
                    725                 730                 735

Leu Leu Glu Arg Val Asn Thr Glu Ile His Phe Val Thr Lys Cys Ala
                740                 745                 750

Phe Gln Pro Pro Pro Ser Cys Leu Arg Phe Val Gln Thr Asn Ile Ser
            755                 760                 765

Arg Leu Leu Gln Glu Thr Ser Glu Gln Leu Val Ala Leu Lys Pro Trp
770                 775                 780

Ile Thr Arg Gln Asn Phe Ser Arg Cys Leu Glu Leu Gln Cys Gln Pro
785                 790                 795                 800

Asp Ser Ser Thr Leu Pro Pro Trp Ser Pro Arg Pro Leu Glu Ala
                805                 810                 815

Thr Ala Pro Thr Ala Pro Gln Pro Pro Leu Leu Leu Leu Leu Leu Leu
                820                 825                 830

Pro Val Gly Leu Leu Leu Ala Ala Ala Trp Cys Leu His Trp Gln
                835                 840                 845

Arg Thr Arg Arg Thr Pro Arg Pro Gly Glu Gln Val Pro Pro Val
850                 855                 860

Pro Ser Pro Gln Asp Leu Leu Leu Val Glu His
865                 870                 875

<210> SEQ ID NO 37
<211> LENGTH: 875
<212> TYPE: PRT
<213> ORGANISM: Artificial Sequence
<220> FEATURE:
<223> OTHER INFORMATION: hIL12aIL21IL12bFLT3L protein heterodimer

<400> SEQUENCE: 37

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
        50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Ser Gly
        195                 200                 205
```

Gly Gly Gly Ser Gln Gly Gln Asp Arg His Met Ile Arg Met Arg Gln
            210             215                 220

Leu Ile Asp Ile Val Asp Gln Leu Lys Asn Tyr Val Asn Asp Leu Val
225                 230                 235                 240

Pro Glu Phe Leu Pro Ala Pro Glu Asp Val Glu Thr Asn Cys Glu Trp
                245                 250                 255

Ser Ala Phe Ser Cys Phe Gln Lys Ala Gln Leu Lys Ser Ala Asn Thr
            260                 265                 270

Gly Asn Asn Glu Arg Ile Ile Asn Val Ser Ile Lys Lys Leu Lys Arg
            275                 280                 285

Lys Pro Pro Ser Thr Asn Ala Gly Arg Arg Gln Lys His Arg Leu Thr
290                 295                 300

Cys Pro Ser Cys Asp Ser Tyr Glu Lys Lys Pro Pro Lys Glu Phe Leu
305                 310                 315                 320

Glu Arg Phe Lys Ser Leu Leu Gln Lys Met Ile His Gln His Leu Ser
                325                 330                 335

Ser Arg Thr His Gly Ser Glu Asp Ser Ile Trp Glu Leu Lys Lys Asp
            340                 345                 350

Val Tyr Val Glu Leu Asp Trp Tyr Pro Asp Ala Pro Gly Glu Met
                355                 360                 365

Val Val Leu Thr Cys Asp Thr Pro Glu Glu Asp Gly Ile Thr Trp Thr
370                 375                 380

Leu Asp Gln Ser Ser Glu Val Leu Gly Ser Gly Lys Thr Leu Thr Ile
385                 390                 395                 400

Gln Val Lys Glu Phe Gly Asp Ala Gly Gln Tyr Thr Cys His Lys Gly
                405                 410                 415

Gly Glu Val Leu Ser His Ser Leu Leu Leu Leu His Lys Lys Glu Asp
            420                 425                 430

Gly Ile Trp Ser Thr Asp Ile Leu Lys Asp Gln Lys Glu Pro Lys Asn
            435                 440                 445

Lys Thr Phe Leu Arg Cys Glu Ala Lys Asn Tyr Ser Gly Arg Phe Thr
450                 455                 460

Cys Trp Trp Leu Thr Thr Ile Ser Thr Asp Leu Thr Phe Ser Val Lys
465                 470                 475                 480

Ser Ser Arg Gly Ser Ser Asp Pro Gln Gly Val Thr Cys Gly Ala Ala
                485                 490                 495

Thr Leu Ser Ala Glu Arg Val Arg Gly Asp Asn Lys Glu Tyr Glu Tyr
            500                 505                 510

Ser Val Glu Cys Gln Glu Asp Ser Ala Cys Pro Ala Ala Glu Glu Ser
            515                 520                 525

Leu Pro Ile Glu Val Met Val Asp Ala Val His Lys Leu Lys Tyr Glu
530                 535                 540

Asn Tyr Thr Ser Ser Phe Phe Ile Arg Asp Ile Ile Lys Pro Asp Pro
545                 550                 555                 560

Pro Lys Asn Leu Gln Leu Lys Pro Leu Lys Asn Ser Arg Gln Val Glu
                565                 570                 575

Val Ser Trp Glu Tyr Pro Asp Thr Trp Ser Thr Pro His Ser Tyr Phe
            580                 585                 590

Ser Leu Thr Phe Cys Val Gln Val Gln Gly Lys Ser Lys Arg Glu Lys
            595                 600                 605

Lys Asp Arg Val Phe Thr Asp Lys Thr Ser Ala Thr Val Ile Cys Arg
610                 615                 620

Lys Asn Ala Ser Ile Ser Val Arg Ala Gln Asp Arg Tyr Tyr Ser Ser

```
                     625                 630                 635                 640
    Ser Trp Ser Glu Trp Ala Ser Val Pro Cys Ser Gly Gly Gly Ser
                    645                 650                 655

Gly Gly Gly Ser Gly Gly Gly Ser Thr Gln Asp Cys Ser Phe
                660                 665                 670

Gln His Ser Pro Ile Ser Ser Asp Phe Ala Val Lys Ile Arg Glu Leu
                675                 680                 685

Ser Asp Tyr Leu Leu Gln Asp Tyr Pro Val Thr Val Ala Ser Asn Leu
    690                 695                 700

Gln Asp Glu Glu Leu Cys Gly Gly Leu Trp Arg Leu Val Leu Ala Gln
    705                 710                 715                 720

Arg Trp Met Glu Arg Leu Lys Thr Val Ala Gly Ser Lys Met Gln Gly
                    725                 730                 735

Leu Leu Glu Arg Val Asn Thr Glu Ile His Phe Val Thr Lys Cys Ala
                    740                 745                 750

Phe Gln Pro Pro Pro Ser Cys Leu Arg Phe Val Gln Thr Asn Ile Ser
                755                 760                 765

Arg Leu Leu Gln Glu Thr Ser Glu Gln Leu Val Ala Leu Lys Pro Trp
    770                 775                 780

Ile Thr Arg Gln Asn Phe Ser Arg Cys Leu Glu Leu Gln Cys Gln Pro
    785                 790                 795                 800

Asp Ser Ser Thr Leu Pro Pro Pro Trp Ser Pro Arg Pro Leu Glu Ala
                    805                 810                 815

Thr Ala Pro Thr Ala Pro Gln Pro Pro Leu Leu Leu Leu Leu Leu
                820                 825                 830

Pro Val Gly Leu Leu Leu Leu Ala Ala Ala Trp Cys Leu His Trp Gln
                835                 840                 845

Arg Thr Arg Arg Arg Thr Pro Arg Pro Gly Glu Gln Val Pro Pro Val
                850                 855                 860

Pro Ser Pro Gln Asp Leu Leu Leu Val Glu His
    865                 870                 875

<210> SEQ ID NO 38
<211> LENGTH: 2616
<212> TYPE: DNA
<213> ORGANISM: Artificial Sequence
<220> FEATURE:
<223> OTHER INFORMATION: nucleotide sequence encoding
      mIL12aIL2IL12bGMCSF protein heterodimer

<400> SEQUENCE: 38
atgtgtcaat cacgctacct cctcttttg gccaccttg ccctcctaaa ccacctcagt     60
ttggccaggg tcattccagt ctctggacct gccaggtgtc ttagccagtc ccgaaacctg    120
ctgaagacca cagatgacat ggtgaagacg gccagagaaa aactgaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gccccccacag aagacgtctt tgatgatgac cctgtgcctt    360
ggtagcatct atgaggactt gaagatgtac cagacagagt ccaggccat caacgcagca    420 cttcagaatc acaaccatca gcagatcatt ctagacaagg catgctggt ggccatcgat    480 gagctgatgc agtctctgaa tcataatggc gagactctgc cagaaacc tctgtggga    540 gaagcagacc cttacagagt gaaaatgaag ctctgcatcc tgcttcacgc cttcagcacc    600
cgcgtcgtga ccatcaacag ggtgatgggc tatctgagct ccgccggtgg aggaggttct    660
```

| | |
|---|---|
| ggaggcggtg gaagtggtgg cggaggtagc gcacccactt caagctccac ttcaagctct | 720 |
| acagcggaag cacagcagca gcagcagcag cagcagcagca cctggagcag | 780 |
| ctgttgatgg acctacagga gctcctgagc aggatggaga attacaggaa cctgaaactc | 840 |
| cccaggatgc tcaccttcaa attttacttg cccaagcagg ccacagaatt gaaagatctt | 900 |
| cagtgcctag aagatgaact tggacctctg cggcatgttc tggatttgac tcaaagcaaa | 960 |
| agctttcaat tggaagatgc tgagaatttc atcagcaata tcagagtaac tgttgtaaaa | 1020 |
| ctaaagggct ctgacaacac atttgagtgc caattcgatg atgagtcagc aactgtggtg | 1080 |
| gactttctga ggagatggat agccttctgt caaagcatca tctcaacaag ccctcaagag | 1140 |
| ggcagaggaa gtcttctaac atgcggtgac gtggaggaga atcccggccc tatgtgtcct | 1200 |
| cagaagctaa ccatctcctg gtttgccatc gttttgctgg tgtctccact catggccatg | 1260 |
| tgggagctgg agaaagacgt ttatgttgta gaggtggact ggactccga tgcccctgga | 1320 |
| gaaacagtga acctcacctg tgacacgcct gaagaagatg acatcacctg gacctcagac | 1380 |
| cagagacatg gagtcatagg ctctggaaag accctgacca tcactgtcaa agagtttcta | 1440 |
| gatgctggcc agtacacctg ccacaaagga ggcgagactc tgagccactc acatctgctg | 1500 |
| ctccacaaga aggaaaatgg aatttggtcc actgaaattt taaaaaattt caaaaacaag | 1560 |
| actttcctga agtgtgaagc accaaattac tccggacggt tcacgtgctc atggctggtg | 1620 |
| caaagaaaca tggacttgaa gttcaacatc aagagcagta gcagttcccc tgactctcgg | 1680 |
| gcagtgacat gtggaatggc gtctctgtct gcagagaagg tcacactgga ccaaagggac | 1740 |
| tatgagaagt attcagtgtc ctgccaggag gatgtcacct gcccaactgc cgaggagacc | 1800 |
| ctgcccattg aactggcgtt ggaagcacgg cagcagaata aatatgagaa ctacagcacc | 1860 |
| agcttcttca tcagggacat catcaaacca gacccgccca gaacttgca gatgaagcct | 1920 |
| ttgaagaact cacaggtgga ggtcagctgg gagtaccctg actcctggag cactccccat | 1980 |
| tcctacttct ccctcaagtt ctttgttcga atccagcgca agaaagaaaa gatgaaggag | 2040 |
| acagaggagg ggtgtaacca gaaaggtgcg ttcctcgtag agaagacatc taccgaagtc | 2100 |
| caatgcaaag gcgggaatgt ctgcgtgcaa gctcaggatc gctattacaa ttcctcgtgc | 2160 |
| agcaagtggg catgtgttcc ctgcagggtc cgatccggag gcggtggaag tggcggtgga | 2220 |
| ggctctggag gtgcggaag cgcacccacc cgctcaccca tcactgtcac ccggccttgg | 2280 |
| aagcatgtag aggccatcaa agaagccctg aacctcctgg atgacatgcc tgtcacgttg | 2340 |
| aatgaagagg tagaagtcgt ctctaacgag ttctccttca gaagctaac atgtgtgcag | 2400 |
| acccgcctga gatattcga gcagggtcta cggggcaatt tcaccaaact caagggcgcc | 2460 |
| ttgaacatga cagccagcta ctaccagaca tactgccccc caactccgga aacggactgt | 2520 |
| gaaacacaag ttaccaccta tgcggatttc atagacagcc ttaaaacctt tctgactgat | 2580 |
| atccccttg aatgcaaaaa accaggccaa aaatga | 2616 |

<210> SEQ ID NO 39
<211> LENGTH: 2610
<212> TYPE: DNA
<213> ORGANISM: Artificial Sequence
<220> FEATURE:
<223> OTHER INFORMATION: nucleotide sequence encoding
      mIL2IL12aIL12bGMCSF protein heterodimer

<400> SEQUENCE: 39

| | |
|---|---|
| atgtacagca tgcagctcgc atcctgtgtc acattgacac ttgtgctcct tgtcaacagc | 60 |

```
gcacccactt caagctccac ttcaagctct acagcggaag cacagcagca gcagcagcag    120
cagcagcagc agcagcagca cctggagcag ctgttgatgg acctacagga gctcctgagc    180
aggatggaga attacaggaa cctgaaactc cccaggatgc tcaccttcaa attttacttg    240
cccaagcagg ccacagaatt gaaagatctt cagtgcctag aagatgaact tggacctctg    300
cggcatgttc tggatttgac tcaaagcaaa agctttcaat tggaagatgc tgagaatttc    360
atcagcaata tcagagtaac tgttgtaaaa ctaaagggct ctgacaacac atttgagtgc    420
caattcgatg atgagtcagc aactgtggtg gactttctga ggagatggat agccttctgt    480
caaagcatca tctcaacaag ccctcaaggt ggaggaggtt ctggaggcgg tggaagtggt    540
ggcggaggta gcagggtcat tccagtctct ggacctgcca ggtgtcttag ccagtcccga    600
aacctgctga agaccacaga tgacatggtg aagacggcca gagaaaaact gaaacattat    660
tcctgcactg ctgaagacat cgatcatgaa gacatcacac gggaccaaac cagcacattg    720
aagacctgtt taccactgga actacacaag aacgagagtt gcctggctac tagagagact    780
tcttccacaa caagagggag ctgcctgccc ccacagaaga cgtctttgat gatgaccctg    840
tgccttggta gcatctatga ggacttgaag atgtaccaga cagagttcca ggccatcaac    900
gcagcacttc agaatcacaa ccatcagcag atcattctag acaagggcat gctggtggcc    960
atcgatgagc tgatgcagtc tctgaatcat aatggcgaga ctctgcgcca gaaacctcct    1020
gtgggagaag cagaccctta cagagtgaaa atgaagctct gcatcctgct tcacgccttc    1080
agcacccgcg tcgtgaccat caacaggggtg atgggctatc tgagctccgc cgagggcaga    1140
ggaagtcttc taacatgcgg tgacgtggag gagaatcccg gccctatgtg tcctcagaag    1200
ctaaccatct cctggtttgc catcgttttg ctggtgtctc cactcatggc catgtgggag    1260
ctggagaaag acgtttatgt tgtagaggtg gactggactc ccgatgcccc tggagaaaca    1320
gtgaacctca cctgtgacac gcctgaagaa gatgacatca cctggaccct agaccagaga    1380
catggagtca taggctctgg aaagaccctg accatcactg tcaaagagtt tctagatgct    1440
ggccagtaca cctgccacaa aggaggcgag actctgagcc actcacatct gctgctccac    1500
aagaaggaaa atggaatttg gtccactgaa atttttaaaaa atttcaaaaa caagactttc    1560
ctgaagtgtg aagcaccaaa ttactccgga cggttcacgt gctcatggct ggtgcaaaga    1620
aacatggact gaagttcaa catcaagagc agtagcagtt cccctgactc tcgggcagtg    1680
acatgtggaa tggcgtctct gtctgcagag aaggtcacac tggaccaaag ggactatgag    1740
aagtattcag tgtcctgcca ggaggatgtc acctgcccaa ctgccgagga gaccctgccc    1800
attgaactgg cgttggaagc acggcagcag aataaatatg agaactacag caccagcttc    1860
ttcatcaggg acatcatcaa accagaccgg cccaagaact gcagatgaa gcctttgaag    1920 aactcacagg tggaggtcag ctgggagtac cctgactcct ggagcactcc ccattcctac    1980 ttctcccctca gttctttgt tcgaatccag cgcaagaaag aaaagatgaa ggagacagag    2040 gagggtgta accagaaagg tgcgttcctc gtagagaaga catctaccga agtccaatgc    2100
aaaggcggga atgtctgcgt gcaagctcag gatcgctatt acaattcctc gtgcagcaag    2160
tgggcatgtg ttccctgcag ggtccgatcc ggaggcggtg gaagtggcgg tggaggctct    2220
ggaggtggcg gaagcgcacc cacccgctca cccatcactg tcacccggcc ttggaagcat    2280
gtagaggcca tcaaagaagc cctgaacctc ctggatgaca tgcctgtcac gttgaatgaa    2340
gaggtagaag tcgtctctaa cgagttctcc ttcaagaagc taacatgtgt gcagacccgc    2400
```

| ctgaagatat tcgagcaggg tctacggggc aatttcacca aactcaaggg cgccttgaac | 2460 |
| atgacagcca gctactacca gacatactgc cccccaactc cggaaacgga ctgtgaaaca | 2520 |
| caagttacca cctatgcgga tttcatagac agccttaaaa cctttctgac tgatatcccc | 2580 |
| tttgaatgca aaaaccagg ccaaaaatga | 2610 |

<210> SEQ ID NO 40
<211> LENGTH: 2601
<212> TYPE: DNA
<213> ORGANISM: Artificial Sequence
<220> FEATURE:
<223> OTHER INFORMATION: nucleotide sequence encoding
    mIL12aIL2GMCSFIL12b protein heterodimer

<400> SEQUENCE: 40

| atgtgtcaat cacgctacct cctcttttg gccacccttg ccctcctaaa ccacctcagt | 60 |
| ttggccaggg tcattccagt ctctggacct gccaggtgtc ttagccagtc ccgaaacctg | 120 |
| ctgaagacca cagatgacat ggtgaagacg gccagagaaa aactgaaaca ttattcctgc | 180 |
| actgctgaag acatcgatca tgaagacatc acacgggacc aaaccagcac attgaagacc | 240 |
| tgtttaccac tggaactaca caagaacgag agttgcctgg ctactagaga gacttcttcc | 300 |
| acaacaagag ggagctgcct gcccccacag aagacgtctt tgatgatgac cctgtgcctt | 360 |
| ggtagcatct atgaggactt gaagatgtac cagacagagt tccaggccat caacgcagca | 420 |
| cttcagaatc acaaccatca gcagatcatt ctagacaagg gcatgctggt ggccatcgat | 480 |
| gagctgatgc agtctctgaa tcataatggc gagactctgc gccagaaacc tcctgtggga | 540 |
| gaagcagacc cttacagagt gaaaatgaag ctctgcatcc tgcttcacgc cttcagcacc | 600 |
| cgcgtcgtga ccatcaacag ggtgatgggc tatctgagct ccgccggtgg aggaggttct | 660 |
| ggaggcggtg gaagtggtgg cggaggtagc gcacccactt caagctccac ttcaagctct | 720 |
| acagcggaag cacagcagca gcagcagcag cagcagcagc agcagcagca cctggagcag | 780 |
| ctgttgatgg acctacagga gctcctgagc aggatggaga attacaggaa cctgaaactc | 840 |
| cccaggatgc tcaccttcaa atttactttg cccaagcagg ccacagaatt gaaagatctt | 900 |
| cagtgcctag aagatgaact tggacctctg cggcatgttc tggatttgac tcaaagcaaa | 960 |
| agctttcaat ggaagatgct gagaattttc atcagcaata tcagagtaac tgttgtaaaa | 1020 |
| ctaaagggct ctgacaacac atttgagtgc caattcgatg atgagtcagc aactgtggtg | 1080 |
| gactttctga ggagatggat agccttctgt caaagcatca tctcaacaag ccctcaagag | 1140 |
| ggcagaggaa gtcttctaac atgcggtgac gtggaggaga tcccggccc tatgtggctg | 1200 |
| cagaatttac ttttcctggg cattgtggtc tacagcctct cagcacccac ccgctcaccc | 1260 |
| atcactgtca cccggccttg gaagcatgta gaggccatca agaagcccct gaacctcctg | 1320 |
| gatgacatgc ctgtcacgtt gaatgaagag gtagaagtcg tctctaacga gttctcctcc | 1380 |
| aagaagctaa catgtgtgca gacccgcctg aagatattcg agcagggtct acggggcaat | 1440 |
| ttcaccaaac tcaagggcgc cttgaacatg acagccagct actaccagac atactgcccc | 1500 |
| ccaactccgg aaacggactg tgaaacacaa gttaccacct atgcggattt catagacagc | 1560 |
| cttaaaacct ttctgactga tatccccttt gaatgcaaaa accaggcca aaaggaggc | 1620 |
| ggtggaagtg gcggtggagg ctctggaggt ggcggaagca tgtgggagct ggagaaagac | 1680 |
| gtttatgttg tagaggtgga ctggactccc gatgccctg agaaacagt gaacctcacc | 1740 |
| tgtgacacgc ctgaagaaga tgacatcacc tggacctcag accagagaca tggagtcata | 1800 |

| | |
|---|---|
| ggctctggaa agaccctgac catcactgtc aaagagtttc tagatgctgg ccagtacacc | 1860 |
| tgccacaaag gaggcgagac tctgagccac tcacatctgc tgctccacaa gaaggaaaat | 1920 |
| ggaatttggt ccactgaaat tttaaaaaat ttcaaaaaca agactttcct gaagtgtgaa | 1980 |
| gcaccaaatt actccggacg gttcacgtgc tcatggctgg tgcaaagaaa catggacttg | 2040 |
| aagttcaaca tcaagagcag tagcagttcc cctgactctc gggcagtgac atgtggaatg | 2100 |
| gcgtctctgt ctgcagagaa ggtcacactg gaccaaaggg actatgagaa gtattcagtg | 2160 |
| tcctgccagg aggatgtcac ctgcccaact gccgaggaga ccctgcccat tgaactggcg | 2220 |
| ttggaagcac ggcagcagaa taaatatgag aactacagca ccagcttctt catcagggac | 2280 |
| atcatcaaac cagacccgcc caagaacttg cagatgaagc ctttgaagaa ctcacaggtg | 2340 |
| gaggtcagct gggagtaccc tgactcctgg agcactcccc attcctactt ctcccctcaag | 2400 |
| ttctttgttc gaatccagcg caagaaagaa aagatgaagg agacagagga ggggtgtaac | 2460 |
| cagaaaggtg cgttcctcgt agagaagaca tctaccgaag tccaatgcaa aggcgggaat | 2520 |
| gtctgcgtgc aagctcagga tcgctattac aattcctcgt gcagcaagtg ggcatgtgtt | 2580 |
| ccctgcaggg tccgatccta g | 2601 |

<210> SEQ ID NO 41
<211> LENGTH: 2595
<212> TYPE: DNA
<213> ORGANISM: Artificial Sequence
<220> FEATURE:
<223> OTHER INFORMATION: nucleotide sequence encoding
    mIL2IL12aGMCSFIL12b protein heterodimer

<400> SEQUENCE: 41

| | |
|---|---|
| atgtacagca tgcagctcgc atcctgtgtc acattgacac ttgtgctcct tgtcaacagc | 60 |
| gcacccactt caagctccac ttcaagctct acagcggaag cacagcagca gcagcagcag | 120 |
| cagcagcagc agcagcagca cctggagcag ctgttgatgg acctacagga gctcctgagc | 180 |
| aggatggaga attacaggaa cctgaaactc cccaggatgc tcaccttcaa attttacttg | 240 |
| cccaagcagg ccacagaatt gaaagatctt cagtgcctag aagatgaact tggacctctg | 300 |
| cggcatgttc tggatttgac tcaaagcaaa agctttcaat tggaagatgc tgagaatttc | 360 |
| atcagcaata tcagagtaac tgttgtaaaa ctaaagggct ctgacaacac atttgagtgc | 420 |
| caattcgatg atgagtcagc aactgtggtg gactttctga gagatgatga gccttctgtc | 480 |
| caaagcatca tctcaacaag ccctcaaggt ggaggaggtt ctggaggcgg tggaagtggt | 540 |
| ggcggaggta gcagggtcat tccagtctct ggacctgcca ggtgtcttag ccagtcccga | 600 |
| aacctgctga agaccacaga tgacatggtg aagacggcca gagaaaaact gaaacattat | 660 |
| tcctgcactg ctgaagacat cgatcatgaa gacatcacac gggaccaaac cagcacattg | 720 |
| aagacctgtt taccactgga actacacaag aacgagagtt gcctggctac tagagagact | 780 |
| tcttccacaa caagagggag ctgcctgccc ccacagaaga cgtctttgat gatgaccctg | 840 |
| tgccttggta gcatctatga ggacttgaag atgtaccaga cagagttcca ggccatcaac | 900 |
| gcagcacttc agaatcacaa ccatcagcag atcattctag acaagggcat gctggtggcc | 960 |
| atcgatgagc tgatgcagtc tctgaatcat aatggcgaga ctctgcgcca gaaacctcct | 1020 |
| gtgggagaag cagacccctta cagagtgaaa atgaagctct gcatcctgct tcacgccttc | 1080 |
| agcacccgcg tcgtgaccat caacagggtg atgggctatc tgagctccgc cgagggcaga | 1140 |
| ggaagtcttc taacatgcgg tgacgtggag gagaatcccg gccctatgtg gctgcagaat | 1200 |

```
ttacttttcc tgggcattgt ggtctacagc ctctcagcac ccacccgctc acccatcact   1260
gtcacccggc cttggaagca tgtagaggcc atcaaagaag ccctgaacct cctggatgac   1320
atgcctgtca cgttgaatga agaggtagaa gtcgtctcta acgagttctc cttcaagaag   1380
ctaacatgtg tgcagacccg cctgaagata ttcgagcagg gtctacgggg caatttcacc   1440
aaactcaagg gcgccttgaa catgacagcc agctactacc agacatactg ccccccaact   1500
ccggaaacgg actgtgaaac acaagttacc acctatgcgg atttcatcga cagccttaaa   1560 accttttctga ctgatatccc ctttgaatgc aaaaaaccag gccaaaaagg aggcggtgga   1620
agtggcggtg gaggctctgg aggtggcgga agcatgtggg agctgagaaa agacgtttat   1680
gttgtagagg tggactggac tcccgatgcc cctggagaaa cagtgaacct cacctgtgac   1740
acgcctgaag aagatgacat cacctggacc tcagaccaga cacatggagt cataggctct   1800
ggaaagaccc tgaccatcac tgtcaaagag tttctagatg ctggccagta cacctgccac   1860
aaaggaggcg agactctgag ccactcacat ctgctgctcc acaagaagga aaatggaatt   1920
tggtccactg aaatttttaaa aaatttcaaa acaagactt tcctgaagtg tgaagcacca   1980
aattactccg acggttcac gtgctcatgg ctggtgcaaa gaaacatgga cttgaagttc   2040
aacatcaaga gcagtagcag ttcccctgac tctcgggcag tgacatgtgg aatggcgtct   2100
ctgtctgcag agaaggtcac actggaccaa agggactatg agaagtattc agtgtcctgc   2160
caggaggatg tcacctgccc aactgccgag gagaccctgc ccattgaact ggcgttggaa   2220
gcacggcagc agaataaata tgagaactac agcaccagct tcttcatcag ggacatcatc   2280
aaaccagacc cgcccaagaa cttgcagatg aagcctttga gaactcaca ggtggaggtc   2340 agctgggagt accctgactc ctggagcact ccccattcct acttctccct caagttcttt   2400
gttcgaatcc agcgcaagaa agaaaagatg aaggagacag gaggggtg taaccagaaa   2460 ggtgcgttcc tcgtagagaa gacatctacc gaagtccaat gcaaaggcgg gaatgtctgc   2520
gtgcaagctc aggatcgcta ttacaattcc tcgtgcagca gtgggcatg tgttccctgc   2580 agggtccgat cctag                                                   2595
```

<210> SEQ ID NO 42
<211> LENGTH: 2616
<212> TYPE: DNA
<213> ORGANISM: Artificial Sequence
<220> FEATURE:
<223> OTHER INFORMATION: nucleotide sequence encoding
      mIL12aGMCSFIL12bIL2 protein heterodimer

<400> SEQUENCE: 42

```
atgtgtcaat cacgctacct cctcttttg gccacccttg ccctcctaaa ccacctcagt    60
ttggccaggg tcattccagt ctctggacct gccaggtgtc ttagccagtc ccgaaacctg   120
ctgaagacca cagatgacat ggtgaagacg gccagagaaa aactgaaaca ttattcctgc   180
actgctgaag acatcgatca tgaagacatc acacgggacc aaaccagcac attgaagacc   240
tgtttaccac tggaactaca caagaacgag agttgcctgg ctactagaga gacttcttcc   300
acaacaagag ggagctgcct gccccccacag aagacgtctt tgatgatgac cctgtgcctt   360
ggtagcatct atgaggactt gaagatgtac cagacagagt ccaggccat caacgcagca   420 cttcagaatc acaaccatca gcagatcatt ctagacaagg gcatgctggt ggccatcgat   480
gagctgatga gtctctgaa tcataatggc gagactctgc gccagaaacc tcctgtggga   540
gaagcagacc cttacagagt gaaaatgaag ctctgcatcc tgcttcacgc cttcagcacc   600
```

```
cgcgtcgtga ccatcaacag ggtgatgggc tatctgagct ccgccggtgg aggaggttct    660
ggaggcggtg gaagtggtgg cggaggtagc gcacccaccc gctcacccat cactgtcacc    720
cggccttgga agcatgtaga ggccatcaaa gaagccctga acctcctgga tgacatgcct    780
gtcacgttga atgaagaggt agaagtcgtc tctaacgagt tctccttcaa gaagctaaca    840
tgtgtgcaga cccgcctgaa gatattcgag cagggtctac ggggcaattt caccaaactc    900
aagggcgcct tgaacatgac agccagctac taccagacat actgcccccc aactccggaa    960
acggactgtg aaacacaagt taccacctat gcggatttca gacagcct aaaacccttt     1020
ctgactgata tccccttga atgcaaaaaa ccaggccaaa agagggcag aggaagtctt     1080
ctaacatgcg gtgacgtgga ggagaatccc ggccctatgt gtcctcagaa gctaaccatc    1140
tcctggtttg ccatcgtttt gctggtgtct ccactcatgg ccatgtggga gctggagaaa    1200
gacgtttatg ttgtagaggt ggactggact cccgatgccc tggagaaac agtgaacctc     1260
acctgtgaca cgcctgaaga agatgacatc acctggacct cagaccagag acatggagtc    1320
ataggctctg gaaagaccct gaccatcact gtcaaagagt ttctagatgc tggccagtac    1380
acctgccaca aggaggcga gactctgagc cactcacatc tgctgctcca caagaaggaa    1440
aatggaattt ggtccactga aattttaaaa aatttcaaaa acaagacttt cctgaagtgt    1500
gaagcaccaa attactccgg acggttcacg tgctcatggc tggtgcaaag aaacatggac    1560
ttgaagttca acatcaagag cagtagcagt tcccctgact ctcgggcagt gacatgtgga    1620
atggcgtctc tgtctgcaga aaggtcaca ctggaccaaa gggactatga aagtattca     1680
gtgtcctgcc aggaggatgt cacctgccca actgccgagg agaccctgcc cattgaactg    1740
gcgttggaag cacggcagca gaataaatat gagaactaca gcaccagctt cttcatcagg    1800
gacatcatca accagacccc gcccaagaac ttgcagatga gccttgaa gaactcacag     1860
gtggaggtca gctgggagta ccctgactcc tggagcactc ccattccta cttctccctc    1920
aagttctttt tcgaatcca gcgcaagaaa gaaaagatga aggagacaga ggaggggtgt     1980
aaccagaaag gtgcgttcct cgtagagaag acatctaccg aagtccaatg caaaggcggg    2040
aatgtctgcg tgcaagctca ggatcgctat tacaattcct cgtgcagcaa gtgggcatgt    2100
gttccctgca gggtccgatc cggaggcggt ggaagtggcg gtggaggctc tggaggtggc    2160
ggaagcgcac ccacttcaag ctccacttca agctctacag cggaagcaca gcagcagcag    2220
cagcagcagc agcagcagca gcagcacctg agcagctgt tgatggacct acaggagctc    2280
ctgagcagga tggagaatta caggaacctg aaactcccca ggatgctcac cttcaaattt    2340
tacttgccca gcaggccac agaattgaaa gatcttcagt gcctagaaga tgaacttgga    2400
cctctgcggc atgttctgga tttgactcaa agcaaaagct ttcaattgga agatgctgag    2460
aatttcatca gcaatatcag agtaactgtt gtaaaactaa agggctctga acacacattt    2520
gagtgccaat tcgatgatga gtcagcaact gtggtggact ttctgaggag atggatagcc    2580
ttctgtcaaa gcatcatctc aacaagccct caataa                              2616
```

<210> SEQ ID NO 43
<211> LENGTH: 2556
<212> TYPE: DNA
<213> ORGANISM: Artificial Sequence
<220> FEATURE:
<223> OTHER INFORMATION: nucleotide sequence encoding
      mIL12aIL7IL12bGMCSF protein heterodimer

<400> SEQUENCE: 43

```
atgtgtcaat cacgctacct cctcttttg gccacccttg ccctcctaaa ccacctcagt      60
ttggccaggg tcattccagt ctctggacct gccaggtgtc ttagccagtc ccgaaacctg     120
ctgaagacca cagatgacat ggtgaagacg gccagagaaa aactgaaaca ttattcctgc     180
actgctgaag acatcgatca tgaagacatc acacgggacc aaaccagcac attgaagacc     240
tgtttaccac tggaactaca caagaacgag agttgcctgg ctactagaga gacttcttcc     300
acaacaagag ggagctgcct gcccccacag aagacgtctt tgatgatgac cctgtgcctt     360
ggtagcatct atgaggactt gaagatgtac cagacagagt tccaggccat caacgcagca     420
cttcagaatc acaaccatca gcagatcatt ctagacaagg gcatgctggt ggccatcgat     480
gagctgatgc agtctctgaa tcataatggc gagactctgc gccagaaacc tcctgtggga     540
gaagcagacc cttacagagt gaaaatgaag ctctgcatcc tgcttcacgc cttcagcacc     600
cgcgtcgtga ccatcaacag ggtgatgggc tatctgagct ccgccggtgg aggaggttct     660
ggaggcggtg gaagtggtgg cggaggtagc gagtgccaca ttaaagacaa agaaggtaaa     720
gcatatgaga gtgtactgat gatcagcatc gatgaattgg acaaaatgac aggaactgat     780
agtaattgcc cgaataatga accaaacttt tttagaaaac atgtatgtga tgatacaaag     840
gaagctgctt ttctaaatcg tgctgctcgc aagttgaagc aatttcttaa aatgaatatc     900
agtgaagaat tcaatgtcca cttactaaca gtatcacaag gcacacaaac actggtgaac     960
tgcacaagta aggaagaaaa aaacgtaaag gaacagaaaa agaatgatgc atgtttccta    1020
aagagactac tgagagaaat aaaaacttgt tggaataaaa ttttgaaggg cagtatagag    1080
ggcagaggaa gtcttctaac atgcggtgac gtggaggaga tcccggccc tatgtgtcct    1140
cagaagctaa ccatctcctg gtttgccatc gttttgctgg tgtctccact catggccatg    1200
tgggagctgg agaaagacgt ttatgttgta gaggtggact ggactcccga tgcccctgga    1260
gaaacagtga acctcacctg tgacacgcct gaagaagatg acatcacctg gacctcagac    1320
cagagacatg gagtcatagg ctctggaaag accctgacca tcactgtcaa agagtttcta    1380
gatgctggcc agtacacctg ccacaaagga ggcgagactc tgagccactc acatctgctg    1440
ctccacaaga aggaaaatgg aatttggtcc actgaaattt taaaaaattt caaaaacaag    1500
actttcctga agtgtgaagc accaaattac tccggacggt tcacgtgctc atggctggtg    1560
caaagaaaca tggacttgaa gttcaacatc aagagcagta gcagttcccc tgactctcgg    1620
gcagtgacat gtggaatggc gtctctgtct gcagagaagg tcacactgga ccaaagggac    1680
tatgagaagt attcagtgtc ctgccaggag gatgtcacct gcccaactgc cgaggagacc    1740
ctgcccattg aactggcgtt ggaagcacgg cagcagaata aatatgagaa ctacagcacc    1800
agcttcttca tcagggacat catcaaacca gacccgccca agaacttgca gatgaagcct    1860
ttgaagaact cacaggtgga ggtcagctgg gagtaccctg actcctggag cactccccat    1920
tcctacttct ccctcaagtt ctttgttcga atccagcgca agaaagaaaa gatgaaggag    1980
acagaggagg ggtgtaacca gaaaggtgcg ttcctcgtag agaagacatc taccgaagtc    2040
caatgcaaag gcgggaatgt ctgcgtgcaa gctcaggatc gctattacaa ttcctcgtgc    2100
agcaagtggg catgtgttcc ctgcagggtc cgatccggag gcgtggaag tggcggtgga    2160
ggctctggag gtggcggaag cgcacccacc cgctcaccca tcactgtcac ccggccttgg    2220
aagcatgtag aggccatcaa agaagccctg aacctcctgg atgacatgcc tgtcacgttg    2280
aatgaagagg tagaagtcgt ctctaacgag ttctccttca agaagctaac atgtgtgcag    2340
acccgcctga agatattcga gcagggtcta cggggcaatt tcaccaaact caagggcgcc    2400
```

```
ttgaacatga cagccagcta ctaccagaca tactgccccc caactccgga aacggactgt    2460
gaaacacaag ttaccaccta tgcggatttc atagacagcc ttaaaaccTT tctgactgat    2520
atcccctttg aatgcaaaaa accaggccaa aaatga                              2556
```

<210> SEQ ID NO 44
<211> LENGTH: 2568
<212> TYPE: DNA
<213> ORGANISM: Artificial Sequence
<220> FEATURE:
<223> OTHER INFORMATION: nucleotide sequence encoding
       mIL12aIL15IL12bGMCSF protein heterodimer

<400> SEQUENCE: 44

```
atgtgtcaat cacgctacct cctctttttg gccaccttg ccctcctaaa ccacctcagt       60
ttggccaggg tcattccagt ctctggacct gccaggtgtc ttagccagtc ccgaaacctg     120
ctgaagacca cagatgacat ggtgaagacg gccagagaaa aactgaaaca ttattcctgc     180
actgctgaag acatcgatca tgaagacatc acacgggacc aaaccagcac attgaagacc     240
tgtttaccac tggaactaca caagaacgag agttgcctgg ctactagaga gacttcttcc     300
acaacaagag ggagctgcct gcccccacag aagacgtctt tgatgatgac cctgtgcctt     360
ggtagcatct atgaggactt gaagatgtac cagacagagt tccaggccat caacgcagca     420
cttcagaatc acaaccatca gcagatcatt ctagacaagg catgctggt ggccatcgat      480 gagctgatgc agtctctgaa tcataatggc gagactctgc gccagaaacc tcctgtggga     540
gaagcagacc cttacagagt gaaaatgaag ctctgcatcc tgcttcacgc cttcagcacc     600
cgcgtcgtga ccatcaacag ggtgatgggc tatctgagct ccgccggtgg aggaggttct     660
ggaggcggtg gaagtggtgg cggaggtagc ggcattcatg tcttcatttt gggctgtgtc    720
agtgtaggtc tccctaaaac agaggccaac tggatagatg taagatatga cctggagaaa    780
attgaaagcc ttattcaatc tattcatatt gacaccactt atacactga cagtgacttt      840 catcccagtt gcaaagttac tgcaatgaac tgctttctcc tggaattgca ggttatttta    900
catgagtaca gtaacatgac tcttaatgaa acagtaagaa acgtgctcta ccttgcaaac    960
agcactctgt cttctaacaa gaatgtagca gaatctggct gcaaggaatg tgaggagctg   1020
gaggagaaaa ccttcacaga ttttttgcaa agctttatac gcattgtcca aatgttcatc    1080
aacacgtccg agggcagagg aagtcttcta acatgcggtg acgtggagga gaatcccggc    1140
cctatgtgtc ctcagaagct aaccatctcc tggtttgcca tcgttttgct ggtgtctcca    1200
ctcatggcca tgtgggagct ggagaaagac gtttatgttg tagaggtgga ctggactccc    1260
gatgcccctg gagaaacagt gaacctcacc tgtgacacgc ctgaagaaga tgacatcacc    1320
tggacctcag accagagaca tggagtcata ggctctggaa agaccctgac catcactgtc    1380
aaagagtttc tagatgctgg ccagtacacc tgccacaaag aggcgagac tctgagccac    1440 tcacatctgc tgctccacaa gaaggaaaat ggaatttggt ccactgaaat tttaaaaaat   1500
ttcaaaaaca gactttcct gaagtgtgaa gcaccaaatt actccggacg gttcacgtgc    1560
tcatggctgg tgcaaagaaa catggacttg aagttcaaca tcaagagcag tagcagttcc    1620
cctgactctc gggcagtgac atgtggaatg cgtctctgt ctgcagagaa ggtcacactg     1680
gaccaaaggg actatgagaa gtattcagtg tcctgccagg aggatgtcac ctgcccaact    1740
gccgaggaga ccctgcccat tgaactggcg ttggaagcac ggcagcagaa taaatatgag    1800
aactacagca ccagcttctt catcagggac atcatcaaac cagacccgcc caagaacttg    1860
```

```
cagatgaagc ctttgaagaa ctcacaggtg gaggtcagct gggagtaccc tgactcctgg    1920
agcactcccc attcctactt ctccctcaag ttctttgttc gaatccagcg caagaaagaa    1980
aagatgaagg agacagagga ggggtgtaac cagaaaggtg cgttcctcgt agagaagaca    2040
tctaccgaag tccaatgcaa aggcgggaat gtctgcgtgc aagctcagga tcgctattac    2100
aattcctcgt gcagcaagtg ggcatgtgtt ccctgcaggg tccgatccgg aggcggtgga    2160
agtggcggtg gaggctctgg aggtggcgga agcgcaccca cccgctcacc catcactgtc    2220
acccggcctt ggaagcatgt agaggccatc aaagaagccc tgaacctcct ggatgacatg    2280
cctgtcacgt tgaatgaaga ggtagaagtc gtctctaacg agttctcctt caagaagcta    2340
acatgtgtgc agacccgcct gaagatattc gagcagggtc tacggggcaa tttcaccaaa    2400
ctcaagggcg ccttgaacat gacagccagc tactaccaga catactgccc cccaactccg    2460
gaaacggact gtgaaacaca agttaccacc tatgcggatt tcatagacag ccttaaaacc    2520
tttctgactg atatccccct tgaatgcaaa aaaccaggcc aaaaatga                 2568

<210> SEQ ID NO 45
<211> LENGTH: 2556
<212> TYPE: DNA
<213> ORGANISM: Artificial Sequence
<220> FEATURE:
<223> OTHER INFORMATION: nucleotide sequence encoding
      mIL12aIL21IL12bGMCSF protein heterodimer

<400> SEQUENCE: 45
atgtgtcaat cacgctacct cctcttttg gccaccccttg ccctcctaaa ccacctcagt      60
ttggccaggg tcattccagt ctctggacct gccaggtgtc ttagccagtc ccgaaacctg    120
ctgaagacca cagatgacat ggtgaagacg gccagagaaa aactgaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gcccccacag aagacgtctt tgatgatgac cctgtgcctt    360
ggtagcatct atgaggactt gaagatgtac cagacagagt tccaggccat caacgcagca    420
cttcagaatc acaaccatca gcagatcatt ctagacaagg gcatgctggt ggccatcgat    480
gagctgatgc agtctctgaa tcataatggc gagactctgc cccagaaacc tcctgtggga    540
gaagcagacc cttacagagt gaaaatgaag ctctgcatcc tgcttcacgc cttcagcacc    600
cgcgtcgtga ccatcaacag ggtgatggc tatctgagcc ccgccggtgg aggaggttct    660
ggaggcggtg gaagtggtgg cggaggtagc cataaatcaa gccccaaggg gccagatcgc    720
ctcctgatta gacttcgtca ccttattgac attgttgaac agctgaaaat ctatgaaaat    780
gacttggatc ctgaacttct atcagctcca caagatgtaa agggcactg tgagcatgca    840 gcttttgcct gttttcagaa ggccaaactc aagccatcaa ccctggaaa caataagaca    900 ttcatcattg acctcgtggc ccagctcagg aggaggctgc ctgccaggag ggagggaaag    960
aaacagaagc acatagctaa tgcccttcc tgtgattcgt atgagaaaag gacacccaaa    1020
gaattcctag aaagactaaa atggctcctt caaagatga ttcatcagca tctctccgag    1080
ggcagaggaa gtcttctaac atgcggtgac gtggaggaga tcccggcccc tatgtgtcct    1140
cagaaagcta accatctcct gtttgccatc gttttgctgg tgtctccact catggccatg    1200
tgggagctga gaaagacgt ttatgttgta gaggtggact ggactccgga tgcccctgga    1260
gaaacagtga acctcacctg tgacacgcct gaagaagatg acatcacctg gacctcagac    1320
```

```
cagagacatg gagtcatagg ctctggaaag accctgacca tcactgtcaa agagtttcta    1380
gatgctggcc agtacacctg ccacaaagga ggcgagactc tgagccactc acatctgctg    1440
ctccacaaga aggaaaatgg aatttggtcc actgaaattt taaaaaattt caaaaacaag    1500
actttcctga agtgtgaagc accaaattac tccggacggt tcacgtgctc atggctggtg    1560
caaagaaaca tggacttgaa gttcaacatc aagagcagta gcagttcccc tgactctcgg    1620
gcagtgacat gtggaatggc gtctctgtct gcagagaagg tcacactgga ccaaagggac    1680
tatgagaagt attcagtgtc ctgccaggag gatgtcacct gcccaactgc cgaggagacc    1740
ctgcccattg aactggcgtt ggaagcacgg cagcagaata aatatgagaa ctacagcacc    1800
agcttcttca tcagggacat catcaaacca gacccgccca agaacttgca gatgaagcct    1860
ttgaagaact cacaggtgga ggtcagctgg gagtaccctg actcctggag cactccccat    1920
tcctacttct ccctcaagtt ctttgttcga atccagcgca agaaagaaaa gatgaaggag    1980
acagaggagg ggtgtaacca gaaaggtgcg ttcctcgtag agaagacatc taccgaagtc    2040
caatgcaaag gcgggaatgt ctgcgtgcaa gctcaggatc gctattacaa ttcctcgtgc    2100
agcaagtggg catgtgttcc ctgcagggtc cgatccggag gcggtggaag tggcggtgga    2160
ggctctggag gtggcggaag cgcacccacc cgctcaccca tcactgtcac ccggccttgg    2220
aagcatgtag aggccatcaa gaagccctg  aacctcctgg atgacatgcc tgtcacgttg    2280
aatgaagagg tagaagtcgt ctctaacgag ttctccttca agaagctaac atgtgtgcag    2340
acccgcctga aatattcga  gcagggtcta cgggggcaatt tcaccaaaact caagggcgcc    2400 ttgaacatga cagccagcta ctaccagaca tactgcccc  caactccgga aacggactgt    2460
gaaacacaag ttaccaccta tgcggatttc atagacagcc ttaaaacctt tctgactgat    2520 atccccttg aatgcaaaaa accaggccaa aaatga                                2556
```

<210> SEQ ID NO 46
<211> LENGTH: 2862
<212> TYPE: DNA
<213> ORGANISM: Artificial Sequence
<220> FEATURE:
<223> OTHER INFORMATION: nucleotide sequence encoding
      mIL12aIL2IL12bFLT3L protein heterodimer

<400> SEQUENCE: 46

```
atgtgtcaat cacgctacct cctcttttg gccaccttg ccctcctaaa ccacctcagt      60
ttggccaggg tcattccagt ctctggacct gccaggtgtc ttagccagtc ccgaaacctg    120
ctgaagacca cagatgacat ggtgaagacg gccagagaaa actgaaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gcccccacag aagacgtctt tgatgatgac cctgtgcctt    360
ggtagcatct atgaggactt gaagatgtac cagacagagt ccaggccat  caacgcagca    420 cttcagaatc acaaccatca gcagatcatt ctagacaagg gcatgctggt ggccatcgat    480
gagctgatgc agtctctgaa tcataatggc gagactctgc gccagaaacc tcctgtggga    540
gaagcagacc cttacagagt gaaaatgaag ctctgcatcc tgcttcacgc cttcagcacc    600
cgcgtcgtga ccatcaacag ggtgatgggc tatctgagct ccgccggtgg aggaggttct    660
ggaggcggtg gaagtggtgg cggaggtagc gcacccactt caagctccac ttcaagctct    720
acagcggaag cacagcagca gcagcagcag cagcagcagc agcagcagca cctggagcag    780
```

```
ctgttgatgg acctacagga gctcctgagc aggatggaga attacaggaa cctgaaactc    840
cccaggatgc tcaccttcaa attttacttg cccaagcagg ccacagaatt gaaagatctt    900
cagtgcctag aagatgaact tggacctctg cggcatgttc tggatttgac tcaaagcaaa    960
agctttcaat tggaagatgc tgagaatttc atcagcaata tcagagtaac tgttgtaaaa   1020
ctaaagggct ctgacaacac atttgagtgc caattcgatg atgagtcagc aactgtggtg   1080
gactttctga ggagatggat agccttctgt caaagcatca tctcaacaag ccctcaagag   1140
ggcagaggaa gtcttctaac atgcggtgac gtggaggaga atcccggccc tatgtgtcct   1200
cagaagctaa ccatctcctg gtttgccatc gttttgctgg tgtctccact catggccatg   1260
tgggagctgg agaaagacgt ttatgttgta gaggtggact ggactcccga tgcccctgga   1320
gaaacagtga acctcacctg tgacacgcct gaagaagatg acatcacctg gacctcagac   1380
cagagacatg gagtcatagg ctctggaaag accctgacca tcactgtcaa agagtttcta   1440
gatgctggcc agtacacctg ccacaaagga ggcgagactc tgagccactc acatctgctg   1500
ctccacaaga aggaaaatgg aatttggtcc actgaaattt taaaaatttt caaaaacaag   1560
actttcctga agtgtgaagc accaaattac tccggacggt tcacgtgctc atggctggtg   1620
caaagaaaca tggacttgaa gttcaacatc aagagcagta gcagttcccc tgactctcgg   1680
gcagtgacat gtggaatggc gtctctgtct gcagagaagg tcacactgga ccaaagggac   1740
tatgagaagt attcagtgtc ctgccaggag gatgtcacct gcccaactgc cgaggagacc   1800
ctgcccattg aactggcgtt ggaagcacgg cagcagaata aatatgagaa ctacagcacc   1860
agcttcttca tcagggacat catcaaacca gacccgccca gaacttgca gatgaagcct    1920
ttgaagaact cacaggtgga ggtcagctgg gagtaccctg actcctggag cactccccat   1980
tcctacttct ccctcaagtt ctttgttcga atccagcgca agaaagaaaa gatgaaggag   2040
acagaggagg ggtgtaacca gaaaggtgcg ttcctcgtag agaagacatc taccgaagtc   2100
caatgcaaag gcgggaatgt ctgcgtgcaa gctcaggatc gctattacaa ttcctcgtgc   2160
agcaagtggg catgtgttcc ctgcagggtc cgatccggag gcggtggaag tggcggtgga   2220
ggctctggag gtggcggaag cgggacacct gactgttact tcagccacag tcccatctcc   2280
tccaacttca aagtgaagtt tagagagttg actgaccacc tgcttaaaga ttacccagtc   2340
actgtggccg tcaatcttca ggacgagaag cactgcaagg ccttgtggag cctcttccta   2400
gcccagcgct ggatagagca actgaagact gtggcagggt ctaagatgca aacgcttctg   2460
gaggacgtca acaccgagat acattttgtc acctcatgta ccttccagcc cctaccagaa   2520
tgtctgcgat tcgtccagac caacatctcc cacctcctga aggacacctg cacacagctg   2580
cttgctctga gccctgtat cgggaaggcc tgccagaatt tctctcggtg cctggaggtg   2640
cagtgccagc cggactcctc caccctgctg ccccaaggaa gtcccatagc cctagaagcc   2700
acggagctcc cagagcctcg gcccaggcag ctgttgctcc tgctgctgct gctgctgcct   2760
ctcacactgg tgctgctggc agccgcctgg ggccttcgct ggcaaagggc aagaaggagg   2820
ggggagctcc accctggggt gccccctcccc tcccatccct ag                      2862
```

<210> SEQ ID NO 47  
<211> LENGTH: 2802  
<212> TYPE: DNA  
<213> ORGANISM: Artificial Sequence  
<220> FEATURE:  
<223> OTHER INFORMATION: nucleotide sequence encoding  
    mIL12aIL7IL12bFLT3L protein heterodimer

<400> SEQUENCE: 47

```
atgtgtcaat cacgctacct cctcttttg gccaccctg ccctcctaaa ccacctcagt      60
ttggccaggg tcattccagt ctctggacct gccaggtgtc ttagccagtc ccgaaacctg    120
ctgaagacca cagatgacat ggtgaagacg gccagagaaa aactgaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gcccccacag aagacgtctt tgatgatgac cctgtgcctt    360
ggtagcatct atgaggactt gaagatgtac cagacagagt tccaggccat caacgcagca    420
cttcagaatc acaaccatca gcagatcatt ctagacaagg gcatgctggt ggccatcgat    480
gagctgatgc agtctctgaa tcataatggc gagactctgc gccagaaacc tcctgtggga    540
gaagcagacc cttacagagt gaaaatgaag ctctgcatcc tgcttcacgc cttcagcacc    600
cgcgtcgtga ccatcaacag ggtgatgggc tatctgagct ccgccggtgg aggaggttct    660
ggaggcggtg gaagtggtgg cggaggtagc gagtgccaca ttaaagacaa agaaggtaaa    720
gcatatgaga gtgtactgat gatcagcatc gatgaattgg acaaaatgac aggaactgat    780
agtaattgcc cgaataatga accaaacttt tttagaaaac atgtatgtga tgatacaaag    840
gaagctgctt ttctaaatcg tgctgctcgc aagttgaagc aatttcttaa aatgaatatc    900
agtgaagaat tcaatgtcca cttactaaca gtatcacaag gcacacaaac actggtgaac    960
tgcacaagta aggaagaaaa aaacgtaaag gaacagaaaa agaatgatgc atgtttccta   1020
aagagactac tgagagaaat aaaaacttgt tggaataaaa ttttgaaggg cagtatagag   1080
ggcagaggaa gtcttctaac atgcggtgac gtggaggaga tcccggccc tatgtgtcct   1140
cagaagctaa ccatctcctg gtttgccatc gttttgctgg tgtctccact catggccatg   1200
tgggagctgg agaaagacgt ttatgttgta gaggtggact ggactcccga tgccctggga   1260
gaaacagtga acctcacctg tgacacgcct gaagaagatg acatcacctg gacctcagac   1320
cagagacatg gagtcatagg ctctggaaag accctgacca tcactgtcaa agagtttcta   1380
gatgctggcc agtacacctg ccacaaagga ggcgagactc tgagccactc acatctgctg   1440
ctccacaaga aggaaaatgg aatttggtcc actgaaattt taaaaaattt caaaacaag   1500
actttcctga gtgtgaagc accaaattac tccggacggt tcacgtgctc atggctggtg   1560
caaagaaaca tggacttgaa gttcaacatc aagagcagta gcagttcccc tgactctcgg   1620
gcagtgacat gtggaatggc gtctctgtct gcagagaagg tcacactgga ccaaagggac   1680
tatgagaagt attcagtgtc ctgccaggag gatgtcacct gcccaactgc cgaggagacc   1740
ctgcccattg aactggcgtt ggaagcacgg cagcagaata aatatgagaa ctacagcacc   1800
agcttcttca tcagggacat catcaaacca gacccgccca gaacttgca gatgaagcct   1860
ttgaagaact cacaggtgga ggtcagctgg gagtaccctg actcctggag cactccccat   1920
tcctacttct ccctcaagtt ctttgttcga atccagcgca agaaagaaaa gatgaaggag   1980
acagaggagg ggtgtaacca gaaaggtgcg ttcctcgtag agaagacatc taccgaagtc   2040
caatgcaaag gcgggaatgt ctgcgtgcaa gctcaggatc gctattacaa ttcctcgtgc   2100
agcaagtggg catgtgttcc ctgcagggtc cgatccggag gcggtggaag tggcggtgga   2160
ggctctggag gtgcggaag cgggacacct gactgttact tcagccacag tcccatctcc   2220
tccaacttca aagtgaagtt tagagagttg actgaccacc tgcttaaaga ttacccagtc   2280
```

-continued

```
actgtggccg tcaatcttca ggacgagaag cactgcaagg ccttgtggag cctcttccta    2340
gcccagcgct ggatagagca actgaagact gtggcagggt ctaagatgca aacgcttctg    2400
gaggacgtca acaccgagat acattttgtc acctcatgta ccttccagcc cctaccagaa    2460
tgtctgcgat tcgtccagac caacatctcc cacctcctga aggacacctg cacacagctg    2520
cttgctctga gccctgtat cgggaaggcc tgccagaatt tctctcggtg cctggaggtg    2580
cagtgccagc cggactcctc caccctgctg cccccaagga gtcccatagc cctagaagcc    2640
acggagctcc cagagcctcg gcccaggcag ctgttgctcc tgctgctgct gctgctgcct    2700
ctcacactgg tgctgctggc agccgcctgg ggccttcgct ggcaaagggc aagaaggagg    2760
ggggagctcc accctggggt gccccctcccc tcccatccct ag                      2802
```

<210> SEQ ID NO 48
<211> LENGTH: 2814
<212> TYPE: DNA
<213> ORGANISM: Artificial Sequence
<220> FEATURE:
<223> OTHER INFORMATION: nucleotide sequence encoding
    mIL12aIL15IL12bFLT3L protein heterodimer

<400> SEQUENCE: 48

```
atgtgtcaat cacgctacct cctcttttg gccaccttg ccctcctaaa ccacctcagt        60
ttggccaggg tcattccagt ctctggacct gccaggtgtc ttagccagtc ccgaaacctg     120
ctgaagacca cagatgacat ggtgaagacg gccagagaaa aactgaaaca ttattcctgc     180
actgctgaag acatcgatca tgaagacatc acacgggacc aaaccagcac attgaagacc     240
tgtttaccac tggaactaca caagaacgag agttgcctgg ctactagaga gacttcttcc     300
acaacaagag ggagctgcct gcccccacag aagacgtctt tgatgatgac cctgtgcctt     360
ggtagcatct atgaggactt gaagatgtac cagacagagt tccaggccat caacgcagca     420
cttcagaatc acaaccatca gcagatcatt ctagacaagg gcatgctggt ggccatcgat     480
gagctgatgc agtctctgaa tcataatggc gagactctgc gccagaaacc tcctgtggga     540
gaagcagacc cttacagagt gaaaatgaag ctctgcatcc tgcttcacgc cttcagcacc     600
cgcgtcgtga ccatcaacag ggtgatgggc tatctgagct ccgccggtgg aggaggttct     660
ggaggcggtg aagtggtgg cggaggtagc ggcattcatg tcttcatttt gggctgtgtc     720
agtgtaggtc tccctaaaac agaggccaac tggatagatg taagatatga cctggagaaa     780
attgaaagcc ttattcaatc tattcatatt gacaccactt tatacactga cagtgacttt     840
catcccagtt gcaaagttac tgcaatgaac tgctttctcc tggaattgca ggttattta      900
catgagtaca gtaacatgac tcttaatgaa acagtaagaa acgtgctcta ccttgcaaac     960
agcactctgt cttctaacaa gaatgtagca gaatctggct gcaaggaatg tgaggagctg    1020
gaggagaaaa ccttcacaga gttttgcaa agctttatac gcattgtcca atgttcatc      1080
aacacgtccg agggcagagg aagtcttcta acatgcggtg acgtgtgagga gaatcccggc   1140
cctatgtgtc ctcagaagct aaccatctcc tggtttgcca tcgttttgct ggtgtctcca    1200
ctcatggcca tgtgggagct ggagaaagac gtttatgttg tagaggtgga ctggactccc    1260
gatgcccctg gagaaacagt gaacctcacc tgtgacacgc ctgaagaaga tgacatcacc    1320
tggacctcag accagagaca tggagtcata ggctctggaa agaccctgac catcactgtc    1380
aaagagtttc tagatgctgg ccagtacacc tgccacaaag aggcgagac tctgagccac    1440
tcacatctgc tgctccacaa gaaggaaaat ggaatttggt ccactgaaat tttaaaaaat    1500
```

```
ttcaaaaaca agactttcct gaagtgtgaa gcaccaaatt actccggacg gttcacgtgc   1560
tcatggctgg tgcaaagaaa catggacttg aagttcaaca tcaagagcag tagcagttcc   1620
cctgactctc gggcagtgac atgtggaatg gcgtctctgt ctgcagagaa ggtcacactg   1680

gaccaaaggg actatgagaa gtattcagtg tcctgccagg aggatgtcac ctgcccaact   1740
gccgaggaga ccctgcccat tgaactggcg ttggaagcac ggcagcagaa taaatatgag   1800
aactacagca ccagcttctt catcagggac atcatcaaac cagacccgcc caagaacttg   1860
cagatgaagc ctttgaagaa ctcacaggtg gaggtcagct gggagtaccc tgactcctgg   1920
agcactcccc attcctactt ctccctcaag ttctttgttc gaatccagcg caagaaagaa   1980
aagatgaagg agacagagga ggggtgtaac cagaaaggtg cgttcctcgt agagaagaca   2040
tctaccgaag tccaatgcaa aggcgggaat gtctgcgtgc aagctcagga tcgctattac   2100
aattcctcgt gcagcaagtg ggcatgtgtt ccctgcaggg tccgatccgg aggcggtgga   2160
agtggcggtg gaggctctgg aggtggcgga agcgggacac ctgactgtta cttcagccac   2220
agtcccatct cctccaactt caaagtgaag tttagagagt tgactgacca cctgcttaaa   2280
gattacccag tcactgtggc cgtcaatctt caggacgaga agcactgcaa ggccttgtgg   2340
agcctcttcc tagcccagcg ctggatagag caactgaaga ctgtggcagg gtctaagatg   2400
caaacgcttc tggaggacgt caacaccgag atacattttg tcacctcatg taccttccag   2460
cccctaccag aatgtctgcg attcgtccag accaacatct cccacctcct gaaggacacc   2520
tgcacacagc tgcttgctct gaagccctgt atcgggaagg cctgccagaa tttctctcgg   2580
tgcctggagg tgcagtgcca gccggactcc tccaccctgc tgccccccaag gagtcccata   2640
gccctagaag ccacggagct cccagagcct cggcccaggc agctgttgct cctgctgctg   2700
ctgctgctgc ctctcacact ggtgctgctg gcagccgcct ggggccttcg ctggcaaagg   2760

gcaagaagga ggggggagct ccaccctggg gtgcccctcc cctcccatcc ctag         2814
```

<210> SEQ ID NO 49
<211> LENGTH: 2802
<212> TYPE: DNA
<213> ORGANISM: Artificial Sequence
<220> FEATURE:
<223> OTHER INFORMATION: nucleotide sequence encoding
      mIL12aIL21IL12bFLT3L protein heterodimer

<400> SEQUENCE: 49

```
atgtgtcaat cacgctacct cctcttttg gccacccttg ccctcctaaa ccacctcagt     60
ttggccaggg tcattccagt ctctggacct gccaggtgtc ttagccagtc ccgaaacctg    120
ctgaagacca cagatgacat ggtgaagacg gccagagaaa aactgaaaca ttattcctgc    180
actgctgaag acatcgatca tgaagacatc acacgggacc aaaccagcac attgaagacc    240
tgtttaccac tggaactaca caagaacgag agttgcctgg ctactagaga gacttcttcc    300
acaacaagag ggagctgcct gcccccacag aagacgtctt tgatgatgac cctgtgcctt    360
ggtagcatct atgaggactt gaagatgtac cagacagagt tccaggccat caacgcagca    420
cttcagaatc acaaccatca gcagatcatt ctagacaagg gcatgctggt ggccatcgat    480
gagctgatgc agtctctgaa tcataatggc gagactctgc gccagaaacc tcctgtggga    540
gaagcagacc cttacagagt gaaaatgaag ctctgcatcc tgcttcacgc cttcagcacc    600
cgcgtcgtga ccatcaacag ggtgatgggc tatctgagct ccgccggtgg aggaggttct    660
ggaggcggtg gaagtggtgg cggaggtagc cataaatcaa gcccccaagg gccagatcgc    720
```

```
ctcctgatta gacttcgtca ccttattgac attgttgaac agctgaaaat ctatgaaaat    780
gacttggatc ctgaacttct atcagctcca caagatgtaa aggggcactg tgagcatgca    840
gcttttgcct gttttcagaa ggccaaactc aagccatcaa accctggaaa caataagaca    900
ttcatcattg acctcgtggc ccagctcagg aggaggctgc ctgccaggag ggaggaaag     960
aaacagaagc acatagctaa atgcccttcc tgtgattcgt atgagaaaag gacacccaaa   1020
gaattcctag aaagactaaa atggctcctt caaaagatga ttcatcagca tctctccgag   1080
ggcagaggaa gtcttctaac atgcggtgac gtggaggaga atccgggccc tatgtgtcct   1140
cagaagctaa ccatctcctg gtttgccatc gttttgctgg tgtctccact catggccatg   1200
tgggagctgg agaaagacgt ttatgttgta gaggtggact ggactcccga tgcccctgga   1260
gaaacagtga acctcacctg tgacacgcct gaagaagatg acatcacctg gacctcagac   1320
cagagacatg gagtcatagg ctctggaaag accctgacca tcactgtcaa agagtttcta   1380
gatgctggcc agtacacctg ccacaaagga ggcgagactc tgagccactc acatctgctg   1440
ctccacaaga aggaaaatgg aatttggtcc actgaaattt aaaaaatttt caaaaacaag   1500
actttcctga agtgtgaagc accaaattac tccggacggt tcacgtgctc atggctggtg   1560
caaagaaaca tggacttgaa gttcaacatc aagagcagta gcagttcccc tgactctcgg   1620
gcagtgacat gtggaatggc gtctctgtct gcagagaagg tcacactgga ccaaagggac   1680
tatgagaagt attcagtgtc ctgccaggag gatgtcacct gcccaactgc cgaggagacc   1740
ctgcccattg aactggcgtt ggaagcacgg cagcagaata aatatgagaa ctacagcacc   1800
agcttcttca tcagggacat catcaaacca gacccgccca gaacttgca gatgaagcct   1860
ttgaagaact cacaggtgga ggtcagctgg gagtaccctg actcctggag cactccccat   1920
tcctacttct ccctcaagtt ctttgttcga atccagcgca agaaagaaaa gatgaaggag   1980
acagaggagg ggtgtaacca gaaaggtgcg ttcctcgtag agaagacatc taccgaagtc   2040
caatgcaaag gcgggaatgt ctgcgtgcaa gctcaggatc gctattacaa ttcctcgtgc   2100
agcaagtggg catgtgttcc ctgcagggtc cgatccggag gcggtggaag tggcggtgga   2160
ggctctggag gtgcggaag cgggacacct gactgttact tcagccacag tcccatctcc   2220
tccaacttca aagtgaagtt tagagagttg actgaccacc tgcttaaaga ttacccagtc   2280
actgtggccg tcaatcttca ggacgagaag cactgcaagg ccttgtggag cctcttccta   2340
gcccagcgct ggatagagca actgaagact gtggcagggt ctaagatgca aacgcttctg   2400
gaggacgtca cacccgagat acattttgtc acctcatgta ccttccagcc cctaccagaa   2460
tgtctgcgat tcgtccagac caacatctcc acctcctga aggacacctg cacacagctg   2520
cttgctctga gccctgtat cgggaaggcc tgccagaatt tctctcggtg cctggaggtg   2580
cagtgccagc cggactcctc caccctgctg ccccaagga gtcccatagc cctagaagcc   2640
acggagctcc cagagcctcg gcccaggcag ctgttgctcc tgctgctgct gctgctgcct   2700
ctcacactgg tgctgctggc agccgcctgg ggccttcgct ggcaaagggc aagaaggagg   2760
ggggagctcc accctggggt gccctccccc tcccatccct ag                     2802
```

<210> SEQ ID NO 50
<211> LENGTH: 2670
<212> TYPE: DNA
<213> ORGANISM: Artificial Sequence
<220> FEATURE:
<223> OTHER INFORMATION: nucleotide sequence encoding
      hIL12aIL2IL12bGMCSF protein heterodimer

<400> SEQUENCE: 50

```
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc     180
gtggccactc cagacccagg aatgttccca tgccttcacc actcccaaaa cctgctgagg     240
gccgtcagca acatgctcca gaaggccaga caaactctag aatttttaccc ttgcacttct     300
gaagagattg atcatgaaga tatcacaaaa gataaaacca gcacagtgga ggcctgttta     360
ccattggaat taaccaagaa tgagagttgc ctaaattcca gagagacctc tttcataact     420
aatgggagtt gcctggcctc cagaaagacc tcttttatga tggccctgtg ccttagtagt     480
atttatgaag acttgaagat gtaccaggtg gagttcaaga ccatgaatgc aaagcttctg     540
atggatccta agaggcagat cttctagat caaaacatgc tggcagttat tgatgagctg     600
atgcaggccc tgaatttcaa cagtgagact gtgccacaaa aatcctccct gaagaaccg     660
gatttttata aaactaaaat caagctctgc atacttcttc atgctttcag aattcgggca     720
gtgactattg atagagtgat gagctatctg aatgcttccg gtggaggagg ttctggaggc     780
ggtggaagtg gtggcggagg tagcgcacct acttcaagtt ctacaaagaa aacacagcta     840
caactggagc atttactgct ggatttacag atgattttga atggaattaa taattacaag     900
aatcccaaac tcaccaggat gctcacattt aagttttaca tgcccaagaa ggccacagaa     960
ctgaaacatc ttcagtgtct agaagaagaa ctcaaacctc tggaggaagt gctaaattta    1020
gctcaaagca aaaactttca cttaagaccc agggacttaa tcagcaatat caacgtaata    1080
gttctggaac taagggatc tgaaacaaca ttcatgtgtg aatatgctga tgagacagca    1140
accattgtag aatttctgaa cagatggatt acctttttgtc aaagcatcat ctcaacactg    1200
actgagggca gaggaagtct tctaacatgc ggtgacgtgg aggagaatcc cggccctatg    1260
tgtcaccagc agttggtcat ctcttggttt tccctggttt ttctggcatc tcccctcgtg    1320
gccatatggg aactgaagaa agatgtttat gtcgtagaat tggattggta tccggatgcc    1380
cctgagaaaa tggtggtcct cacctgtgac accctgaag aagatggtat cacctggacc    1440
ttggaccaga gcagtgaggt cttaggctct ggcaaaaccc tgaccatcca agtcaaagag    1500
tttgagatgc ctgccagta cacctgtcac aaaggaggcg aggttctaag ccattcgctc    1560
ctgctgcttc acaaaaagga agatggaatt tggtccactg atattttaaa ggaccagaaa    1620
gaacccaaaa ataagacctt tctaagatgc gaggccaaga attattctgg acgtttcacc    1680
tgctggtggc tgacgacaat cagtactgat ttgacattca gtgtcaaaag cagcagaggc    1740
tcttctgacc cccaagggt gacgtgcgga gctgctacac tctctgcaga gagagtcaga    1800
ggggacaaca aggagtatga gtactcagtg gagtgccagg aggacagtgc ctgcccagct    1860
gctgaggaga gtctgcccat tgaggtcatg gtggatgccg ttcacaagct caagtatgaa    1920
aactacacca gcagcttctt catcagggac atcatcaaac tgacccacc caagaacttg    1980
cagctgaagc cattaaagaa ttctcggcag gtggaggtca gctgggagta ccctgacacc    2040
tggagtactc cacattccta cttctcctg acattctgcg ttcaggtcca gggcaagagc    2100
aagagagaaa agaaagatag agtcttcacg gacaagacct cagccacggt catctgccgc    2160
aaaaatgcca gcattagcgt gcgggcccag gaccgctact atagctcatc ttggagcgaa    2220
tgggcatctg tgccctgcag tggaggcggt ggaagtggcg gtgaggctc tggaggtggc    2280
ggaagcgcac ccgcccgctc gcccagcccc agcacgcagc cctgggagca tgtgaatgcc    2340
```

| | |
|---|---|
| atccaggagg cccggcgtct cctgaacctg agtagagaca ctgctgctga gatgaatgaa | 2400 |
| acagtagaag tcatctcaga aatgtttgac ctccaggagc cgacctgcct acagacccgc | 2460 |
| ctggagctgt acaagcaggg cctgcggggc agcctcacca agctcaaggg ccccttgacc | 2520 |
| atgatggcca gccactacaa gcagcactgc cctccaaccc cggaaacttc ctgtgcaacc | 2580 |
| cagattatca cctttgaaag tttcaaagag aacctgaagg actttctgct tgtcatcccc | 2640 |
| tttgactgct gggagccagt ccaggagtga | 2670 |

<210> SEQ ID NO 51
<211> LENGTH: 2727
<212> TYPE: DNA
<213> ORGANISM: Artificial Sequence
<220> FEATURE:
<223> OTHER INFORMATION: nucleotide sequence encoding
    hIL12aIL7IL12bGMCSF protein heterodimer

<400> SEQUENCE: 51

| | |
|---|---|
| atgtggcccc ctgggtcagc ctcccagcca ccgccctcac ctgccgcggc cacaggtctg | 60 |
| catccagcgg ctcgccctgt gtccctgcag tgccggctca gcatgtgtcc agcgcgcagc | 120 |
| ctcctccttg tggctaccct ggtcctcctg gaccacctca gtttggccag aaacctcccc | 180 |
| gtggccactc agacccagg aatgttccca tgccttcacc actcccaaaa cctgctgagg | 240 |
| gccgtcagca acatgctcca gaaggccaga caaactctag aattttaccc ttgcacttct | 300 |
| gaagagattg atcatgaaga tatcacaaaa gataaaacca gcacagtgga ggcctgttta | 360 |
| ccattggaat taccaagaa tgagagttgc ctaaattcca gagagacctc tttcataact | 420 |
| aatgggagtt gcctggcctc agaaagacc tcttttatga tggccctgtg ccttagtagt | 480 |
| atttatgaag acttgaagat gtaccaggtg gagttcaaga ccatgaatgc aaagcttctg | 540 |
| atggatccta agaggcagat ctttctagat caaaacatgc tggcagttat tgatgagctg | 600 |
| atgcaggccc tgaatttcaa cagtgagact gtgccacaaa aatcctccct tgaagaaccg | 660 |
| gatttttata aaactaaaat caagctctgc atacttcttc atgcttcag aattcgggca | 720 |
| gtgactattg atagagtgat gagctatctg aatgcttccg gtggaggagg ttctggaggc | 780 |
| ggtggaagtg gtggcggagg tagcgattgt gatattgaag gtaaagatgg caaacaatat | 840 |
| gagagtgttc taatggtcag catcgatcaa ttattggaca gcatgaaaga aattggtagc | 900 |
| aattgcctga ataatgaatt aacttttttt aaaagacata tctgtgatgc taataaggaa | 960 |
| ggtatgtttt tattccgtgc tgctcgcaag ttgaggcaat tcttaaaat gaatagcact | 1020 |
| ggtgattttg atctccactt attaaaagtt tcagaaggca caacaatact gttgaactgc | 1080 |
| actggccagg ttaaaggaag aaaaccagct gccctgggtg aagcccaacc aacaaagagt | 1140 |
| ttggaagaaa ataaatcttt aaaggaacag aaaaaactga atgacttgtg tttcctaaag | 1200 |
| agactattac aagagataaa acttgttgg aataaaattt tgatgggcac taagaaacac | 1260 |
| gagggcagag gaagtcttct aacatgcggt gacgtggagg agaatcccgg ccctatgtgt | 1320 |
| caccagcagt tggtcatctc ttggttttcc ctggtttttc tggcatctcc cctcgtggcc | 1380 |
| atatgggaac tgaagaaaga tgtttatgtc gtagaattgg attggtatcc ggatgcccct | 1440 |
| ggagaaatgg tggtcctcac ctgtgacacc cctgaagaag atggtatcac ctggaccttg | 1500 |
| gaccagagca gtgaggtctt aggctctggc aaaaccctga ccatccaagt caaagagttt | 1560 |
| ggagatgctg ccagtacac ctgtcacaaa ggaggcgagt tctaagcca ttcgctcctg | 1620 |
| ctgcttcaca aaaaggaaga tggaatttgg tccactgata ttttaaagga ccagaaagaa | 1680 |

```
cccaaaaata agacctttct aagatgcgag gccaagaatt attctggacg tttcacctgc    1740
tggtggctga cgacaatcag tactgatttg acattcagtg tcaaaagcag cagaggctct    1800
tctgaccccc aagggggtgac gtgcggagct gctacactct ctgcagagag agtcagaggg   1860
gacaacaagg agtatgagta ctcagtggag tgccaggagg acagtgcctg cccagctgct    1920
gaggagagtc tgcccattga ggtcatggtg gatgccgttc acaagctcaa gtatgaaaac    1980
tacaccagca gcttcttcat cagggacatc atcaaacctg acccacccaa gaacttgcag    2040
ctgaagccat taagaattc tcggcaggtg gaggtcagct gggagtaccc tgacacctgg    2100
agtactccac attcctactt ctccctgaca ttctgcgttc aggtccaggg caagagcaag    2160
agagaaaaga agatagagt cttcacggac aagacctcag ccacggtcat ctgccgcaaa    2220
aatgccagca ttagcgtgcg ggcccaggac cgctactata gctcatcttg gagcgaatgg    2280
gcatctgtgc cctgcagtgg aggcggtgga agtggcggtg gaggctctgg aggtggcgga    2340
agcgcacccg cccgctcgcc cagccccagc acgcagccct gggagcatgt gaatgccatc    2400
caggaggccc ggcgtctcct gaacctgagt agagacactg ctgctgagat gaatgaaaca    2460
gtagaagtca tctcagaaat gtttgacctc caggagccga cctgcctaca gacccgcctg    2520
gagctgtaca gcagggcct gcgggggcagc ctcaccaagc tcaagggccc cttgaccatg    2580
atggccagcc actacaagca gcactgccct ccaaccccgg aaacttcctg tgcaacccag    2640
attatcacct ttgaaagttt caagagaaac ctgaaggact ttctgcttgt catcccttt     2700 gactgctggg agccagtcca ggagtga                                      2727

<210> SEQ ID NO 52
<211> LENGTH: 2670
<212> TYPE: DNA
<213> ORGANISM: Artificial Sequence
<220> FEATURE:
<223> OTHER INFORMATION: nucleotide sequence encoding
      hIL12aIL15IL12bGMCSF protein heterodimer

<400> SEQUENCE: 52
atgtggcccc ctgggtcagc ctcccagcca ccgccctcac ctgccgcggc cacaggtctg     60
catccagcgg ctcgccctgt gtccctgcag tgccggctca gcatgtgtcc agcgcgcagc    120
ctcctccttg tggctaccct ggtcctcctg gaccacctca gtttggccag aaacctcccc    180
gtggccactc cagacccagg aatgttccca tgccttcacc actcccaaaa cctgctgagg    240
gccgtcagca acatgctcca gaaggccaga caaactctag aattttaccc ttgcacttct    300
gaagagattg atcatgaaga tatcacaaaa gataaaacca gcacagtgga ggcctgttta    360
ccattggaat taaccaagaa tgagagttgc ctaaattcca gagagaccct tttcataact    420
aatgggagtt gcctggcctc cagaaagacc tcttttatga tggcctgtg ccttagtagt    480 atttatgaag acttgaagat gtaccaggtg agttcaagac ccatgaatgc aaagcttctg    540
atggatccta agaggcagat cttctctaga tcaaaacatg ctggcagttat tgatgagctg    600 atgcaggccc tgaatttcaa cagtgagact gtgccacaaa atcctccct gaagaaccg    660 gatttttata aaactaaaat caagctctgc atacttcttc atgctttcag aattcgggca    720
gtgactattg atagagtgat gagctatctg aatgcttccg gtggaggag tctggaggc    780 ggtggaagtg gtggcggagg tagcggcatt catgtcttca tttttgggctg tttcagtgca    840 gggcttccta aaacagaagc caactgggtg aatgtaataa gtgatttgaa aaaaattgaa    900
gatcttattc aatctatgca tattgatgct actttatata cggaaagtga tgttcaccc    960
```

```
agttgcaaag taacagcaat gaagtgcttt ctcttggagt tacaagttat ttcacttgag    1020
tccggagatg caagtattca tgatacagta gaaaatctga tcatcctagc aaacaacagt    1080
ttgtcttcta atgggaatgt aacagaatct ggatgcaaag aatgtgagga actggaggaa    1140
aaaaatatta aagaattttt gcagagtttt gtacatattg tccaaatgtt catcaacact    1200
tctgagggca gaggaagtct tctaacatgc ggtgacgtgg aggagaatcc cggccctatg    1260
tgtcaccagc agttggtcat ctcttggttt tccctggttt ttctggcatc tccctcgtg    1320 gccatatggg aactgaagaa agatgtttat gtcgtagaat tggattggta tccggatgcc    1380
cctggagaaa tggtggtcct cacctgtgac acccctgaag aagatggtat cacctggacc    1440
ttggaccaga gcagtgaggt cttaggctct ggcaaaaccc tgaccatcca agtcaaagag    1500
tttggagatg ctggccagta cacctgtcac aaaggaggcg aggttctaag ccattcgctc    1560
ctgctgcttc acaaaaagga agatggaatt tggtccactg atatttaaa ggaccagaaa    1620 gaacccaaaa ataagacctt tctaagatgc gaggccaaga attattctgg acgtttcacc    1680
tgctggtggc tgacgacaat cagtactgat ttgacattca gtgtcaaaag cagcagaggc    1740
tcttctgacc cccaaggggt gacgtgcgga gctgctacac tctctgcaga gagagtcaga    1800
ggggacaaca aggagtatga gtactcagtg gagtgccagg aggacagtgc ctgcccagct    1860
gctgaggaga gtctgcccat tgaggtcatg gtggatgccg ttcacaagct caagtatgaa    1920
aactacacca gcagcttctt catcagggac atcatcaaac ctgacccacc caagaacttg    1980
cagctgaagc cattaaagaa ttctcggcag gtggaggtca gctgggagta ccctgacacc    2040
tggagtactc cacattccta cttctccctg acattctgcg ttcaggtcca gggcaagagc    2100
aagagagaaa agaaagatag agtcttcacg gacaagacct cagccacggt catctgccgc    2160
aaaaatgcca gcattagcgt gcgggcccag gaccgctact atagctcatc ttggagcgaa    2220
tgggcatctg tgccctgcag tggaggcggt ggaagtggcg gtggaggctc tggaggtggc    2280
ggaagcgcac ccgcccgctc gcccagcccc agcacgcagc cctgggagca tgtgaatgcc    2340
atccaggagg cccggcgtct cctgaacctg agtagagaca ctgctgctga tgaatgaa    2400 acagtagaag tcatctcaga aatgtttgac ctccaggagc cgacctgcct acagacccgc    2460
ctggagctgt acaagcaggg cctgcggggc agcctcacca agctcaaggg ccccttgacc    2520
atgatggcca gccactacaa gcagcactgc cctccaaccc cggaaacttc ctgtgcaacc    2580
cagattatca cctttgaaag tttcaaagag aacctgaagg actttctgct tgtcatcccc    2640
tttgactgct gggagccagt ccaggagtga                                     2670
```

<210> SEQ ID NO 53
<211> LENGTH: 2670
<212> TYPE: DNA
<213> ORGANISM: Artificial Sequence
<220> FEATURE:
<223> OTHER INFORMATION: nucleotide sequence encoding
      hIL12aIL21IL12bGMCSF protein heterodimer

<400> SEQUENCE: 53

```
atgtggcccc tgggtcagc ctcccagcca ccgccctcac ctgccgcggc cacaggtctg     60
catccagcgg ctcgccctgt gtccctgcag tgccggctca gcatgtgtcc agcgcgcagc    120
ctcctccttg tggctaccct ggtcctcctg gaccacctca gtttggccag aaacctcccc    180
gtggccactc cagacccagg aatgttccca tgccttcacc actcccaaaa cctgctgagg    240
gccgtcagca acatgctcca gaaggccaga caaactctag aattttaccc ttgcacttct    300
```

```
gaagagattg atcatgaaga tatcacaaaa gataaaacca gcacagtgga ggcctgttta    360
ccattggaat taaccaagaa tgagagttgc ctaaattcca gagagacctc tttcataact    420
aatgggagtt gcctggcctc cagaaagacc tcttttatga tggccctgtg ccttagtagt    480
atttatgaag acttgaagat gtaccaggtg gagttcaaga ccatgaatgc aaagcttctg    540
atggatccta agaggcagat ctttctagat caaaacatgc tggcagttat tgatgagctg    600
atgcaggccc tgaatttcaa cagtgagact gtgccacaaa atcctccct tgaagaaccg    660 gatttttata aaactaaaat caagctctgc atacttcttc atgctttcag aattcgggca    720
gtgactattg atagagtgat gagctatctg aatgcttccg gtggaggagg ttctggaggc    780
ggtggaagtg gtggcggagg tagccaaggt caagatcgcc acatgattag aatgcgtcaa    840
cttatagata ttgttgatca gctgaaaaat tatgtgaatg acttggtccc tgaatttctg    900
ccagctccag aagatgtaga gacaaactgt gagtggtcag cttttttcctg ctttcagaag    960 gcccaactaa agtcagcaaa tacaggaaac aatgaaagga taatcaatgt atcaattaaa    1020
aagctgaaga ggaaaccacc ttccacaaat gcagggagaa gacagaaaca cagactaaca    1080
tgcccttcat gtgattctta tgagaaaaaa ccacccaaag aattcctaga aagattcaaa    1140
tcacttctcc aaaagatgat tcatcagcat ctgtcctcta gaacacacgg aagtgaagat    1200
tccgagggca gaggaagtct tctaacatgc ggtgacgtgg aggagaatcc cggccctatg    1260
tgtcaccagc agttggtcat ctcttggttt tccctggttt ttctggcatc tccctcgtg    1320 gccatatggg aactgaagaa agatgtttat gtcgtagaat tggattggta tccggatgcc    1380
cctggagaaa tggtggtcct cacctgtgac accccctgaag aagatggtat cacctggacc    1440
ttggaccaga gcagtgaggt cttaggctct ggcaaaaccc tgaccatcca agtcaaagag    1500
tttggagatg ctggccagta cacctgtcac aaaggaggcg aggttctaag ccattcgctc    1560
ctgctgcttc acaaaaagga agatggaatt tggtccactg atatttaaa ggaccagaaa    1620 gaacccaaaa ataagacctt tctaagatgc gaggccaaga attattctgg acgtttcacc    1680
tgctggtggc tgacgacaat cagtactgat ttgacattca gtgtcaaaag cagcagaggc    1740
tcttctgacc cccaaggggt gacgtgcgga gctgctacac tctctgcaga gagagtcaga    1800
ggggacaaca aggagtatga gtactcagtg gagtgccagg aggacagtgc ctgcccagct    1860
gctgaggaga gtctgccccat tgaggtcatg gtggatgccg ttcacaagct caagtatgaa    1920
aactacacca gcagcttctt catcagggac atcatcaaac ctgacccacc caagaacttg    1980
cagctgaagc cattaaagaa ttctcggcag gtggaggtca gctgggagta ccctgacacc    2040
tggagtactc cacattccta cttctccctg acattctgcg ttcaggtcca gggcaagagc    2100
aagagagaaa agaaagatag agtcttcacg gacaagacct cagccacggt catctgccgc    2160
aaaaatgcca gcattagcgt gcgggcccag gaccgctact atagctcatc ttggagcgaa    2220
tgggcatctg tgcctgcag tggaggcggt ggaagtggcg gtgaggctc tggaggtggc    2280 ggaagcgcac ccgcccgctc gcccagcccc agcacgcagc cctgggagca gtgaatgcc    2340 atccaggagg cccggcgtct cctgaacctg agtagagaca ctgctgctga gatgaatgaa    2400
acagtagaag tcatctcaga aatgtttgac ctccaggagc cgacctgcct acagacccgc    2460
ctggagctgt acaagcaggg cctgcggggc agcctcacca agctcaaggg cccccttgacc    2520 atgatggcca gccactacaa gcagcactgc cctccaaccc cggaaacttc ctgtgcaacc    2580
cagattatca cctttgaaag tttcaaagag aacctgaagg actttctgct tgtcatcccc    2640
```

| | |
|---|---|
| tttgactgct gggagccagt ccaggagtga | 2670 |

<210> SEQ ID NO 54
<211> LENGTH: 2916
<212> TYPE: DNA
<213> ORGANISM: Artificial Sequence
<220> FEATURE:
<223> OTHER INFORMATION: nucleotide sequence encoding
    hIL12aIL2IL12bFLT3L protein heterodimer

<400> SEQUENCE: 54

| | |
|---|---|
| atgtggcccc ctgggtcagc ctcccagcca ccgccctcac ctgccgcggc cacaggtctg | 60 |
| catccagcgg ctcgccctgt gtccctgcag tgccggctca gcatgtgtcc agcgcgcagc | 120 |
| ctcctccttg tggctaccct ggtcctcctg gaccacctca gtttggccag aaacctcccc | 180 |
| gtggccactc cagacccagg aatgttccca tgccttcacc actcccaaaa cctgctgagg | 240 |
| gccgtcagca acatgctcca gaaggccaga caaactctag aattttaccc ttgcacttct | 300 |
| gaagagattg atcatgaaga tatcacaaaa gataaaacca gcacagtgga ggcctgttta | 360 |
| ccattggaat taccaagaa tgagagttgc ctaaattcca gagagacctc tttcataact | 420 |
| aatgggagtt gcctggcctc agaaagacc tcttttatga tggccctgtg ccttagtagt | 480 |
| atttatgaag acttgaagat gtaccaggtg gagttcaaga ccatgaatgc aaagcttctg | 540 |
| atggatccta gaggcagat cttctctaga caaaacatgc tggcagttat tgatgagctg | 600 |
| atgcaggccc tgaatttcaa cagtgagact gtgccacaaa atcctccct gaagaaccg | 660 |
| gatttttata aaactaaaat caagctctgc atacttcttc atgctttcag aattcgggca | 720 |
| gtgactattg atagagtgat gagctatctg aatgcttccg gtgaggagg ttctggaggc | 780 |
| ggtggaagtg gtggcggagg tagcgcacct acttcaagtt ctacaaagaa aacacagcta | 840 |
| caactggagc atttactgct ggatttacag atgattttga tggaattaa taattacaag | 900 |
| aatcccaaac tcaccaggat gctcacattt aagttttaca tgcccaagaa ggccacagaa | 960 |
| ctgaaacatc ttcagtgtct agaagaagaa ctcaaacctc tggaggaagt gctaaattta | 1020 |
| gctcaaagca aaaactttca cttaagaccc agggacttaa tcagcaatat caacgtaata | 1080 |
| gttctggaac taaagggatc tgaaacaaca ttcatgtgtg aatatgctga tgagacagca | 1140 |
| accattgtag aatttctgaa cagatggatt accttttgtc aaagcatcat ctcaacactg | 1200 |
| actgagggca gaggaagtct tctaaacatgc ggtgacgtgg aggagaatcc cggccctatg | 1260 |
| tgtcaccagc agttggtcat ctcttggttt tccctggttt ttctggcatc tcccctcgtg | 1320 |
| gccatatggg aactgaagaa agatgtttat gtcgtagaat tggattggta tccggatgcc | 1380 |
| cctggagaaa tggtggtcct cacctgtgac accctgaag aagatggtat cacctggacc | 1440 |
| ttggaccaga gcagtgaggt cttaggctct ggcaaaaccc tgaccatcca agtcaaagag | 1500 |
| tttggagatg ctgccagta cacctgtcac aaaggaggcg aggttctaag ccattcgctc | 1560 |
| ctgctgcttc acaaaaagga agatggaatt tggtccactg atatttaaa ggaccagaaa | 1620 |
| gaacccaaaa ataagacctt tctaagatgc gaggccaaga attattctgg acgtttcacc | 1680 |
| tgctggtggc tgacgacaat cagtactgat ttgacattca gtgtcaaaag cagcagaggc | 1740 |
| tcttctgacc cccaagggt gacgtgcgga gctgctacac tctctgcaga gagagtcaga | 1800 |
| ggggacaaca aggagtatga gtactcagtg gagtgccagg aggacagtgc ctgcccagct | 1860 |
| gctgaggaga gtctgccat tgaggtcatg gtggatgccg ttcacaagct caagtatgaa | 1920 |
| aactacacca gcagcttctt catcagggac atcatcaaac ctgacccacc caagaacttg | 1980 |

```
cagctgaagc cattaaagaa ttctcggcag gtggaggtca gctgggagta ccctgacacc    2040
tggagtactc cacattccta cttctccctg acattctgcg ttcaggtcca gggcaagagc    2100
aagagagaaa agaaagatag agtcttcacg acaagacct cagccacggt catctgccgc     2160
aaaaatgcca gcattagcgt gcgggcccag gaccgctact atagctcatc ttggagcgaa    2220
tgggcatctg tgccctgcag tggaggcggt ggaagtggcg gtggaggctc tggaggtggc    2280
ggaagcaccc aggactgctc cttccaacac agccccatct cctccgactt cgctgtcaaa    2340
atccgtgagc tgtctgacta cctgcttcaa gattacccag tcaccgtggc ctccaacctg    2400
caggacgagg agctctgcgg gggcctctgg cggctggtcc tggcacagcg ctggatggag    2460
cggctcaaga ctgtcgctgg gtccaagatg caaggcttgc tggagcgcgt gaacacggag    2520
atacactttg tcaccaaatg tgcctttcag ccccccccca gctgtcttcg cttcgtccag    2580
accaacatct cccgcctcct gcaggagacc tccgagcagc tggtggcgct gaagccctgg    2640
atcactcgcc agaacttctc ccggtgcctg gagctgcagt gtcagccgga ctcctcaacc    2700
ctgccacccc catggagtcc ccggcccctg gaggccacag cccgacagc cccgcagccc     2760 cctctgctcc tcctactgct gctgcccgtg ggcctcctgc tgctggccgc tgcctggtgc    2820
ctgcactggc agaggacgcg gcggaggaca ccccgcccctg gggagcaggt gccccccgtc    2880
cccagtcccc aggacctgct gcttgtggag cactga                              2916
```

<210> SEQ ID NO 55
<211> LENGTH: 2973
<212> TYPE: DNA
<213> ORGANISM: Artificial Sequence
<220> FEATURE:
<223> OTHER INFORMATION: nucleotide sequence encoding
      hIL12aIL7IL12bFLT3L protein heterodimer

<400> SEQUENCE: 55

```
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg gaccacctca gtttggccag aaacctcccc    180
gtggccactc cagacccagg aatgttccca tgccttcacc actcccaaaa cctgctgagg    240
gccgtcagca acatgctcca gaaggccaga caaactctag aattttaccc ttgcacttct    300
gaagagattg atcatgaaga tatcacaaaa gataaaacca gcacagtgga ggcctgttta    360
ccattggaat taaccaagaa tgagagttgc ctaaattcca gagagacctc tttcataact    420
aatgggagtt gcctggcctc agaaaagacc tcttttatga tggcccctgtg ccttagtagt    480 atttatgaag acttgaagat gtaccaggtg gagttcaaga ccatgaatgc aaagcttctg    540
atggatccta agaggcagat ctttctagat caaaacatgc tggcagttat tgatgagctg    600
atgcaggccc tgaatttcaa cagtgagact gtgccacaaa atcctccct gaagaaccg      660 gatttttata aaactaaaat caagctctgc atacttcttc atgctttcag aattcgggca    720
gtgactattg atagagtgat gagctatctg aatgcttccg gtggaggagg ttctggaggc    780
ggtggaagtg gtggcggagg tagcgattgt gatattgaag gtaaagatgg caaacaatat    840
gagagtgttc taatggtcag catcgatcaa ttattggaca gcatgaaaga aattggtagc    900
aattgcctga ataatgaatt taactttttt aaaagacata tctgtgatgc taataaggaa    960
ggtatgtttt tattccgtgc tgctcgcaag ttgaggcaat tccttaaaat gaatagcact   1020
ggtgattttg atctccactt attaaaagtt tcagaaggca caacaatact gttgaactgc   1080
```

-continued

```
actggccagg ttaaaggaag aaaaccagct gccctgggtg aagcccaacc aacaaagagt      1140
ttggaagaaa ataaatcttt aaaggaacag aaaaaactga atgacttgtg tttcctaaag      1200
agactattac aagagataaa aacttgttgg aataaaattt tgatgggcac taaagaacac      1260
gagggcagag gaagtcttct aacatgcggt gacgtggagg agaatcccgg ccctatgtgt      1320
caccagcagt tggtcatctc ttggttttcc ctggtttttc tggcatctcc cctcgtggcc      1380
atatgggaac tgaagaaaga tgtttatgtc gtagaattgg attggtatcc ggatgcccct      1440
ggagaaatgg tggtcctcac ctgtgacacc cctgaagaag atggtatcac ctggaccttg      1500
gaccagagca gtgaggtctt aggctctggc aaaaccctga ccatccaagt caaagagttt      1560
ggagatgctg gccagtacac ctgtcacaaa ggaggcgagg ttctaagcca ttcgctcctg      1620
ctgcttcaca aaaggaaga tggaatttgg tccactgata tttaaagga ccagaaagaa      1680 cccaaaaata gacctttct aagatgcgag gccaagaatt attctggacg tttcacctgc      1740
tggtggctga cgacaatcag tactgatttg acattcagtg tcaaaagcag cagaggctct      1800
tctgaccccc aaggggtgac gtgcggagct gctacactct ctgcagagag agtcagaggg      1860
gacaacaagg agtatgagta ctcagtggag tgccaggagg acagtgcctg cccagctgct      1920
gaggagagtc tgcccattga ggtcatggtg gatgccgttc acaagctcaa gtatgaaaac      1980
tacaccagca gcttcttcat cagggacatc atcaaacctg acccacccaa gaacttgcag      2040
ctgaagccat taaagaattc tcggcaggtg gaggtcagct gggagtaccc tgacacctgg      2100
agtactccac attcctactt ctccctgaca ttctgcgttc aggtccaggg caagagcaag      2160
agagaaaaga aagatagagt cttcacggac aagacctcag ccacggtcat ctgccgcaaa      2220
aatgccagca ttagcgtgcg ggcccaggac cgctactata gctcatcttg gagcgaatgg      2280
gcatctgtgc cctgcagtgg aggcggtgga agtggcggtg gaggctctgg aggtggcgga      2340
agcacccagg actgctcctt ccaacacagc cccatctcct ccgacttcgc tgtcaaaatc      2400
cgtgagctgt ctgactacct gcttcaagat tacccagtca ccgtggcctc caacctgcag      2460
gacgaggagc tctgcggggg cctctggcgg ctggtcctgg cacagcgctg gatggagcgg      2520
ctcaagactg tcgctgggtc caagatgcaa ggcttgctgg agcgcgtgaa cacggagata      2580
cactttgtca ccaaatgtgc ctttcagccc cccccagct gtcttcgctt cgtccagacc      2640
aacatctccc gcctcctgca ggagacctcc gagcagctgg tggcgctgaa gccctggatc      2700
actcgccaga acttctcccg gtgcctggag ctgcagtgtc agcccgactc ctcaaccctg      2760
ccacccccat ggagtccccg gcccctggag gccacagccc cgacagcccc gcagcccccct      2820 ctgctcctcc tactgctgct gccccgtgggc ctcctgctgc tggccgctgc ctggtgcctg      2880
cactggcaga ggacgcggcg gaggacaccc cgccctgggg agcaggtgcc cccgtcccc      2940 agtccccagg acctgctgct tgtggagcac tga                                    2973
```

<210> SEQ ID NO 56
<211> LENGTH: 2916
<212> TYPE: DNA
<213> ORGANISM: Artificial Sequence
<220> FEATURE:
<223> OTHER INFORMATION: nucleotide sequence encoding
      hIL12aIL15IL12bFLT3L protein heterodimer

<400> SEQUENCE: 56

```
atgtggcccc ctgggtcagc ctcccagcca ccgccctcac ctgccgcggc cacaggtctg        60
catccagcgg ctcgccctgt gtccctgcag tgccggctca gcatgtgtcc agcgcgcagc       120
```

```
ctcctccttg tggctaccct ggtcctcctg gaccacctca gtttggccag aaacctcccc      180
gtggccactc cagacccagg aatgttccca tgccttcacc actcccaaaa cctgctgagg      240
gccgtcagca acatgctcca gaaggccaga caaactctag aattttaccc ttgcacttct      300
gaagagattg atcatgaaga tatcacaaaa gataaaacca gcacagtgga ggcctgttta      360
ccattggaat taaccaagaa tgagagttgc ctaaattcca gagagacctc tttcataact      420
aatgggagtt gcctggcctc cagaaagacc tcttttatga tggccctgtg ccttagtagt      480
atttatgaag acttgaagat gtaccaggtg gagttcaaga ccatgaatgc aaagcttctg      540
atggatccta agaggcagat ctttctagat caaaacatgc tggcagttat tgatgagctg      600
atgcaggccc tgaatttcaa cagtgagact gtgccacaaa atcctcccct tgaagaaccg      660 gattttata aaactaaaat caagctctgc atacttcttc atgctttcag aattcgggca      720
gtgactattg atagagtgat gagctatctg aatgcttccg tggaggagg ttctggaggc      780 ggtggaagtg gtggcggagg tagcggcatt catgtcttca ttttgggctg tttcagtgca      840
gggcttccta aaacagaagc caactgggtg aatgtaataa gtgatttgaa aaaaattgaa      900
gatcttattc aatctatgca tattgatgct actttatata cggaaagtga tgttcacccc      960
agttgcaaag taacagcaat gaagtgcttt ctcttggagt tacaagttat ttcacttgag     1020
tccggagatg caagtattca tgatacagta gaaaatctga tcatcctagc aaacaacagt     1080
ttgtcttcta atgggaatgt aacagaatct ggatgcaaag aatgtgagga actggaggaa     1140
aaaaatatta agaattttt gcagagtttt gtacatattg tccaaatgtt catcaacact     1200
tctgagggca gaggaagtct tctaacatgc ggtgacgtgg aggagaatcc cggccctatg     1260
tgtcaccagc agttggtcat ctcttggttt tccctggttt ttctggcatc tcccctcgtg     1320
gccatatggg aactgaagaa agatgtttat gtcgtagaat tggattggta ccgatgcc      1380 cctggagaaa tggtggtcct cacctgtgac accctgaag aagatggtat cacctggacc     1440
ttggaccaga gcagtgaggt cttaggctct ggcaaaaccc tgaccatcca agtcaaagag     1500
tttggagatg ctggccagta cacctgtcac aaaggaggcg aggttctaag ccattcgctc     1560
ctgctgcttc acaaaaagga agatggaatt tggtccactg atatttaaa ggaccagaaa     1620 gaacccaaaa ataagacctt tctaagatgc gaggccaaga attattctgg acgtttcacc     1680
tgctggtggc tgacgacaat cagtactgat ttgacattca gtgtcaaaag cagcagaggc     1740
tcttctgacc cccaaggggt gacgtgcgga gctgctacac tctctgcaga gagagtcaga     1800
ggggacaaca aggagtatga gtactcagtg gagtgccagg aggacagtgc ctgcccagct     1860
gctgaggaga gtctgccat tgaggtcatg gtggatgccg ttcacaagct caagtatgaa     1920
aactacacca gcagcttctt catcagggac atcatcaaac ctgacccacc caagaacttg     1980
cagctgaagc cattaaagaa ttctcggcag gtggaggtca gctgggagta ccctgacacc     2040
tggagtactc cacattccta cttctccctg acattctgcg ttcaggtcca gggcaagagc     2100
aagagagaaa agaaagatag agtcttcacg gacaagacct cagccacggt catctgccgc     2160
aaaaatgcca gcattagcgt gcgggcccag gaccgctact atagctcatc ttggagcgaa     2220
tgggcatctg tgccctgcag tggaggcggt ggaagtggcg gtgaggctc tggaggtggc     2280 ggaagcaccc aggactgctc cttccaacac agccccatct cctccgactt cgctgtcaaa     2340
atccgtgagc tgtctgacta cctgcttcaa gattacccag tcaccgtggc ctccaacctg     2400
caggacgagg agctctgcgg gggcctctgg cggctggtcc tggcacagcg ctggatggag     2460
cggctcaaga ctgtcgctgg gtccaagatg caaggcttgc tggagcgcgt gaacacggag     2520
```

```
atacactttg tcaccaaatg tgcctttcag cccccccca gctgtcttcg cttcgtccag    2580
accaacatct cccgcctcct gcaggagacc tccgagcagc tggtggcgct gaagccctgg    2640
atcactcgcc agaacttctc ccggtgcctg gagctgcagt gtcagcccga ctcctcaacc    2700
ctgccacccc catggagtcc ccggcccctg gaggccacag cccgacagc cccgcagccc    2760 cctctgctcc tcctactgct gctgcccgtg ggcctcctgc tgctggccgc tgcctggtgc    2820
ctgcactggc agaggacgcg gcggaggaca ccccgccctg gggagcaggt gccccccgtc    2880
cccagtcccc aggacctgct gcttgtggag cactga                              2916
```

<210> SEQ ID NO 57
<211> LENGTH: 2916
<212> TYPE: DNA
<213> ORGANISM: Artificial Sequence
<220> FEATURE:
<223> OTHER INFORMATION: nucleotide sequence encoding
      hIL12aIL21IL12bFLT3L protein heterodimer

<400> SEQUENCE: 57

```
atgtggcccc ctgggtcagc ctcccagcca ccgccctcac ctgccgcggc cacaggtctg      60
catccagcgg ctcgccctgt gtccctgcag tgccggctca gcatgtgtcc agcgcgcagc     120
ctcctccttg tggctaccct ggtcctcctg accacctca gtttggccag aaacctcccc      180
gtggccactc cagacccagg aatgttccca tgccttcacc actcccaaaa cctgctgagg     240
gccgtcagca acatgctcca gaaggccaga caaactctag aattttaccc ttgcacttct     300
gaagagattg atcatgaaga tatcacaaaa gataaaacca gcacagtgga ggcctgttta     360
ccattggaat taaccaagaa tgagagttgc ctaaattcca gagagacctc tttcataact     420
aatgggagtt gcctggcctc agaaagacc tcttttatga tggccctgtg ccttagtagt     480
atttatgaag acttgaagat gtaccaggtg gagttcaaga ccatgaatgc aaagcttctg     540
atggatccta gaggcagat ctttctagat caaaacatgc tggcagttat tgatgagctg     600
atgcaggccc tgaatttcaa cagtgagact gtgccacaaa atcctccct tgaagaaccg     660 gattttata aaactaaaat caagctctgc atacttcttc atgctttcag aattcgggca     720
gtgactattg atagagtgat gagctatctg aatgcttccg gtggaggagg ttctggaggc     780
ggtggaagtg gtggcggagg tagccaaggt caagatcgcc acatgattag aatgcgtcaa     840
cttatagata ttgttgatca gctgaaaaat tatgtgaatg acttggtccc tgaatttctg     900
ccagctccag aagatgtaga gacaaactgt gagtggtcag cttttttcctg ctttcagaag     960 gcccaactaa agtcagcaaa tacaggaaac aatgaaagga ataatcaatgt atcaattaaa    1020 aagctgaaga gaaaccacc ttccacaaat gcagggagaa gacagaaaca cagactaaca    1080
tgcccttcat gtgattctta tgagaaaaaa ccacccaaag aattcctaga agattcaaaa    1140
tcacttctcc aaaagatgat tcatcagcat ctgtcctcta gaacacacgg aagtgaagat    1200
tccgagggca gaggaagtct tctaacatgc ggtgacgtgg aggagaatcc cggccctatg    1260
tgtcaccagc agttggtcat ctcttggttt tccctggttt ttctggcatc tcccctcgtg    1320
gccatatggg aactgaagaa agatgtttat gtcgtagaat ggattggta tccgatgcc    1380 cctggagaaa tggtggtcct cacctgtgac acccctgaag aagatggtat cacctggacc    1440
ttggaccaga gcagtgaggt cttaggctct ggcaaaaccc tgaccatcca agtcaaagag    1500
tttggagatg ctggccagta cacctgtcac aaaggaggcg aggttctaag ccattcgctc    1560
ctgctgcttc acaaaaagga agatggaatt tggtccactg atattttaaa ggaccagaaa    1620
```

```
gaacccaaaa ataagacctt tctaagatgc gaggccaaga attattctgg acgtttcacc    1680
tgctggtggc tgacgacaat cagtactgat ttgacattca gtgtcaaaag cagcagaggc    1740
tcttctgacc cccaagggt gacgtgcgga gctgctacac tctctgcaga gagagtcaga    1800
ggggacaaca aggagtatga gtactcagtg gagtgccagg aggacagtgc ctgcccagct    1860
gctgaggaga gtctgcccat tgaggtcatg gtggatgccg ttcacaagct caagtatgaa    1920
aactacacca gcagcttctt catcagggac atcatcaaac ctgacccacc caagaacttg    1980
cagctgaagc cattaaagaa ttctcggcag gtggaggtca gctgggagta ccctgacacc    2040
tggagtactc cacattccta cttctccctg acattctgcg ttcaggtcca ggcaagagc    2100 aagagagaaa agaaagatag agtcttcacg gacaagacct cagccacggt catctgccgc    2160
aaaaatgcca gcattagcgt gcgggcccag gaccgctact atagctcatc ttggagcgaa    2220
tgggcatctg tgccctgcag tggaggcggt ggaagtggcg gtggaggctc tggaggtggc    2280
ggaagcaccc aggactgctc cttccaacac agccccatct cctccgactt cgctgtcaaa    2340
atccgtgagc tgtctgacta cctgcttcaa gattacccag tcaccgtggc ctccaacctg    2400 caggacgag agctctgcgg gggcctctgg cggctggtcc tggcacagcg ctggatggag    2460
cggctcaaga ctgtcgctgg gtccaagatg caaggcttgc tggagcgcgt gaacacggag    2520
atacactttg tcaccaaatg tgcctttcag ccccccccca gctgtcttcg cttcgtccag    2580
accaacatct cccgcctcct gcaggagacc tccgagcag tggtggcgct gaagccctgg    2640
atcactcgcc agaacttctc ccggtgcctg gagctgcagt gtcagcccga ctcctcaacc    2700
ctgccacccc catggagtcc ccggcccctg gaggccacag cccgacagc cccgcagccc    2760 cctctgctcc tcctactgct gctgcccgtg ggcctcctgc tgctggccgc tgcctggtgc    2820
ctgcactggc agaggacgcg gcggaggaca ccccgccctg gggagcaggt gcccccgtc    2880 cccagtcccc aggacctgct gcttgtggag cactga                              2916
```

<210> SEQ ID NO 58
<211> LENGTH: 18
<212> TYPE: PRT
<213> ORGANISM: Artificial Sequence
<220> FEATURE:
<223> OTHER INFORMATION: amino acid sequence of 2A self-splicing peptide

<400> SEQUENCE: 58

Glu Gly Arg Gly Ser Leu Leu Thr Cys Gly Asp Val Glu Glu Asn Pro
1               5                   10                  15

Gly Pro

<210> SEQ ID NO 59
<211> LENGTH: 54
<212> TYPE: DNA
<213> ORGANISM: Artificial Sequence
<220> FEATURE:
<223> OTHER INFORMATION: nucleotide sequence encoding 2A self-splicing
      peptide

<400> SEQUENCE: 59
gagggcagag gaagtcttct aacatgcggt gacgtggagg agaatcccgg ccct           54

<210> SEQ ID NO 60
<211> LENGTH: 357
<212> TYPE: PRT
<213> ORGANISM: Artificial Sequence
<220> FEATURE:

<223> OTHER INFORMATION: mIL12a-mIL2 first polypeptide chain

<400> SEQUENCE: 60

```
Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Ile Ile
        115                 120                 125

Leu Asp Lys Gly Met Leu Val Ala Ile Asp Glu Leu Met Gln Ser Leu
    130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Ser Gly Gly Gly Ser Gly Gly Gly Ser
        195                 200                 205

Ala Pro Thr Ser Ser Ser Thr Ser Ser Ser Thr Ala Glu Ala Gln Gln
    210                 215                 220

Gln Gln Gln Gln Gln Gln Gln Gln Gln Gln His Leu Glu Gln Leu Leu
225                 230                 235                 240

Met Asp Leu Gln Glu Leu Leu Ser Arg Met Glu Asn Tyr Arg Asn Leu
                245                 250                 255

Lys Leu Pro Arg Met Leu Thr Phe Lys Phe Tyr Leu Pro Lys Gln Ala
            260                 265                 270

Thr Glu Leu Lys Asp Leu Gln Cys Leu Glu Asp Glu Leu Gly Pro Leu
        275                 280                 285

Arg His Val Leu Asp Leu Thr Gln Ser Lys Ser Phe Gln Leu Glu Asp
    290                 295                 300

Ala Glu Asn Phe Ile Ser Asn Ile Arg Val Thr Val Val Lys Leu Lys
305                 310                 315                 320

Gly Ser Asp Asn Thr Phe Glu Cys Gln Phe Asp Asp Glu Ser Ala Thr
                325                 330                 335

Val Val Asp Phe Leu Arg Arg Trp Ile Ala Phe Cys Gln Ser Ile Ile
            340                 345                 350

Ser Thr Ser Pro Gln
        355
```

<210> SEQ ID NO 61
<211> LENGTH: 357
<212> TYPE: PRT
<213> ORGANISM: Artificial Sequence
<220> FEATURE:

<223> OTHER INFORMATION: mIL2-mIL12a first polypeptide chain

<400> SEQUENCE: 61

Ala Pro Thr Ser Ser Ser Thr Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
            35                  40                  45

Lys Leu Pro Arg Met Leu Thr Phe Lys Phe Tyr Leu Pro Lys Gln Ala
        50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
130                 135                 140

Ser Thr Ser Pro Gln Gly Gly Gly Ser Gly Gly Gly Ser Gly
145                 150                 155                 160

Gly Gly Ser Arg Val Ile Pro Val Ser Gly Pro Ala Arg Cys Leu
                165                 170                 175

Ser Gln Ser Arg Asn Leu Leu Lys Thr Thr Asp Asp Met Val Lys Thr
            180                 185                 190

Ala Arg Glu Lys Leu Lys His Tyr Ser Cys Thr Ala Glu Asp Ile Asp
        195                 200                 205

His Glu Asp Ile Thr Arg Asp Gln Thr Ser Thr Leu Lys Thr Cys Leu
210                 215                 220

Pro Leu Glu Leu His Lys Asn Glu Ser Cys Leu Ala Thr Arg Glu Thr
225                 230                 235                 240

Ser Ser Thr Thr Arg Gly Ser Cys Leu Pro Pro Gln Lys Thr Ser Leu
                245                 250                 255

Met Met Thr Leu Cys Leu Gly Ser Ile Tyr Glu Asp Leu Lys Met Tyr
            260                 265                 270

Gln Thr Glu Phe Gln Ala Ile Asn Ala Ala Leu Gln Asn His Asn His
        275                 280                 285

Gln Gln Ile Ile Leu Asp Lys Gly Met Leu Val Ala Ile Asp Glu Leu
290                 295                 300

Met Gln Ser Leu Asn His Asn Gly Glu Thr Leu Arg Gln Lys Pro Pro
305                 310                 315                 320

Val Gly Glu Ala Asp Pro Tyr Arg Val Lys Met Lys Leu Cys Ile Leu
                325                 330                 335

Leu His Ala Phe Ser Thr Arg Val Val Thr Ile Asn Arg Val Met Gly
            340                 345                 350

Tyr Leu Ser Ser Ala
        355

<210> SEQ ID NO 62
<211> LENGTH: 332
<212> TYPE: PRT
<213> ORGANISM: Artificial Sequence
<220> FEATURE:

<223> OTHER INFORMATION: mIL12a-mGMCSF first polypeptide chain

<400> SEQUENCE: 62

```
Arg Val Ile Pro Val Ser Gly Pro Ala Arg Cys Leu Ser Gln Ser Arg
1               5                   10                  15
Asn Leu Leu Lys Thr Thr Asp Asp Met Val Lys Thr Ala Arg Glu Lys
            20                  25                  30
Leu Lys His Tyr Ser Cys Thr Ala Glu Asp Ile Asp His Glu Asp Ile
        35                  40                  45
Thr Arg Asp Gln Thr Ser Thr Leu Lys Thr Cys Leu Pro Leu Glu Leu
    50                  55                  60
His Lys Asn Glu Ser Cys Leu Ala Thr Arg Glu Thr Ser Ser Thr Thr
65                  70                  75                  80
Arg Gly Ser Cys Leu Pro Pro Gln Lys Thr Ser Leu Met Met Thr Leu
                85                  90                  95
Cys Leu Gly Ser Ile Tyr Glu Asp Leu Lys Met Tyr Gln Thr Glu Phe
            100                 105                 110
Gln Ala Ile Asn Ala Ala Leu Gln Asn His Asn His Gln Ile Ile
        115                 120                 125
Leu Asp Lys Gly Met Leu Val Ala Ile Asp Glu Leu Met Gln Ser Leu
    130                 135                 140
Asn His Asn Gly Glu Thr Leu Arg Gln Lys Pro Pro Val Gly Glu Ala
145                 150                 155                 160
Asp Pro Tyr Arg Val Lys Met Lys Leu Cys Ile Leu Leu His Ala Phe
                165                 170                 175
Ser Thr Arg Val Val Thr Ile Asn Arg Val Met Gly Tyr Leu Ser Ser
            180                 185                 190
Ala Gly Gly Gly Ser Gly Gly Gly Ser Gly Gly Gly Ser
        195                 200                 205
Ala Pro Thr Arg Ser Pro Ile Thr Val Thr Arg Pro Trp Lys His Val
    210                 215                 220
Glu Ala Ile Lys Glu Ala Leu Asn Leu Leu Asp Asp Met Pro Val Thr
225                 230                 235                 240
Leu Asn Glu Glu Val Glu Val Val Ser Asn Glu Phe Ser Phe Lys Lys
                245                 250                 255
Leu Thr Cys Val Gln Thr Arg Leu Lys Ile Phe Glu Gln Gly Leu Arg
            260                 265                 270
Gly Asn Phe Thr Lys Leu Lys Gly Ala Leu Asn Met Thr Ala Ser Tyr
        275                 280                 285
Tyr Gln Thr Tyr Cys Pro Pro Thr Pro Glu Thr Asp Cys Glu Thr Gln
    290                 295                 300
Val Thr Thr Tyr Ala Asp Phe Ile Asp Ser Leu Lys Thr Phe Leu Thr
305                 310                 315                 320
Asp Ile Pro Phe Glu Cys Lys Lys Pro Gly Gln Lys
                325                 330
```

<210> SEQ ID NO 63
<211> LENGTH: 337
<212> TYPE: PRT
<213> ORGANISM: Artificial Sequence
<220> FEATURE:
<223> OTHER INFORMATION: mIL12a-mIL7 first polypeptide chain

<400> SEQUENCE: 63

```
Arg Val Ile Pro Val Ser Gly Pro Ala Arg Cys Leu Ser Gln Ser Arg
1               5                   10                  15
```

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

Thr Arg Asp Gln Thr Ser Thr Leu Lys Thr Cys Leu Pro Leu Glu Leu
    50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Ile Ile
        115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Gly Ser Gly Gly Gly Ser Gly Gly Gly Gly Ser
        195                 200                 205

Glu Cys His Ile Lys Asp Lys Gly Lys Ala Tyr Glu Ser Val Leu
210                 215                 220

Met Ile Ser Ile Asp Glu Leu Asp Lys Met Thr Gly Thr Asp Ser Asn
225                 230                 235                 240

Cys Pro Asn Asn Glu Pro Asn Phe Phe Arg Lys His Val Cys Asp Asp
                245                 250                 255

Thr Lys Glu Ala Ala Phe Leu Asn Arg Ala Ala Arg Lys Leu Lys Gln
            260                 265                 270

Phe Leu Lys Met Asn Ile Ser Glu Glu Phe Asn Val His Leu Leu Thr
        275                 280                 285

Val Ser Gln Gly Thr Gln Thr Leu Val Asn Cys Thr Ser Lys Glu Glu
    290                 295                 300

Lys Asn Val Lys Glu Gln Lys Lys Asn Asp Ala Cys Phe Leu Lys Arg
305                 310                 315                 320

Leu Leu Arg Glu Ile Lys Thr Cys Trp Asn Lys Ile Leu Lys Gly Ser
                325                 330                 335

Ile

<210> SEQ ID NO 64
<211> LENGTH: 341
<212> TYPE: PRT
<213> ORGANISM: Artificial Sequence
<220> FEATURE:
<223> OTHER INFORMATION: mIL12a-mIL15 first polypeptide chain

<400> SEQUENCE: 64

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
            35                  40                  45

Thr Arg Asp Gln Thr Ser Thr Leu Lys Thr Cys Leu Pro Leu Glu Leu
        50                  55                  60

His Lys Asn Glu Ser Cys Leu Ala Thr Arg Glu Thr Ser Ser Thr Thr
65                  70                  75                  80

Arg Gly Ser Cys Leu Pro Pro Gln Lys Thr Ser Leu Met Met Thr Leu
                85                  90                  95

Cys Leu Gly Ser Ile Tyr Glu Asp Leu Lys Met Tyr Gln Thr Glu Phe
            100                 105                 110

Gln Ala Ile Asn Ala Ala Leu Gln Asn His Asn His Gln Gln Ile Ile
        115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
            180                 185                 190

Ala Gly Gly Gly Gly Ser Gly Gly Gly Ser Gly Gly Gly Gly Ser
        195                 200                 205

Gly Ile His Val Phe Ile Leu Gly Cys Val Ser Val Gly Leu Pro Lys
            210                 215                 220

Thr Glu Ala Asn Trp Ile Asp Val Arg Tyr Asp Leu Glu Lys Ile Glu
225                 230                 235                 240

Ser Leu Ile Gln Ser Ile His Ile Asp Thr Thr Leu Tyr Thr Asp Ser
                245                 250                 255

Asp Phe His Pro Ser Cys Lys Val Thr Ala Met Asn Cys Phe Leu Leu
            260                 265                 270

Glu Leu Gln Val Ile Leu His Glu Tyr Ser Asn Met Thr Leu Asn Glu
        275                 280                 285

Thr Val Arg Asn Val Leu Tyr Leu Ala Asn Ser Thr Leu Ser Ser Asn
290                 295                 300

Lys Asn Val Ala Glu Ser Gly Cys Lys Glu Cys Glu Glu Leu Glu Glu
305                 310                 315                 320

Lys Thr Phe Thr Glu Phe Leu Gln Ser Phe Ile Arg Ile Val Gln Met
                325                 330                 335

Phe Ile Asn Thr Ser
            340

<210> SEQ ID NO 65
<211> LENGTH: 337
<212> TYPE: PRT
<213> ORGANISM: Artificial Sequence
<220> FEATURE:
<223> OTHER INFORMATION: mIL12a-mIL21 first polypeptide chain

<400> SEQUENCE: 65

Arg Val Ile Pro Val Ser Gly Pro Ala Arg Cys Leu Ser Gln Ser Arg
1               5                   10                  15

Asn Leu Leu Lys Thr Thr Asp Asp Met Val Lys Thr Ala Arg Glu Lys
            20                  25                  30

Leu Lys His Tyr Ser Cys Thr Ala Glu Asp Ile Asp His Glu Asp Ile
        35                  40                  45

```
Thr Arg Asp Gln Thr Ser Thr Leu Lys Thr Cys Leu Pro Leu Glu Leu
 50                  55                  60

His Lys Asn Glu Ser Cys Leu Ala Thr Arg Glu Thr Ser Ser Thr Thr
 65                  70                  75                  80

Arg Gly Ser Cys Leu Pro Pro Gln Lys Thr Ser Leu Met Met Thr Leu
                 85                  90                  95

Cys Leu Gly Ser Ile Tyr Glu Asp Leu Lys Met Tyr Gln Thr Glu Phe
             100                 105                 110

Gln Ala Ile Asn Ala Ala Leu Gln Asn His Asn His Gln Gln Ile Ile
             115                 120                 125

Leu Asp Lys Gly Met Leu Val Ala Ile Asp Glu Leu Met Gln Ser Leu
130                 135                 140

Asn His Asn Gly Glu Thr Leu Arg Gln Lys Pro Pro Val Gly Glu Ala
145                 150                 155                 160

Asp Pro Tyr Arg Val Lys Met Lys Leu Cys Ile Leu Leu His Ala Phe
                165                 170                 175

Ser Thr Arg Val Val Thr Ile Asn Arg Val Met Gly Tyr Leu Ser Ser
                180                 185                 190

Ala Gly Gly Gly Ser Gly Gly Gly Ser Gly Gly Gly Gly Ser
                195                 200                 205

His Lys Ser Ser Pro Gln Gly Pro Asp Arg Leu Leu Ile Arg Leu Arg
210                 215                 220

His Leu Ile Asp Ile Val Glu Gln Leu Lys Ile Tyr Glu Asn Asp Leu
225                 230                 235                 240

Asp Pro Glu Leu Leu Ser Ala Pro Gln Asp Val Lys Gly His Cys Glu
                245                 250                 255

His Ala Ala Phe Ala Cys Phe Gln Lys Ala Lys Leu Lys Pro Ser Asn
                260                 265                 270

Pro Gly Asn Asn Lys Thr Phe Ile Ile Asp Leu Val Ala Gln Leu Arg
                275                 280                 285

Arg Arg Leu Pro Ala Arg Arg Gly Gly Lys Lys Gln Lys His Ile Ala
                290                 295                 300

Lys Cys Pro Ser Cys Asp Ser Tyr Glu Lys Arg Thr Pro Lys Glu Phe
305                 310                 315                 320

Leu Glu Arg Leu Lys Trp Leu Leu Gln Lys Met Ile His Gln His Leu
                325                 330                 335

Ser

<210> SEQ ID NO 66
<211> LENGTH: 452
<212> TYPE: PRT
<213> ORGANISM: Artificial Sequence
<220> FEATURE:
<223> OTHER INFORMATION: mIL12b-mGMCSF second polypeptide chain

<400> SEQUENCE: 66

Met Trp Glu Leu Glu Lys Asp Val Tyr Val Val Glu Val Asp Trp Thr
  1               5                  10                  15

Pro Asp Ala Pro Gly Glu Thr Val Asn Leu Thr Cys Asp Thr Pro Glu
                 20                  25                  30

Glu Asp Asp Ile Thr Trp Thr Ser Asp Gln Arg His Gly Val Ile Gly
                 35                  40                  45

Ser Gly Lys Thr Leu Thr Ile Thr Val Lys Glu Phe Leu Asp Ala Gly
             50                  55                  60

Gln Tyr Thr Cys His Lys Gly Gly Glu Thr Leu Ser His Ser His Leu
```

```
            65                  70                  75                  80
Leu Leu His Lys Lys Glu Asn Gly Ile Trp Ser Thr Glu Ile Leu Lys
                    85                  90                  95

Asn Phe Lys Asn Lys Thr Phe Leu Lys Cys Glu Ala Pro Asn Tyr Ser
                100                 105                 110

Gly Arg Phe Thr Cys Ser Trp Leu Val Gln Arg Asn Met Asp Leu Lys
                115                 120                 125

Phe Asn Ile Lys Ser Ser Ser Ser Pro Asp Ser Arg Ala Val Thr
130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
                180                 185                 190

Gln Asn Lys Tyr Glu Asn Tyr Ser Thr Ser Phe Phe Ile Arg Asp Ile
                195                 200                 205

Ile Lys Pro Asp Pro Pro Lys Asn Leu Gln Met Lys Pro Leu Lys Asn
210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
                260                 265                 270

Leu Val Glu Lys Thr Ser Thr Glu Val Gln Cys Lys Gly Gly Asn Val
                275                 280                 285

Cys Val Gln Ala Gln Asp Arg Tyr Tyr Asn Ser Ser Cys Ser Lys Trp
290                 295                 300

Ala Cys Val Pro Cys Arg Val Arg Ser Gly Gly Gly Ser Gly Gly
305                 310                 315                 320

Gly Gly Ser Gly Gly Gly Gly Ser Ala Pro Thr Arg Ser Pro Ile Thr
                325                 330                 335

Val Thr Arg Pro Trp Lys His Val Glu Ala Ile Lys Glu Ala Leu Asn
                340                 345                 350

Leu Leu Asp Asp Met Pro Val Thr Leu Asn Glu Glu Val Glu Val Val
                355                 360                 365

Ser Asn Glu Phe Ser Phe Lys Lys Leu Thr Cys Val Gln Thr Arg Leu
370                 375                 380

Lys Ile Phe Glu Gln Gly Leu Arg Gly Asn Phe Thr Lys Leu Lys Gly
385                 390                 395                 400

Ala Leu Asn Met Thr Ala Ser Tyr Tyr Gln Thr Tyr Cys Pro Pro Thr
                405                 410                 415

Pro Glu Thr Asp Cys Glu Thr Gln Val Thr Thr Tyr Ala Asp Phe Ile
                420                 425                 430

Asp Ser Leu Lys Thr Phe Leu Thr Asp Ile Pro Phe Glu Cys Lys Lys
                435                 440                 445

Pro Gly Gln Lys
        450

<210> SEQ ID NO 67
<211> LENGTH: 452
<212> TYPE: PRT
<213> ORGANISM: Artificial Sequence
```

<220> FEATURE:
<223> OTHER INFORMATION: mGMCSF-mIL12b second polypeptide chain

<400> SEQUENCE: 67

```
Ala Pro Thr Arg Ser Pro Ile Thr Val Thr Arg Pro Trp Lys His Val
1               5                   10                  15

Glu Ala Ile Lys Glu Ala Leu Asn Leu Leu Asp Asp Met Pro Val Thr
            20                  25                  30

Leu Asn Glu Glu Val Glu Val Val Ser Asn Glu Phe Ser Phe Lys Lys
        35                  40                  45

Leu Thr Cys Val Gln Thr Arg Leu Lys Ile Phe Glu Gln Gly Leu Arg
    50                  55                  60

Gly Asn Phe Thr Lys Leu Lys Gly Ala Leu Asn Met Thr Ala Ser Tyr
65                  70                  75                  80

Tyr Gln Thr Tyr Cys Pro Pro Thr Pro Glu Thr Asp Cys Glu Thr Gln
                85                  90                  95

Val Thr Thr Tyr Ala Asp Phe Ile Asp Ser Leu Lys Thr Phe Leu Thr
            100                 105                 110

Asp Ile Pro Phe Glu Cys Lys Lys Pro Gly Gln Lys Gly Gly Gly Gly
        115                 120                 125

Ser Gly Gly Gly Gly Ser Gly Gly Gly Ser Met Trp Glu Leu Glu
    130                 135                 140

Lys Asp Val Tyr Val Val Glu Val Asp Trp Thr Pro Asp Ala Pro Gly
145                 150                 155                 160

Glu Thr Val Asn Leu Thr Cys Asp Thr Pro Glu Glu Asp Asp Ile Thr
                165                 170                 175

Trp Thr Ser Asp Gln Arg His Gly Val Ile Gly Ser Gly Lys Thr Leu
            180                 185                 190

Thr Ile Thr Val Lys Glu Phe Leu Asp Ala Gly Gln Tyr Thr Cys His
        195                 200                 205

Lys Gly Gly Glu Thr Leu Ser His Ser His Leu Leu Leu His Lys Lys
    210                 215                 220

Glu Asn Gly Ile Trp Ser Thr Glu Ile Leu Lys Asn Phe Lys Asn Lys
225                 230                 235                 240

Thr Phe Leu Lys Cys Glu Ala Pro Asn Tyr Ser Gly Arg Phe Thr Cys
                245                 250                 255

Ser Trp Leu Val Gln Arg Asn Met Asp Leu Lys Phe Asn Ile Lys Ser
            260                 265                 270

Ser Ser Ser Ser Pro Asp Ser Arg Ala Val Thr Cys Gly Met Ala Ser
        275                 280                 285

Leu Ser Ala Glu Lys Val Thr Leu Asp Gln Arg Asp Tyr Glu Lys Tyr
    290                 295                 300

Ser Val Ser Cys Gln Glu Asp Val Thr Cys Pro Thr Ala Glu Glu Thr
305                 310                 315                 320

Leu Pro Ile Glu Leu Ala Leu Glu Ala Arg Gln Gln Asn Lys Tyr Glu
                325                 330                 335

Asn Tyr Ser Thr Ser Phe Phe Ile Arg Asp Ile Ile Lys Pro Asp Pro
            340                 345                 350

Pro Lys Asn Leu Gln Met Lys Pro Leu Lys Asn Ser Gln Val Glu Val
        355                 360                 365

Ser Trp Glu Tyr Pro Asp Ser Trp Ser Thr Pro His Ser Tyr Phe Ser
    370                 375                 380

Leu Lys Phe Phe Val Arg Ile Gln Arg Lys Lys Glu Lys Met Lys Glu
385                 390                 395                 400
```

```
Thr Glu Glu Gly Cys Asn Gln Lys Gly Ala Phe Leu Val Glu Lys Thr
            405                 410                 415

Ser Thr Glu Val Gln Cys Lys Gly Gly Asn Val Cys Val Gln Ala Gln
            420                 425                 430

Asp Arg Tyr Tyr Asn Ser Ser Cys Ser Lys Trp Ala Cys Val Pro Cys
            435                 440                 445

Arg Val Arg Ser
        450

<210> SEQ ID NO 68
<211> LENGTH: 477
<212> TYPE: PRT
<213> ORGANISM: Artificial Sequence
<220> FEATURE:
<223> OTHER INFORMATION: mIL12b-mIL2 second polypeptide chain

<400> SEQUENCE: 68

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
            20                  25                  30

Glu Asp Asp Ile Thr Trp Thr Ser Asp Gln Arg His Gly Val Ile Gly
        35                  40                  45

Ser Gly Lys Thr Leu Thr Ile Thr Val Lys Glu Phe Leu Asp Ala Gly
    50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
            100                 105                 110

Gly Arg Phe Thr Cys Ser Trp Leu Val Gln Arg Asn Met Asp Leu Lys
        115                 120                 125

Phe Asn Ile Lys Ser Ser Ser Ser Pro Asp Ser Arg Ala Val Thr
    130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
        195                 200                 205

Ile Lys Pro Asp Pro Pro Lys Asn Leu Gln Met Lys Pro Leu Lys Asn
    210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Glu Val Gln Cys Lys Gly Gly Asn Val
        275                 280                 285

Cys Val Gln Ala Gln Asp Arg Tyr Tyr Asn Ser Ser Cys Ser Lys Trp
    290                 295                 300
```

Ala Cys Val Pro Cys Arg Val Arg Ser Gly Gly Gly Ser Gly Gly
305                 310                 315                 320

Gly Gly Ser Gly Gly Gly Ser Ala Pro Thr Ser Ser Thr Ser
            325                 330                 335

Ser Ser Thr Ala Glu Ala Gln Gln Gln Gln Gln Gln Gln Gln Gln
            340                 345                 350

Gln Gln His Leu Glu Gln Leu Leu Met Asp Leu Gln Glu Leu Leu Ser
            355                 360                 365

Arg Met Glu Asn Tyr Arg Asn Leu Lys Leu Pro Arg Met Leu Thr Phe
            370                 375                 380

Lys Phe Tyr Leu Pro Lys Gln Ala Thr Glu Leu Lys Asp Leu Gln Cys
385                 390                 395                 400

Leu Glu Asp Glu Leu Gly Pro Leu Arg His Val Leu Asp Leu Thr Gln
                405                 410                 415

Ser Lys Ser Phe Gln Leu Glu Asp Ala Glu Asn Phe Ile Ser Asn Ile
            420                 425                 430

Arg Val Thr Val Val Lys Leu Lys Gly Ser Asp Asn Thr Phe Glu Cys
            435                 440                 445

Gln Phe Asp Asp Glu Ser Ala Thr Val Val Asp Phe Leu Arg Arg Trp
450                 455                 460

Ile Ala Phe Cys Gln Ser Ile Ile Ser Thr Ser Pro Gln
465                 470                 475

<210> SEQ ID NO 69
<211> LENGTH: 534
<212> TYPE: PRT
<213> ORGANISM: Artificial Sequence
<220> FEATURE:
<223> OTHER INFORMATION: mIL12b-mFLT3L second polypeptide chain

<400> SEQUENCE: 69

Met Trp Glu Leu Glu Lys Asp Val Tyr Val Val Glu Val Asp Trp Thr
1               5                   10                  15

Pro Asp Ala Pro Gly Glu Thr Val Asn Leu Thr Cys Asp Thr Pro Glu
                20                  25                  30

Glu Asp Ile Thr Trp Thr Ser Asp Gln Arg His Gly Val Ile Gly
            35                  40                  45

Ser Gly Lys Thr Leu Thr Ile Thr Val Lys Glu Phe Leu Asp Ala Gly
        50                  55                  60

Gln Tyr Thr Cys His Lys Gly Gly Glu Thr Leu Ser His Ser His Leu
65                  70                  75                  80

Leu Leu His Lys Lys Glu Asn Gly Ile Trp Ser Thr Glu Ile Leu Lys
                85                  90                  95

Asn Phe Lys Asn Lys Thr Phe Leu Lys Cys Glu Ala Pro Asn Tyr Ser
                100                 105                 110

Gly Arg Phe Thr Cys Ser Trp Leu Val Gln Arg Asn Met Asp Leu Lys
            115                 120                 125

Phe Asn Ile Lys Ser Ser Ser Ser Pro Asp Ser Arg Ala Val Thr
130                 135                 140

Cys Gly Met Ala Ser Leu Ser Ala Glu Lys Val Thr Leu Asp Gln Arg
145                 150                 155                 160

Asp Tyr Glu Lys Tyr Ser Val Ser Cys Gln Glu Asp Val Thr Cys Pro
                165                 170                 175

Thr Ala Glu Glu Thr Leu Pro Ile Glu Leu Ala Leu Glu Ala Arg Gln
            180                 185                 190

Gln Asn Lys Tyr Glu Asn Tyr Ser Thr Ser Phe Phe Ile Arg Asp Ile
            195                 200                 205

Ile Lys Pro Asp Pro Lys Asn Leu Gln Met Lys Pro Leu Lys Asn
210                 215                 220

Ser Gln Val Glu Val Ser Trp Glu Tyr Pro Asp Ser Trp Ser Thr Pro
225                 230                 235                 240

His Ser Tyr Phe Ser Leu Lys Phe Phe Val Arg Ile Gln Arg Lys Lys
                245                 250                 255

Glu Lys Met Lys Glu Thr Glu Glu Gly Cys Asn Gln Lys Gly Ala Phe
            260                 265                 270

Leu Val Glu Lys Thr Ser Thr Val Gln Cys Lys Gly Gly Asn Val
        275                 280                 285

Cys Val Gln Ala Gln Asp Arg Tyr Tyr Asn Ser Ser Cys Ser Lys Trp
290                 295                 300

Ala Cys Val Pro Cys Arg Val Arg Ser Gly Gly Gly Ser Gly Gly
305                 310                 315                 320

Gly Gly Ser Gly Gly Gly Ser Gly Thr Pro Asp Cys Tyr Phe Ser
                325                 330                 335

His Ser Pro Ile Ser Ser Asn Phe Lys Val Lys Phe Arg Glu Leu Thr
            340                 345                 350

Asp His Leu Leu Lys Asp Tyr Pro Val Thr Val Ala Val Asn Leu Gln
            355                 360                 365

Asp Glu Lys His Cys Lys Ala Leu Trp Ser Leu Phe Leu Ala Gln Arg
        370                 375                 380

Trp Ile Glu Gln Leu Lys Thr Val Ala Gly Ser Lys Met Gln Thr Leu
385                 390                 395                 400

Leu Glu Asp Val Asn Thr Glu Ile His Phe Val Thr Ser Cys Thr Phe
                405                 410                 415

Gln Pro Leu Pro Glu Cys Leu Arg Phe Val Gln Thr Asn Ile Ser His
            420                 425                 430

Leu Leu Lys Asp Thr Cys Thr Gln Leu Leu Ala Leu Lys Pro Cys Ile
        435                 440                 445

Gly Lys Ala Cys Gln Asn Phe Ser Arg Cys Leu Glu Val Gln Cys Gln
    450                 455                 460

Pro Asp Ser Ser Thr Leu Leu Pro Pro Arg Ser Pro Ile Ala Leu Glu
465                 470                 475                 480

Ala Thr Glu Leu Pro Glu Pro Arg Pro Arg Gln Leu Leu Leu Leu
                485                 490                 495

Leu Leu Leu Leu Pro Leu Thr Leu Val Leu Leu Ala Ala Trp Gly
            500                 505                 510

Leu Arg Trp Gln Arg Ala Arg Arg Arg Gly Glu Leu His Pro Gly Val
            515                 520                 525

Pro Leu Pro Ser His Pro
    530

<210> SEQ ID NO 70
<211> LENGTH: 345
<212> TYPE: PRT
<213> ORGANISM: Artificial Sequence
<220> FEATURE:
<223> OTHER INFORMATION: hIL12a-hIL2 first polypeptide chain

<400> SEQUENCE: 70

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
            130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Ser Gly Gly Gly Gly Ser Gly
            195                 200                 205

Gly Gly Gly Ser Ala Pro Thr Ser Ser Ser Thr Lys Lys Thr Gln Leu
            210                 215                 220

Gln Leu Glu His Leu Leu Leu Asp Leu Gln Met Ile Leu Asn Gly Ile
225                 230                 235                 240

Asn Asn Tyr Lys Asn Pro Lys Leu Thr Arg Met Leu Thr Phe Lys Phe
                245                 250                 255

Tyr Met Pro Lys Lys Ala Thr Glu Leu Lys His Leu Gln Cys Leu Glu
            260                 265                 270

Glu Glu Leu Lys Pro Leu Glu Glu Val Leu Asn Leu Ala Gln Ser Lys
            275                 280                 285

Asn Phe His Leu Arg Pro Arg Asp Leu Ile Ser Asn Ile Asn Val Ile
            290                 295                 300

Val Leu Glu Leu Lys Gly Ser Glu Thr Thr Phe Met Cys Glu Tyr Ala
305                 310                 315                 320

Asp Glu Thr Ala Thr Ile Val Glu Phe Leu Asn Arg Trp Ile Thr Phe
                325                 330                 335

Cys Gln Ser Ile Ile Ser Thr Leu Thr
            340                 345

<210> SEQ ID NO 71
<211> LENGTH: 364
<212> TYPE: PRT
<213> ORGANISM: Artificial Sequence
<220> FEATURE:
<223> OTHER INFORMATION: hIL12a-hIL7 first polypeptide chain

<400> SEQUENCE: 71

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

```
Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
 50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
                100                 105                 110

Gln Val Glu Phe Lys Thr Met Asn Ala Lys Leu Leu Met Asp Pro Lys
                115                 120                 125

Arg Gln Ile Phe Leu Asp Gln Asn Met Leu Ala Val Ile Asp Glu Leu
            130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Gly Ser Gly Gly Gly Gly Ser Gly
            195                 200                 205

Gly Gly Ser Asp Cys Asp Ile Glu Gly Lys Asp Gly Lys Gln Tyr
        210                 215                 220

Glu Ser Val Leu Met Val Ser Ile Asp Gln Leu Leu Asp Ser Met Lys
225                 230                 235                 240

Glu Ile Gly Ser Asn Cys Leu Asn Asn Glu Phe Asn Phe Phe Lys Arg
                245                 250                 255

His Ile Cys Asp Ala Asn Lys Glu Gly Met Phe Leu Phe Arg Ala Ala
            260                 265                 270

Arg Lys Leu Arg Gln Phe Leu Lys Met Asn Ser Thr Gly Asp Phe Asp
        275                 280                 285

Leu His Leu Leu Lys Val Ser Glu Gly Thr Thr Ile Leu Leu Asn Cys
        290                 295                 300

Thr Gly Gln Val Lys Gly Arg Lys Pro Ala Ala Leu Gly Glu Ala Gln
305                 310                 315                 320

Pro Thr Lys Ser Leu Glu Glu Asn Lys Ser Leu Lys Glu Gln Lys Lys
                325                 330                 335

Leu Asn Asp Leu Cys Phe Leu Lys Arg Leu Leu Gln Glu Ile Lys Thr
            340                 345                 350

Cys Trp Asn Lys Ile Leu Met Gly Thr Lys Glu His
        355                 360

<210> SEQ ID NO 72
<211> LENGTH: 345
<212> TYPE: PRT
<213> ORGANISM: Artificial Sequence
<220> FEATURE:
<223> OTHER INFORMATION: hIL12a-hIL15 first polypeptide chain

<400> SEQUENCE: 72

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30
```

```
Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
 50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
            130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Gly Gly Gly Gly Ser Gly Gly Gly Gly Ser Gly
            195                 200                 205

Gly Gly Ser Gly Ile His Val Phe Ile Leu Gly Cys Phe Ser Ala
        210                 215                 220

Gly Leu Pro Lys Thr Glu Ala Asn Trp Val Asn Val Ile Ser Asp Leu
225                 230                 235                 240

Lys Lys Ile Glu Asp Leu Ile Gln Ser Met His Ile Asp Ala Thr Leu
                245                 250                 255

Tyr Thr Glu Ser Asp Val His Pro Ser Cys Lys Val Thr Ala Met Lys
            260                 265                 270

Cys Phe Leu Leu Glu Leu Gln Val Ile Ser Leu Glu Ser Gly Asp Ala
            275                 280                 285

Ser Ile His Asp Thr Val Glu Asn Leu Ile Ile Leu Ala Asn Asn Ser
        290                 295                 300

Leu Ser Ser Asn Gly Asn Val Thr Glu Ser Gly Cys Lys Glu Cys Glu
305                 310                 315                 320

Glu Leu Glu Glu Lys Asn Ile Lys Glu Phe Leu Gln Ser Phe Val His
                325                 330                 335

Ile Val Gln Met Phe Ile Asn Thr Ser
            340                 345

<210> SEQ ID NO 73
<211> LENGTH: 345
<212> TYPE: PRT
<213> ORGANISM: Artificial Sequence
<220> FEATURE:
<223> OTHER INFORMATION: hIL12a-hIL21 first polypeptide chain

<400> SEQUENCE: 73

Arg Asn Leu Pro Val Ala Thr Pro Asp Pro Gly Met Phe Pro Cys Leu
 1               5                  10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45
```

His Glu Asp Ile Thr Lys Asp Lys Thr Ser Thr Val Glu Ala Cys Leu
 50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
                100                 105                 110

Gln Val Glu Phe Lys Thr Met Asn Ala Lys Leu Leu Met Asp Pro Lys
            115                 120                 125

Arg Gln Ile Phe Leu Asp Gln Asn Met Leu Ala Val Ile Asp Glu Leu
        130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
                180                 185                 190

Tyr Leu Asn Ala Ser Gly Gly Gly Ser Gly Gly Gly Ser Gly
            195                 200                 205

Gly Gly Gly Ser Gln Gly Gln Asp Arg His Met Ile Arg Met Arg Gln
        210                 215                 220

Leu Ile Asp Ile Val Asp Gln Leu Lys Asn Tyr Val Asn Asp Leu Val
225                 230                 235                 240

Pro Glu Phe Leu Pro Ala Pro Glu Asp Val Glu Thr Asn Cys Glu Trp
                245                 250                 255

Ser Ala Phe Ser Cys Phe Gln Lys Ala Gln Leu Lys Ser Ala Asn Thr
                260                 265                 270

Gly Asn Asn Glu Arg Ile Ile Asn Val Ser Ile Lys Lys Leu Lys Arg
            275                 280                 285

Lys Pro Pro Ser Thr Asn Ala Gly Arg Arg Gln Lys His Arg Leu Thr
        290                 295                 300

Cys Pro Ser Cys Asp Ser Tyr Glu Lys Lys Pro Pro Lys Glu Phe Leu
305                 310                 315                 320

Glu Arg Phe Lys Ser Leu Leu Gln Lys Met Ile His Gln His Leu Ser
                325                 330                 335

Ser Arg Thr His Gly Ser Glu Asp Ser
            340                 345

<210> SEQ ID NO 74
<211> LENGTH: 448
<212> TYPE: PRT
<213> ORGANISM: Artificial Sequence
<220> FEATURE:
<223> OTHER INFORMATION: hIL12b-hGMCSF second polypeptide chain

<400> SEQUENCE: 74

Ile Trp Glu Leu Lys Lys Asp Val Tyr Val Val Glu Leu Asp Trp Tyr
 1               5                  10                  15

Pro Asp Ala Pro Gly Glu Met Val Val Leu Thr Cys Asp Thr Pro Glu
                 20                  25                  30

Glu Asp Gly Ile Thr Trp Thr Leu Asp Gln Ser Ser Glu Val Leu Gly
             35                  40                  45

Ser Gly Lys Thr Leu Thr Ile Gln Val Lys Glu Phe Gly Asp Ala Gly
         50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
            85                  90                  95

Asp Gln Lys Glu Pro Lys Asn Lys Thr Phe Leu Arg Cys Glu Ala Lys
        100                 105                 110

Asn Tyr Ser Gly Arg Phe Thr Cys Trp Trp Leu Thr Thr Ile Ser Thr
    115                 120                 125

Asp Leu Thr Phe Ser Val Lys Ser Ser Arg Gly Ser Ser Asp Pro Gln
130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
290                 295                 300

Cys Ser Gly Gly Gly Ser Gly Gly Gly Ser Gly Gly Gly Gly
305                 310                 315                 320

Ser Ala Pro Ala Arg Ser Pro Ser Pro Ser Thr Gln Pro Trp Glu His
                325                 330                 335

Val Asn Ala Ile Gln Glu Ala Arg Arg Leu Leu Asn Leu Ser Arg Asp
            340                 345                 350

Thr Ala Ala Glu Met Asn Glu Thr Val Glu Val Ile Ser Glu Met Phe
        355                 360                 365

Asp Leu Gln Glu Pro Thr Cys Leu Gln Thr Arg Leu Glu Leu Tyr Lys
370                 375                 380

Gln Gly Leu Arg Gly Ser Leu Thr Lys Leu Lys Gly Pro Leu Thr Met
385                 390                 395                 400

Met Ala Ser His Tyr Lys Gln His Cys Pro Pro Thr Pro Glu Thr Ser
                405                 410                 415

Cys Ala Thr Gln Ile Ile Thr Phe Glu Ser Phe Lys Glu Asn Leu Lys
            420                 425                 430

Asp Phe Leu Leu Val Ile Pro Phe Asp Cys Trp Glu Pro Val Gln Glu
        435                 440                 445

<210> SEQ ID NO 75
<211> LENGTH: 530
<212> TYPE: PRT
<213> ORGANISM: Artificial Sequence
<220> FEATURE:

<223> OTHER INFORMATION: hIL12b-hFLT3L second polypeptide chain

<400> SEQUENCE: 75

```
Ile Trp Glu Leu Lys Lys Asp Val Tyr Val Val Glu Leu Asp Trp Tyr
1               5                   10                  15
Pro Asp Ala Pro Gly Glu Met Val Val Leu Thr Cys Asp Thr Pro Glu
            20                  25                  30
Glu Asp Gly Ile Thr Trp Thr Leu Asp Gln Ser Ser Glu Val Leu Gly
        35                  40                  45
Ser Gly Lys Thr Leu Thr Ile Gln Val Lys Glu Phe Gly Asp Ala Gly
    50                  55                  60
Gln Tyr Thr Cys His Lys Gly Gly Glu Val Leu Ser His Ser Leu Leu
65                  70                  75                  80
Leu Leu His Lys Lys Glu Asp Gly Ile Trp Ser Thr Asp Ile Leu Lys
                85                  90                  95
Asp Gln Lys Glu Pro Lys Asn Lys Thr Phe Leu Arg Cys Glu Ala Lys
            100                 105                 110
Asn Tyr Ser Gly Arg Phe Thr Cys Trp Trp Leu Thr Thr Ile Ser Thr
        115                 120                 125
Asp Leu Thr Phe Ser Val Lys Ser Ser Arg Gly Ser Ser Asp Pro Gln
    130                 135                 140
Gly Val Thr Cys Gly Ala Ala Thr Leu Ser Ala Glu Arg Val Arg Gly
145                 150                 155                 160
Asp Asn Lys Glu Tyr Glu Tyr Ser Val Glu Cys Gln Glu Asp Ser Ala
                165                 170                 175
Cys Pro Ala Ala Glu Glu Ser Leu Pro Ile Glu Val Met Val Asp Ala
            180                 185                 190
Val His Lys Leu Lys Tyr Glu Asn Tyr Thr Ser Ser Phe Phe Ile Arg
        195                 200                 205
Asp Ile Ile Lys Pro Asp Pro Pro Lys Asn Leu Gln Leu Lys Pro Leu
    210                 215                 220
Lys Asn Ser Arg Gln Val Glu Val Ser Trp Glu Tyr Pro Asp Thr Trp
225                 230                 235                 240
Ser Thr Pro His Ser Tyr Phe Ser Leu Thr Phe Cys Val Gln Val Gln
                245                 250                 255
Gly Lys Ser Lys Arg Glu Lys Lys Asp Arg Val Phe Thr Asp Lys Thr
            260                 265                 270
Ser Ala Thr Val Ile Cys Arg Lys Asn Ala Ser Ile Ser Val Arg Ala
        275                 280                 285
Gln Asp Arg Tyr Tyr Ser Ser Ser Trp Ser Glu Trp Ala Ser Val Pro
    290                 295                 300
Cys Ser Gly Gly Gly Ser Gly Gly Gly Ser Gly Gly Gly Gly Gly Gly
305                 310                 315                 320
Ser Thr Gln Asp Cys Ser Phe Gln His Ser Pro Ile Ser Ser Asp Phe
                325                 330                 335
Ala Val Lys Ile Arg Glu Leu Ser Asp Tyr Leu Leu Gln Asp Tyr Pro
            340                 345                 350
Val Thr Val Ala Ser Asn Leu Gln Asp Glu Glu Leu Cys Gly Gly Leu
        355                 360                 365
Trp Arg Leu Val Leu Ala Gln Arg Trp Met Glu Arg Leu Lys Thr Val
    370                 375                 380
Ala Gly Ser Lys Met Gln Gly Leu Leu Glu Arg Val Asn Thr Glu Ile
385                 390                 395                 400
```

-continued

```
His Phe Val Thr Lys Cys Ala Phe Gln Pro Pro Ser Cys Leu Arg
            405             410             415

Phe Val Gln Thr Asn Ile Ser Arg Leu Leu Gln Glu Thr Ser Glu Gln
            420             425             430

Leu Val Ala Leu Lys Pro Trp Ile Thr Arg Gln Asn Phe Ser Arg Cys
            435             440             445

Leu Glu Leu Gln Cys Gln Pro Asp Ser Ser Thr Leu Pro Pro Pro Trp
    450             455             460

Ser Pro Arg Pro Leu Glu Ala Thr Ala Pro Thr Ala Pro Gln Pro Pro
465             470             475             480

Leu Leu Leu Leu Leu Leu Leu Pro Val Gly Leu Leu Leu Leu Ala Ala
            485             490             495

Ala Trp Cys Leu His Trp Gln Arg Thr Arg Arg Arg Thr Pro Arg Pro
            500             505             510

Gly Glu Gln Val Pro Pro Val Pro Ser Pro Gln Asp Leu Leu Leu Val
            515             520             525

Glu His
    530
```

PROTEIN HETERODIMER AND USE THEREOF

CROSS REFERENCE TO RELATED APPLICATIONS

This application is a national stage application claiming priority under 35 U.S.C. § 371 to Patent Cooperation Treaty application PCT/CN2019/098300, filed Jul. 30, 2019, which claims the benefit of Chinese Appl. No. 201810853384.X, filed Jul. 30, 2018, the text of each of which is incorporated by reference to the extent allowed.

SEQUENCE LISTING

The instant application contains a Sequence Listing which has been submitted electronically in ASCII format and is hereby incorporated by reference in its entirety. Said ASCII copy, created on Aug. 10, 2021, is named 534338USSL.txt and is 300,763 bytes in size.

FIELD OF THE INVENTION

The present application relates to the field of tumor treatment. In particular, the present application relates to a protein heterodimer and use thereof.

BACKGROUND OF THE INVENTION

Tumor is a disease that seriously threatens the health of human beings. In recent years, immunotherapy as a novel therapy has shown a great potential in the tumor treatment. Cytokine is a very important immune signal in the body, and the cytokine fusion protein technology is another important research aspect of the current tumor immunotherapy. In such a method, two or more cytokines are fused together by utilizing the genetic engineering technology based on the fact that these cytokines have the same or relevant functional activities and different acting targets. However, the effect of tumor treatment by using the cytokine protein fusion technology at present is not yet satisfactory, and needs to be improved in many aspects.

SUMMARY OF THE INVENTION

The present application provides a protein heterodimer having at least beneficial effect including good antitumor effect, as well as use thereof.

In an aspect, the present application provides a protein heterodimer including a first polypeptide chain and a second polypeptide chain different from the first polypeptide chain, wherein the first polypeptide chain includes IL12a and a first factor fused to the IL12a, the second polypeptide chain includes IL12b and a second factor fused to the IL12b, and wherein the first factor and the second factor are each independently selected from a group consisting of IL2, GMCSF, IL7, IL15, IL21 and FLT3L.

In certain embodiments, the first factor is different from the second factor.

In certain embodiments, the first factor and the second factor are different from each other and selected from a group consisting of cytokine group A and the cytokine group B, respectively, wherein the cytokine group A is selected from the group consisting of IL2, IL7, IL15 and IL21, and the cytokine group B is selected from the group consisting of GMCSF and FLT3L.

In certain embodiments, in the first polypeptide chain, the C-terminus of the IL12a is directly or indirectly fused to the N-terminus of the first factor. In certain embodiments, in the first polypeptide chain, the N-terminus of the IL12a is directly or indirectly fused to the C-terminus of the first factor. In certain embodiments, in the second polypeptide chain, the C-terminus of the IL12b is directly or indirectly fused to the N-terminus of the second factor. In certain embodiments, in the second polypeptide chain, the N-terminus of the IL12b is directly or indirectly fused to the C-terminus of the second factor.

In certain embodiments, the first factor and the second factor are selected from the group consisting of:
1) the first factor is IL2, and the second factor is GMCSF;
2) the first factor is IL7, and the second factor is GMCSF;
3) the first factor is IL15, and the second factor is GMCSF;
4) the first factor is IL21, and the second factor is GMCSF;
5) the first factor is IL2, and the second factor is FLT3L;
6) the first factor is IL7, and the second factor is FLT3L;
7) the first factor is IL15, and the second factor is FLT3L;
8) the first factor is IL21, and the second factor is FLT3L;
9) the first factor is GMCSF, and the second factor is IL2;
10) the first factor is GMCSF, and the second factor is IL7;
11) the first factor is GMCSF, and the second factor is IL15;
12) the first factor is GMCSF, and the second factor is IL21;
13) the first factor is FLT3L, and the second factor is IL2;
14) the first factor is FLT3L, and the second factor is IL7;
15) the first factor is FLT3L, and the second factor is IL15; and,
16) the first factor is FLT3L, and the second factor is IL21.

In certain embodiments, the IL12a, the IL12b, the first factor and the second factor are derived from mammals.

In certain embodiments, the IL12a, the IL12b, the first factor and the second factor are derived from the same origin.

In certain embodiments, the first polypeptide chain includes a sequence as set forth in any one of SEQ ID NO: 60-65 and SEQ ID NO: 70-73.

In certain embodiments, the second polypeptide chain includes a sequence as set forth in any one of SEQ ID NO: 66-69 and SEQ ID NO: 74-75.

In certain embodiments, the protein heterodimer includes a sequence as set forth in any one of SEQ ID NO: 18-37.

In another aspect, the present application provides one or more isolated nucleic acid molecules encoding the protein heterodimer.

In certain embodiments, the nucleic acid molecule includes a sequence as set forth in any one of SEQ ID NO: 38-57.

In another aspect, the present application provides an expression vector including a nucleotide sequence encoding the protein heterodimer.

In another aspect, the present application provides a host cell including the expression vector.

In another aspect, the present application provides a pharmaceutical composition including the protein heterodimer, the nucleic acid molecule, the vector and/or the host cell, and a pharmaceutically acceptable carrier.

In another aspect, the present application provides a method of preparing the protein heterodimer including the step of culturing the host cell under conditions that the protein heterodimer can be expressed.

In another aspect, the present application provides use of the protein heterodimer and the pharmaceutical composition in preparation of a drug for treating tumors.

In certain embodiments, the tumors include melanoma.

Persons skilled in the art can recognize other aspects and advantages of the present application from the following detailed description. The following detailed description only shows and indicates exemplary embodiments of the present application. As those skilled in the art will appreciate, the disclosure of the present application enables persons skilled in the art to modify the disclosed embodiments without departing from the spirit and scope of the present invention involved in the present application. Correspondingly, the drawings and the description in the specification of the present application are only exemplary, and not restrictive.

BRIEF DESCRIPTION OF THE DRAWINGS

The specific features of the invention involved by the present application are as shown in the appended claims. By reference to the exemplary embodiments detailedly described below and the accompanying drawings, the characteristics and advantages of the present invention involved in the present application can be better understood. The drawings are briefly described as follows.

FIGS. 2A-2C show schematic structural view of the protein heterodimer.

In FIGS. 1 and 4-16, each broken line represents the tumor area of a mouse, for example, 5 broken lines represent the data of 5 mice in an experiment the fraction represents the ratio of tumor-clearing mice to tumor-inoculated mice, for example, 10/10 represents that the ratio of the tumor-clearing mice/the tumor-inoculated mice is 10/10=100%.

DETAILED DESCRIPTION OF THE EMBODIMENTS

Figure 1:
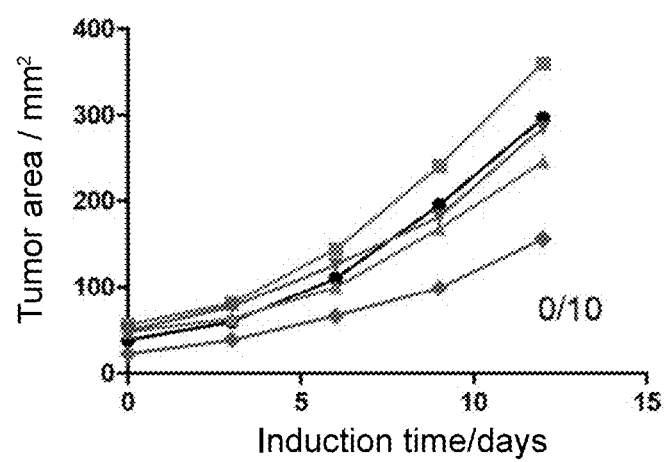
FIG. 1 shows the growth of tumor. Each broken line represents the tumor area of a mouse, for example, 5 broken lines represent the data of 5 mice in an experiment; the fraction represents the ratio of tumor-clearing mice to tumor-inoculated mice, for example, 10/10 represents that the ratio of the tumor-clearing mice/the tumor-inoculated mice is 10/10=100%.
Figure 2B:
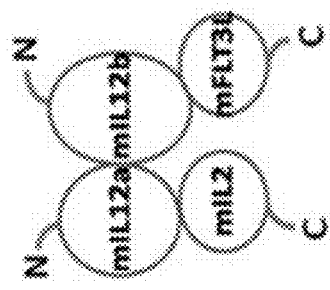
Figure 2B:
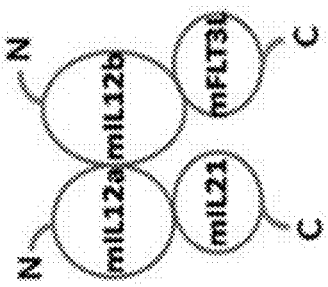
Figure 2B:
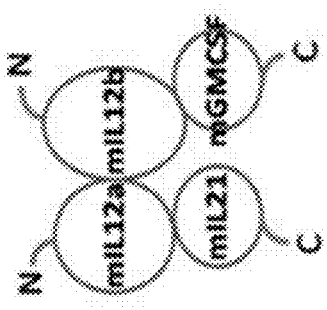
Figure 2B:
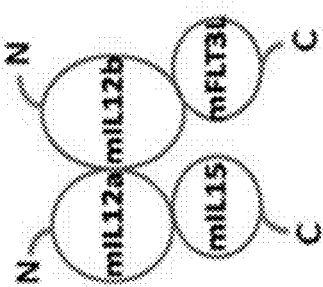
Figure 2B:
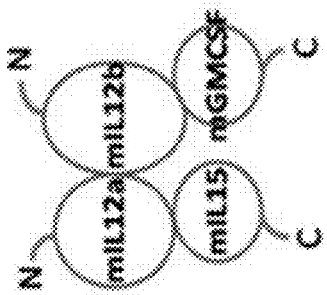
Figure 2B:
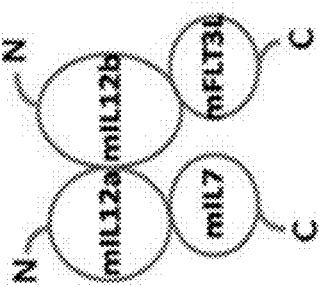
Figure 2C:
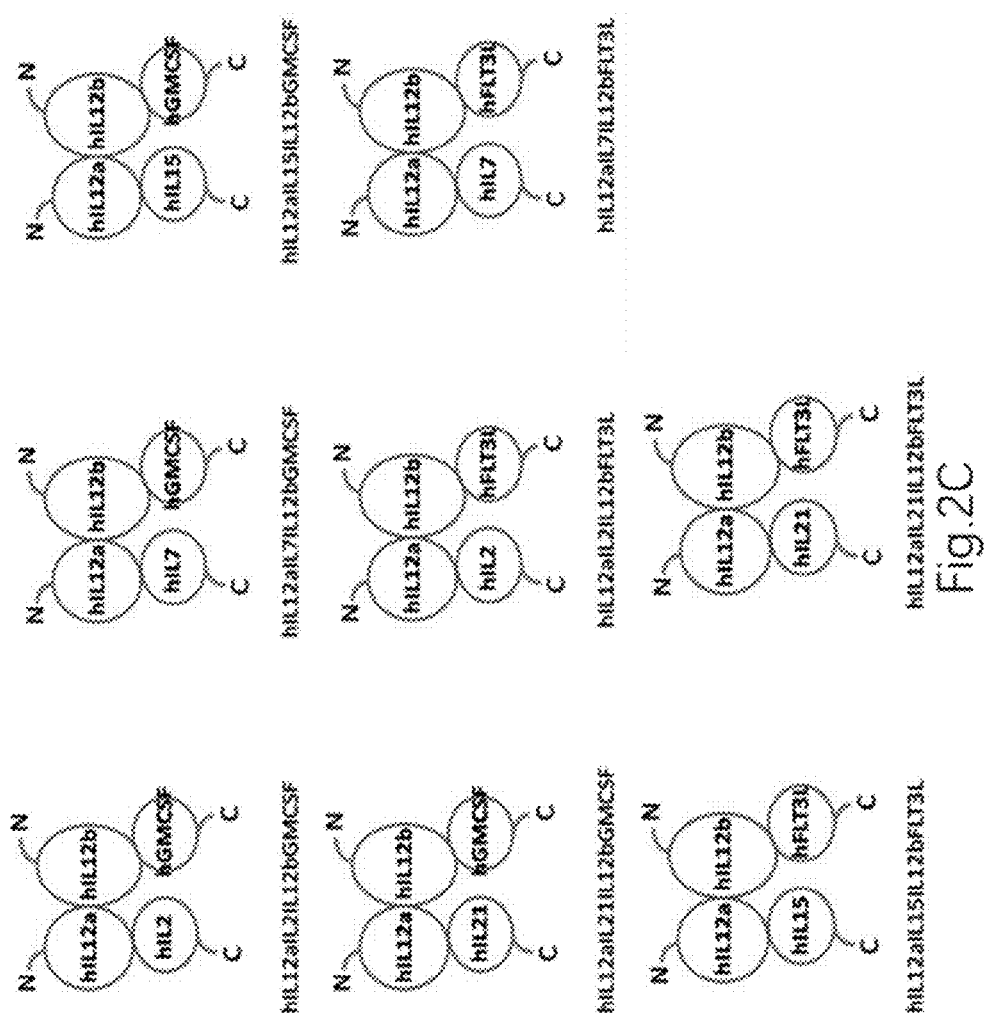

Hereinafter the embodiments of the present application are described by specific examples. Persons skilled in the art can readily understand other advantages and effects of the present invention of the present application from the disclosure of the specification.

In the present application, the term "fusion protein" refers generally to a protein consisting of two or more polypeptides. In the fusion protein, the polypeptides can have different properties that can be biological properties, such as, in vitro or in vivo activity; or can be simple chemical or physical properties, such as, binding to a target molecule, catalytic reaction, or the like. In the fusion protein, the polypeptides can be directly bonded, or can be indirectly bonded via a linker (e.g., a peptide linker) or a spacer. The fusion protein can be expressed by a fusion gene, and the nucleotide sequence encoding a polypeptide in the fusion gene can be accompanied in the frame by a nucleotide sequence encoding another polypeptide different from the polypeptide. The fusion gene can be expressed by a recombinant host cell as a single protein.

In the present application, the term "cytokine fusion protein" refers generally to include a fusion protein of two or more cytokines. The cytokine fusion protein can be obtained by gene recombination technology. The cytokine fusion protein can not only have the unique biological activities of the contained cytokines or substantially improve some of the activities, but also can exert complex biological functions that are not available in simple combinations of individual cytokines by complementary and synergistic effects of biological activities, or even may produce some new structures and biological functions. In the present application, the cytokine fusion protein can be a protein heterodimer.

In the present application, the term "protein heterodimer" is a dimer consisting of two different polypeptide chains. In the present application, the protein heterodimer can include a first polypeptide chain and a second polypeptide chain, wherein the first polypeptide chain is different from the second polypeptide chain, and wherein the first polypeptide chain can include IL12a and the first factor fused to the IL12a, the second polypeptide chain can include IL12b and a second factor fused to the IL12b.

In the present application, the term "cytokine" refers generally to a small molecular protein that is primarily secreted by immune cells and can serve to adjust the cellular functions. The cytokines play an important regulatory role in the interaction, growth, and differentiation of cells. For instance, the cytokine can be selected from the group consisting of interleukins and colony stimulating factors. In the present application, interleukins are a type of cytokines that are generated by a plurality of cells and act on a plurality of cells. Interleukins play important roles in information transmission; activation and regulation of immune cells; mediation of activation, proliferation and differentiation of T and B cells; and inflammatory reaction. For instance, the interleukins can be one or more selected from the group consisting of IL12, IL2, IL15, IL21 and IL7. In the present application, the colony stimulating factors can be cytokines that can stimulate different hematopoietic stem cells to form cell colonies in a semi-solid medium. The colony stimulating cytokines produce an effect of promoting the proliferation and differentiation of hematopoietic stem cells in different developmental stages. For instance, according to the acting scope of colony stimulating factors, the colony stimulating factors can be named as granulocyte colony stimulating factors (G-CSF), macrophage colony stimulating factors (M-CSF), granulocyte and macrophage colony stimulating factors (GM-CSF), and multipotent colony stimulating factors (multi-CSF, IL3), respectively. For instance, the colony stimulating factors can be one or more selected from the group consisting of FMS-related tyrosine kinase 3 ligand (FTL3L) and granulocyte macrophage colony stimulating factors (GMCSF).

In the present application, the term "IL12" refers generally to interleukins-12. In the present application, IL12 and IL-12 can be used interchangeably. IL12 can stimulate the proliferation of activated T cells, promote the differentiation of Th0 cells to Th1 cells; and can also induce the cytotoxic activity of CTL and NK cells and promote their secretion of cytokines, such as, IFN-γ, TNF-α, GM-CSF, etc.; or promote the expression of NK cells and IL-2Ra receptors and CD56 molecules, and enhance the ADCC effect on tumor cells. IL12 is a heterodimer including p40 subunit (40 kd) and p35 subunit (35 kd), both of which can be linked via a disulfide bond. For instance, the p35 subunits within mouse IL12 (mIL12) can include the amino acid sequence as set forth in SEQ ID NO:1, and the p40 subunits can include the amino acid sequence as set forth in SEQ ID NO:2. Alternatively, for example, the p35 subunits within human IL12 (hIL12) can include the amino acid sequence as set forth in SEQ ID NO:9, p40 subunit can include the amino acid sequence as set forth in SEQ ID NO:10.

In the present application, the term "IL2" refers generally to interleukins-2. IL2 plays an important role in the immune response, antiviral infection of organisms, and the like, and can stimulate the proliferation of T cells initiated by specific antigens. Meanwhile, IL2 can activate T cells, promote the production of cytokines; stimulate the proliferation of NK cells, enhance the NK killing activity and produce cytokines, induce the production of LAK cells; promote the proliferation of B cells and secret antibodies; and activate macrophages. For instance, mouse IL2 (mIL2) can include the amino acid sequence as set forth in SEQ ID NO:3. Alternatively, for example, human cytokine IL2 (hIL2) can include the amino acid sequence as set forth in SEQ ID NO:11.

In the present application, the term "IL15" refers generally to interleukins-15. IL15 is produced by a plurality of cells including activated mononuclear macrophages, epidermal cells and fibroblasts, etc., that can induce the proliferation and differentiation of B cells. For instance, mouse IL15 (mIL15) can include the amino acid sequence as set forth in SEQ ID NO:4. Alternatively, for example, human IL15 (hIL15) can include the amino acid sequence as set forth in SEQ ID NO:12.

In the present application, the term "IL7" refers generally to interleukin-7. IL7 is mainly secreted by thymus and bone marrow stromal cells, and belongs to glycoproteins with a molecular weight of 25000-28000. The signal transduction pathway mediated by IL7 and a receptor thereof is mainly achieved by three pathways, such as, Janus kinase, activator of signal transduction and transcription, and phosphoinositide 3-kinase. For example, mouse IL7 (mIL7) can include an amino acid sequence as set forth in SEQ ID NO:5. Alternatively, for example, human IL7 (hIL7) can include an amino acid sequence as set forth in SEQ ID NO:13.

In the present application, the term "IL21" refers generally to interleukin-21. IL21 is secreted by activated CD4+ T-cells. IL21 participates in the proliferation of B-cells, and the deletion of IL21 gene can cause that the organisms are more likely to be infected by bacteria or viruses. Studies indicate that the expression level of IL2 receptor protein (CD25) can be influenced by regulating the Bcl-6 protein. For example, mouse IL21 (mIL21) can include an amino acid sequence as set forth in SEQ ID NO:6. Alternatively, for example, human IL21 (hIL21) can include an amino acid sequence as set forth in SEQ ID NO:14.

In the present application, the term "FTL3L" refers generally to a ligand of FMS-associated tyrosine kinase 3. FTL3L can regulate the proliferation and differentiation of non-erythroid hematopoietic stem cells, promote the proliferation, differentiation and maturation of pre-B lymphocytes, dendritic cells, NK cells and cytotoxic T lymphocytes, and has an important anti-tumor effect. For example, mouse FTL3L (mFTL3L) can include an amino acid sequence as set forth in SEQ ID NO:7. Alternatively, for example, human FTL3L (hFTL3L) can include an amino acid sequence as set forth in SEQ ID NO:15.

In the present application, the term "GMCSF" refers generally to granulocyte macrophage colony stimulating factor. GMCSF can stimulate the proliferation, differentiation and activation of granulocytes and macrophages, increase hematopoietic function, and can also enhance a variety of functions of neutrophils, eosinophils and monocytes. GMCSF can improve the immune activity that the immune effector cells phagocytize bacteria and kill cancer cells, and facilitates the recovery of neutropenia caused by tumor chemotherapy and bone marrow transplantation. For example, mouse GMCSF (mGMCSF) can include an amino acid sequence as set forth in SEQ ID NO:8. Alternatively, for example, human GMCSF (hGMCSF) can include an amino acid sequence as set forth in SEQ ID NO:16.

In the present application, the term "nucleic acid molecule" generally refers to any length of isolated form of nucleotide, deoxyribonucleotide or ribonucleotide or their analogues that are isolated from its natural environment or artificially synthesized. In the present application, the nucleic acid molecule can encode the protein heterodimer including a nucleotide sequence as set forth in any one of SEQ ID NO.38-57.

In the present application, the term "vector" refers generally to a nucleic acid molecule capable of self-replicating in a suitable host. The vector can transfer the incorporated nucleic acid molecule into and/or between the host cells. The vector can include a vector that is mainly used for incorporating DNA or RNA into a cell, a vector that is mainly used for the replication of DNA or RNA, and a vector that is mainly used for transcription and/or translation of DNA or RNA. The vector can further include those having a plurality of the above-described functions. The vector can be a polynucleotide that can be transcribed and translated to a peptide when introduced into a suitable host cell. Typically, the vector can produce the desired expression product by culturing a proper host cell including the vector.

In the present application, the term "host cell" refers generally to an individual cell, cell line or cell culture that can include or has included a plasmid or vector including the nucleic acid molecule of the present application, or can express the protein heterodimer of the present application. The cell can include offsprings of a single host cell. Due to natural, accidental, or intentional mutation, daughter cells may not be completely identical to the original parent cells in morphology or genome, as long as they can express the protein heterodimers of the present application. The host cell can be produced by transfecting the host cell with the vector of the present application in vitro. In the present application, the host cell capable of expressing the protein heterodimer of the present application can be produced by transfecting B16 (rtTA) tumor cells or 293A cells with virus expressing the vector.

In the present application, the term "pharmaceutically acceptable carrier" refers generally to one of the ingredients of a pharmaceutical composition which can include buffers, antioxidants, preservatives, low molecular weight polypeptides, proteins, hydrophilic polymers, amino acids, hydrocarbons, chelants, counter ions, metal complexes and/or nonionic surfactants, etc. For example, the pharmaceutically acceptable vector can include excipients, e.g., the excipients can be selected from a group consisting of starches, dextrin, sucrose, lactose, magnesium stearate, calcium sulfate, carboxymethyl cellulose, talc powder, calcium alginate gel, chitosan, and nano-spheres, etc. For example, the pharmaceutically acceptable carrier can also be selected from a group consisting of pH regulators, osmotic pressure regulator, solubilizers, and antimicrobials.

In the present application, the term "tumor" generally refers to or describes a physiological condition typically characterized by the dysfunction of cell proliferation or survival. For example, the tumor can be selected from a group of lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, anterior adenocarcinoma, testicular cancer, renal cancer, bladder cancer, eyelid cancer, leukemia and lymphoma.

Protein Heterodimers

In an aspect, the present application provides a protein heterodimer including a first polypeptide chain and a second polypeptide chain different from the first peptide chain, wherein the first polypeptide chain can include IL12a and a first factor fused to the IL12a, the second peptide chain can include IL12b and a second factor fused to IL12b, and wherein the first and the second factors can be each independently selected from a group consisting of IL2, GMCSF, IL7, IL15, IL21 and FLT3L.

In the present application, the first factor can be different from the second factor. In the present application, the protein heterodimer can be a cytokine fusion protein in which two or more of the cytokines, i.e., IL12 and IL2, GMCSF, IL7, IL15, IL21 and FLT3L can be fused together by gene recombination technology. The protein heterodimer can not only have the unique biological activities of its components, but also play a biological function that is not possessed by individual cytokines through the complementary and synergistic effect of biological activities, or even produce some new structures and biological functions.

In the present application, the first factor and the second factor can be each independently selected from cytokine group A and cytokine group B, respectively, wherein the cytokine group A can be selected from the following groups: IL2, IL7, IL15 and IL21, and the cytokine group B can be selected from the following groups: GMCSF and FLT3L.

For example, the first factor can be selected as IL2 in the cytokine group A, and the second factor can be selected as GMCSF in the cytokine group B; or the first factor can be selected as IL7 in the cytokine group A, and the second factor can be selected as GMCSF in the cytokine group B; or the first factor can be selected as IL15 in the cytokine group A, and the second factor can be selected as GMCSF in the cytokine group B; or the first factor can be selected as IL21 in the cytokine group A, and the second factor can be selected as GMCSF in the cytokine group B; or the first factor can be selected as IL2 in the cytokine group A, and the second factor can be selected as FLT3L in the cytokine group B; or the first factor can be selected as IL7 in the cytokine group A, and the second factor can be selected as FLT3L in the cytokine group B; or the first factor can be selected as IL15 in the cytokine group A, and the second factor can be selected as FLT3L in the cytokine group B; or the first factor can be selected as IL21 in the cytokine group A, and the second factor can be selected as FLT3L in the cytokine group B; or the second factor can be selected as IL2 in the cytokine group A, and the first factor can be selected as GMCSF in the cytokine group B; or the second factor can be selected as IL7 in the cytokine group A, and the first factor can be selected as GMCSF in the cytokine group B; or the second factor can be selected as IL15 in the cytokine group A, and the first factor can be selected as GMCSF in the cytokine group B; or the second factor can be selected as IL21 in the cytokine group A, and the first factor can be selected as GMCSF in the cytokine group B; or the second factor can be selected as IL2 in the cytokine group A, and the first factor can be selected as FLT3L in the cytokine group B; or the second factor can be selected as IL7 in the cytokine group A, and the first factor can be selected as FLT3L in the cytokine group B; or the second factor can be selected as IL15 in the cytokine group A, and the first factor can be selected as FLT3L in the cytokine group B; or the second factor can be selected as IL21 in the cytokine group A, and the first factor can be selected as FLT3L in the cytokine group B.

In the present application, in the first peptide chain, the C-terminus of IL12a can be directly or indirectly fused to the N-terminus of the first factor. For example, in the first polypeptide chain, the C-terminus of IL12a can be directly or indirectly fused to the N-terminus of IL2; or in the first polypeptide chain, the C-terminus of IL12a can be directly or indirectly fused to the N-terminus of IL7; or in the first polypeptide chain, the C-terminus of IL12a can be directly or indirectly fused to the N-terminus of IL15; or in the first polypeptide chain, the C-terminus of IL12a can be directly or indirectly fused to the N-terminus of IL21; or in the first polypeptide chain, the C-terminus of IL12a can be directly or indirectly fused to the N-terminus of GMCSF; or in the first polypeptide chain, the C-terminus of IL12a can be directly or indirectly fused to the N-terminus of FLT3L.

In the present application, in the first peptide chain, the N-terminus of the IL12a can be directly or indirectly fused to the C-terminus of the first factor. For example, in the first peptide chain, the N-terminus of the IL12a can be directly or indirectly fused to the C-terminus of the IL2; or in the first peptide chain, the N-terminus of the IL12a can be directly or indirectly fused to the C-terminus of the IL7; or in the first peptide chain, the N-terminus of the IL12a can be directly or indirectly fused to the C-terminus of the IL15; or in the first peptide chain, the N-terminus of the IL12a can be directly or indirectly fused to the C-terminus of the IL21; or in the first peptide chain, the N-terminus of the IL12a can be directly or indirectly fused to the C-terminus of the GMCSF; or in the first peptide chain, the N-terminus of the IL12a can be directly or indirectly fused to the C-terminus of the FLT3L.

In the present application, in the second polypeptide chain, the C-terminus of the IL12b can be directly or indirectly fused to the N-terminus of the second factor. For example, in the second polypeptide chain, the C-terminus of the IL12b can be directly or indirectly fused to the N-terminus of the IL2; or in the second polypeptide chain, the C-terminus of the IL12b can be directly or indirectly fused to the N-terminus of the IL7; or in the second polypeptide chain, the C-terminus of the IL12b can be directly or indirectly fused to the N-terminus of the IL15; or in the second polypeptide chain, the C-terminus of the IL12b can be directly or indirectly fused to the N-terminus of the IL21; or in the second polypeptide chain, the C-terminus of the IL12b can be directly or indirectly fused to the N-terminus of the GMCSF; or in the second polypeptide chain, the C-terminus of the IL12b can be directly or indirectly fused to the N-terminus of the FLT3L.

In the present application, in the second polypeptide chain, the N-terminus of the IL12b can be directly or indirectly fused to the C-terminus of the second factor. For example, in the second polypeptide chain, the N-terminus of the IL12b can be directly or indirectly fused to the C-terminus of the IL2; or in the second polypeptide chain, the N-terminus of the IL12b can be directly or indirectly fused to the C-terminus of the IL7; or in the second polypeptide chain, the N-terminus of the IL12b can be directly or indirectly fused to the C-terminus of the IL15; or in the second polypeptide chain, the N-terminus of the IL12b can be directly or indirectly fused to the C-terminus of the IL21; or in the second polypeptide chain, the N-terminus of the IL12b can be directly or indirectly fused to the C-terminus of the GMCSF; or in the second polypeptide chain, the N-terminus of the IL12b can be directly or indirectly fused to the C-terminus of the FLT3L.

In the present application, the protein heterodimer can include any arrangement combination of all the positional connection relationships of the cytokines.

In the present application, the first factor and the second factor can be selected from a group consisting of:

1) the first factor can be IL2, and the second factor can be GMCSF;
2) the first factor can be IL7, and the second factor can be GMCSF;
3) the first factor can be IL15, and the second factor can be GMCSF;
4) the first factor can be IL21, and the second factor can be GMCSF;
5) the first factor can be IL2, and the second factor can be FLT3L;
6) the first factor can be IL7, and the second factor can be FLT3L;
7) the first factor can be IL15, and the second factor can be FLT3L;
8) the first factor can be IL21, and the second factor can be FLT3L;
9) the first factor can be GMCSF, and the second factor can be IL2;
10) the first factor can be GMCSF, and the second factor can be IL7;
11) the first factor can be GMCSF, and the second factor can be IL15;
12) the first factor can be GMCSF, and the second factor can be IL21;
13) the first factor can be FLT3L, and the second factor can be IL2;
14) the first factor can be FLT3L, and the second factor can be IL7;
15) the first factor can be FLT3L, and the second factor can be IL15; and
16) the first factor can be FLT3L, and the second factor can be IL21.

In the present application, the IL12a and the first factor and/or the IL12b and the second factor can be linked to each other via a linker peptide. For example, the amino acid sequence of the linker peptide can be as set forth in SEQ ID NO. 17.

In the present application, the IL12a and the IL12b can be covalently bonded to each other via a disulfide bond. In the present application, the first polypeptide chain and the second polypeptide chain can be bonded via a disulfide between the IL12a and the IL12b to form the protein heterodimer. In certain embodiments, a nucleotide sequence encoding a self-cleavage peptide can be included between the nucleotide sequences encoding the first polypeptide chain and the second polypeptide chain. For example, when an expression vector including the aforesaid nucleotide sequence is transcribed and translated, the site of the self-cleavage peptide will be cleaved so as to construct the protein heterodimer including the first polypeptide chain and the second polypeptide chain and formed by a disulfide. In certain embodiments, when constructing the expression vector, the first polypeptide chain and the second polypeptide chain can be linked to each other via a 2A self-splicing peptide or a flexible amino acid joint peptide. For example, the amino acid sequence of the 2A self-splicing peptide can have an amino acid sequence as set forth in SEQ ID NO.58, and the nucleotide sequence encoding 2A self-splicing peptide can be as set forth in SEQ ID NO.59. Alternatively, for example, the flexible amino acid joint peptide can have an amino acid sequence as set forth in SEQ ID. 17.

In certain embodiments, the joint peptide can also be included between the first polypeptide chain and the second polypeptide chain.

For example, in the protein heterodimer, the C-terminus of the IL12a can be fused to the N-terminus of the IL2 to form the first polypeptide chain, and the C-terminus of the IL12b can be fused to the N-terminus of GMCSF to form the second polypeptide chain, so as to form the IL12a-IL2-IL12b-GMCSF protein heterodimer.

For example, in the protein heterodimer, the C-terminus of the IL2 can be fused to the N-terminus of the IL12a to form the first polypeptide chain, and the C-terminus of the IL12b can be fused to the N-terminus of GMCSF to form the second polypeptide chain, so as to form IL2-IL12a-IL12b-GMCSF protein heterodimer.

For example, in the protein heterodimer, the C-terminus of the IL12a can be fused to the N-terminus of the IL2 to form the first polypeptide chain, and the C-terminus of the GMCSF can be fused to the N-terminus of the IL12b to form the second polypeptide chain, so as to form IL12a-IL2-GMCSF-IL12b protein heterodimer.

For example, in the protein heterodimer, the C-terminus of the IL2 can be fused to the N-terminus of the IL12a to form the first polypeptide chain, and the C-terminus of the GMCSF can be fused to the N-terminus of the IL12b to form the second polypeptide chain, so as to form IL2-IL12a-GMCSF-IL12b protein heterodimer.

For example, in the protein heterodimer, the C-terminus of the IL12a can be fused to the N-terminus of the GMCSF to form the first polypeptide chain, and the C-terminus of the IL12b can be fused to the N-terminus of the IL2 to form the second polypeptide chain, so as to form IL12a-GMCSF-IL12b-IL2 protein heterodimer.

For example, in the protein heterodimer, the C-terminus of the IL12a can be fused to the N-terminus of the IL7 to form the first polypeptide chain, and the C-terminus of the IL12b can be fused to the N-terminus of GMCSF to form the second polypeptide chain, so as to form IL12a-IL7-IL12b-GMCSF protein heterodimer.

For example, in the protein heterodimer, the C-terminus of the IL12a can be fused to the N-terminus of the IL15 to form the first polypeptide chain, and the C-terminus of the IL12b can be fused to the N-terminus of GMCSF to form the second polypeptide chain, so as to form IL12a-IL15-IL12b-GMCSF protein heterodimer.

For example, in the protein heterodimer, the C-terminus of the IL12a can be fused to the N-terminus of the IL21 to form the first polypeptide chain, and the C-terminus of the IL12b can be fused to the N-terminus of GMCSF to form the second polypeptide chain, so as to form IL12a-IL21-IL12b-GMCSF protein heterodimer.

For example, in the protein heterodimer, the C-terminus of the IL12a can be fused to the N-terminus of the IL2 to form the first polypeptide chain, and the C-terminus of the IL12b can be fused to the N-terminus of the FLT3L to form the second polypeptide chain, so as to form IL12a-IL2-IL12b-FLT3L protein heterodimer.

For example, in the protein heterodimer, the C-terminus of the IL12a can be fused to the N-terminus of the IL7 to form the first polypeptide chain, and the C-terminus of the IL12b can be fused to the N-terminus of the FLT3L to form the second polypeptide chain, so as to form IL12a-IL7-IL12b-FLT3L protein heterodimer.

For example, in the protein heterodimer, the C-terminus of the IL12a can be fused to the N-terminus of the IL15 to form the first polypeptide chain, and the C-terminus of the IL12b can be fused to the N-terminus of the FLT3L to form the second polypeptide chain, so as to form IL12a-IL15-IL12b-FLT3L protein heterodimer.

For example, in the protein heterodimer, the C-terminus of the IL12a can be fused to the N-terminus of the IL21 to form the first polypeptide chain, and the C-terminus of the IL12b can be fused to the N-terminus of the FLT3L to form the second polypeptide chain, so as to form IL12a-IL21-IL12b-FLT3L protein heterodimer.

In the present application, the IL12a, the IL12b, the first factor and the second factor can be derived from mammals. For example, the mammals can be selected from a group consisting of: human, mouse, rat, monkey, dog, pig, sheep, cow and cat. In the present application, the mammals can be selected from a group consisting of: human, mouse. For example, the IL12a, IL12b, IL2, GMCSF, IL7, IL15, IL21 and FLT3L can be selected from mouse; and the mouse-originated IL12a, IL12b, IL2, GMCSF, IL7, IL15, IL21 and FLT3L can be abbreviated as mIL12a, mIL12b, mIL2, mGMCSF, mIL7, mIL15, mIL21 and mFLT3L. For example, the IL12a, IL12b, IL2, GMCSF, IL7, IL15, IL21 and FLT3L can be selected from human, the human-originated IL12a, IL12b, IL2, GMCSF, IL7, IL15, IL21 and FLT3L can be abbreviated as hIL12a, hIL12b, hIL2, hGMCSF, hIL7, hIL15, hIL21 and hFLT3L.

In the present application, the IL12a, the IL12b, the first factor and the second factor can be from the same origin.

In the present application, the first polypeptide chain can include a sequence as set forth in any one of SEQ ID NO.60-65 and SEQ ID NO.70-73.

In the present application, the second polypeptide chain can include a sequence as set forth in any one of SEQ ID NO.66-69 and SEQ ID NO.74-75.

In the present application, the protein heterodimer can include a sequence as set forth in any one of SEQ ID NO.18-37.

For example, in the protein heterodimer, the C-terminus of the mIL12a and the N-terminus of the mIL2 can be fused to form the mIL12a-mIL2 first polypeptide chain (with a sequence as set forth in SEQ ID NO.60), and the C-terminus of the mIL12b and the N-terminus of the mGMCSF can be fused to form the mIL12b-mGMCSF second polypeptide chain (with a sequence as set forth in SEQ ID NO.66), so as to form the mIL12a-mIL2-mIL12b-mGMCSF protein heterodimer (with a sequence as set forth in SEQ ID NO.18).

For example, in the protein heterodimer, the C-terminus of the mIL2 and the N-terminus of the mIL12a can be fused to form the mIL2-mIL12a first polypeptide chain (with a sequence as set forth in SEQ ID NO.61), and the C-terminus of the mIL12b and the N-terminus of the mGMCSF can be fused to form the mIL12b-mGMCSF second polypeptide chain (with a sequence as set forth in SEQ ID NO.66), so as to form the mIL2-mIL12a-mIL12b-mGMCSF protein heterodimer (with a sequence as set forth in SEQ ID NO.19).

For example, in the protein heterodimer, the C-terminus of the mIL12a and the N-terminus of the mIL2 can be fused to form the mIL12a-mIL2 first polypeptide chain (with a sequence as set forth in SEQ ID NO.60), and the C-terminus of the mGMCSF and the N-terminus of the mIL12b can be fused to form the mGMCSF-mIL12b second polypeptide chain (with a sequence as set forth in SEQ ID NO.67), so as to form the mIL12a-mIL2-mGMCSF-mIL12b protein heterodimer (with a sequence as set forth in SEQ ID NO.20).

For example, in the protein heterodimer, the C-terminus of the mIL2 and the N-terminus of the mIL12a can be fused to form the mIL2-mIL12a first polypeptide chain (with a sequence as set forth in SEQ ID NO.61), and the C-terminus of the mGMCSF and the N-terminus of the mIL12b can be fused to form the mGMCSF-mIL12b second polypeptide chain (with a sequence as set forth in SEQ ID NO.67), so as to form the mIL2-mIL12a-mGMCSF-mIL12b protein heterodimer (with a sequence as set forth in SEQ ID NO.21).

For example, in the protein heterodimer, the C-terminus of the mIL12a and the N-terminus of the mGMCSF can be fused to form the mIL12a-mGMCSF first polypeptide chain (with a sequence as set forth in SEQ ID NO.62), and the C-terminus of the mIL12b and the N-terminus of the mIL2 can be fused to form the mIL12b-mIL2 second polypeptide chain (with a sequence as set forth in SEQ ID NO.68), so as to form the mIL12a-mGMCSF-mIL12b-mIL2 protein heterodimer (with a sequence as set forth in SEQ ID NO.22).

For example, in the protein heterodimer, the C-terminus of the mIL12a and the N-terminus of the mIL7 can be fused to form the mIL12a-mIL7 first polypeptide chain (with a sequence as set forth in SEQ ID NO.63), and the C-terminus of the mIL12b and the N-terminus of the mGMCSF can be fused to form the mIL12b-mGMCSF second polypeptide chain (with a sequence as set forth in SEQ ID NO.66), so as to form the mIL12a-mIL7-mIL12b-mGMCSF protein heterodimer (with a sequence as set forth in SEQ ID NO.23).

For example, in the protein heterodimer, the C-terminus of the mIL12a and the N-terminus of the mIL5 can be fused to form the mIL12a-mIL15 first polypeptide chain (with a sequence as set forth in SEQ ID NO.64), and the C-terminus of the mIL12b and the N-terminus of the mGMCSF can be fused to form the mIL12b-mGMCSF second polypeptide chain (with a sequence as set forth in SEQ ID NO.66), so as to form the mIL12a-mIL15-mIL12b-mGMCSF protein heterodimer (with a sequence as set forth in SEQ ID NO.24).

For example, in the protein heterodimer, the C-terminus of the mIL12a and the N-terminus of the mIL21 can be fused to form the mIL12a-mIL21 first polypeptide chain (with a sequence as set forth in SEQ ID NO.65), and the C-terminus of the mIL12b and the N-terminus of the mGMCSF can be fused to form the mIL12b-mGMCSF second polypeptide chain (with a sequence as set forth in SEQ ID NO.66), so as to form the mIL12a-mIL21-mIL12b-mGMCSF protein heterodimer (with a sequence as set forth in SEQ ID NO.25).

For example, in the protein heterodimer, the C-terminus of the mIL12a and the N-terminus of the mIL2 can be fused to form the mIL12a-mIL2 first polypeptide chain (with a sequence as set forth in SEQ ID NO.60), and the C-terminus of the mIL12b and the N-terminus of the mFLT3L can be fused to form the mIL12b-mFLT3L second polypeptide chain (with a sequence as set forth in SEQ ID NO.69), so as to form the mIL12a-mIL2-mIL12b-mFLT3L protein heterodimer (with a sequence as set forth in SEQ ID NO.26).

For example, in the protein heterodimer, the C-terminus of the mIL12a and the N-terminus of the mIL7 can be fused to form the mIL12a-mIL7 first polypeptide chain (with a sequence as set forth in SEQ ID NO.63), and the C-terminus of the mIL12b and the N-terminus of the mFLT3L can be fused to form the mIL12b-mFLT3L second polypeptide chain (with a sequence as set forth in SEQ ID NO.69), so as to form the mIL12a-mIL7-mIL12b-mFLT3L protein heterodimer (with a sequence as set forth in SEQ ID NO.27).

For example, in the protein heterodimer, the C-terminus of the mIL12a and the N-terminus of the mIL5 can be fused to form the mIL12a-mIL15 first polypeptide chain (with a sequence as set forth in SEQ ID NO.64), and the C-terminus of the mIL12b and the N-terminus of the mFLT3L can be fused to form the mIL12b-mFLT3L second polypeptide chain (with a sequence as set forth in SEQ ID NO.69), so as to form the mIL12a-mIL15-mIL12b-mFLT3L protein heterodimer (with a sequence as set forth in SEQ ID NO.28).

For example, in the protein heterodimer, the C-terminus of the mIL12a and the N-terminus of the mIL21 can be fused to form the mIL12a-mIL21 first polypeptide chain (with a sequence as set forth in SEQ ID NO.65), and the C-terminus of the mIL12b and the N-terminus of the mFLT3L can be fused to form the mIL12b-mFLT3L second polypeptide chain (with a sequence as set forth in SEQ ID NO.69), so as to form the mIL12a-mIL21-mIL12b-mFLT3L protein heterodimer (with a sequence as set forth in SEQ ID NO.29).

For example, in the protein heterodimer, the C-terminus of the hIL12a and the N-terminus of the hIL2 can be fused to form the hIL12a-hIL2 first polypeptide chain (with a sequence as set forth in SEQ ID NO.70), and the C-terminus of the hIL12b and the N-terminus of the hGMCSF can be fused to form the hIL12b-hGMCSF second polypeptide chain (with a sequence as set forth in SEQ ID NO.74), so as to form the hIL12a-hIL2-hIL12b-hGMCSF protein heterodimer (with a sequence as set forth in SEQ ID NO.30).

For example, in the protein heterodimer, the C-terminus of the hIL12a and the N-terminus of the hIL7 can be fused to form the hIL12a-hIL7 first polypeptide chain (with a sequence as set forth in SEQ ID NO.71), and the C-terminus of the hIL12b and the N-terminus of the hGMCSF can be fused to form the hIL12b-hGMCSF second polypeptide chain (with a sequence as set forth in SEQ ID NO.74), so as to form the hIL12a-hIL7-hIL12b-hGMCSF protein heterodimer (with a sequence as set forth in SEQ ID NO.31).

For example, in the protein heterodimer, the C-terminus of the hIL12a and the N-terminus of the hIL15 can be fused to form the hIL12a-hIL15 first polypeptide chain (with a sequence as set forth in SEQ ID NO.72), and the C-terminus of the hIL12b and the N-terminus of the hGMCSF can be fused to form the hIL12b-hGMCSF second polypeptide chain (with a sequence as set forth in SEQ ID NO.74), so as to form the hIL12a-hIL15-hIL12b-hGMCSF protein heterodimer (with a sequence as set forth in SEQ ID NO.32).

For example, in the protein heterodimer, the C-terminus of the hIL12a and the N-terminus of the hIL21 can be fused to form the hIL12a-hIL21 first polypeptide chain (with a sequence as set forth in SEQ ID NO.73), and the C-terminus of the hIL12b and the N-terminus of the hGMCSF can be fused to form the hIL12b-hGMCSF second polypeptide chain (with a sequence as set forth in SEQ ID NO.74), so as to form the hIL12a-hIL21-hIL12b-hGMCSF protein heterodimer (with a sequence as set forth in SEQ ID NO.33).

For example, in the protein heterodimer, the C-terminus of the hIL12a and the N-terminus of the hIL2 can be fused to form the hIL12a-hIL2 first polypeptide chain (with a sequence as set forth in SEQ ID NO.70), and the C-terminus of the hIL12b and the N-terminus of the hFLT3L can be fused to form the hIL12b-hFLT3L second polypeptide chain (with a sequence as set forth in SEQ ID NO.75), so as to form the hIL12a-hIL2-hIL12b-hFLT3L protein heterodimer (with a sequence as set forth in SEQ ID NO.34).

For example, in the protein heterodimer, the C-terminus of the hIL12a and the N-terminus of the hIL7 can be fused to form the hIL12a-hIL7 first polypeptide chain (with a sequence as set forth in SEQ ID NO.71), and the C-terminus of the hIL12b and the N-terminus of the hFLT3L can be fused to form the hIL12b-hFLT3L second polypeptide chain (with a sequence as set forth in SEQ ID NO.75), so as to form the hIL12a-hIL7-hIL12b-hFLT3L protein heterodimer (with a sequence as set forth in SEQ ID NO.35).

For example, in the protein heterodimer, the C-terminus of the hIL12a and the N-terminus of the hIL15 can be fused to form the hIL12a-hIL15 first polypeptide chain (with a sequence as set forth in SEQ ID NO.72), and the C-terminus of the hIL12b and the N-terminus of the hFLT3L can be fused to form the hIL12b-hFLT3L second polypeptide chain (with a sequence as set forth in SEQ ID NO.75), so as to form the hIL12a-hIL15-hIL12b-hFLT3L protein heterodimer (with a sequence as set forth in SEQ ID NO.36).

For example, in the protein heterodimer, the C-terminus of the hIL12a and the N-terminus of the hIL21 can be fused to form the hIL12a-hIL21 first polypeptide chain (with a sequence as set forth in SEQ ID NO.73), and the C-terminus of the hIL12b and the N-terminus of the hFLT3L can be fused to form the hIL12b-hFLT3L second polypeptide chain (with a sequence as set forth in SEQ ID NO.75), so as to form the hIL12a-hIL21-hIL12b-hFLT3L protein heterodimer (with a sequence as set forth in SEQ ID NO.37).

In the present application, the mIL12a-mIL2-mIL12b-mGMCSF, mIL2-mIL12a-mIL12b-mGMCSF, mIL12a-mIL2-mGMCSF-mIL12b, mIL2-mIL12a-mGMCSF-mIL12b, mIL12a-mGMCSF-mIL12b-mIL2, mIL12a-mIL7-mIL12b-mGMCSF, mIL12a-mIL15-mIL12b-mGMCSF, mIL12a-mIL21-mIL12b-mGMCSF, mIL12a-mIL2-mIL12b-mFLT3L, mIL12a-mIL7-mIL12b-mFLT3L, mIL12a-mIL15-mIL12b-mFLT3L, mIL12a-mIL21-mIL12b-mFLT3L, hIL12a-hIL2-hIL12b-hGMCSF, hIL12a-hIL7-hIL12b-hGMCSF, hIL12a-hIL15-hIL12b-hGMCSF, hIL12a-hIL21-hIL12b-hGMCSF, hIL12a-hIL2-hIL12b-hFLT3L, hIL12a-hIL7-hIL12b-hFLT3L, hIL12a-hIL15-hIL12b-hFLT3L and hIL12a-hIL21-hIL12b-hFLT3L can be sequentially abbreviated as mIL12aIL2IL12bGMCSF, mIL2IL12aIL12bGMCSF, mIL12aIL2GMCSFIL12b, mIL2IL12aGMCSFIL12b, mIL12aGMCSFIL12bIL2, mIL12aIL7IL12bGMCSF, mIL12aIL151L12bGMCSF, mIL12aIL21IL12bGMCSF, mIL12aIL2IL12bFLT3L, mIL12aIL71L12bFLT3L, mIL12aIL15IL12bFLT3L, mIL12aIL21IL12bFLT3L, hIL12aIL2IL12bGMCSF, hIL12aIL7IL12bGMCSF, hIL12aIL15IL12bGMCSF, hIL12aIL21IL12bGMCSF, hIL12aIL2IL12bFLT3L, hIL12aIL7IL12bFLT3L, hIL12aIL15IL12bFLT3L and hIL12aIL21IL12bFLT3L, respectively. The protein heterodimer can have a structure as shown in FIG. 2.

In the present application, the protein heterodimer can be used for treating tumors.

In another aspect, the present application provides use of the protein heterodimer in preparation of a drug for use in the treatment of tumors.

The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

Nucleic Acid Molecule, Expression Vector, Host Cell, Pharmaceutical Composition, and Preparation Method In another aspect, the present application provides one or more isolated nucleic molecule encoding the protein heterodimer. For example, the nucleic acid molecule can include a sequence as set forth in any one of SEQ ID NO.38-57. For example, the nucleotide sequences encoding the mIL12aIL2IL12bGMCSF, mIL2IL12aIL12bGMCSF, mIL12aIL2GMCSFIL12b, mIL2IL12aGMCSFIL12b, mIL12aGMCSFIL12bIL2, mIL12aIL7IL12bGMCSF, mIL12aIL15IL12bGMCSF, mIL12aIL21IL12bGMCSF, mIL12aIL21L12bFLT3L, mIL12aIL7IL12bFLT3L, mIL12aIL15IL12bFLT3L, mIL12aIL21IL12bFLT3L, hIL12aIL2IL12bGMCSF, hIL12aIL7IL12bGMCSF, hIL12aIL15IL12bGMCSF, hIL12aIL21IL12bGMCSF, hIL12aIL2IL12bFLT3L, hIL12aIL7IL12bFLT3L, hIL12aIL15IL12bFLT3L and hIL12aIL21IL12bFLT3L can be SEQ ID NO.38, SEQ ID NO.39, SEQ ID NO.40, SEQ ID NO.41, SEQ ID NO.42, SEQ ID NO.43, SEQ ID NO.44, SEQ ID NO.45, SEQ ID NO.46, SEQ ID NO.47, SEQ ID NO.48, SEQ ID NO.49, SEQ ID NO.50, SEQ ID NO.51, SEQ ID NO.52, SEQ ID NO.53, SEQ ID NO.54, SEQ ID NO.55, SEQ ID NO.56 and SEQ ID NO.57, respectively.

In the present application, the nucleic acid molecule can be used for treating tumors.

In another aspect, the present application provides use of the nucleic acid molecule in preparation of a drug for use in the treatment of tumors.

The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

In another aspect, the present application provides an expression vector including a nucleotide sequence encoding the protein heterodimer. In the present application, the nucleotide sequences encoding mIL12aIL2IL12bGMCSF, mIL2IL12aIL12bGMCSF, mIL12aIL2GMCSFIL12b, mIL2IL12aGMCSFIL12b, mIL12aGMCSFIL12bIL2, mIL12aIL7IL12bGMCSF, mIL12aIL15IL12bGMCSF, mIL12aIL21IL12bGMCSF, mIL12aIL2IL12bFLT3L, mIL12aIL7IL12bFLT3L, mIL12aIL15IL12bFLT3L and mIL12aIL21IL12bFLT3L respectively can be incorporated into the nucleotide sequence of pLentis-PTRE-MCS-PGK-PURO, thereby constructing regulable expression vectors pLentis-PTRE-mIL12aIL2IL12bGMCSF-PGK-PURO, pLentis-PTRE-mIL2IL12aIL12bGMCSF-PGK-PURO, pLentis-PTRE-mIL12aIL2GMCSFIL12b-PGK-PURO, pLentis-PTRE-mIL2IL12aGMCSFIL12b-PGK-PURO, pLentis-PTRE-mIL12aGMCSF IL12bIL2-PGK-PURO, pLentis-PTRE-mIL12aIL7IL12bGMCSF-PGK-PURO, pLentis-PTRE-mIL12aIL15IL12bGMCSF-PGK-PURO, pLentis-PTRE-mIL12aIL21IL12bGMCSF-PGK-PURO, pLentis-PTRE-mIL12 aIL2IL12bFLT3L-PGK-PURO, pLentis-PTRE-mIL12aIL7IL12bFLT3L-PGK-PURO, pLentis-PTRE-mIL12 aIL15IL12bFLT3L-PGK-PURO and pLentis-PTRE-mIL12aIL21IL12bFLT3L-PGK-PURO. For example, hIL12aIL2IL12bGMCSF, hIL12aIL7IL12bGMCSF, hIL12aIL15IL12bGMCSF, hIL12aIL21IL12bGMCSF, hIL12aIL2IL12bFLT3L, hIL12aIL7IL12bFLT3L, hIL12aIL15IL12bFLT3L and hIL12aIL21IL12bFLT3L can be incorporated into pLentis-CMV-MCS-IRES-PURO, respectively, thereby constructing the expression vectors pLentis-CMV-hIL12 aIL2IL12bGMCSF-IRES-PURO, pLentis-CMV-hIL12 aIL7IL12bGMCSF-IRES-PURO, pLentis-CMV-hIL12 aIL15IL12bGMCSF-IRES-PURO, pLentis-CMV-hIL12 aIL21IL12bGMCSF-IRE S-PURO, pLentis-CMV-hIL12 aIL2IL12bFLT3L-IRES-PURO, pLentis-CMV-hIL12 aIL7IL12bFLT3L-IRES-PURO, pLentis-CMV-hIL12aIL15IL12bFLT3L-IRES-PURO and pLentis-CMV-hIL12 aIL21IL12bFLT3L-IRES-PURO In the present application, the expression vector can be used for treating tumors.

In another aspect, the present application provides use of the expression vector in preparation of a drug for use in the treatment of tumors. The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

In the present application, the method of constructing a vector and plasmid, e.g., a method of incorporating a gene encoding the protein into the vector and plasmid or a method of introducing a plasmid into a host cell is well-established for persons skilled in the art, and is described in a variety of publications, including Sambrook, J., Fritsch, E. F. and Maniais, T. (1989) Molecular Cloning: A Laboratory Manual, 2nd edition, Cold spring Harbor Laboratory Press.

In another aspect, the present application provides a host cell including expression vector. In the present application, the host cell can be produced by transfecting B16 (rtTA) tumor cells with the expression vector. For example, the viruses of pLentis-PTRE-mIL12aIL2IL12bGMCSF-PGK-PURO, pLentis-PTRE-mIL2IL12aIL12bGMCSF-PGK-PURO, pLentis-PTRE-mIL12aIL2GMCSFIL12b-PGK-PURO, pLentis-PTRE-mIL2IL12aGMCSFIL12b-PGK-PURO, pLentis-PTRE-mIL12aGMCSFIL12bIL2-PGK-PURO, pLentis-PTRE-mIL12 aIL7IL12bGMCSF-PGK-PURO, pLentis-PTRE-mIL12 aIL15IL12bGMCSF-PGK-PURO, pLentis-PTRE-mIL12aIL21IL12bGMCSF-PGK-PURO, pLentis-PTRE-mIL12aIL2IL12bFLT3L-PGK-PURO, pLentis-PTRE-mIL12aIL7IL12bFLT3L-PGK-PURO, pLentis-PTRE-mIL12aIL15IL12bFLT3L-PGK-PURO and pLentis-PTRE-mIL12aIL21IL12bFLT3L-PGK-PURO expression vectors are used to transfect B16 (rtTA) tumor cells, respectively, thereby obtaining B16 (rtTA)-mIL12aIL2IL12bGMCSF, B16 (rtTA)-mIL2IL12aIL12bGMCSF, B16 (rtTA)-mIL12aIL2GMCSFIL12b, B16 (rtTA)-mIL2IL12aGMCSFIL12b, B16 (rtTA)- mIL12aGMCSFIL12bIL2, B16 (rtTA)-mIL12aIL7IL1-2bGMCSF, B16 (rtTA)-mIL12aIL15IL12bGMCSF, B16 (rtTA)-mIL12aIL21IL12bGMCSF, B16 (rtTA)-mIL12aIL-2IL12bFLT3L, B16 (rtTA)-mIL12aIL7IL12bFLT3L, B16 (rtTA)-mIL12aIL15IL12bFLT3L and B16 (rtTA)-mIL12aIL21IL12bFLT3L host cells. For example, the viruses of pLentis-CMV-hIL12aIL2IL12bGMCSF-IRES-PURO, pLentis-CMV-hIL12 aIL7IL12bGMCSF-IRES-PURO, pLentis-CMV-hIL12 aIL15IL12bGMCSF-IRES-PURO, pLentis-CMV-hIL12 aIL21IL12bGMCSF-IRES-PURO, pLentis-CMV-hIL12aIL2IL12bFLT3L-IRES-PURO, pLentis-CMV-hIL12aIL7IL12bFLT3L-IRES-PURO and pLentis-CMV-hIL12aIL15IL12bFLT3L-IRES-PURO, pLentis-CMV-hIL12aIL21IL12bFLT3L-IRES-PURO expression vectors can be used to transfect 293A cells, thereby obtaining 293A-hIL12aIL2IL12bGMCSF, 293A-hIL12aIL7IL12bGMCSF, 293A-hIL12aIL15IL12bGMCSF, 293A-hIL12aIL21IL12bGMCSF, 293A-hIL12aIL2IL12bFLT3L, 293A-hIL12aIL71L12bFLT3L, 293A-hIL12aIL15IL12bFLT3L and 293A-hIL12aIL2-1IL12bFLT3L host cells.

In the present application, the host cell can be used for treating tumors. The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

In another aspect, the present application provides use of the host cell in preparation of a drug for use in the treatment of tumors. The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

The present application provides a protein heterodimer, a nucleic acid molecule, an expression vector, a host cell, a pharmaceutical composition for use in the treatment of tumors.

A method of treating tumors including the step of administering the protein heterodimer, the nucleic acid molecule, the expression vector, the host cell and/or the pharmaceutical composition to a subject in need thereof.

The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

In another aspect, the present application provides a method of preparing the protein heterodimer including the step of culturing the host cell under conditions that can express the protein heterodimer.

Pharmaceutical Composition and Use Thereof

In another aspect, the present application provides a pharmaceutical composition including the protein heterodimer, the nucleic acid molecule, the vector and/or the host cell, and a pharmaceutically acceptable carrier.

The pharmaceutically acceptable carrier can include buffers, antioxidants, preservatives, low molecular weight polypeptides, proteins, hydrophilic polymers, amino acids, hydrocarbons, chelators, counterions, metal complexes and/or nonionic surfactants, etc. For example, the pharmaceutically acceptable carrier can include excipients, e.g., the excipients can be selected from a group consisting of: starches, dextrins, sucrose, lactose, magnesium stearate, calcium sulfate, carboxymethyl cellulose, talc powder, calcium alginate gel, chitosan, and nano-spheres, etc. For example, the pharmaceutically acceptable carrier can also be selected from a group consisting of: pH regulators, osmotic pressure regulators, solubilizers, and antimicrobials.

In the present application, the pharmaceutical composition can be formulated for oral administration, intravenous administration, intramuscular administration, in-situ intratumoral administration, inhalation, rectal administration, vaginal administration, transdermal administration or administration by subcutaneous reservoir.

In the present application, the pharmaceutical composition can be used for treating tumors. The tumors can be selected from a group consisting of: melanoma, lung cancer, esophageal cancer, gastric cancer, colorectal cancer, liver cancer, breast cancer, cervical cancer, thyroid cancer, brain and central nervous system cancer, pancreatic cancer, oral cancer, nasopharyngeal cancer, head and neck cancer, laryngeal cancer, bone cancer, skin cancer, ovarian cancer, prostate cancer, testicular cancer, renal cancer, bladder cancer, eyelid cancer, leukemia and lymphoma.

In the present application, the pharmaceutical composition can be used to inhibit the growth of tumors. For example, the pharmaceutical composition of the present application can inhibit or delay the development or progression of diseases, can reduce the tumor size (or even substantially eliminate the tumor) by promoting the expression of cytokines, and/or can alleviate and/or stabilize the disease conditions.

In the present application, the pharmaceutical composition can include a therapeutically effective amount of the protein heterodimer, the nucleic acid molecule, the vector and/or the host cell. The therapeutically effective amount is a dose capable of preventing and/or treating (at least partially treating) a disease or disorder (e.g., cancer) and/or any complication thereof in a subject having or at a risk of developing the disease or disorder.

In another aspect, the present application provides a method of ameliorating or treating tumors including administering the protein heterodimer, the nucleic acid molecule, the expression vector, the host cell and/or the pharmaceutical composition.

In the present application, the administration mode can include oral administration, intravenous administration, intramuscular administration, in-situ intratumoral administration, inhalation, rectal administration, vaginal administration, transdermal administration or administration by subcutaneous reservoir.

The following examples are intended to illustrate the embodiments of the present invention, and are not intended to limit the scope of the description or claims by any way.

EXAMPLES

Reagents: The DMEM medium, 1640 medium and fetal bovine serum were purchased from Lifetechnologies Inc.;

the cell culture bottles and culture plates were purchased from Corning Inc.; doxycycline (DOX) was purchased from Shanghai Shenggong Bioengineering Co., Ltd.; puromycin and blasticidin were purchased from Chemicon Inc.; the restriction endonuclease was purchased from Takara Inc. and NEB Inc.; the ligase was purchased from NEB company; the DNA polymerase was purchased from Takara company; the plasmid extraction kit and the gel recovery kit were purchased from OmegaBiotech, Inc.; the primer synthesis was completed by Shanghai Shenggong Bioengineering Co., Ltd.; the gene synthesis was completed by Nanjing Kingsley company; and the ELISA kit was purchased from Boster company. The cytokines mIL12, mGMCSF, mFLT3L, mIL2, mIL15, mIL21, mIL7, hIL12, hGMCSF, hFLT3L, hIL2, hIL15, hIL21 and hIL7 were purchased from Peprotech, Inc.

Please refer to FIGS. 1 and 4-6 for some experimental results of the examples. In FIGS. 1 and 4-16, each broken line represents the tumor area of a mouse, for example, 5 broken lines represent the data of 5 mice in an experiment; the fraction represents the ratio of tumor-clearing mice to tumor-inoculated mice, for example, 10/10 represents that the ratio of the tumor-clearing mice/the tumor-inoculated mice is 10/10=100%.

Example 1

Preparation of Tumor Cells Expressing Regulable Protein 1.1 Construction of the First Expression Vector pLentis-CMV-rtTA-IRES-Bsd A DNA sequence of rtTA having BamHI and EcoRI sites attached to both ends thereof (GenBank: ALK44378.1) was synthesized, and the synthetic product was ligated to a vector pUC57. The pUC57 vector having rtTA ligated thereto was digested with an enzyme digestion system as follows: 6 µg of pUC57 vector plasmid having rtTA ligated thereto, 4 µl of digestion buffer, 1 µl of BamHI and 1 µl of EcoRI, water was added to a total volume of 40 µl, and stood at 37° C. for 12 hours. The EP tube was removed, and 4.4 µl of 10× loading buffer was added. Electrophoresis was performed with 1% agarose gel, followed by recovery of rtTA fragments for further use.

In the EP tube, the vector pLentis-CMV-IRES-Bsd was digested with the following system: 2 µg of pLentis-CMV-IRES-Bsd vector plasmid, 3 µl of digestion buffer, 1 µl of BamHI and 1 µl of EcoRI, water was added to a total volume of 30 µl, and stood at 37° C. for 12 hours. The EP tube was removed, and 3.3 µl of 10× loading buffer was added. Electrophoresis was performed with 1% agarose gel, followed by recovery of pLentis-CMV-IRES-Bsd vector fragments for further use.

The pLentis-CMV-IRES-Bsd and rtTA were ligated with the following system: 2 µl of pLentis-CMV-IRES-Bsd, 2 µl of rtTA, 1 µl of ligase buffer, 0.5 µl of T4DNA ligase and 4.5 µl of water stood at room temperature for 4 hours of ligation. Then, the ligation system was transformed into competent *E. coli*. On the second day, the colonies were picked from the transformed plates, and cultured overnight in LB medium at 37° C. in a shaker. The plasmids were extracted from the cultured bacteria using a plasmid extraction kit. A digestion was used to identify whether the rtTA fragment was successfully ligated into the pLentis-CMV-IRES-Bsd vector, and then the correct vector was sequenced to confirm that the first expression vector pLentis-CMV-rtTA-IRES-Bsd was successfully constructed.

1.2 Preparation of Virus of First Expression Vector pLentis-CMV-rtTA-IRES-Bsd

1) The cultured 293FT cells were digested. After counting, $3\times10^6$ cells/well were plated into a 10 cm culture dish, and the volume of culture medium was 10 ml.

2) At the night of the second day, the cells were observed for their status. If the cell status was appropriately good, they were subject to transfection. Into the culture plate, chloroquine was added to a final concentration of 25 µM. To a test tube were added sterile water and the following plasmids (5 µg of pMD2.G+15 µg of pSPAX2+20 µg of pLentis-CMV-rtTA-IRES-Bsd) with a total volume of 1045 µl, followed by adding 155 µl of 2MCaCl$_2$. After uniformly mixing, 1200 µl of 2×HBS was finally added dropwise under shaking. After the completion of addition, the mixture was immediately added into the cell culture wells, and gently shaken for mixing well.

3) In the morning of the third day, the cells were observed for their status, and the medium was replaced with 10 ml of fresh DMEM medium.

4) In the morning of the fifth day, the cells were observed for their status. The supernatant in the culture dish was collected, filtered by 0.45 µm filter, and centrifuged at 50000 g in a high-speed centrifuge tube for 2 hours. The supernatant was carefully discarded. The liquid was absorbed with absorbent paper as much as possible, and the precipitate was re-suspended in 500 µl of HBSS. After 2 hours of dissolution, the solution was subpackaged in vials, and stored at −70° C. to give the virus of the first expression vector pLentis-CMV-rtTA-IRES-Bsd.

1.3. Transfection of B16 Tumor Cells with Virus of First Expression Vector pLentis-CMV-rtTA-IRES-Bsd The cultured mouse melanoma cells B16 were digested and inoculated into a 6-well plate with $10^5$ cells/well. The culture volume was 1 ml. After 24 hours, 10 µl of the virus of the first expression vector pLentis-CMV-rtTA-IRES-Bsd was added, and cultured in an incubator for additional 24 hours. The supernatant was discarded and replaced with fresh medium for further culture. After the cells were full, they were transferred to a culture flask, and blasticidin at an appropriate concentration was added for further culture. Further culture was performed, the medium was changed every two days, and the concentration of blasticidin was kept at 8 µg/ml. After one week of screening, the surviving cells were cells stably expressing regulatory proteins, which are named B16 (rtTA).

Example 2

Effect of Induced Expression of Green Fluorescent Protein (GFP) on Tumor Growth 2.1. Construction of Regulable Expression Vector Encoding Green Fluorescent Protein (GFP)

The primers were used to amplify GFP gene with GFP gene as template. The PCR conditions were in accordance with Prime StarHSDNApolymerase instructions. After agarose gel electrophoresis, PCR was recovered by gel recovery kit, and then digested by BamHI and EcoRI with the following system: 30 µg of PCR recovery product, 4 µl of digestion buffer, 1 µl of BamHI and 1 µl of EcoRI, water was added to a total volume of 40 µl, and stood at 37° C. for 12 hours. The EP tube was removed, and 4.4 µl of 10× loading buffer was added. Electrophoresis was performed with 1% agarose gel, followed by recovery of GFP gene fragments for further use.

The regulable expression vector was digested with the following system: 2 μg of pLentis-PTRE-MCS-PGK-PURO plasmid, 3 μl of digestion buffer, 1 μl of BamHI and 1 μl of EcoRI, water was added to a total volume of 30 μl, and stood at 37° C. for 12 hours. The EP tube was removed, and 3.3 μl of 10× loading buffer was added. Electrophoresis was performed with 1% agarose gel, followed by recovery of vector fragments for further use. The pLentis-PTRE-MCS-PGK-PURO and GFP were ligated with the follow ligation system: 2 μl of pLentis-PTRE-MCS-PGK-PURO, 2 μl of GFP, 1 μl of ligase buffer, 0.5 μl of T4DNA ligase and 4.5 μl of water. The mixture stood at room temperature for 4 hours of ligation. Then, the ligation system was transformed into competent E. coli. On the second day, the colonies were picked from the transformed plates, and cultured overnight in LB medium at 37° C. in a shaker. The plasmids were extracted from the cultured bacteria using a plasmid extraction kit. Digestion was used to identify whether the fragment was successfully ligated into the vector, and then the correct vector was sequenced to confirm that the second expression vector pLentis-PTRE-GFP-PGK-PURO was successfully constructed.

2.2 Preparation of Cells Regulable to Express GFP

A virus of GFP expression vector was prepared in accordance with the same method as the virus of the first expression vector to give the virus of the second expression vector pLentis-PTRE-GFP-PGK-PURO.

The cultured B16 (rtTA) tumor cells were digested and inoculated into a 6-well plate with $10^5$ cells/well. The culture volume was 1 ml. After 24 hours, 10 μl of the virus of the second expression vector pLentis-PTRE-GFP-PGK-PURO was added, and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to express GFP, which are named B16 (rtTA)-GFP.

2.3. Effect of Regulated Expression of GFP on Tumor Growth

The B16 (rtTA)-GFP cells in logarithmic phase were digested, and diluted with HBSS to 2×$10^6$ cells/ml. 8-10 week-old C57BL/6 female mice (purchased from Beijing Huafukang Biotechnology Co., Ltd.) were injected at their right backs with 1 ml syringe at 50 μL/mouse (10 mice in total). After tumor growth, the mice were fed with water containing 2 g/L of doxycycline. The tumor growth of mice was recorded, as shown in FIG. 1. The results show that the induced expression of GFP does not produce any inhibitory effect on tumor growth (each broken line represents the tumor area status in one mouse).

Example 3

Design of Protein Heterodimer

The following protein heterodimers were designed: mIL2IL12aIL12bGMCSF, mIL12aIL2GMCSFIL12b, mIL2IL12aGMCSFIL12b, mIL12aGMCSFIL12bIL2, mIL12aIL7IL12bGMCSF, mIL12aIL15IL12bGMCSF, mIL12aIL21IL12bGMCSF, mIL12aIL2IL12bFLT3L, mIL12aIL7IL12bFLT3L, mIL12aIL15Th12bFLT3L, mIL12aIL21IL12bFLT3L, hIL12aIL2IL12bGMCSF, hIL12aIL7IL12bGMCSF, hIL12aIL15Th12bGMCSF, hIL12aIL21IL12bGMCSF, hIL12aIL2IL12bFLT3L, hIL12aIL7IL12bFLT3L, hIL12aIL15Th12bFLT3L and hIL12aIL21IL12bFLT3L. The structures of the protein heterodimers are shown in FIG. 2.

Example 4

Effect of Induced Expression of mIL12aIL2IL12bGMCSF on Tumor Growth 4.1. Construction of Regulable Expression Vector of mIL12aIL2IL12bGMCSF A sequence encoding mIL12aIL2IL12bGMCSF having BamHI, BglII and XhoI, EcoRI digestion sites attached to both ends thereof was synthesized, and then digested by BamHI or BglII and XhoI or EcoRI with the following system: 5 μg of mIL12aIL2IL12bGMCSF plasmid, 4 μl of digestion buffer, 1 μl of BamHI and 1 μl of XhoI, water was added to a total volume of 40 μl, and stood at 37° C. for 12 hours. The EP tube was removed, and 4.4 μl of 10× loading buffer was added. Electrophoresis was performed with 1% agarose gel, followed by recovery of mIL12aIL2IL12bGMCSF gene fragments for further use.

The amino acid sequence of mIL12aIL2IL12bGMCSF protein heterodimer is as set forth in SEQ ID NO. 18, and the nucleotide sequence encoding the mIL12aIL2IL12bGMCSF is as set forth in SEQ ID NO. 38.

The regulable expression vector pLentis-PTRE-MCS-PGK-PURO was digested with the following system: 2 μg of pLentis-PTRE-MCS-PGK-PURO vector plasmid, 3 μl of digestion buffer, 1 μl of BamHI and 1 μl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL2IL12bGMCSF were ligated with the following ligation system: 2 μl of pLentis-PTRE-MCS-PGK-PURO, 2 μl of mIL12aIL2IL12bGMCSF, 1 μl of ligase buffer, 0.5 μl of T4DNA ligase and 4.5 μl of water. The mixture stood at room temperature for 4 hours of ligation. Then, the ligation system was transformed into competent E. coli. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL12aIL2IL12bGMCSF-PGK-PURO.

4.2 Preparation of Cells Regulable to Expressing mIL12aIL2IL12bGMCSF

A virus of the mIL12aIL2IL12bGMCSF expression vector was prepared in accordance with the same method as the virus of the first expression vector to obtain the virus of the second expression vector pLentis-PTRE-mIL12aIL2IL12bGMCSF-PGK-PURO.

The cultured B16 (rtTA) tumor cells were digested and inoculated into a 6-well plate with $10^5$ cells/well. The culture volume was 1 ml. After 24 hours, 10 μl of the virus of the second expression vector pLentis-PTRE-mIL12aIL2IL12bGMCSF-PGK-PURO was added, and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to express mIL12aIL2IL12bGMCSF, which are named B16 (rtTA)-mIL12aIL2IL12bGMCSF.

4.3. In Vitro Detection of Effect of Induced Expression of mIL12aIL2IL12bGMCSF

Figure 3:
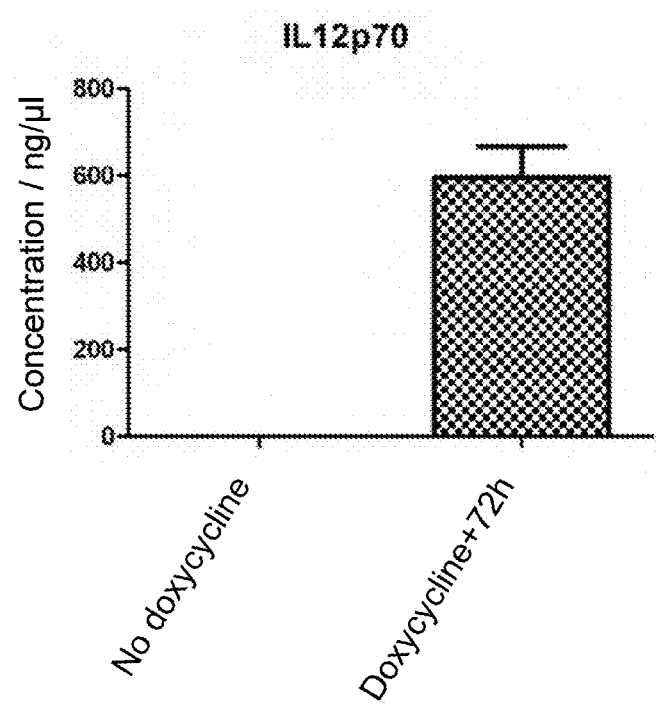
FIG. 3 shows the expression of the protein heterodimer of mIL12aIL2IL12bGMCSF.

The B16 (rtTA)-mIL12aIL2IL12bGMCSF cells were placed into a 24-well plate with $5\times10^4$ cells/well. After 24 hours, 100 ng/ml of DOX was added to the wells, and cultured for additional 72 hours. The supernatant was collected. A mouse IL12p70 ELISA kit was used to detect the expression level of the fusion protein in the supernatant in accordance with the instructions of the kit. The wells without DOX induction were used as control. As shown in FIG. 3, the addition of DOX induces the expression of mIL12aIL2IL12bGMCSF fusion protein.

4.4. Effect of Induced Expression of mIL12aIL2IL12bGMCSF on Tumor Growth

Figure 4:
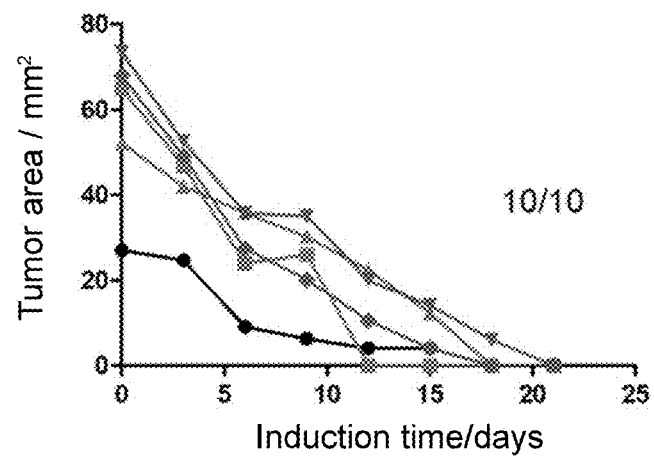
FIG. 4 shows the regression induced by the protein heterodimer of mIL12aIL2IL12bGMCSF.

The B16 (rtTA)-mIL12aIL2IL12bGMCSF cells in logarithmic phase were digested, and diluted with HBSS to $2\times10^6$ cells/ml. 8-10 week-old C57BL/6 female mice were injected at their right backs with 1 ml syringe at 50 µL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 10/10, as shown in FIG. 4. The mIL12aIL2IL12bGMCSF can induce tumor regression in all the mice.

Example 5

Effect of Induced Expression of mIL2IL12aIL12bGMCSF on Tumor Growth 5.1. Construction of Regulable Expression Vector of mIL2IL12aIL12bGMCSF The coding sequence of mIL2IL12aIL12bGMCSFF having BamHI, BglII and XhoI, EcoRI digestion sites attached to both sides thereof was synthesized, and digested by BamHI or BglII and XhoI or EcoRI with the following system: 5 µg of mIL2IL12aIL12bGMCSF plasmid, 4 µl of digestion buffer, 1 µl of BamHI and 1 µl of XhoI, water was added to a total volume of 40 µl, and stood at 37° C. for 12 hours. The EP tube was removed, and 4.4 µl of 10× loading buffer was added. Electrophoresis was performed with 1% agarose gel, followed by recovery of mIL2IL12aIL12bGMCSF gene fragments for further use.

The amino acid sequence of mIL2IL12aIL12bGMCSF protein heterodimer is as set forth in SEQ ID NO. 19, and the nucleotide sequence encoding mIL2IL12aIL12bGMCSF was SEQ ID NO. 39.

The regulable expression vector pLentis-PTRE-MCS-PGK-PURO was digested with the following system: 2 µg of pLentis-PTRE-MCS-PGK-PURO vector plasmid, 3 µl of digestion buffer, 1 µl of BamHI and 1 µl of XhoI, water was added to a total volume of 30 µl, and stood at 37° C. for 12 hours. The EP tube was removed, and 3.3 µl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL2IL12aIL12bGMCSF were ligated with the following ligation system: 2 µl of pLentis-PTRE-MCS-PGK-PURO, 2 µl of mIL2IL12aIL12bGMCSF, 1 µl of ligase buffer, 0.5 µl of T4DNA ligase and 4.5 µl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture cells, and digestion was used to identify whether the fragment was successfully ligated into the vector. Then, the correct vectors were sequenced to confirm the successful construction of the second expression vector pLentis-PTRE-mIL2IL12aIL12bGMCSF-PGK-PURO.

5.2 Preparation of Cells Regulable to Express mIL2IL12aIL12bGMCSF

A virus of the mIL2IL12aIL12bGMCSF expression vector was prepared in accordance with the same method as the virus of the first expression vector to obtain the virus of the second expression vector pLentis-PTRE-mIL2IL12aIL12bGMCSF-PGK-PURO.

The cultured B16 (rtTA) tumor cells were digested and inoculated into a 6-well plate with $10^5$ cells/well. The culture volume was 1 ml. After 24 hours, 10 µl of the virus of the second expression vector pLentis-PTRE-mIL2IL12aIL12bGMCSF-PGK-PURO was added, and cultured in an incubator for additional 24 hours. The supernatant was discarded and replaced with fresh medium for further culture. After the cells were full, they were transferred to a culture flask, and puromycin was added to a final concentration of 3 µg/ml. After culture for additional 3 days, the surviving cells were cells regulable to express mIL2IL12aIL12bGMCSF, which are named B16 (rtTA)-mIL2IL12aIL12bGMCSF.

5.3 Effect of Induced Expression of mIL2IL12aIL12bGMCSF on Tumor Growth

Figure 5:
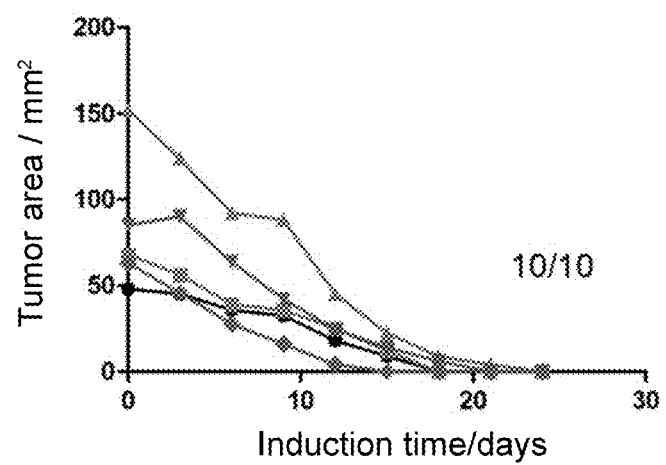
FIG. 5 shows the regression induced by the protein heterodimer of mIL2IL12aIL12bGMCSF.

The B16 (rtTA)-mIL2IL12aIL12bGMCSF cells in logarithmic phase were digested, and diluted with HBSS to $2\times10^6$ cells/ml. 8-10 week-old C57BL/6 female mice were injected at their right backs with 1 ml syringe at 50 µL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 10/10, as shown in FIG. 5. The mIL2IL12aIL12bGMCSF can induce tumor regression in all the mice.

Example 6

Effect of Induced Expression of mIL12aIL2GMCSFIL12b on Tumor Growth 6.1. Construction of Regulable Expression Vector of mIL12aIL2GMCSFIL12b A sequence encoding mIL12aIL2GMCSFIL12b gene was synthesized, and BamHI, BglII and XhoI, EcoRI digestion sites were attached to both ends thereof. Then, it was digested by BamHI or BglII and XhoI or EcoRI with the following system: 5 µg of mIL12aIL2GMCSFIL12b plasmid, 4 µl of digestion buffer, 1 µl of BamHI and 1 µl of XhoI, water was added to a total volume of 40 µl, and stood at 37° C. for 12 hours. The EP tube was removed, and 4.4 µl of 10× loading buffer was added. Electrophoresis was performed with 1% agarose gel, followed by recovery of mIL12aIL2GMCSFIL12b gene fragments for further use.

The amino acid sequence of mIL12aIL2GMCSFIL12b protein heterodimer is as set forth in SEQ ID NO. 20, and the nucleotide sequence encoding the mIL12aIL2GMCSFIL12b is as set forth in SEQ ID NO. 40.

The regulable expression vector pLentis-PTRE-MCS-PGK-PURO was digested with the following system: 2 µg of pLentis-PTRE-MCS-PGK-PURO vector plasmid, 3 µl of digestion buffer, 1 μl of BamHI and 1 μl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MC S-PGK-PURO and mIL12aIL2GMCSFIL12b were ligated with the following ligation system: 2 μl of pLentis-PTRE-MCS-PGK-PURO, 2 μl of mIL12aIL2GMCSFIL12b, 1 μl of ligase buffer, 0.5 μl of T4DNA ligase and 4.5 μl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL12aIL2GMCSFIL12b-PGK-PURO.

6.2 Preparation of Cells Regulable to Express mIL12aIL2GMCSFIL12b

The virus of the mIL12aIL2GMCSFIL12b expression vector was prepared with the same method as the virus of the first expression vector to obtain the virus of the second Regulable Expression Vector pLentis-PTRE-mIL12aIL2GMCSFIL12b-PGK-PUR.

The cultured B16 (rtTA) tumor cells were digested and inoculated into a 6-well plate with $10^5$ cells/well. The culture volume was 1 ml. After 24 hours, 10 μl of the virus of the second regulable expression vector pLentis-PTRE-mIL12aIL2GMCSFIL12b-PGK-PURO was added, and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to express mIL12aIL2GMCSFIL12b, which are named B16 (rtTA)-mIL12aIL2GMCSFIL12b.

6.3. Effect of Induced Expression of mIL12aIL2GMCSFIL12b on Tumor Growth

Figure 6:
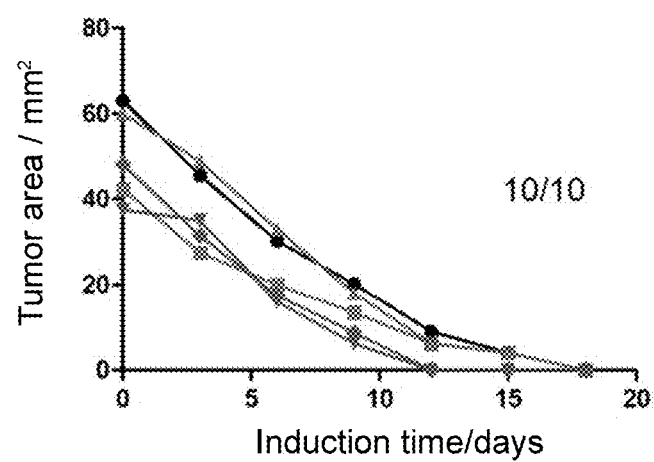
FIG. 6 shows the regression induced by the protein heterodimer of mIL12aIL2GMCSFIL12b.

The B16 (rtTA)-mIL12aIL2GMCSFIL12b cells in logarithmic phase were digested, and diluted with HBSS to $2\times10^6$ cells/ml. 8-10 week-old C57BL/6 female mice were injected at their right backs with 1 ml syringe at 50 μL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 10/10, as shown in FIG. 6. The mIL12aIL2GMCSFIL12b can induce tumor regression in all the mice.

Example 7

Effect of Induced Expression of mIL2IL12aGMCSFIL12b on Tumor Growth 7.1 Construction of Regulable Expression Vector of mIL2IL12aGMCSFIL12b The coding sequence of mIL2IL12aGMCSFIL12b with BamHI, BglII and XhoI, EcoRI digestion sites attached to both sides thereof was synthesized, and then digested by BamHI or BglII and XhoI or EcoRI with the following system: 5 μg of mIL2IL12aGMCSFIL12b plasmid, 4 μl of digestion buffer, 1 μl of BamHI and 1 μl of XhoI, water was added to a total volume of 40 μl, and stood at 37° C. for 12 hours. The EP tube was removed, and 4.4 μl of 10× loading buffer was added. Electrophoresis was performed with 1% agarose gel, followed by recovery of mIL2IL12aGMCSFIL12b gene fragments for further use.

The amino acid sequence of mIL2IL12aGMCSFIL12b protein heterodimer is as set forth in SEQ ID NO. 21, and the nucleotide sequence encoding mIL2IL12aGMCSFIL12b is as set forth in SEQ ID NO. 41.

The regulable expression vector pLentis-PTRE-MCS-PGK-PURO was digested with the following system: 2 μg of pLentis-PTRE-MCS-PGK-PURO plasmid, 3 μl of digestion buffer, 1 μl of BamHI, 1 μl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL2IL12aGMCSFIL12b were ligated with the following ligation system: 2 μl of pLentis-PTRE-MCS-PGK-PURO, 2 μl of mIL2IL12aGMCSFIL12b, 1 μl of ligase buffer, 0.5 μl of T4DNA ligase and 4.5 μl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL2IL12aGMCSF IL12b-PGK-PURO.

7.2 Preparation of Cells Regulable to Express mIL2IL12aGMCSFIL12b

The virus of mIL2IL12aGMCSFIL12b expression vector was prepared in accordance with the same method as the virus of the first expression vector to obtain the virus of the second expression vector pLentis-PTRE-mIL2IL12aGMCSFIL12b-PGK-PURO.

The cultured B16 (rtTA) tumor cells were digested and inoculated into a 6-well plate with $10^5$ cells/well. The culture volume was 1 ml. After 24 hours, 10 μl of the virus of the second regulable expression vector pLentis-PTRE-mIL2IL12aGMCSFIL12b-PGK-PURO was added and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulably expressing mIL2IL12aGMCSFIL12b, which are named B16 (rtTA)-mIL12aIL2GMCSFIL12b.

7.3 Effect of Induced Expression of mIL2IL12aGMCSFIL12b on Tumor Growth

Figure 7:
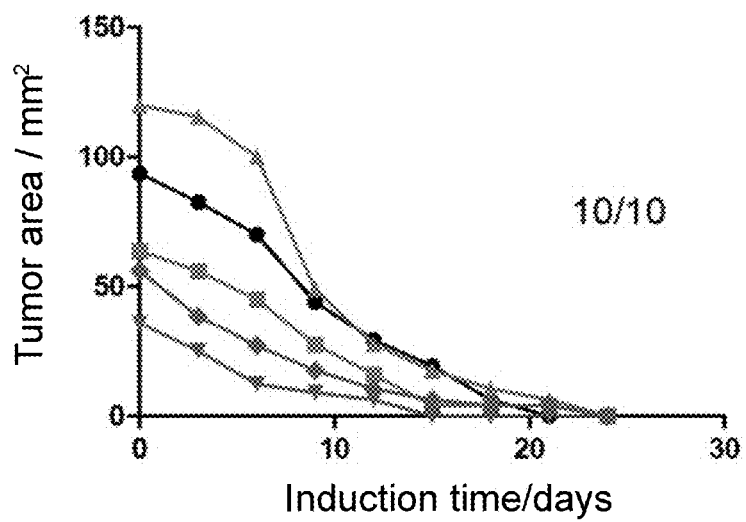
FIG. 7 shows the regression induced by the protein heterodimer of mIL2IL12aGMCSFIL12b.

The B16 (rtTA)-mIL2IL12aGMCSFIL12b cells in logarithmic growth phase were digested and diluted with HBSS to $2\times10^6$ cells/ml. 8-10 week-old C57BL/6 female mice was injected with 1 ml syringe at their right backs with 50 μL/mouse (10 mice in total). After tumor growth, the mice were fed with water containing 2 g/L of doxycycline. The tumor growth and tumor clearance were recorded. The ratio of the number of tumor-clearing mice to the total number of mice=10/10. As shown in FIG. 7, mIL2IL12aGMCSFIL12b can induce tumor regression in all the mice.

Example 8

Effect of Induced Expression of mIL12aGMCSFIL12bIL2 on Tumor Growth 8.1 Construction of Regulable Expression Vector of mIL12aGMCSFIL12bIL2

The coding sequence of mIL12aGMCSFIL12bIL2 with BamHI, BglII and XhoI, EcoRI digestion sites attached to both ends thereof was synthesized, and then digested by BamHI or BglII and XhoI or EcoRI with the following system: 5 μg of mIL12aGMCSFIL12bIL2 plasmid, 4 μl of digestion buffer, 1 μl of BamHI and 1 μl of XhoI, water was added to a total volume of 40 and stood at 37° C. for 12 hours. The EP tube was removed, and 4.4 μl of 10× loading buffer was added. Electrophoresis was performed with 1% agarose gel, followed by recovery of mIL12aGMCSFIL12bIL2 gene fragments for further use.

The amino acid sequence of mIL12aGMCSFIL12bIL2 protein heterodimer is as set forth in SEQ ID NO. 22, and the nucleotide sequence encoding mIL12aGMCSFIL12bIL2 was SEQ ID NO. 42.

The regulable expression vector pLentis-PTRE-MCS-PGK-PURO was digested with the following system: 2 μg of pLentis-PTRE-MCS-PGK-PURO plasmid, 3 μl of digestion buffer, 1 μl of BamHI and 1 μl of XhoI, adding water to a total volume of 30 μl of, and standing at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aGMCSFIL12bIL2 were ligated with the following ligation system: 2 μl of pLentis-PTRE-MCS-PGK-PURO, 2 μl of mIL12aGMCSFIL12bIL2, 1 μl of ligase buffer, 0.5 μl of T4DNA ligase and 4.5 μl of water. The mixture stood at room temperature for 4 hours of ligation. Then, the ligation system was transformed into competent $E.\ coli$. On the second day, the colonies were picked from the transformed plates, and cultured overnight in LB medium at 37° C. in a shaker. Plasmid extract kit was used to extract the plasmid from the culture cells, and digestion was used to identify whether the fragment was successfully ligated into the vector. Then, the correct vectors were sequenced to confirm the successful construction of the second expression vector pLentis-PTRE-mIL12aGMCSFIL12bIL2-PGK-PURO.

8.2 Preparation of Cells Regulable to Express mIL12aGMCSFIL12bIL2

The mIL12aGMCSFIL12bIL2 expression vector was prepared in accordance with the same method as the virus of the first expression vector to obtain the virus of the second expression vector pLentis-PTRE-mIL12aGMCSFIL1-2bIL2-PGK-PURO.

The cultured B16 (rtTA) tumor cells were digested and inoculated into a 6-well plate with $10^5$ cells/well. The culture volume was 1 ml. After 24 hours, 10 μl of the virus of the second regulable expression vector pLentis-PTRE-mIL12aGMCSFIL12bIL2-PGK-PURO was added and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to expressing mIL12aGMCSFIL12bIL2, which are named B16 (rtTA)-mIL12aGMCSFIL12bIL2.

8.3 Effect of Induced Expression of mIL12aGMCSFIL12bIL2 on Tumor Growth

Figure 8:
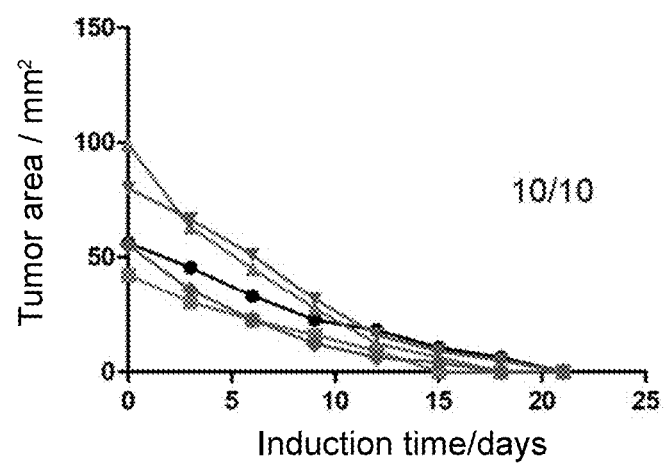
FIG. 8 shows the regression induced by the protein heterodimer of mIL12aGMCSFIL12bIL2.

The B16 (rtTA)-mIL12aGMCSFIL12bIL2 cells in logarithmic growth phase was digested and diluted with HBSS to $2×10^6$ cells/ml. 8-10 week-old C57BL/6 female mouse was injected with 1 ml syringe at their right backs at 50 μl/mouse (10 mice in total). After tumor growth, the mice were fed with water containing 2 g/L of DOX. The tumor growth status and the tumor clearance in mice were recorded. The ratio of the number of tumor-clearing mice to the total number of mice was 10/10. As shown in FIG. 8, the results show that mIL12aGMCSFIL12bIL2 can induce the tumor regression in all the mice.

Example 9

Effect of Induced Expression of hIL12aIL2IL12bGMCSF on Tumor Growth 9.1 Construction of hIL12aIL2IL12bGMCSF Regulable Expression Vector A sequence encoding hIL12aIL2IL12bGMCSF having BamHI, BglII and XhoI, EcoRI digestion sites attached to both ends thereof was synthesized, and then digested by BamHI or BglII and XhoI or EcoRI with the following system: 5 μg of hIL12aIL2IL12bGMCSF plasmid, 4 μl of digestion buffer, 1 μl of BamHI and 1 μl of XhoI, water was added to a total volume of 40 μl, and stood at 37° C. for 12 hours. The EP tube was removed, and 4.4 μl of 10× loading buffer was added. Electrophoresis was performed with 1% agarose gel, followed by recovery of hIL12aIL2IL12bGMCSF gene fragments for further use.

The amino acid sequence of hIL12aIL2IL12bGMCSF protein heterodimer is as set forth in SEQ ID NO. 30, and the nucleotide sequence encoding hIL12aIL2IL12bGMCSF is as set forth in SEQ ID NO. 50.

The regulable expression vector pLentis-PTRE-MCS-PGK-PURO was digested with the following system: 2 μg of pLentis-PTRE-MCS-PGK-PURO plasmid, 3 μl of digestion buffer, 1 μl of BamHI and 1 μl of XhoI, water was added to a total volume of 30 and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MC S-PGK-PURO and hIL12aIL2IL12bGMCSF were ligated with the following ligation system: 2 μl of pLentis-PTRE-MCS-PGK-PURO, 2 μl of hIL12aIL2IL12bGMCSF, 1 μl of ligase buffer, 0.5 μl of T4DNA ligase and 4.5 μl of water. The mixture stood at room temperature for 4 hours of ligation. Then, the ligation system was transformed into competent $E.\ coli$. On the second day, the colonies were picked from the transformed plates, and cultured overnight in LB medium at 37° C. in a shaker. Plasmid extract kit was used to extract the plasmid from the culture cells, and digestion was used to identify whether the fragment was successfully ligated into the vector. Then, the correct vectors were sequenced to confirm the successful construction of the second expression vector pLentis-PTRE-hIL12aIL2IL12bGMCSF-PGK-PURO.

9.2 Preparation of Cells Regulable to Express hIL12aIL2IL12bGMCSF

The hIL12aIL2IL12bGMCSF expression vector was prepared in accordance with the same method as the virus of the first expression vector to obtain the virus of the second expression vector pLentis-PTRE-hIL12aIL2IL12bGMCSF-PGK-PURO.

The cultured B16 (rtTA) tumor cells were digested and inoculated into a 6-well plate with $10^5$ cells/well. The culture volume was 1 ml. After 24 hours, 10 µl of the virus of the second expression vector pLentis-PTRE-hIL12aIL2IL12bGMCSF-PGK-PURO was added and cultured in an incubator for additional 24 hours. The supernatant was discarded and replaced with fresh medium for further culture. After the cells were full, they were transferred to a culture flask, and puromycin was added to a final concentration of 3 µg/ml. After culture for additional 3 days, the surviving cells were cells regulable to express hIL12aIL2IL12bGMCSF, which are named B16 (rtTA)-hIL12aIL2IL12bGMCSF.

9.3. Effect of Induced Expression of hIL12aIL2IL12bGMCSF on Tumor Growth

Figure 9:
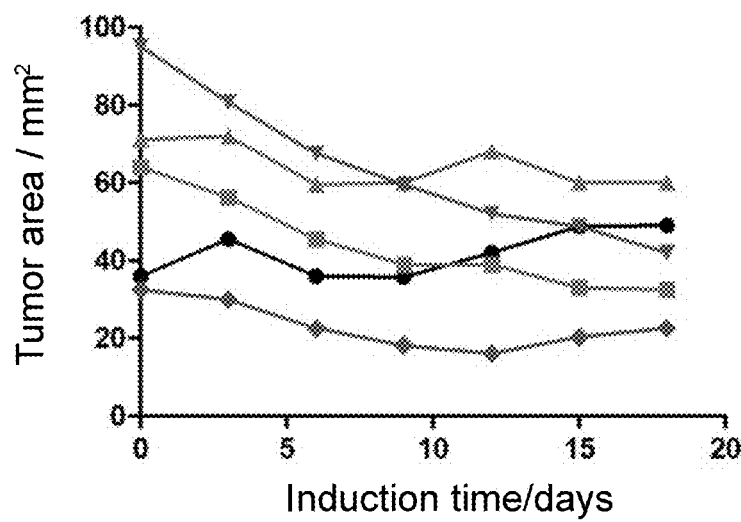
FIG. 9 shows the regression induced by the protein heterodimer of hIL12aIL2IL12bGMCSF.

The B16 (rtTA)-hIL12aIL2IL12bGMCSF cells in logarithmic phase were digested, and diluted with HBSS to $2\times10^6$ cells/ml. 8-10 week-old C57BL/6 female mice were injected at their right backs with 1 ml syringe at 50 µL/mouse (10 mice in total). After tumor growth, the mice were fed with water containing 2 g/L of doxycycline. The tumor growth and the tumor clearance of mice were recorded, as shown in FIG. 9, the hIL12aIL2IL12bGMCSF can inhibit the growth of tumors in the mice to a certain extent.

Example 10

Effect of Induced Expression of mIL12aIL7IL12bGMCSF on Tumor Growth 10.1 Construction of mIL12aIL7IL12bGMCSF Regulable Expression Vector A sequence encoding mIL12aIL7IL12bGMCSF gene having BamHI, BglII and XhoI, EcoRI digestion sites attached to both ends thereof was synthesized, and then digested by BamHI or BglII and XhoI or EcoRI with the following system: 5 µg of mIL12aIL7IL12bGMCSF plasmid, 4 µl of digestion buffer, 1 µl of BamHI and 1 µl of XhoI, water was added to a total volume of 40 µl, and stood at 37° C. for 12 hours. The EP tube was removed, and 4.4 µl of 10× loading buffer was added. Electrophoresis was performed with 1% agarose gel, followed by recovery of mIL12aIL7IL12bGMCSF gene fragments for further use.

The amino acid sequence of mIL12aIL7IL12bGMCSF protein heterodimer is as set forth in SEQ ID NO. 23, and the nucleotide sequence encoding mIL12aIL7IL12bGMCSF is as set forth in SEQ ID NO. 43.

The regulable expression vector pLentis-PTRE-MCS-PGK-PURO was digested with the following system: 2 µg of pLentis-PTRE-MCS-PGK-PURO vector plasmid, 3 µl of digestion buffer, 1 µl of BamHI, 1 µl of XhoI, water was added to a total volume of 30 µl, and stood at 37° C. for 12 hours. The EP tube was removed, and 3.3 µl of 10× loading buffer was added. Electrophoresis was performed with 1% agarose gel, followed by recovery of pLentis-PTRE-MCS-PGK-PURO vector fragments for further use.

The pLentis-PTRE-MC S-PGK-PURO and mIL12aIL7IL12bGMCSF were ligated with the following ligation system: 2 µl of pLentis-PTRE-MCS-PGK-PURO, 2 µl of mIL12aIL7IL12bGMCSF, 1 µl of ligase buffer, 0.5 µl of T4DNA ligase and 4.5 µl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture cells, and digestion was used to identify whether the fragment was successfully ligated into the vector. Then, the correct vectors were sequenced to confirm the successful construction of the second expression vector pLentis-PTRE-mIL12aIL7IL12bGMCSF-PGK-PURO.

10.2 Preparation of Cells Regulable to Express mIL12aIL7IL12bGMCSF

The virus of the mIL12aIL7IL12bGMCSF expression vector was prepared in accordance with the same method as the virus of the first expression vector to obtain the virus of the second expression vector pLentis-PTRE-mIL12aIL7IL12bGMCSF-PGK-PURO.

The cultured B16 (rtTA) tumor cells were digested and inoculated into a 6-well plate with $10^5$ cells/well. The culture volume was 1 ml. After 24 hours, 10 µl of the virus of the second regulable expression vector pLentis-PTRE-mIL12aIL7IL12bGMCSF-PGK-PURO was added and cultured in an incubator for additional 24 hours. The supernatant was discarded and replaced with fresh medium for further culture. After the cells were full, they were transferred to a culture flask, and puromycin was added to a final concentration of 3 µg/ml. After culture for additional 3 days, the surviving cells were cells regulable to express mIL12aIL7IL12bGMCSF, which are named B16 (rtTA)-mIL12aIL7IL12bGMCSF.

10.3. Effect of Induced Expression of mIL12aIL7IL12bGMCSF on Tumor Growth

Figure 10:
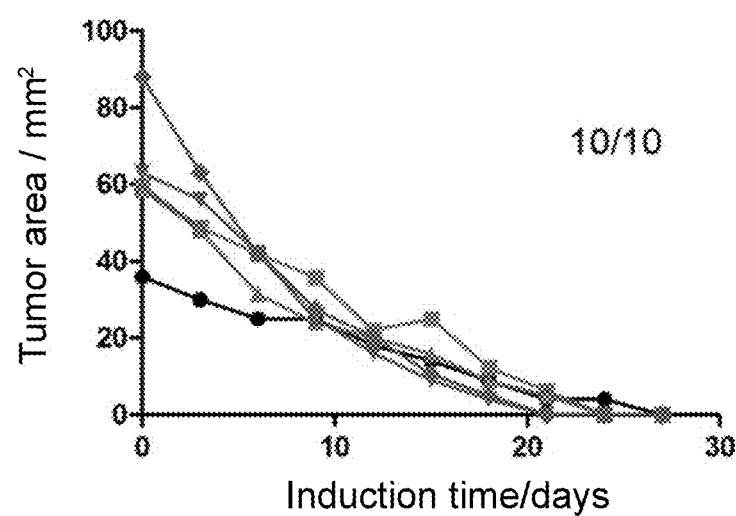
FIG. 10 shows the regression induced by the protein heterodimer of mIL12aIL7IL12bGMCSF.

The B16 (rtTA)-mIL12aIL7IL12bGMCSF cells in logarithmic growth phase were digested and diluted with HBSS to $2\times10^6$ cells/ml. 8-10 week-old C57BL/6 female mice were injected with 1 ml syringe at their right backs with 50 µL/mouse. After tumor growth, the mice were fed with water containing 2 g/L of doxycycline. The tumor growth and tumor clearance were recorded. The ratio of the number of tumor-clearing mice to the total number of mice was 10/10. As shown in FIG. 10, mIL12aIL7IL12bGMCSF can induce tumor regression in all the mice.

Example 11

Effect of Induced Expression of mIL12aIL15IL12bGMCSF on Tumor Growth 11.1 Construction of mIL12aIL15IL12bGMCSF Regulable Expression Vector A sequence encoding mIL12aIL15IL12bGMCSF gene having BamHI, BglII and XhoI, EcoRI digestion sites attached to both ends thereof was synthesized, and then digested by BamHI or BglII and XhoI or EcoRI with the following system: 5 µg of mIL12aIL7IL12bGMCSF plasmid, 4 µl of digestion buffer, 1 µl of BamHI and 1 µl of XhoI, water was added to a total volume of 40 and stood at 37° C. for 12 hours. The EP tube was removed, and 4.4 µl of 10× loading buffer was added. Electrophoresis was performed with 1% agarose gel, followed by recovery of mIL12aIL15IL12bGMCSF gene fragments for further use.

The amino acid sequence of mIL12aIL15IL12bGMCSF protein heterodimer is as set forth in SEQ ID NO. 24, and the nucleotide sequence encoding mIL12aIL15IL12bGMCSF is as set forth in SEQ ID NO. 44.

The regulable expression vector pLentis-PTRE-MCS-PGK-PURO was digested with the following system: 2 µg of pLentis-PTRE-MCS-PGK-PURO vector plasmid, 3 µl of digestion buffer, 1 µl of BamHI and 1 µl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL15IL12bGMCSF were ligated with the following ligation system: 2 μl of pLentis-PTRE-MCS-PGK-PURO, 2 μl of mIL12aIL15IL12bGMCSF, 1 μl of ligase buffer, 0.5 μl of T4DNA ligase and 4.5 μl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture cells, and digestion was used to identify whether the fragment was successfully ligated into the vector. Then, the correct vectors were sequenced to confirm the successful construction of the second expression vector pLentis-PTRE-mIL12aIL15Th12bGMCSF-PGK-PURO.

11.2 Preparation of Cells Regulable to Express mIL12aIL15IL12bGMCSF

The virus of the mIL12aIL15IL12bGMCSF expression vector was prepared in accordance with the same method as the virus of the first expression vector to obtain the virus of the second expression vector pLentis-PTRE-mIL12aIL15IL12bGMCSF-PGK-PURO.

The cultured B16 (rtTA) tumor cells were digested and inoculated into a 6-well plate with $10^5$ cells/well. The culture volume was 1 ml. After 24 hours, 10 μl of the virus of the second regulable expression vector pLentis-PTRE-mIL12aIL15IL12bGMCSF-PGK-PURO was added and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to express mIL12aIL15IL12bGMCSF, which are named B16 (rtTA)-mIL12aIL15IL12bGMCSF.

11.3 Effect of Induced Expression of mIL12aIL15IL12bGMCSF on Tumor Growth

Figure 11:
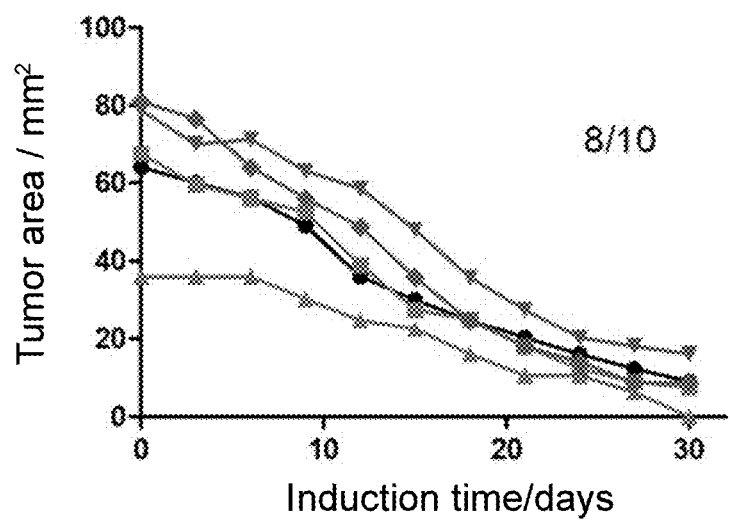
FIG. 11 shows the regression induced by the protein heterodimer of mIL12aIL15IL12bGMCSF.

The B16 (rtTA)-mIL12aIL15IL12bGMCSF cells in logarithmic phase were digested, and diluted with HBSS to $2\times10^6$ cells/ml. 8-10 week old C57BL/6 female mice were injected at their right backs with 1 ml syringe at 50 μL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 8/10, as shown in FIG. 11. The mIL12aIL15IL12bGMCSF can induce tumor regression in part of the mice.

Example 12

Effect of Induced Expression of mIL12aIL21IL12bGMCSF Effect of on Tumor Growth 12.1 Construction of mIL12aIL21IL12bGMCSF Regulable Expression Vector A sequence encoding mIL12aIL21IL12bGMCSF gene having BamHI, BglII and XhoI, EcoRI digestion sites attached to both ends thereof was synthesized, and then digested by BamHI or BglII and XhoI or EcoRI with the following system: 5 μg of mIL12aIL21IL12bGMCSF plasmid, 4 μl of digestion buffer, 1 μl of BamHI and 1 μl of XhoI, water was added to a total volume of 40 μl, and stood at 37° C. for 12 hours. The EP tube was removed, and 4.4 μl of 10× loading buffer was added. Electrophoresis was performed with 1% agarose gel, followed by recovery of mIL12aIL21IL12bGMCSF gene fragments for further use.

The amino acid sequence of mIL12aIL21IL12bGMCSF protein heterodimer is as set forth in SEQ ID NO. 25, and the nucleotide sequence encoding mIL12aIL21IL12bGMCSF is as set forth in SEQ ID NO. 45.

The regulable expression vector pLentis-PTRE-MCS-PGK-PURO was digested with the following system: 2 μg of pLentis-PTRE-MCS-PGK-PURO vector plasmid, 3 μl of digestion buffer, 1 μl of BamHI, 1 μl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL21IL12bGMCSF were ligated with the following ligation system: 2 μl of pLentis-PTRE-MCS-PGK-PURO, 2 μl of mIL12aIL21IL12bGMCSF, 1 μl of ligase buffer, 0.5 μl of T4DNA ligase and 4.5 μl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL12aIL21IL12bGMCSF-PGK-PURO.

12.2 Preparation of Cells Regulable to Express mIL12aIL21IL12bGMCSF

The mIL12aIL21IL12bGMCSF expression vector was prepared in accordance with the same method as the virus of the first expression vector to obtain the virus of the second expression vector pLentis-PTRE-mIL12aIL21IL12bGMCSF-PGK-PURO.

The cultured B16 (rtTA) tumor cells were digested and inoculated into a 6-well plate with $10^5$ cells/well. The culture volume was 1 ml. After 24 hours, 10 μl of the virus of the second expression vector pLentis-PTRE-mIL12aIL21IL12bGMCSF-PGK-PURO was added and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to express mIL12aIL21IL12bGMCSF, which are named B16 (rtTA)-mIL12aIL21IL12bGMCSF.

12.3. Effect of Induced Expression of mIL12aIL21IL12bGMCSF on Tumor Growth

Figure 12:
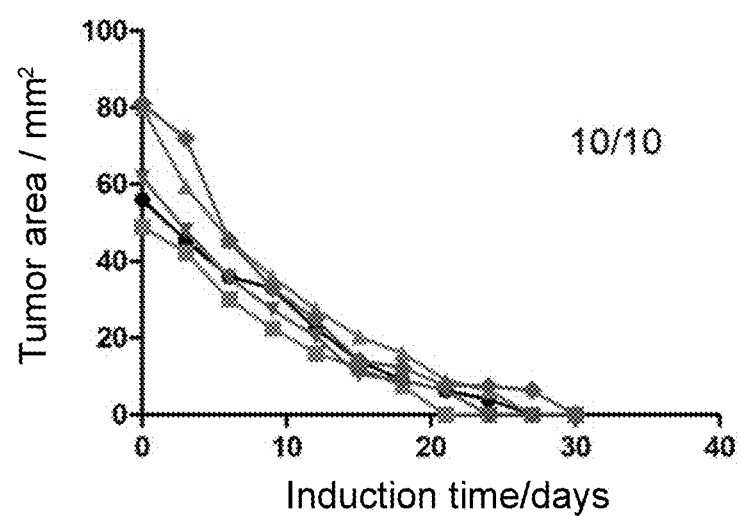
FIG. 12 shows the regression induced by the protein heterodimer of mIL12aIL21IL12bGMCSF.

The B16 (rtTA)-mIL12aIL21IL12bGMCSF cells in logarithmic phase were digested, and diluted with HBSS to $2\times10^6$ cells/ml. 8-10 week-old C57BL/6 female mice were injected at their right backs with 1 ml syringe at 50 μL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 10/10, as shown in FIG. 12. The mIL12aIL21IL12bGMCSF can induce tumor regression in all the mice.

Example 13

Effect of Induced Expression of mIL12aIL2IL12bFLT3L on Tumor Growth 13.1 Construction of Regulable Expression Vector of mIL12aIL2IL12bFLT3L A sequence encoding the mIL12aIL2IL12bFLT3L gene having BamHI, BglII and XhoI, EcoRI digestion sites attached to both ends thereof was synthesized, and then digested by BamHI or BglII and XhoI or EcoRI with the following system: 5 µg of mIL12aIL2IL12bFLT3L plasmid, 4 µl of digestion buffer, 1 µl of BamHI and 1 µl of XhoI, water was added to a total volume of 40 µl, and stood at 37° C. for 12 hours. The EP tube was removed, and 4.4 µl of 10× loading buffer was added. Electrophoresis was performed with 1% agarose gel, followed by recovery of mIL12aIL2IL12bFLT3L gene fragments for further use.

The amino acid sequence of mIL12aIL2IL12bFLT3L protein heterodimer is as set forth in SEQ ID NO. 26, and the nucleotide sequence encoding mIL12aIL2IL12bFLT3L is as set forth in SEQ ID NO. 46.

The regulable expression vector pLentis-PTRE-MCS-PGK-PURO was digested with the following system: 2 µg of pLentis-PTRE-MCS-PGK-PURO vector plasmid, 3 µl of digestion buffer, 1 µl of BamHI and 1 µl of XhoI, water was added to a total volume of 30 µl, and stood at 37° C. for 12 hours. The EP tube was removed, and 3.3 µl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL2IL12bFLT3L were ligated with the following ligation system: 2 µl of pLentis-PTRE-MCS-PGK-PURO, 2 µl of mIL12aIL2IL12bFLT3L, 1 µl of ligase buffer, 0.5 µl of T4DNA ligase and 4.5 µl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL12aIL2IL12bFLT3L-PGK-PURO.

13.2 Preparation of Cells Regulable to Express mIL12aIL2IL12bFLT3L

The mIL12aIL2IL12bFLT3L expression vector was prepared in accordance with the same method as the virus of the first expression vector to obtain the virus of the second expression vector pLentis-PTRE-mIL12aIL2IL12bFLT3L-PGK-PURO.

The cultured B16 (rtTA) tumor cells were inoculated into a 6-well plate with $10^5$ cells/well. The culture volume was 1 ml. After 24 hours, 10 µl of the virus of the aforesaid second regulable expression vector pLentis-PTRE-mIL12aIL2IL12bFLT3L-PGK-PURO was added and cultured in an incubator for additional 24 hours. The supernatant was discarded and replaced with fresh medium for further culture. After the cells were full, they were transferred to a culture flask, and puromycin was added to a final concentration of 3 µg/ml. After culture for additional 3 days, the surviving cells were cells regulable to express mIL12aIL2IL12bFLT3L, which are named B16 (rtTA)-mIL12aIL2IL12bFLT3L.

13.3. Effect of Induced Expression of mIL12aIL2IL12bFLT3L on Tumor Growth

Figure 13:
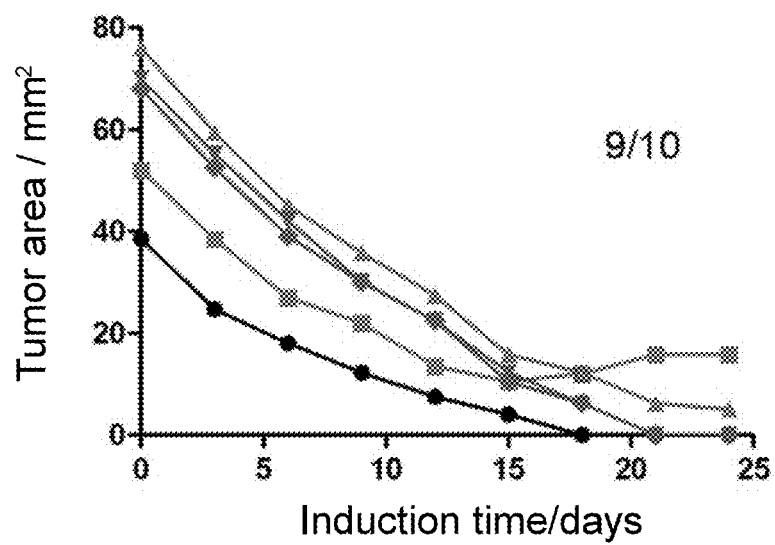
FIG. 13 shows the regression induced by the protein heterodimer of mIL12aIL2IL12bFLT3L.

The B16 (rtTA)-mIL12aIL2IL12bFLT3L cells in logarithmic phase were digested, and diluted with HBSS to $2 \times 10^6$ cells/ml. 8-10 week-old C57BL/6 female mice were injected at their right backs with 1 ml syringe at 50 µL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 9/10, as shown in FIG. 13. The mIL12aIL2IL12bFLT3L can induce tumor regression in part of the mice.

Example 14

Effect of Induced Expression of mIL12aIL7IL12bFLT3L on Tumor Growth 14.1 Construction of Regulable Expression Vector of mIL12aIL7IL12bFLT3L A sequence encoding the mIL12aIL7IL12bFLT3L gene having BamHI, BglII and XhoI, EcoRI digestion sites attached to both ends thereof was synthesized, and then digested by BamHI or BglII and XhoI or EcoRI with the following system: 5 µg of mIL12aIL7IL12bFLT3L plasmid, 4 µl of digestion buffer, 1 µl of BamHI and 1 µl of XhoI, water was added to a total volume of 40 µl, and stood at 37° C. for 12 hours. The EP tube was removed, and 4.4 µl of 10× loading buffer was added. Electrophoresis was performed with 1% agarose gel, followed by recovery of mIL12aIL7IL12bFLT3L gene fragments for further use.

The amino acid sequence of mIL12aIL7IL12bFLT3L protein heterodimer is as set forth in SEQ ID NO. 27, and the nucleotide sequence encoding mIL12aIL7IL12bFLT3L is as set forth in SEQ ID NO. 47.

The regulable expression vector pLentis-PTRE-MCS-PGK-PURO was digested with the following system: 2 µg of pLentis-PTRE-MCS-PGK-PURO plasmid, 3 µl of digestion buffer, 1 µl of BamHI and 1 µl of XhoI, water was added to a total volume of 30 µl, and stood at 37° C. for 12 hours. The EP tube was removed, and 3.3 µl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL7IL12bFLT3L were ligated with the following ligation system: 2 µl of pLentis-PTRE-MCS-PGK-PURO, 2 µl of mIL12aIL7IL12bFLT3L, 1 µl of ligase buffer, 0.5 µl of T4DNA ligase and 4.5 µl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL12aIL7IL12bFLT3L-PGK-PURO.

14.2 Preparation of Cells Regulable to Express mIL12aIL7IL12bFLT3L

The mIL12aIL7IL12bFLT3L expression vector was prepared in accordance with the same method as the virus of the first expression vector to obtain the virus of the second expression vector pLentis-PTRE-mIL12aIL7IL12bFLT3L-PGK-PURO.

The cultured B16 (rtTA) tumor cells were inoculated into a 6-well plate with 10⁵ cells/well. The culture volume was 1 ml. After 24 hours, 10 μl of the virus of the aforesaid second expression vector pLentis-PTRE-mIL12aIL7IL12bFLT3L-PGK-PURO was added and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulable to express mIL12aIL7IL12bFLT3L, which are named B16 (rtTA)-mIL12aIL7IL12bFLT3L.

14.3 Effect of Induced Expression of mIL12aIL7IL12bFLT3L on Tumor Growth

Figure 14:
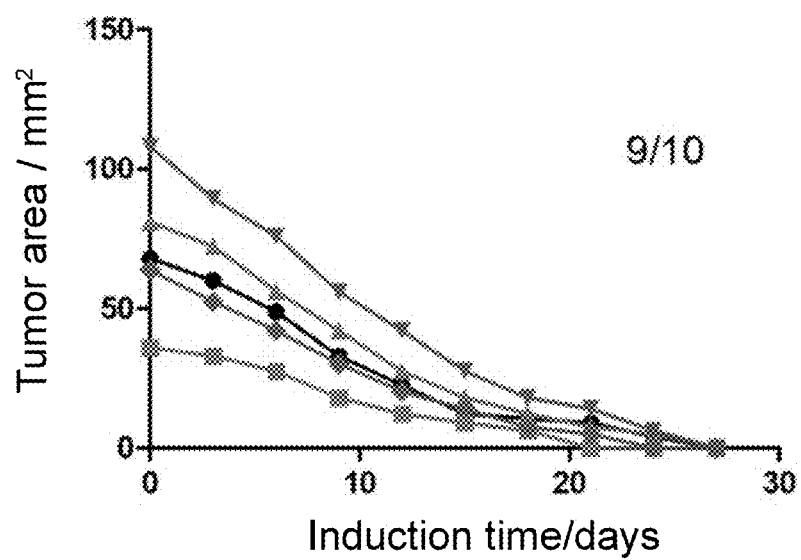
FIG. 14 shows the regression induced by the protein heterodimer of mIL12aIL7IL12bFLT3L.

The B16 (rtTA)-mIL12aIL7IL12bFLT3L cells in logarithmic phase were digested, and diluted with HBSS to 2×10⁶ cells/ml. 8-10 week old C57BL/6 female mice were injected at their right backs with 1 ml syringe at 50 μL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 9/10, as shown in FIG. 14. The mIL12aIL7IL12bFLT3L can induce tumor regression in part of the mice.

Example 15

Effect of Induced Expression of mIL12aIL15IL12bFLT3L on Tumor Growth 15.1 Construction of Regulable Expression Vector of mIL12aIL15Th12bFLT3L A sequence encoding the mIL12aIL15IL12bFLT3L gene having BamHI, BglII and XhoI, EcoRI digestion sites attached to both ends thereof was synthesized, and then digested by BamHI or BglII and XhoI or EcoRI with the following system: 5 μg of mIL12aIL15IL12bFLT3L plasmid, 4 μl of digestion buffer, 1 μl of BamHI and 1 μl of XhoI, water was added to a total volume of 40 μl, and stood at 37° C. for 12 hours. The EP tube was removed, and 4.4 μl of 10× loading buffer was added. Electrophoresis was performed with 1% agarose gel, followed by recovery of mIL12aIL15IL12bFLT3L gene fragments for further use.

The amino acid sequence of mIL12aIL15IL12bFLT3L protein heterodimer is as set forth in SEQ ID NO. 28, and the nucleotide sequence encoding mIL12aIL15IL12bFLT3L is as set forth in SEQ ID NO. 48.

The regulable expression vector pLentis-PTRE-MCS-PGK-PURO was digested with the following system: 2 μg of pLentis-PTRE-MCS-PGK-PURO vector plasmid, 3 μl of digestion buffer, 1 μl of BamHI, 1 μl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL15IL12bFLT3L were ligated with the following ligation system: 2 μl of pLentis-PTRE-MCS-PGK-PURO, 2 μl of mIL12aIL15IL12bFLT3L, 1 μl of ligase buffer, 0.5 μl of T4DNA ligase and 4.5 μl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture cells, and digestion was used to identify whether the fragment was successfully ligated into the vector. Then, the correct vectors were sequenced to confirm the successful construction of the second expression vector pLentis-PTRE-mIL12aIL15Th12bFLT3L-PGK-PURO.

15.2 Preparation of Cells Regulable to Express mIL12aIL15IL12bFLT3L

The mIL12aIL15IL12bFLT3L expression vector was prepared in accordance with the same method as the virus of the first expression vector to obtain the virus of the second expression vector pLentis-PTRE-mIL12aIL15Th12bFLT3L-PGK-PURO.

The cultured B16 (rtTA) tumor cells were inoculated into a 6-well plate with 10⁵ cells/well. The culture volume was 1 ml. After 24 hours, 10 μl of the virus of the aforesaid second expression vector pLentis-PTRE-mIL12aIL15IL12bFLT3L-PGK-PURO was added and cultured in an incubator for additional 24 hours. The supernatant was discarded and replaced with fresh medium for further culture. After the cells were full, they were transferred to a culture flask, and puromycin was added to a final concentration of 3 μg/ml. After culture for additional 3 days, the surviving cells were cells regulably expressing mIL12aIL15IL12bFLT3L, which are named B16 (rtTA)-mIL12aIL15IL12bFLT3L.

15.3 Effect of Induced Expression of mIL12aIL15IL12bFLT3L on Tumor Growth

Figure 15:
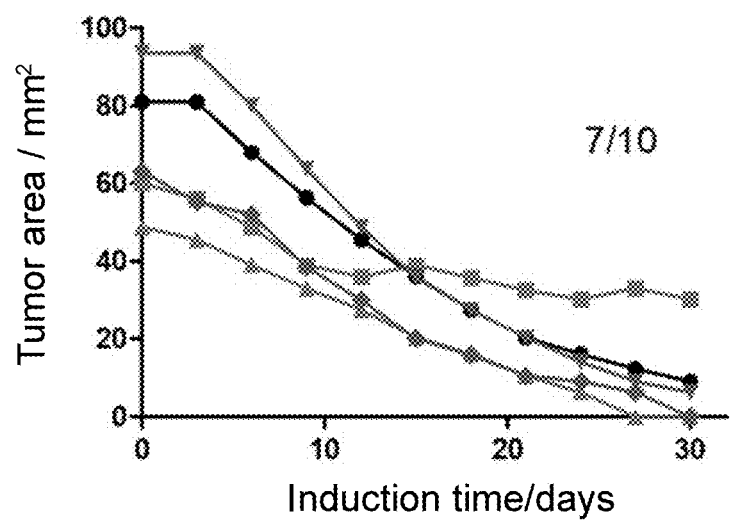
FIG. 15 shows the regression induced by the protein heterodimer of mIL12aIL15IL12bFLT3L.

The B16 (rtTA)-mIL12aIL15IL12bFLT3L cells in logarithmic phase were digested, and diluted with HBSS to 2×10⁶ cells/ml. 8-10 week-old C57BL/6 female mice were injected at their right backs with 1 ml syringe at 50 μL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 7/10, as shown in FIG. 15. The mIL12aIL15IL12bFLT3L can induce tumor regression in part of the mice.

Example 16

Effect of Induced Expression of mIL12aIL21IL12bFLT3L on Tumor Growth 16.1 Construction of Regulable Expression Vector of mIL12aIL21IL12bFLT3L A sequence encoding the mIL12aIL21IL12bFLT3L having BamHI, BglII and XhoI, EcoRI digestion sites attached to both ends thereof was synthesized, and then digested by BamHI or BglII and XhoI or EcoRI with the following system: 5 μg of mIL12aIL21IL12bFLT3L plasmid, 4 μl of digestion buffer, 1 μl of BamHI and 1 μl of XhoI, water was added to a total volume of 40 μl, and stood at 37° C. for 12 hours. The EP tube was removed, and 4.4 μl of 10× loading buffer was added. Electrophoresis was performed with 1% agarose gel, followed by recovery of mIL12aIL21IL12bFLT3L gene fragments for further use.

The amino acid sequence of mIL12aIL21IL12bFLT3L protein heterodimer is as set forth in SEQ ID NO. 29, and the nucleotide sequence encoding mIL12aIL21IL12bFLT3L is as set forth in SEQ ID NO. 49.

The regulable expression vector pLentis-PTRE-MCS-PGK-PURO was digested with the following system: 2 μg of pLentis-PTRE-MCS-PGK-PURO plasmid, 3 μl of digestion buffer, 1 μl of BamHI, 1 μl of XhoI, water was added to a total volume of 30 μl, and stood at 37° C. for 12 hours. The EP tube was removed, and 3.3 μl of 10× loading buffer was added. Electrophoresis was performed with 1% agarose gel, followed by recovery of pLentis-PTRE-MCS-PGK-PURO vector fragments for further use.

The pLentis-PTRE-MCS-PGK-PURO and mIL12aIL21IL12bFLT3L were ligated with the following ligation system: 2 µl of pLentis-PTRE-MCS-PGK-PURO, 2 µl of mIL12aIL21IL12bFLT3L, 1 µl of ligase buffer, 0.5 µl of T4DNA ligase and 4.5 µl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction of the second expression vector pLentis-PTRE-mIL12aIL21IL12bFLT3L-PGK-PURO.

16.2 Preparation of Cells Regulable to Express mIL12aIL21IL12bFLT3L

The virus of the mIL12aIL21IL12bFLT3L expression vector was prepared in accordance with the same method as the virus of the first expression vector to obtain the virus of the second expression vector pLentis-PTRE-mIL12aIL21IL12bFLT3L-PGK-PURO.

The cultured B16 (rtTA) tumor cells were digested and inoculated into a 6-well plate with $10^5$ cells/well. The culture volume was 1 ml. After 24 hours, 10 µl of the virus of the second regulable expression vector pLentis-PTRE-mIL12aIL21IL12bFLT3L-PGK-PURO was added and cultured in an incubator for additional 24 hours. The supernatant was discarded and replaced with fresh medium for further culture. After the cells were full, they were transferred to a culture flask, and puromycin was added to a final concentration of 3 µg/ml. After culture for additional 3 days, the surviving cells were cells regulable to express mIL12aIL21IL12bFLT3L, which are named B16 (rtTA)-mIL12aIL21IL12bFLT3L.

16.3 Effect of Induced Expression of mIL12aIL21IL12bFLT3L on Tumor Growth

Figure 16:
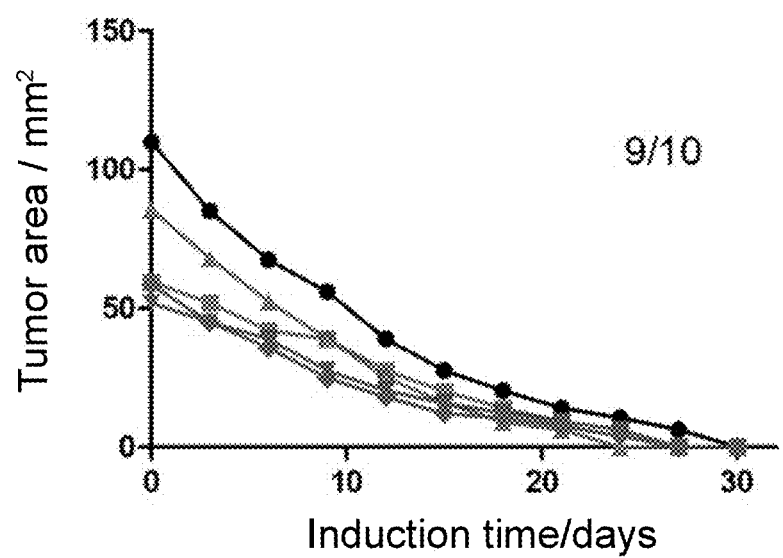
FIG. 16 shows the regression induced by the protein heterodimer of mIL12aIL21IL12bFLT3L.

The B16 (rtTA)-mIL12aIL21IL12bFLT3L cells in logarithmic phase were digested, and diluted with HBSS to $2\times10^6$ cells/ml. 8-10 week-old C57BL/6 female mice were injected at their right backs with 1 ml syringe at 50 µL/mouse (10 mice in total). After tumor growth, the mice were fed with water containing 2 g/L of doxycycline. The tumor growth and the tumor clearance of mice were recorded. The ratio of the number of tumor-clearing mice to the total number of mice was 9/10, as shown in FIG. 16. The mIL12aIL21IL12bFLT3L can induce tumor regression in part of the mice.

Example 17

Construction of Cells Expressing Human hIL12aIL2IL12bGMCSF, human hIL12aIL7IL12bGMCSF, human hIL12aIL15IL12bGMCSF, human hIL12aIL21IL12bGMCSF, human hIL12aIL2IL12bFLT3L, human hIL12aIL7IL12bFLT3L, human hIL12aIL15IL12bFLT3L, human hIL12aIL21IL12bFLT3L 17.1 Construction of Vector Regulable to Express Target Gene In the EP tube, the vector pLentis-CMV-MCS-IRES-PURO was digested with the following system: 2 µg of pLentis-CMV-MCS-IRES-PURO vector plasmid, 3 µl of digestion buffer, 1 µl of BamHI and 1 µl of XhoI, water was added to a total volume of 30 µl, and stood at 37° C. for 12 hours. The EP tube was removed, and 3.3 µl of 10× loading buffer was added. Electrophoresis was performed with 1% agarose gel, followed by recovery of pLentis-CMV-MCS-IRES-PURO vector fragments for further use.

DNA sequences of human hIL12aIL2IL12bGMCSF, human hIL12aIL7IL12bGMCSF, human hIL12aIL15IL12bGMCSF, human hIL12aIL21IL12bGMCSF, human hIL12aIL2IL12bFLT3L, human hIL12aIL7IL12bFLT3L, human hIL12aIL15Th12bFLT3L and human hIL12aIL21IL12bFLT3L were synthesized, respectively. During synthesis, BamHI or BglII digestion site was added to its 5' end, and XhoI or EcoRI digestion site was added to its 3' end. The synthesized plasmids with target gene were digested with the following system: 5 µg of plasmid, 4 µl of digestion buffer, 1 µl of BamHI and 1 µl of XhoI, water was added to a total volume of 40 µl, and stood at 37° C. for 12 hours. The EP tube was removed, and 4.4 µl of 10× loading buffer was added. Electrophoresis was performed with 1% agarose gel, followed by recovery of fragments for further use.

The amino acid sequence of hIL12aIL2IL12bGMCSF protein heterodimer is as set forth in SEQ ID NO. 30, and the nucleotide sequence encoding hIL12aIL2IL12bGMCSF is as set forth in SEQ ID NO. 50.

The amino acid sequence of hIL12aIL7IL12bGMCSF protein heterodimer is as set forth in SEQ ID NO. 31, and the nucleotide sequence encoding hIL12aIL7IL12bGMCSF is as set forth in SEQ ID NO. 51.

The amino acid sequence of hIL12aIL15IL12bGMCSF protein heterodimer is as set forth in SEQ ID NO. 32, and the nucleotide sequence encoding hIL12aIL15IL12bGMCSF is as set forth in SEQ ID NO. 52.

The amino acid sequence of hIL12aIL21IL12bGMCSF protein heterodimer is as set forth in SEQ ID NO. 33, and the nucleotide sequence encoding hIL12aIL21IL12bGMCSF is as set forth in SEQ ID NO. 53.

The amino acid sequence of hIL12aIL2IL12bFLT3L protein heterodimer is as set forth in SEQ ID NO. 34, and the nucleotide sequence encoding hIL12aIL2IL12bFLT3L is as set forth in SEQ ID NO. 54.

The amino acid sequence of hIL12aIL7IL12bFLT3L protein heterodimer is as set forth in SEQ ID NO. 35, and the nucleotide sequence encoding hIL12aIL7IL12bFLT3L is as set forth in SEQ ID NO. 55.

The amino acid sequence of hIL12aIL15IL12bFLT3L protein heterodimer is as set forth in SEQ ID NO. 36, and the nucleotide sequence encoding hIL12aIL15IL12bFLT3L is as set forth in SEQ ID NO. 56.

The amino acid sequence of hIL12aIL21IL12bFLT3L protein heterodimer is as set forth in SEQ ID NO. 37, and the nucleotide sequence encoding hIL12aIL21IL12bFLT3L is as set forth in SEQ ID NO. 57.

The pLentis-CMV-MCS-IRES-PURO and human hIL12aIL2IL12bGMCSF, human hIL12aIL7IL12bGMCSF, human hIL12aIL15IL12bGMCSF, human hIL12aIL21IL12bGMCSF, human hIL12aIL2IL12bFLT3L, human hIL12aIL7IL12bFLT3L, human hIL12aIL15IL12bFLT3L and human hIL12aIL21IL12bFLT3L were ligated with the following system respectively: 2 µl of pLentis-CMV-MCS-IRES-PURO vector fragments, 2 µl of gene fragments, 1 µl of ligase buffer, 0.5 µl of T4 DNA ligase and 4.5 µl of water. The mixture stood at room temperature for 4 hours of ligation. Then, the ligation system was transformed into competent *E. coli*. On the second day, the colonies were picked from the transformed plates, and cultured overnight in LB medium at 37° C. in a shaker. Plasmid extract kit was used to extract the plasmid from the culture bacteria, and digestion was used to identify whether the fragment was successfully ligated into the vector. Then, the correct vectors were sequenced to confirm the successful construction. The vectors expressing the target gene pLentis-CMV-hIL12aIL2IL12bGMCSF-IRES-PURO, vector pLentis-CMV-hIL12aIL7IL12bGMCSF-IRES-PURO, vector pLentis-CMV-hIL12aIL15IL12bGMCSF-IRES-PURO, vector pLentis-CMV-hIL12aIL21IL12bGMCSF-IRES-PURO, vector pLentis-CMV-hIL12aIL2IL12bFLT3L-IRES-PURO, vector pLentis-CMV-hIL12aIL7IL12bFLT3L-IRES-PURO, vector pLentis-CMV-hIL12aIL15IL12bFLT3L-IRES-PURO and vector pLentis-CMV-hIL12aIL21IL12bFLT3L-IRES-PURO were obtained.

17.2 Preparation of Cells Regulable to Express Target Gene

1) The cultured 293FT cells were digested. After counting, 3×10$^6$ cells/well were plated into a 10 cm culture dish, and the volume of culture medium was 10 ml. 5 plates in total were plated.

2) On the night of the second day, the cells were observed for their status. If the cells exhibited good status, transfection was conducted. Chloroquine was added into the culture plate to a final concentration of 25 μM. To a test tube were added sterile water and the following plasmids (pMD2.G 6 μg+pSPAX2 15 μg+expression vector 20 μg) with a total volume of 1045 μl. Then, 2M CaCl$_2$ (155 μl) was added and mixed well. Finally, 1200 μl of 2×HBS was added dropwise under shaking. After the completion of addition, the mixture was rapidly added into the cell culture wells, and gently shaken and mixed well.

3) In the morning of the third day, the cells were observed for their status, and the medium was replaced with 10 ml of fresh DMEM medium.

4) In the morning of the fifth day, the cells were observed for their status. The supernatant in the culture dish was collected, filtered by a 0.45 μm filter, and centrifuged at 50000 g in a high-speed centrifuge tube for 2 hours. The supernatant was carefully discarded. The liquid was removed with absorbent paper as much as possible, and the precipitate was re-suspended in 200 μl of HBSS. After 2 hours of dissolution, it was subpackaged to vials, and stored at −70° C.

17.3 Preparation of Cells Regulable to Express Target Gene

The cultured 293A cells were inoculated into a 6-well plate with 10$^5$ cells/well. The culture volume was 1 ml. After 24 hours, 10 μl of virus expressing the aforesaid target gene was added and cultured in an incubator for additional 24 hours. The supernatant was discarded and replaced with fresh medium for further culture. After the cells were full, they were transferred to a culture flask, and puromycin was added to a final concentration of 3 μg/ml for further culture. The medium was replaced every 2 days, and the concentration of puromycin was maintained. After one week of screening, the surviving cells are cells stably expressing the cytokines, which are named 293A-hIL12aIL2IL12bGMCSF, 293A-hIL12aIL7IL12bGMCSF, 293A-hIL12aIL15IL12bGMCSF, 293A-hIL12aIL21IL12bGMCSF, 293A-hIL12aIL2IL12bFLT3L, 293A-hIL12aIL7IL12bFLT3L, 293A-hIL12aIL15IL12bFLT3L, 293A-hIL12aIL21IL12bFLT3L, respectively.

Figure 17:
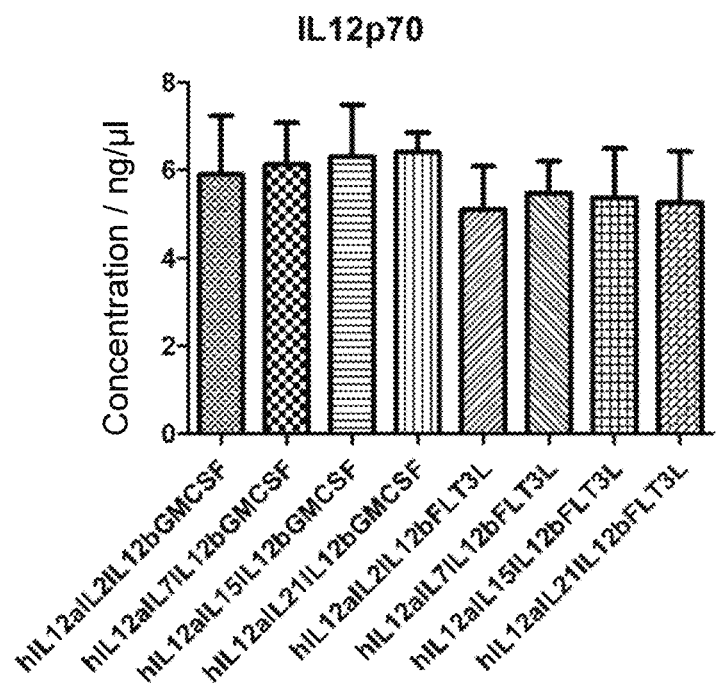
FIG. 17 shows the construction of the protein heterodimer.

The constructed expression cells were plated into a 24-well plate with 5×10$^4$ cells/well. After 96 hours of culture, the supernatant was collected, and detected by human IL12p70 ELISA kit for the expression of fusion protein in the supernatant in accordance with the instructions. As shown in FIG. 17, all these cells can produce a large amount of IL12p70, and thus the cells expressing the fusion protein were successfully constructed.

The aforesaid detailed description is provided in an illustrative and exemplary manner, and is not intended to limit the scope of the appended claims. Various modifications of embodiments currently listed herein are apparent for persons skilled in the art, and are encompassed within the scope of the appended claims and their equivalents.

The invention claimed is:

1. A protein heterodimer comprising:
a first polypeptide chain; and
a second polypeptide chain different from said first polypeptide chain,
wherein the first polypeptide chain comprises IL (interleukin) 12a and a first factor fused to the IL12a,
wherein the second polypeptide chain comprises IL12b and a second factor fused to the IL12b, and
wherein the first and the second factors are each independently selected from a cytokine group consisting of IL2, GMCSF (granulocyte-macrophage colony-stimulating factor), IL7, IL15, IL21, and FLT3L (FMS-like tyrosine kinase 3 ligand), wherein the first polypeptide chain comprises the sequence selected from the group consisting of SEQ ID NOs: 60-65 and SEQ IIS NOs: 70-73.

2. A protein heterodimer comprising:
a first polypeptide chain; and
a second polypeptide chain different from said first polypeptide chain,
wherein the first polypeptide chain comprises IL (interleukin)12a and a first factor fused to the IL12a,
wherein the second polypeptide chain comprises IL12b and a second factor fused to the IL12b, and
wherein the first and the second factors are each independently selected from a cytokine group consisting of IL2, GMCSF (granulocyte-macrophage colony-stimulating factor), IL15, IL21, and FLT3L (FMS-like tyrosine kinase 3 ligand),
wherein the second polypeptide chain comprises the sequence selected from the group consisting of SEQ ID NOs: 66-69 and SEQ ID NOs: 74-75.

3. A protein heterodimer, comprising
a first polypeptide chain; and
a second polypeptide chain different from said first polypeptide chain,
wherein the first polypeptide chain comprises IL (interleukin) 12a and a first factor fused to the IL12a,
wherein the second polypeptide chain comprises IL12b and a second factor fused to the IL12b, and
wherein the first and the second factors are each independently selected from a cytokine group consisting of IL2, GMCSF (granulocyte-macrophage colony-stimulating factor), IL7, IL15, IL21, and FLT3L (FMS-like tyrosine kinase 3 ligand),
wherein the protein heterodimer comprises the sequence selected from the group consisting of SEQ ID NOs:18-37.

4. An isolated nucleic acid molecule, encoding the protein heterodimer of claim 3.

5. The nucleic acid molecule of claim 4, comprising the sequence selected from the group consisting of SEQ ID NOs: 38-57.

6. A method of ameliorating or treating a tumor in a subject in need thereof, the method comprising:
administering an effective amount of the protein heterodimer of claim 1 to the subject, thereby ameliorating or treating the tumor, wherein the tumor comprises melanoma.

7. A method of ameliorating; or treating a tumor in a subject in need thereof, the method comprising:
administering an effective amount of the protein heterodimer of claim 2 to the subject, thereby ameliorating or treating tumor, wherein said tumor comprises melanoma.

8. A method of ameliorating or treating a tumor in a subject in need thereof, the method comprising:
administering an effective amount of the protein heterodimer of claim 3 to the subject, thereby ameliorating or treating the tumor, wherein said tumor comprises melanoma.

* * * * *